(12) United States Patent
Cunningham

(10) Patent No.: US 8,367,319 B2
(45) Date of Patent: *Feb. 5, 2013

(54) METHODS AND COMPOSITIONS FOR THE IDENTIFICATION OF ANTIBIOTICS THAT ARE NOT SUSCEPTIBLE TO ANTIBIOTIC RESISTANCE

(75) Inventor: Phillip R. Cunningham, Troy, MI (US)

(73) Assignee: Wayne State University, Detroit, MI (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/771,340

(22) Filed: Apr. 30, 2010

(65) Prior Publication Data

US 2011/0256533 A1 Oct. 20, 2011

Related U.S. Application Data

(60) Continuation of application No. 11/436,349, filed on May 18, 2006, now Pat. No. 7,709,196, which is a division of application No. 10/612,224, filed on Jul. 1, 2003, now Pat. No. 7,081,341.

(60) Provisional application No. 60/393,237, filed on Jul. 1, 2002, provisional application No. 60/452,012, filed on Mar. 5, 2003.

(51) Int. Cl.
*C12Q 1/70* (2006.01)
*C12N 15/70* (2006.01)
*C12N 15/00* (2006.01)
*C12N 1/21* (2006.01)
*C12P 21/00* (2006.01)

(52) U.S. Cl. ........... 435/6; 435/471; 435/440; 435/70.1; 435/252.3

(58) Field of Classification Search .................. None
See application file for complete search history.

(56) References Cited

U.S. PATENT DOCUMENTS

| 4,772,555 A | 9/1988 | De Boer |
| 4,873,316 A | 10/1989 | Meade et al. |
| 5,821,058 A | 10/1998 | Smith et al. |
| 5,981,280 A | 11/1999 | Fang et al. |

FOREIGN PATENT DOCUMENTS

| WO | WO-96/06106 | 2/1996 |
| WO | WO-00/32619 | 6/2000 |
| WO | WO-01/42445 | 6/2001 |
| WO | WO-02/29019 | 4/2002 |
| WO | WO-03/029459 | 4/2003 |
| WO | WO-2006/115570 | 11/2006 |

OTHER PUBLICATIONS

Asai, T., (1999) Construction and Initial Characterization of Escherichia coli Strains with Few or No Intact Chromosomal rRNA Operons; J. Bacteriol. 181: 3803-3809.
Baldari et al. (1987) A novel leader peptide which allows efficient secretion of a fragment of human interleukin 1β in Saccharomyces cerevisiae; EMBO J. 6:229-234.
Banerji et al. (1983) A lymphocyte-specific cellular enhancer is located downstream of the joining region in immunoglobulin heavy chain genes. Cell 33:729-740.
Bottger, E., et al., "Resistance to drugs targeting protein synthesis in mycobacteria," Trends in Microbiology; 2(10):416-421 (1994).
Brosius, J., et al. (1981) Construction and Fine Mapping of Recombinant Plasmids Containing the rrnB Ribosomal RNA Operon of E. coli; Plasmid 6: 112-118.
Brow, D. A. & Noller, H. F. (1983) Protection of Ribosomal RNA from Kethoxal in Polyribosomes; J. Mol. Biol. 163:112-118.
Byrne and Ruddle (1989) Multiplex gene regulation: A two-tiered approach to transgene regulation in transgenic mice; Proc. Natl. Acad. Sci. USA 86:5473-5477.
Calame and Eaton (1988) Transcriptional controlling elements in the immunoglobulin and T cell receptor loci. Adv. Immunol. 43:235-275.
Calos, M.P. (1978) DNA sequence for a low-level promoter of the lac repressor gene and an 'up' promoter mutation; Nature 274:762-765.
Capaldi, D. & Reese, C. (1994) Use of the 1-(2-fluorophenyl)-4-methoxypiperidin-4-yl (Fpmp) and related protecting groups in oligoribonucleotide synthesis: stability of internucleotide linkages to aqueous acid; Nucl. Acids Res. 22:2209-2216.
Carter-Muenchau, P. & Wolf, R. E. (1989) Growth-rate dependent regulation of 6-phosphogluconate dehydrogenase level mediated by an anti-Shine-Dalgarno sequence located within the Escherichia coli gnd structural gene; Proc. Natl. Acad. Sci. USA 86:1138-1142.
Chen, H., et al. (1994) Determination of the optimal aligned spacing between the Shine-Dalgarno sequence and the translation initiation codon of Escherichia coli mRNAs; Nucl. Acids Res. 22: 4953-4957.
Cunningham, P., et al. (1993) Functional effects of base changes which further define the decoding center of Escherichia coli 16S ribosomal RNA: mutation of C1404, G1405, C1496, G1497, and U1498. Biochemistry 32: 7172-7180.
de Boer, H. A., et al. (1983) The tac promoter: A functional hybrid derived from the trp and lac promoters; Proc. Natl Acad. Sci. USA 80:21-25.
Denman, R. et al. (1989) In vitro assembly of 30S and 70S bacterial ribosomes from 16S RNA containing single base substitutions, insertions, and deletions around the decoding site (C1400). Biochemistry 28:1002-1011.
Dower, W. J., et al. (1988) High efficiency transformation of E. coli by high voltage electroporation; Nucl. Acids Res. 16: 6127.
Edlund et al. (1985) Cell-Specific Expression of the Rat Insulin Gene: Evidence for Role of Two Distinct 5' Flanking Elements; Science 230:912-916.
Goeddel (1990) Systems for Heterologous Gene Expression; Methods Enzymol. 185:3-7.

(Continued)

Primary Examiner — Nancy T Vogel
(74) Attorney, Agent, or Firm — Senniger Powers LLP

(57) ABSTRACT

Compositions and methods are provided to identify functional mutant ribosomes that may be used as drug targets. The compositions and methods allow isolation and analysis of mutations that would normally be lethal and allow direct selection of rRNA mutants with predetermined levels of ribosome function. The compositions and methods of the present invention may be used to identify antibiotics to treat a large number of human pathogens through the use of genetically engineered rRNA genes from a variety of species. The invention further provides novel plasmid constructs to be used in the methods of the invention.

17 Claims, 47 Drawing Sheets

OTHER PUBLICATIONS

Gottesman, S. (1990) Minimizing Proteolysis in *Escherichia coli*: Genetic Solutions; Methods Enzymol. 185:119-128.

Govantes, F. et al. (1998) Mechanism of translational coupling in the nifLA operon of *Klebsiella pneumoniae*; EMBO J. 17(8):2368-2377.

Gutell, R. R. (1994) Collection of small subunit (16S- and 16S-like) ribosomal RNA structures: 1994; Nucl. Acids Res. 22: 3502-3507.

Hanahan, D. (1983) Studies on Transformation of *Escherichia coli* with Plasmids; J. Mol. Biol. 166:557-580.

Herr, W., et al. (1979) Mechanism of Ribosomal Subunit Association: Discrimination of Specific Sites in 16S RNA Essential for Association Activity; J. Mol. Biol. 130: 433-449.

Higuchi, R. (1989) Using PCR to Engineer DNA; PCR Technology (Erlich, H.A., ed.), pp. 61-70, Stockton Press, New York.

Hui, A., et al. (1987) Directing Ribosomes to a Single mRNA Species: A Method to Study Ribosomal RNA Mutations and Their Effects on Translation of a Single Messenger in *Escherichia coli*; Methods Enzymol. 153: 432-452.

Hui, A., et al. (1987) Specialized ribosome system: Preferential translation of a single mRNA species by a subpopulation of a mutated ribosomes in *Escherichia coli*; Proc. Natl. Acad. Sci. U.S.A. 84: 4762-4766.

Kaufman et al. (1987) Translation efficiency of polycistronic mRNAs and their utilization to express heterologous genes in Mammalian Cells. EMBO J. 6:187-195.

Kessel and Gruss (1990) Murine Developmental Control Genes; Science 249:374-379.

Koosha, H., et al. (2000) Alterations in the peptidyltransferase and decoding domains of ribosomal RNA suppress mutations in the elongation factor G gene; RNA. 6: 1166-1173.

Kozak, M., "Regulation of translation via mRNA structure in prokaryotes and eukaryotes," Gene, 361:13-37 (2005).

Kurjan and Herskowitz (1982) Structure of a yeast pheromone gene (MF alpha): a putative alpha-factor precursor contains four tandem copies of mature alpha-factor. Cell 30:933-943.

Laios, E., et al. (2004) "Combinatorial genetic technology for the development of new anti-infectives"; *Arch Pathol Lab Med.*; Dec; 128 (12); pp. 1351-1359.

Lee, K., et al. (1996) Genetic analyais of the Shine-Dalgarno interaction: Selection of alternative functional mRNA-rRNA combinations; RNA 2: 1270-1285.

Lee, K., et al. (2001) Genetic Approaches to Studying Protein Synthesis: Effects of Mutations at Pseudouridine 516 and A535 in *Escherichia coli* 16S rRNA. Symposium: Translational Control: A Mechanistic Perspective at the Experimental Biology 2001 Meeting.

Lee, K., et al. (1997) In Vivo Determination of RNA Structure-Function Relationships: Analysis of the 790 Loop in Ribosomal RNA; J. Mol. Biol. 269:732-743.

Lee, K., et al. (2001) "Genetic approaches to studying protein synthesis: effects of mutations at Psi516 and A535 in *Escherichia coli* 16S rRNA"; *J Nutr* 131:2994S-3004S.

Luria, S.E. & Burrous, J.W. (1957) Hybridization between *Escherichia coli* and shigella; J. Bacteriol. 74:461-476.

Maden, B. E. (1990) The Numerous Modified Nucleotides in Eukaryotic Ribosomal RNA; Prog. Nucleic Acid Res. Mol. Biol. 39: 241-303.

Maidak, B. L. et al. (1996) The Ribosomal Database Project (RDP); Nucl. Acids Res. 24: 82-85.

Makosky, P. C. et al. (1987) Spectinomycin resistance at site 1192 in 16S ribosomal RNA of *E. coli*: an analysis of three mutants. Biochimie 69: 885-889.

Miller, J.H. (1992) Procedures for Working with *lac*; A Short Course in Bacterial Genetics, (Miller, J. H., ed.), pp. 71-80, Cold Spring Harbor Laboratory Press, Cold Spring Harbor, NY.

Moazed, D. & Noller, H.F. (1986) Interconversion of Active and Inactive 30 S Ribosomal Subunits is Accompanied by a Conformational Change in the Decoding Region of 16S rRNA; J. Mol. Biol. 191:483-493.

Morosyuk S. V., et al. (2000) Structure and Function of the Conserved 690 Hairpin in *Escherichia coli* 16 S Ribosomal RNA: Analysis of the Stem Nucleotides; J. Mol. Biol. 300 (1):113-126.

Morosyuk S. V., et al. (2001) Structure and Function of the Conserved 690 Hairpin in *Escherichia coli* 16 S Ribosomal RNA. II. NMR Solution Structure; J. Mol. Biol. 307 (1):197-211.

Morosyuk S. V., et al. (2001) Structure and Function of the Conserved 690 Hairpin in *Escherichia coli* 16 S Ribosomal RNA. III. Functional Analysis of the 690 Loop; J. Mol. Biol. 307 (1):213-228.

Nielsen, D. A. et al. (1989) A highly sensitive, mixed-phase assay for chloramphenicol acetyltransferase activity in transfected cells. Anal. Biochem. *Anal. Biochem.* 179: 19-23.

O'Connor, M. et al. (2001) Enhancement of translation by the epsilon element is independent of the sequence of the 460 region of 16S rRNA; Nucl. Acids Res. 29: 1420-1425.

O'Connor, M., et al. (2001) Mutagenesis of the peptidyltransferase center of 23S rRNA: the invariant U2449 is dispensable; Nucl. Acids Res. 29: 710-715.

Pinkert et al. (1987) An albumin enhancer located 10 kb upstream functions along with its promoter to direct efficient, liver-specific expression in transgenic mice; Genes Dev. 1:268-277.

Powers, T. et al. (1991) A functional pseudoknot in 16S ribosomal RNA; EMBO J. 10: 2203-2214.

Queen, C. & Baltimore, D. (1983) Immunoglobulin gene transcription is activated by downstream sequence elements. Cell 33:741-748.

Schottel, J. L., et al. (1984) Effects of alterations in the translation control region on bacterial gene expression: use of *cat* gene constructs transcribed from the *lac* promoter as a model system; Gene 28: 177-193.

Schultz et al. (1987) Expression and secretion in yeast of a 400-kDa envelope glycoprotein derived from Epstein-Barr virus; Gene 54:113-123.

Seed, B. (1987) An LFA-3 cDNA encodes a phospholipid-linked membrane protein homologous to its receptor CD2; Nature 329:840.

Sergiev, P. V., et al. (2000) Mutations at Position A960 of *E. coli* 23 S Ribosomal RNA Influence the Structure of 5 S Ribosomal RNA and the Peptidyltransferase Region of 23 S Ribosomal RNA; J. Mol. Biol. 299:379-389.

Sigmund, C. D., et al. (1984) Antibiotic resistance in 16S and 23S ribosomal RNA genes of *Escherichia coli*; Nucl. Acids Res. 12: 4653-4663.

Sigmund, C. D., et al. (1988) Antibiotic Resistance Mutations in Ribosomal RNA Genes of *Escherichia coli*; Methods Enzymol. 164: 673-690.

Sigmund, C. D. et al. (1982) Erythromycin resistance due to a mutation in a ribosomal RNA operon of *Escherichia coli*; Proc. Natl. Acad. Sci. U.S.A. 79: 5602-5606.

Smith, D.B. and Johnson, K.S. (1988) Single-step purification of polypeptides expressed in *Escherichia coli* as fusions with glutathione S-transferase; Gene 67:31-40.

Stormo, G. D., et al. (1982) Characterization of translational initiation sites in *E. coli*; Nucleic Acids Res. 10: 2971-2996.

Tapprich, W. & Hill, W. (1986) Involvement of bases 787-795 of *Escherichia coli* 16S ribosomal RNA in ribosomal subunit association; Proc. Natl Acad. Sci. USA 83: 556-56.

Tapprich, W., et al. (1989) Mutation at position 791 *Escherichia coli* 16S ribosomal RNA affects processes involved in the initiation of protein synthesis; Proc. Natl Acad. Sci. USA 86: 4927-4931.

Triman, K., et al. (1989) Isolation of Temperature-sensitive Mutants of 16 S rRNA in *Escherichia coli*; J. Mol. Biol. 209:645-653.

Vila-Sanjurjo, A. et al. (2001) Mutational Analysis of the Conserved Bases C1402 and A1500 in the Center of the Decoding Domain of *Escherichia coli* 16 S rRNA Reveals an Important Tertiary Interaction; J. Mol. Biol. 308: 457-463.

Voulgaris, J., et al. (1999) Increased *rrn* Gene Dosage Causes Intermittent Transcription of rRNA in *Escherichia coli*; J. Bacteriol. 181: 4170-4175.

Wada et al. (1992) Codon usage tabulated from the GenBank genetic sequence data; Nucl. Acids Res. 20:2111-2118.

Winoto and Baltimore (1989) A novel, inducible and T cell-specific enhancer located at the 3' end of the T cell receptor α locus; EMBO J. 8:729-733.

Yanisch-Perron, C., et al. (1985) Improved M13 phage cloning vectors and host strains: nucleotide sequences of the M13mp18 and pUC19 vectors; Gene 33:103-119.

Supplemental European Search Report for EP 03 76 2329 dated Nov. 10, 2005.
Supplemental European Search Report for EP 06 75 9609 dated Jan. 13, 2009.
International Search Report for PCT/US06/18320 dated Nov. 28, 2007.
Adachi, J. A., et al. (2002) "Natural history of enteroaggregative and enterotoxigenic *Escherichia coli* infection among US travelers to Guadalajara, Mexico"; *J Infect Dis* 185:1681-3.
Adang, A. E. P., et al. (1994) "Case Histories of Peptidomimetics: Progression from Peptides to Drugs"; *Recl. Trav. Chim. Pays-Bas* 113:63-78.
Agalarov, S. C., et al. (2000) "Structure of the S15,S6,S18-rRNA complex: assembly of the 30S ribosome central domain"; *Science* 288:107-112.
Ahn, J. M., et al. (2002) "Peptidomimetics and Peptide Backbone Modifications"; *Mini Rev. Med. Chem.* 2:463-473.
Andersson, D. I., et al. (1998) "Antibiotic resistance here to stay? Compensatory mutations restore virulence of resistant bacteria"; *Lakartidningen* 95:3940, 3943-4.
Ang, J. Y., et al. (2004) "Antibacterial resistance"; *Indian J Pediatr* 71:229-39.
Aoki, H., et al. (2002) "Oxazolidinone antibiotics target the P site on *Escherichia coli* ribosomes"; *Antimicrob Agents Chemother* 46:1080-5.
Asai, T., (1999) "Construction and initial characterization of *Escherichia coli* strains with few or no intact chromosomal rRNA operons"; *J. Bacteriol.* 181: 3803-3809.
Baldari et al. (1987) "A novel leader peptide which allows efficient secretion of a fragment of human interleukin 1β in *Saccharomyces cerevisiae*"; *EMBO J.* 6:229-234.
Banerji et al. (1983) "A lymphocyte-specific cellular enhancer is located downstream of the joining region in immunoglobulin heavy chain genes," *Cell* 33:729-740.
Barrick, J. E., et al. (2001) "Selection of RNA-Binding Peptides Using mRNA-Peptide Fusions"; *Methods* 3:287-293.
Barrick, J. E. & Roberts, R. W. (2002) "Sequence Analysis of an Artifical Family of RNA-Binding Peptides"; *Protein Sci.* 11:2688-2696.
Batey, R. T., et al. (1992) "Preparation of isotopically labeled ribonucleotides for multidimensional NMR spectroscopy of RNA"; *Nucleic Acids Res.* 20:4515-4523.
Batey, R. T. & Williamson, J. R. (1996) "Interaction of the *Bacillus stearothermophilus* ribosomal protein S15 with 16 S rRNA: II. Specificity determinants of RNA-protein recognition"; *J Mol Biol* 261:550-67.
Bhattacharya, S. K., et al. (2003) "Multidrug-resistant *Shigella dysenteriae* type 1 in south Asia"; *Lancet Infect Dis* 3:755.
Bjorkman, J., et al. (2000) "Effects of environment on compensatory mutations to ameliorate costs of antibiotic resistance"; *Science* 287:1479-82.
Bodhidatta, L., et al. (2002) "Bacterial enteric pathogens in children with acute dysentery in Thailand: increasing importance of quinolone-resistant *Campylobacter*"; *Southeast Asian J Trop Med Public Health* 33:752-7.
Brodersen, D. E., et al. (2002) "Crystal structure of the 30 S ribosomal subunit from *Thermus thermophilus*: structure of the proteins and their interactions with 16 S RNA"; *J Mol Biol* 316:725-68.
Brosius, J., et al. (1981); "Construction and fine mapping of recombinant plasmids containing the *rrnB* ribosomal RNA operon of *Escherichia coli*"; *Plasmid* 6:112-118.
Brow, D. A. & Noller, H. F. (1983) "Protection of ribosomal RNA from Kethoxal in polyribosomes"; *J. Mol. Biol.* 163:27-46.
Bursavich, M. G. & Rich, D. H. (2002) "Designing Non-Peptide Peptidomimetics in the 21st Century: Inhibitors Targeting Conformational Ensembles"; *J. Med. Chem.* 45(3):541-558.
Byrne and Ruddle (1989) "Multiplex gene regulation: a two-tiered approach to transgene regulation in transgenic mice"; *Proc. Natl. Acad. Sci. USA* 86:5473-5477.
Calame and Eaton (1988) "Transcriptional controlling elements in the immunoglobulin and T cell receptor loci," *Adv. Immunol.* 43:235-275.

Calos, M.P. (1978) "DNA sequence for a low-level promoter of the *lac* repressor gene and an 'up' promoter mutation"; *Nature* 274:762-765.
Cannone, J. J., et al. (2002) "The Comparative RNA Web (CRW) Site: an online database of comparative sequence and structure information for ribosomal, intron, and other RNAs: Correction"; *BMC Bioinformatics* 3:15.
Capaldi, D. & Reese, C. (1994) "Use of the 1-(2-fluorophenyl)-4-methoxypiperidin-4-yl (Fpmp) and related protecting groups in oligoribonucleotide synthesis: stability of internucleotide linkages to aqueous acid"; *Nucl. Acids Res.* 22:2209-2216.
Carter, A. P., et al. (2001) "Crystal structure of an initiation factor bound to the 30S ribosomal subunit"; *Science* 291:498-501.
Carter, A. P., et al.(2000) "Functional insights from the structure of the 30S ribosomal subunit and its interactions with antibiotics"; *Nature* 407:340-8.
Carter-Muenchau, P. & Wolf, R. E. (1989) "Growth-rate dependent regualtion of 6-phosphogluconate dehydrogenase level mediated by an anti-Shine-Dalgarno sequence located within the *Escherichia coli* gnd structural gene"; *Proc. Natl. Acad. Sci. USA* 86:1138-1142.
Castagnoli, L., et al. (2001) "Alternative bacteriophage display systems"; *Comb Chem High Throughput Screen* 4:121-33.
Cha, J., et al. (1993) "New vectors for direct cloning of PCR products"; *Gene* 136:369-70.
Chen, H., et al. (1994) "Determination of the optimal aligned spacing between the Shine-Dalgarno sequence and the translation initiation codon of *Escherichia coli* mRNAs"; *Nucl. Acids Res.* 22: 4953-4957.
Chopra, I., et al. (2003) "The role of mutators in the emergence of antibiotic-resistant bacteria"; *Drug Resist Updat* 6:137-45.
Chow, C. S. & Bogdan, F. M. (1997) "A Structural Basis for RNA-Ligand Interactions"; *Chem. Rev.* 97:1489-1513.
Clarke, S. C., et al. (2003) "Virulence of enteropathogenic *Escherichia coil*, a global pathogen"; *Clin Microbiol Rev* 16(3):365-78.
Clarke, S. C., et al. (2002) "Enteropathogenic *Escherichia coli* infection: history and clinical aspects"; *Br J Biomed Sci* 59:123-7.
Collins, M. & Tami, T. A. (2003) "Methicillin-resistant *Staphylococcus aureus* (MRSA) in the practice of otolaryngology—an emerging community acquired organism?"; *Curr Opin Otolaryngol Head Neck Surg* 11:179-83.
Cunningham, P., et al. (1993) "Functional effects of base changes which further define the decoding center of *Escherichia coli* 16S ribosomal RNA: mutation of C1404, G1405, C1496, G1497, and U1498," *Biochemistry* 32: 7172-7180.
Cunningham, P. R., et al. (1988) "The role of 16S RNA in ribosome function: single base alterations and their effect on in vitro protein synthesis"; *Arch Biol Med Exp* (Santiago) 21:393-401.
Danner, S. & Belasco, J. G. (2001) "T7 phage display: a novel genetic selection system for cloning RNA-binding proteins from cDNA libraries"; *Proc Natl Acad Sci U S A* 98:12954-9.
de Boer, H. A., et al. (1983) "The tac promoter: a functional hybrid derived from the *trp* and *lac* promoters"; *Proc. Natl Acad. Sci. USA* 80:21-25.
De Stasio, E. A., et al. (1989) "Mutations in 16S ribosomal RNA disrupt antibiotic—RNA interactions"; *Embo J* 8:1213-6.
Denman, R. et al. (1989) "In vitro assembly of 30S and 70S bacterial ribosomes from 16S RNA containing single base substitutions, insertions, and deletions around the decoding site (C1400)," *Biochemistry* 28:1002-1011.
Depardieu, F., et al. (2003) "VanD-type vancomycin-resistant *Enterococcus faecium* 10/96A"; *Antimicrob Agents Chemother* 47:7-18.
Dessen, A., et al. (2001) "Molecular mechanisms of antibiotic resistance in gram-positive pathogens"; *Curr Drug Targets Infect Disord* 1:63-77.
Dower, W. J., et al. (1988) "High efficiency transformation of *Escherichia coli* by high voltage electroporation"; *Nucl. Acids Res.* 16: 6127.
Edlund et al. (1985) "Cell-specific expression of the rat insulin gene: evidence for role f two distinct 5' flanking elements"; *Science* 230:912-916.
Enright, M. C. (2003) "The evolution of a resistant pathogen—the case of MRSA"; *Curr Opin Pharmacol* 3:474-9.

Evans, G. A. (2002) "The Oxazolidinones"; *Curr Infect Dis Rep* 4:17-27.

Fauci, A. S., et al.; (2005) "Emerging infectious diseases: a 10-year perspective from the national institute of allergy and infectious diseases." *Emerg Infect Dis*; 11: 519-25.

Fourmy, D., et al. (1996) "Structure of the A site of *Escherichia coli* 16S Ribosomal RNA Complexed with an Aminoglycoside Antibiotic"; *Science* 274:1367-1371.

Gabashvili, I. S., et al. (1999) "Major rearrangements in the 70S ribosomal 3D structure caused by a conformational switch in 16S ribosomal RNA"; *Embo J* 18:6501-7.

Goeddel (1990) "Systems for heterologous gene expression"; *Methods Enzymol*. 185:3-7.

Gomi, H., et al. (2001) "In vitro antimicrobial susceptibility testing of bacterial enteropathogens causing traveler's diarrhea in four geographic regions"; *Antimicrob Agents Chemother* 45:212-6.

Gonzales, R. D., et al. (2001) "Infections due to vancomycin-resistant *Enterococcus faecium* resistant to linezolid"; *Lancet* 357:1179.

Gottesman, S. (1990) "Minimizing proteolysis in *Escherichia coli*: genetic solutions"; *Methods Enzymol*. 185:119-128.

Govantes, F. et al. (1998) "Mechanism of translational coupling in the nifLA operon of *Klebsiella pneumoniae*"; *EMBO J*. 17(8):2368-2377.

Guerrant, R. L., et al. (2002) "Magnitude and impact of diarrheal diseases"; *Arch Med Res* 33:351-5.

Gutell, R. R. (1994) "Collection of small subunit (16S- and 16S-like) ribosomal RNA structures"; *Nucl. Acids Res*. 22: 3502-3507.

Gutell, R. R., et al. (1992) "Identifying constraints on the higher-order structure of RNA: continued development and application of comparative sequence analysis methods"; *Nucleic Acids Res* 20(21):5785-95.

Haddad, J., et al. (2002) "Design of Novel Antibiotics that Bind to the Ribosomal Acyltransfer Site"; *J. Am. Chem. Soc*. 124:3229-3237.

Hanahan, D. (1983) "Studies on transformation of *Escherichia coli* with plasmids"; *J. Mol. Biol*. 166:557-580.

Hancock, R. E. & Chapple, D. S. (1999) "Peptide Antibiotics"; *Antimicrob. Agents Chemother*. 43(6):1317-1323.

Harms, J., et al. (2001) "High Resolution Structure of the Large Ribosomal Subunit from a Mesophilic Eubacterium"; *Cell* 107:679-688.

Hartman, A. B., et al. (2003) "Epidemiology of tetracycline resistance determinants in *Shigella* spp. and enteroinvasive *Escherichia coli*: characterization and dissemination of tet(A)-1"; *J Clin Microbiol* 41:1023-32.

Herr, W., et al. (1979) "Mechanism of ribosomal subunit association: discrimination of specific sites in 16S RNA essential for association activity"; *J. Mol. Biol*. 130: 433-449.

Herrero, I. A., et al. (2002) "Nosocomial spread of linezolid-resistant, vancomycin-resistant *Enterococcus faecium*"; *N Engl J Med* 346:867-9.

Higuchi, R. (1989) "Using PCR to engineer DNA"; PCR Technology (Erlich, H.A., ed.), pp. 61-70, Stockton Press, New York.

Hui, A., et al. (1987) "Specialized ribosome system: preferential translation of a single mRNA species by a subpopulation of a mutated ribosome in *Escherichia coli*"; *Proc. Natl. Acad. Sci. U.S.A*. 84: 4762-4766.

Hui, A., et al. (1987) "Directing ribosomes to a single mRNA species: a method to study ribosomal RNA mutations and their effects on translation of a single messenger in *Escherichia coli*"; *Methods Enzymol*. 153: 432-452.

Hwang, S., et al. (1999) "Inhibition of Gene Expression in Human Cells Through Small Molecule-RNA Interactions"; *Proc. Natl. Acad. Sci. USA* 96:12997-13002.

International Search Report dated Nov. 28, 2007.

John, T. J. (1996) "Emerging & re-emerging bacterial pathogens in India"; *Indian J Med Res* 103:4-18.

Jones, R. N., et al. (2002) "Linezolid-resistant *Enterococcus faecium* isolated from a patient without prior exposure to an oxazolidinone: report from the SENTRY Antimicrobial Surveillance Program"; *Diagn Microbiol Infect Dis* 42:137-9.

Kaufman, et al. (1987) "Translation efficiency of polycistronic mRNAs and their utilization to express heterologous genes in Mammalian Cells"; *EMBO J*. 6:187-195.

Keren-Zur, M., et al. (1979) "Localization of the decoding region on the 30S *Escherichia coli* ribosomal subunit by affinity immunoelectron microscopy"; *Proc Natl Acad Sci U S A* 76:1054-8.

Kessel and Gruss (1990) "Murine developmental control genes"; *Science* 249:374-379.

Khan, W. A., et al. (1996) "Randomised controlled comparison of single-dose ciprofloxacin and doxycycline for cholera caused by *Vibrio cholerae* 01 or 0139"; *Lancet* 348:296-300.

Kieber-Emmons, T., et al. (1997) "Therapeutic Peptides and Peptidomimetics"; *Curr Opin. Biotech*. 8:435-441.

Kloss, P., et al. (1999) "Resistance mutations in 23 S rRNA identify the site of action of the protein synthesis inhibitor linezolid in the ribosomal peptidyl transferase center"; *J Mol Biol* 294:93-101.

Klostermeier, D., et al. (2004) "A three-fluorophore FRET assay for high-throughput screening of small-molecule inhibitors of ribosome assembly"; *Nucleic Acids Res*.; May 17; 32(9); pp. 2707-2715.

Koosha, H., et al. (2000) "Alterations in the peptidyltransferase and decoding domains of ribosomal RNA suppress mutations in the elongation factor G gene"; *RNA*. 6: 1166-1173.

Krzyzosiak, W., et al. (1987) "In vitro synthesis of 16S ribosomal RNA containing single base changes and assembly into a functional 30S ribosome"; *Biochemistry* 26:2353-64.

Kurjan and Herskowitz (1982) "Structure of a yeast pheromone gene (MF alpha): a putative alpha-factor precursor contains four tandem copies of mature alpha-factor," *Cell* 30:933-943.

Lam, K. S., et al. (1995) "Application of a Dual Color Detection Scheme in the Screening of a Random Combinatorial Peptide Library"; *J. Immunol. Methods* 180:219-223.

Lesley, S. A., et al. (1991) "Use of in vitro protein synthesis from polymerase chain reaction-generated templates to study interaction of *Escherichia coli* transcription factors with core RNA polymerase and for epitope mapping of monoclonal antibodies"; *J Biol Chem* 266(4): 2632-8.

Levy, S. B., et al. (2004) "Antibacterial resistance worldwide: causes, challenges and responses." *Nat Med*.; 10:S122-9.

Levy, S. B. (2001) "Antibiotic resistance: consequences of inaction"; *Clin Infect Dis* 33 Suppl 3:S124-9.

Lin-Goerke, J. L., et al. (1997) "PCR-based random mutagenesis using manganese and reduced dNTP concentration"; *Biotechniques* 23:409-12.

Lind, K. E., et al. (2002) "Structure-Based Computational Database Screening, In Vitro Assay, and NMR Assessment of Compunds that Target TAR RNA"; *Chem. Biol*. 9:185-193.

Lindenbaum, J., et al. (1967) "Antibiotic therapy of cholera in children"; *Bull World Health Organ* 37:529-38.

Llano-Sotelo, B., et al. (2002) "Aminoglycosides Modified by Resistance Enzymes Display Diminished Binding to the Bacterial Ribosomal Acyl-Transfer Site"; *Chemistry & Biology* 9:455-463.

Lodmell, J. S. & Dahlberg, A. E. (1997) "A conformational switch in *Escherichia coli* 16S ribosomal RNA during decoding of messenger RNA"; Science 277:1262-7.

Luria, S.E. & Burrous, J.W. (1957); "Hybridization between *Escherichia coli* and *shigella*"; *J. Bacteriol*. 74:461-476.

Lynch, S. R., et al. (2003) "Comparison of X-Ray Crystal Structure of the 30S Subuni-Antibiotic Complex with NMR Structure of Decoding Site Oligonucleotide-Paromomycin Complex"; *Structure* 11:43-53.

Maden, B. E. (1990); "The numerous modified nucleotides in eukaryotic ribosomal RNA"; *Prog. Nucleic Acid Res. Mol. Biol*. 39: 241-303.

Magnet, S. & Blanchard, J.S. (2005) "Molecular insights into aminoglycoside action and resistance"; *Chem Rev*; 105:477-98.

Maidak, B. L. et al. (1996); "The ribosomal database project (RDP)"; *Nucl. Acids Res*. 24: 82-85.

Makosky, P. C. et al. (1987) "Spectinomycin resistance at site 1192 in 16S ribosomal RNA of *E. coli*: an analysis of three mutants," *Biochimie* 69: 885-889.

McManus, M. C. (1997) "Mechanisms of bacterial resistance to antimicrobial agents"; *Am J Health Syst Pharm* 54:1420-33; quiz pp. 1444-1446.

Miller, B. T., et al. (1997) "Peptide Biotinylation with Amine-Reactive Esters: Differential Side Chain Reactivity"; *Peptides* 18:1585-1595.

Miller, J.H. (1992) "A Short Course in Bacterial Genetics", (Miller, J. H., ed.), pp. 71-80, Cold Spring Harbor Laboratory Press, Cold Spring Harbor, NY.

Mirza, S. H., et al. (1996) "Multi-drug resistant typhoid: a global problem"; *J Med Microbiol* 44:317-9.

Moazed, D. & Noller, H.F. (1986) "Interconversion of active and inactive 30S ribosomal subunits is accompanied by a conformation change in the decoding region of 16S rRNA"; *J. Mol. Biol.* 191:483-493.

Morosyuk S. V., et al. (2001) "Structure and function of the conserved 690 hairpin in *Escherichia coli* 16S ribosomal RNA. II. NMR solution structure"; *J. Mol. Biol.* 307 (1):197-211.

Morosyuk S. V., et al. (2001) "Structure and function of the conserved 690 hairpin in *Escherichia coli* 16S ribosomal RNA. III. Functional analysis of the 690 loop"; *J. Mol. Biol.* 307 (1):213-228.

Morosyuk S. V., et al. (2000) "Structure and function of the conserved 690 hairpin in *Escherichia coli* 16S ribosomal RNA"; *J. Mol. Biol.* 300 (1):113-126.

Mucha, P., et al. (2002) "Interaction of RNA with Phage-Display Selected Peptides Analyzed by Capillary Electrophoresis Mobility Shift Assay"; *RNA* 8:698-704.

Mucha, P., et al. (2001) "Anticodon Domain Methylated Nucleosides of Yeast tRNA Phe are Significant Recognition Determinants in the Building of a Phage Display Selected Peptide"; *Biochemistry* 40:14191-14199.

Nandi, S., et al. (2004) "Gram-positive bacteria are a major reservoir of Class 1 antibiotic resistance integrons in poultry litter"; *Proc Natl Acad Sci U S A* 101:7118-22.

Nataro, J. P. & Kaper, J. B. (1998) "Diarrheagenic *Escherichia coli*"; *Clin Microbiol Rev* 11(1):142-201.

Nielsen, D. A. et al. (1989) "A highly sensitive, mixed-phase assay for chloramphenicol acetyltransferase activity in transfected cells," *Anal. Biochem.* 179: 19-23.

Nikonowicz, E. P., et al. (1992) "Preparation of 13C and 15N labelled RNAs for heteronuclear multi-dimensional NMR studies"; *Nucleic Acids Res.* 20(17):4507-4513.

O'Connor, M., et al. (2001) "Enhancement of translation by the epsilon element is independent of the sequence of the 460 region of 16S rRNA"; *Nucl. Acids Res.* 29: 1420-1425.

O'Connor, M., et al. (2001) "Mutagenesis of the peptidyltransferase center of 23S rRNA: the invariant U2449 is dispensable"; *Nucl. Acids Res.* 29: 710-715.

Ogle, J. M., et al. (2001) "Recognition of cognate transfer RNA by the 30S ribosomal subunit"; *Science* 292:897-902.

Oldfield, E. C., 3rd & Wallace, M. R. (2001) "The role of antibiotics in the treatment of infectious diarrhea"; *Gastroenterol Clin North Am* 30:817-36.

Orr, J. W., et al. (1998) "Protein and Mg(2+)-induced conformational changes in the S15 binding site of 16 S ribosomal RNA"; *J. Mol. Biol.* 275:453-464.

Papich, M. G. (2003) "Antimicrobial therapy for gastrointestinal diseases"; *Vet Clin North Am Equine Pract* 19:645-63.

Pelham, H. R. & Jackson, R. J. (1976) "An efficient mRNA-dependent translation system from reticulocyte lysates"; *Eur J Biochem* 67:247-56.

Peske, F., et al. (2004) "Conformational changes of the small ribosomal subunit during elongation factor G-dependent tRNA-mRNA translocation"; *J Mol Biol* 343:1183-94.

Pinkert, et al. (1987) "An albumin enhancer located 10 kb upstream functions along with its promoter to direct efficient, liver-specific expression in transgenic mice"; *Genes Dev.* 1:268-277.

Pioletti, M., et al. (2001) "Crystal structures of complexes of the small ribosomal subunit with tetracycline, edeine and IF3"; *Embo J* 20:1829-39.

Powers, T. et al. (1991) "A functional pseudoknot in 16S ribosomal RNA"; *EMBO J.* 10: 2203-2214.

Prince, J. B., et al. (1982) "Covalent crosslinking of tRNA1Val to 16S RNA at the ribosomal P site: identification of crosslinked residues"; *Proc Natl Acad Sci U S A* 79:5450-4.

Queen, C. & Baltimore, D. (1983) "Immunoglobulin gene transcription is activated by downstream sequence elements." *Cell* 33:741-748.

Recht, M. I., et al. (1999) "Effect of mutations in the A site of 16 S rRNA on aminoglycoside antibiotic-ribosome interaction"; *J Mol Biol*; 286:33-43.

Rodriguez-Correa, D. & Dahlberg, A. E. (2004) "Genetic evidence against the 16S ribosomal RNA helix 27 conformational switch model"; *RNA* 10:28-33.

Rothman, J. H. & Still, W. C. (1997) "Peptide-Binding Antibiotics: A Solid-Phase Assay for Screening Libraries of Vancomycin Mimics for Selective d-Ala-d-Ala Binding"; *Bioorg. Med. Chem. Lett.* 7:3159-3164.

Sander, P., et al. (2002) "Ribosomal and non-ribosomal resistance to oxazolidinones: species-specific idiosyncrasy of ribosomal alterations"; *Mol Microbiol* 46:1295-304.

Schottel, J. L., et al. (1984) "Effects of alterations in the translational control region on bacterial gene expression: use of *cat* gene constructs transcribed from the *lac* promoter as a model system"; *Gene* 28: 177-193.

Schultz et al. (1987) "Expression and secretion in yeast of a 400-kDa envelope glycoprotein derived from Epstein-Barr virus"; *Gene* 54:113-123.

Seed, B. (1987) "An LFA-3 cDNA encodes a phospholipid-linked membrane protein homologous to its receptor CD2"; *Nature* 329:840.

Serganov, A. A., et al. (1996) "The 16S rRNA binding site of *Thermus thermophilus* ribosomal protein S15: comparison with *Escherichia coli* S15, minimum site and structure"; *RNA* 2:1124-1138.

Sergiev, P. V., et al. (2000) "Mutations at position A960 of *Escherichia coli* 23S ribosomal RNA influence the structure of 5S ribosomal RNA and the peptidyltransferase region of 23 S ribosomal RNA"; *J. Mol. Biol.* 299:379-389.

Shine, J. & Dalgarno, L. (1974) "The 3'-terminal sequence of *Escherichia coli* 16S ribosomal RNA: complementarity to nonsense triplets and ribosome binding sites"; *Proc Natl Acad Sci U S A*; 71:1342-6.

Sigmund, C. D., et al. (1988) "Antibiotic resistance mutations in ribosomal RNA genes of *Escherichia coli*"; *Methods Enzymol.* 164: 673-690.

Sigmund, C. D., et al. (1984) "Antibiotic resistance in 16S and 23S ribosomal RNA genes of *Escherichia coli*"; *Nucl. Acids Res.* 12(11):4653-4663.

Sigmund, C. D. et al. (1982) "Erythromycin resistance due to a mutation in a ribosomal RNA operon of *Escherichia coli*"; *Proc. Natl. Acad. Sci. U.S.A.* 79: 5602-5606.

Sirinavin, S. & Garner, P. (2000) "Antibiotics for treating salmonella gut infections"; *Cochrane Database Syst Rev*, CD001167.

Smith, D.B. and Johnson, K.S. (1988); "Single-step purification of polypeptides expressed in *Escherichia coli* as fusions with glutathione S-transferase"; *Gene* 67:31-40.

Stormo, G. D., et al. (1982) "Characterization of translational initiation sites in *Escherichia coli*"; *Nucleic Acids Res.* 10:2971-2996.

Tapprich, W., et al. (1989) "Mutation at position 791 *Escherichia coli* 16S ribosomal RNA affects processes involved in the initiation of protein synthesis"; *Proc. Natl Acad. Sci. USA* 86: 4927-4931.

Tapprich, W. & Hill, W. (1986); "Involvement of bases 787-795 of *Escherichia coli* 16S ribosomal RNA in ribosomal subunit association"; *Proc. Natl Acad. Sci. USA* 83: 556-560.

Triman, K., et al. (1989) "Isolation of temperature-sensitive mutants of 16S rRNA in *Escherichia coli*"; *J. Mol. Biol.* 209:645-653.

Tsiodras, S., et al. (2001) "Linezolid resistance in a clinical isolate of *Staphylococcus aureus*"; *Lancet* 358:207-8.

Vicens, Q. & Westhof, E. (2003) "Crystal structure of geneticin bound to a bacterial 16S ribosomal RNA A site oligonucleotide"; *J Mol Biol* 326:1175-88.

Vicens, Q. & Westhof, E. (2001) "Crystal Structure of Paromomycin Docked into the Eubacterial Ribosomal Decoding A Site"; *Structure* 9:647-658.

Vila-Sanjurjo, A. et al. (2001) "Mutational analysis of the conserved bases C1402 and A1500 in the center of the decoding domain of *Escherichia coli* 16S rRNA reveals an important tertiary interaction"; *J. Mol. Biol.* 308: 457-463.

Vila-Sanjurjo, A., et al. (1999) "Isolation of kasugamycin resistant mutants in the 16 S ribosomal RNA of *Escherichia coli*"; *J Mol Biol* 293:1-8.

Voulgaris, J., et al. (1999) "Increased *rrn* gene dosage causes intermittent transcription of rRNA in *Escherichia coli*"; *J. Bacteriol.* 181:4170-4175.

Wada et al. (1992) "Codon usage tabulated from the Genbank genetic sequence data"; *Nucl. Acids Res.* 20:2111-2118.

Wallace, C. K., et al. (1968) "Optimal antibiotic therapy in cholera"; *Bull World Health Organ* 39:239-45.

Wang, Y., et al. (1997) "Specificity of Aminoglycoside Binding to RNA Constructs Derived from the 16S rRNA Decoding Region and the HIV-RRE Activator Region"; *Biochemistry* 36:768-779.

Wanke, C. A. (2001) "To know *Escherichia coli* is to know bacterial diarrheal disease"; *Clin Infect Dis* 32:1710-2.

Wilson, K. S. & Noller, H. F. (1998) "Mapping the position of translational elongation factor EF-G in the ribosome by directed hydroxyl radical probing"; *Cell* 92:131-9.

Wimberly, B. T., et al. (2000) "Structure of the 30S ribosomal subunit"; *Nature* 407:327-39.

Winkler, F. K., et al. (2001) "Structure-Based Approaches in Modern Drug Discovery Research"; *Ernst Schering Res. Found. Workshop* 34:123-142.

Winoto and Baltimore (1989) "A novel, inducible and T cell-specific enhancer located at the 3' end of the T cell receptor α locus"; *EMBO J.* 8:729-733.

Xiong, L., et al. (2000) "Oxazolidinone resistance mutations in 23S rRNA of *Escherichia coli* reveal the central region of domain V as the primary site of drug action"; *J Bacteriol* 182(19):5325-31.

Yanisch-Perron, C., et al. (1985) "Improved M13 phage cloning vectors and host strains: nucleotide sequences of the M13mp18 and pUC19 vectors"; *Gene* 33:103-119.

Yoshizawa, S., et al. (1998) "Structural Origins of Gentamicin Antibiotic Action"; *EMBO J.* 17:6437-6448.

Yusupov, M. M., et al.(2001) "Crystal Structure of the Ribosome at 5.5 Å Resolution"; *Science* 292:883-896.

Yusupova, G. Z., et al. (2001) "The path of messenger RNA through the ribosome"; *Cell* 106:233-41.

Zhang, K. & Zhao, H. (2000) "Assessing reliability of gene clusters from gene expression data"; *Funct Integr Genomics* 1:156-73.

Zhang, X., et al. (2000) "Quinolone antibiotics induce Shiga toxin-encoding bacteriophages, toxin production, and death in mice"; *J Infect Dis* 181:664-70.

| Nucleotide | Description |
|---|---|
| 1-1542 | 16S rRNA of *Escherichia coli* rrnB operon |
| 1536-1540 | 16S MBS (message binding sequence) GGGAU |
| 1543-1982 | 16S-23S spacer region |
| 1983-4886 | 23S rRNA of *Escherichia coli* rrnB operon |
| 4887-4982 | 23S-5S spacer region |
| 4983-5098 | 5S rRNA of *Escherichia coli* rrnB operon |
| 5102-5145 | terminator T1 of *Escherichia coli* rrnB operon |
| 5276-5305 | terminator T2 of *Escherichia coli* rrnB operon |
| 6575-7432 | *bla* (β-lactamase; ampicillin resistance) |
| 7575-8209 | replication origin |
| 8813-8622 | *rop* (Rop protein) |
| 10201-9467 | GFP (Green Fluorescent Protein) |
| 10213-10209 | GFP RBS (ribosome binding sequence) AUCCC |
| 10270-10230 | *trpc* promoter |
| 10745-10785 | *trpc* promoter |
| 10802-10806 | CAT RBS (ribosome binding sequence) AUCCC |
| 10814-11473 | *cam* (chloramphenicol acetyltransferase: CAT) |
| 11782-11859 | *lac$^q$* promoter |
| 11860-12942 | *lacI$^q$* (lac repressor) |
| 12985-13026 | *lacUV5* promoter |

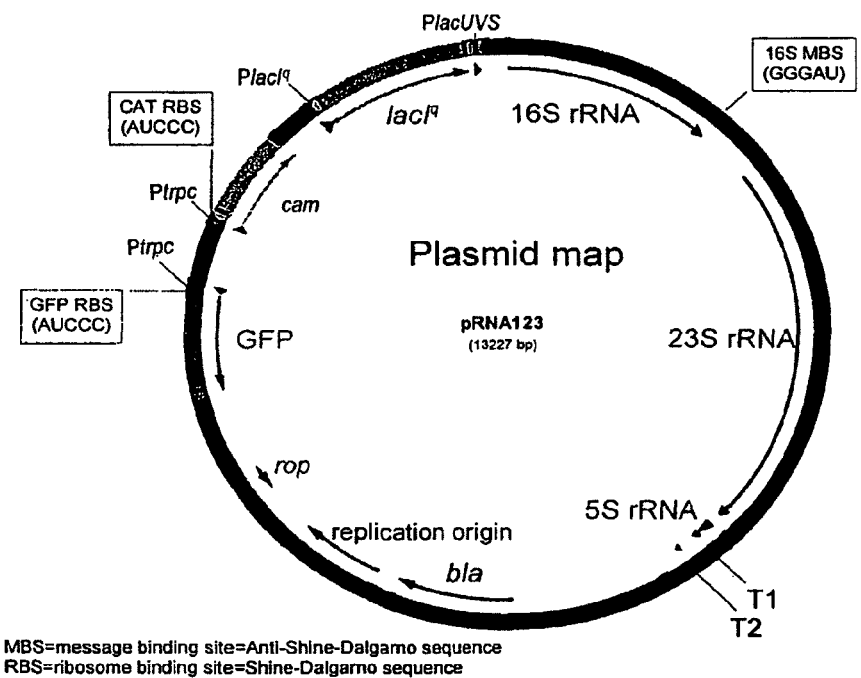

MBS=message binding site=Anti-Shine-Dalgarno sequence
RBS=ribosome binding site=Shine-Dalgarno sequence

*Fig. 1*

| Oligo | Sequence (5' to 3') | Used for |
|---|---|---|
| OL2 | ATAGGGGTTCCGCGCACATT | Primer cam from −268 to −249 |
| IL2 | CTCGAGCCTCCTGAAAGCGGCCG CAACTCAAAAAATACGCCCGGT AGT | Creating a NotI in the upstream of cam |
| OR2 | AAATCGTCGTGGTATTCACT | Primer cam from 473 to 492 |
| IR2 | GCGGCCGCTTTCAGGAGGCTCGA GAAATGGAGAAAAAAATCACT | Creating a NotI in the upstream of cam |
| TRP*-T | GGCCGCTAGCCGGCGAGCTGTTG ACAATTAATCATCGAACTAGTT TAATGTGTGGAAGC | Promoter trpc, top strand |
| TRP*-B | GGCCGCTTCCACACATTAAACTA GTTCGATGATTAATTGTCAACAG CTCGCCGGCTAGC | Promoter trpc, bottom strand |
| SD*-B | TCGAGCACACTGAAAGC | Mutated RBS for pCAM5; top strand |
| SD*-T | GGCCGCTTTCAGTGTGC | Mutated RBS for pCAM5; bottom strand |
| lacU | GGTCATAGGCGGCGCGTGTGTGA AATTGTTATCCGCTCACAATTCC ACACATTATACGAGCCGGAAGC | Creating a NotI and PlacUV5 mutation in the 3' end of lacI |
| lacL | TTGGATCCGACACCATCGAATGG TGCAAACCTT | Creating a BamHI and lacI⁹ mutation in the 5' end of lacI |
| OL4 | GAAGGGATCCGGCGAAGATGTTT CTCTGG | Primer 16S rRNA from −707 to −689; creating a BamHI in the 5' end of 16S rRNA |
| IL4 | GCGGCCGCTTAAAATAATTTTCT GACC | Primer 16S rRNA from −351 to −333; deleting P1P2 and creating a NotI in the 5' end of 16S rRNA |
| OR4 | CCACAAGCTTCGCACCTGAGCGT CAGTCTTC | Primer 16S rRNA from 745 to 765; creating a HindIII in the middle of 16S rRNA |
| IR4 | AAAATTATTTAAGCGGCCGCTG AGAAAAGCGAAGC | Primer 16S rRNA from −184 to −180; deleting P1P2 and creating a NotI in the 5' end of 16S rRNA |
| ASD*-B | GGCGACTTTCACTCACAAAC | Primer tRNAGlu from +8 to +27 |
| ASD*-T | GTCGAAGCTTGGTAACCGTAGGG GAACCTGCGGTTGGATCACACAC TACCCTTAAAGAAGCGTAC | Primer 16S from 1504 to +16, mutating the MBS region from C1536UC1538 to A1536CA1538 |
| Cat-M-XhoI | TTAATGTGTGGAAGCGGCCGCTT TCATATCCCTNNNNAAATGGAG AAAAAATC | Primer cam from −39 to +15; creating 4 nucleotide random mutations |
| Cat-N-NcoI | CAGCCACCTTGTCGCCTTGC | Primer cam from 688 to 706 |

*Fig. 9*

| Plasmid | Description | Reference |
|---|---|---|
| pUC19 | Cloning vector | (67) |
| pBR322 | Cloning vector | (73) |
| pACYC177 | Cloning vector | (72) |
| pKK3535 | pBR322 derivative containing intact rrnB operon | (31) |
| pSPORT1 | pUC19 derivative containing lacI | (57) |
| pJLS1021 | pBR322 derivative containing cam | (58) |
| pSTL102 | pKK3535 containing U1192 in 16S rRNA and G2058 in 23S rRNA | (34) |
| pCAM1 | pJLS1021 plus a NotI site in the upstream of cam | This study |
| pCAM2 | pCAM1 plus Ptrpc between NotI sites in the upstream of cam | This study |
| pCAM4 | pBR322 plus the NaeI fragment of pCAM2 containing cam under Ptrpc | This study |
| pCAM5 | pCAM4 containing RBS (5'-GUGUG) of Hui et al. (1) in cam | This study |
| pCAM9 | pCAM5 containing selected RBS (5'-AUCCC) in cam | This study |
| pCAM10 | pCAM9 containing selected upstream sequence of cam | This study |
| pRNA3 | pUC19 plus lacIq and 5' end of 16S rRNA under PlacUV5 | This study |
| pRNA4 | pACYC177 plus lacIq and rrnB with wild-type MBS under Plac UV5 | This study |
| pRNA5 | pRNA4 containing MBS (5'-CACAC) of Hui et al. (1) in 16S rRNA | This study |
| pRNA6 | pCAM5 plus the BamHI fragment containing lacIq and rrnB from pRNA5 | This study |
| pRNA8 | pCAM5 plus the BamHI fragment containing lacIq and rrnB from pRNA4 | This study |
| pRNA9 | pCAM4 plus the BamHI fragment containing lacIq and rrnB from pRNA4 | This study |
| pRNA100 | pRNA8 containing selected MBS (5'-GGGAU) and RBS (5'-AUCCC) | This study |
| pRNA101 | pRNA100 containing U1192 in 16S rRNA | This study |
| pRNA104 | pRNA101 containing U2058 in 23S rRNA | This study |
| p16ST | pUC19 derivative containing cam, lacIq and 16S rRNA from pRNA100 | This study |
| pRNA122 | pRNA100 containing selected upstream sequence of cam from pCAM10 | This study |
| pRNA170 | pRNA122 containing U1192 in 16S rRNA and U2058 in 23S rRNA | This study |

Fig. 10

| MIC with no induction | MIC with induction | | | | | | | | | |
|---|---|---|---|---|---|---|---|---|---|---|
| | 50 | 100 | 200 | 400 | 500 | 600 | 700 | 800 | 1000 |
| 50 | | | 4 | | | | | | |
| 100 | | 1 | 1 | | | | | | |
| 200 | | | 3 | | | | | | |
| 400 | | | | 51 | 16 | 6 | 1 | | |
| 500 | | | | 121 | 45 | 10 | 2 | | |
| 600 | | | | 72 | 72 | 22 | 1 | 1 | |
| 700 | | | | 4 | 11 | 20 | 3 | 60 | 3 |
| 800 | | | | | | | 1 | 3 | |
| 1000 | | | | | | | | | 1 |

Fig. 11

| Clone | RNA sequences | | $\Delta G^0_{37}$ | MIC | | CAT | | Induction |
|---|---|---|---|---|---|---|---|---|
| | 5' C A R1 R2 R3 R4 R5 C U C G 3' CAT mRNA<br>3' A U U H5 H4 H3 H2 H1 A C U 5' 16S rRNA | | kcal/mol | µg of Cm/mL | | CPM | | |
| | | | | − | + | − | + | −/+ |
| Random | | | -9.8 | 500 | 500 | 2803 ± 68 | 2700 ± 196 | 1.0 |
| pRNA9 | 5' C A G G A G G C U C G 3'<br>3' A U U C C U C C A C U 5' | | -7.8 | 100 | 200 | 4033 ± 1040 | 12437 ± 2491 | 3.1 |
| pRNA6 | 5' C A G U G U G C U C G 3'<br>3' A U U A G A C A C U 5' | | -8.4 | 100 | 500 | 6293 ± 706 | 72206 ± 706 | 11.5 |
| VII30 | 5' C A U A U C C C U C G 3'<br>3' A U U A G G G A C U 5' | | -8.1 | 125 | 500 | 5603 ± 1011 | 47667 ± 891 | 8.5 |
| VII43 | 5' C A A A C A C C U C G 3'<br>3' A U U G G G A G A A C U 5' | | -7.3 | 100 | 500 | 6200 ± 953 | 37311 ± 3978 | 6.0 |
| VII64,<br>VII65 | 5' C A U A C C U C U C G 3'<br>3' A U U G G A G A C U 5' | | -10.9 | 125 | 600 | 7869 ± 416 | 91153 ± 4003 | 11.6 |
| VIII29 | 5' C A A A U C C C U C G 3'<br>3' A U U A G G A G A C U 5' | | -7.7 | 100 | 500 | 6431 ± 816 | 46840 ± 796 | 7.3 |
| VIII46 | 5' C A C A U A C C U C G 3'<br>3' A U U G G A G U A C U 5' | | -7.7 | 150 | 600 | 6794 ± 650 | 44358 ± 4841 | 6.5 |
| VIII77 | 5' C A C G A C C U C G 3'<br>3' A U U G G A G U A C U 5' | | -8.5 | 100 | 500 | 5643 ± 897 | 24888 ± 2388 | 4.4 |
| VIII93 | 5' C A C C A U C C U C G 3'<br>3' A U U G G A G U A C U 5' | | -7.3 | 100 | 650 | 7524 ± 263 | 91809 ± 4542 | 12.7 |
| IX24 | 5' C A C U U C C C U C G 3'<br>3' A U U G G A G U A C U 5' | | -7.7 | 100 | 500 | 5783 ± 971 | 32164 ± 5862 | 5.6 |
| IX32 | 5' C A C C U C C U C G 3'<br>3' A U U G G A G U A C U 5' | | -8.0 | 125 | 600 | 6063 ± 787 | 24581 ± 3009 | 4.1 |
| IX67 | 5' C A U A U C C C U C G 3'<br>3' A U U G G A G A A C U 5' | | | | | | | |

Fig. 12

| Clone | RNA sequences | | MIC ($\mu$g/mL) | |
|---|---|---|---|---|
| | 5' CAUAUCCCUNNNNAAAUG 3' CAT mRNA<br>3' AUUAGGGUACUAGG 5' 16S rRNA | | − | +I |
| Mutated positions | | | | |
| pRNA100 | 5' C A U A U C C C U G G A G A A A U G 3'<br>3' A U U A G G G U A C U A G G 5' | | 100 | 650 |
| pRNA100<br>+ wt MBS | 5' C A U A U C C C U G A G A A A U G 3'<br>3' A U U C A C U A G G 5' | | 50 | 50 |
| pRNA122 | 5' C A U A U C C C U G G U C A A A U G 3'<br>3' A U U A G G G U A C U A G G 5' | | 50 | 600 |
| pRNA122<br>+ wt MBS | 5' C A U A U C C C U G G U C C A A A U G 3'<br>3' A U U C C A C U A G G 5' | | 10 | 10 |
| pRNA125 | 5' C A U A U C C C U G G U G A A A U G 3'<br>3' A U U A G G G U A C U A G G 5' | | 80 | 600 |
| pRNA127 | 5' C A U A U C C C U G G A A A A U G 3'<br>3' A U U A G G G U A C U A G G 5' | | 50 | 600 |
| pRNA128 | 5' C A U A U C C C U G G A C A A A U G 3'<br>3' A U U A G G G U A C U A G G 5' | | 50 | 600 |

*Fig. 13*

| Residue at 516 | Percent plasmid-derived 30S in | | | % CAT |
|---|---|---|---|---|
| | 30S peak | 70S peak | Crude ribosomes | |
| Ψ | 46.5 ± 3.6 | 53.0 ± 4.5 | 47.8 ± 2.8 | 100 |
| A | 54.2 ± 5.4 | 10.6 ± 1.4 | 37.5 ± 3.9 | 0 |
| C | 51.8 ± 0.2 | 27.1 ± 2.9 | 42.9 ± 5.8 | 59.4 |
| G | 67.5 ± 6 | 8.8 ± 0.9 | 44.1 ± 5.2 | 6.3 |

*Fig. 14*

| Clone | Alignment of CAT mRNA and 16S rRNA | | MIC (μg or Cm/mL) | | ΔG3y (kcal/mol) |
|---|---|---|---|---|---|
| Random | 5' C A R1 R2 R3 R4 R5 C U C G 3' CAT mRNA<br>3' A U N5 N4 N3 N2 N1 A C U 5' 16S rRNA | | no IPTG | 1 mM IPTG | |
| wild-type | 5' C A G G A G G C U C G 3'<br>3' A U C C U C C A C U 5' | | 500 | 500 | -9.8 |
| 1 | 5' C A A U C C C U C G 3'<br>3' A U U A G G C A C U 5' | | 100 | 400 | -8.3 |
| 2 | 5' C A U A C U U C U C G 3'<br>3' A U U G G G U A A C U 5' | | 50 | 100 | -4 |
| 3 | 5' C A C A G U C U C G 3'<br>3' A U U A G C A G A C U 5' | | 50 | 100 | -1.9 |
| 4 | 5' C A A A C C A C U C G 3'<br>3' A U U U A G U G A C U 5' | | 50 | 100 | -4.1 |
| 5 | 5' C A U A G C C C U C G 3'<br>3' A U U G G U U A C U 5' | | 50 | 100 | -7.6 |
| 6 | 5' C A U C U C C U C G 3'<br>3' A U U G G A G A C U 5' | | 50 | 100 | -7.4 |
| 7 | 5' C A A U U A U C U C G 3'<br>3' A U U U A A G A C U 5' | | 50 | 100 | -3.1 |
| 8 | 5' C A C A G A A C U C G 3'<br>3' A U U G A C U A A C U 5' | | 100 | 200 | -3.6 |
| 9 | 5' C A A A G U U C U C G 3'<br>3' A U U C A G C A A C U 5' | | 100 | 200 | -0.6 |
| 10 | 5' C A A U U C A C U C G 3'<br>3' A U U A A C U G A C U 5' | | 100 | 400 | -7.7 |
| 11 | 5' C A A C U C A C U C G 3'<br>3' A U U G U G A G A C U 5' | | 100 | 200 | -7.1 |
| 12 | 5' C A A C C C A C U C G 3'<br>3' A U U A G G G U A C U 5' | | 50 | 100 | -6 |
| 13 | 5' C A U C G U U C U C G 3'<br>3' A U U G C A G A A A C U 5' | | 50 | 200 | -2.2 |
| 14 | 5' C A C A C C A C U C G 3'<br>3' A U U U U G G U A C U 5' | | 50 | 100 | -4.7 |
| 15 | 5' C A C C C A C C U C G 3'<br>3' A U U G G G A A C U 5' | | 50 | 200 | -7 |
| 16 | 5' C A U C C C A C U C G 3'<br>3' A U U G G G A C U 5' | | 50 | 100 | -7.3 |
| 17 | 5' C A A A C C C U C G 3'<br>3' A U U A U C A U A C U 5' | | 50 | 100 | 0.8 |
| 18 | 5' C A U A C A U C U C G 3'<br>3' A U U U G A G A A C U 5' | | 50 | 100 | -2.1 |
| 19 | 5' C A A C U C U C U C G 3'<br>3' A U U A G A G A C U 5' | | 50 | 200 | -5.6 |
| 20 | 5' C A A A U C U C G 3'<br>3' A U U U A G A G A C U 5' | | 200 | 500 | -6.2 |
| 21 | 5' C A U A C C U C U C G 3'<br>3' A U U G G A G U A C U 5' | | 200 | 500 | -7.3 |
| 22 | 5' C A U A G U A C U C G 3'<br>3' A U U U A G G U A C U 5' | | 100 | 200 | 0.3 |
| 23 | 5' C A A U C C A C U C G 3'<br>3' A U U A G G U G A C U 5' | | 200 | 400 | -10.6 |
| 24 | 5' C A C A G A U C U C G 3'<br>3' A U U U C G G A C U 5' | | 100 | 200 | -0.2 |

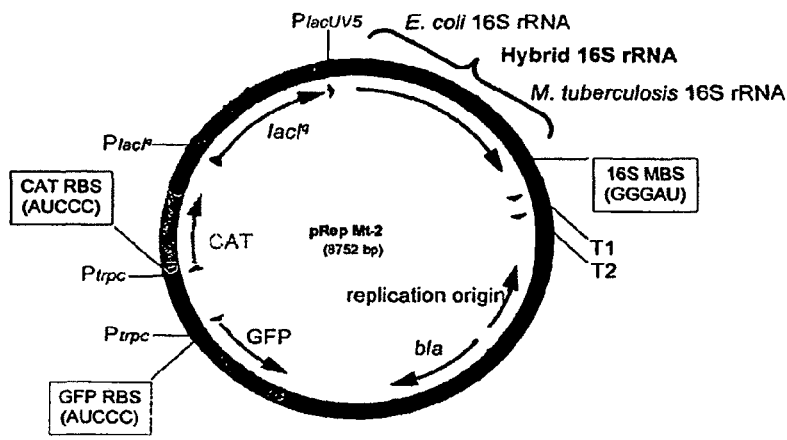

| Nucleotide | Description |
|---|---|
| 1-931 | part of 16S rRNA from *Escherichia coli* rrnB operon |
| 932-1542 | part of 16S rRNA from *Mycobacterium tuberculosis* rrn operon |
| 1536-1540 | 16S MBS (message binding sequence) GGGAU |
| 1791-1834 | terminator T1 of *Escherichia coli* rrnB operon |
| 1965-1994 | terminator T2 of *Escherichia coli* rrnB operon |
| 3054-2438 | replication origin |
| 3214-4074 | *bla* (β-lactamase; ampicillin resistance) |
| 5726-4992 | GFP (Green Fluorescent Protein) |
| 5738-5734 | GFP RBS (ribosome binding sequence) AUCCC |
| 5795-5755 | *trpc* promoter |
| 6270-6310 | *trpc* promoter |
| 6327-6331 | CAT RBS (ribosome binding sequence) AUCCC |
| 6339-6998 | *cam* (chloramphenicol acetyltransferase; CAT) |
| 7307-7384 | *lacIq* promoter |
| 7385-8467 | *lacIq* (lac repressor) |
| 8510-8551 | lacUV5 promoter |

*Fig. 17*

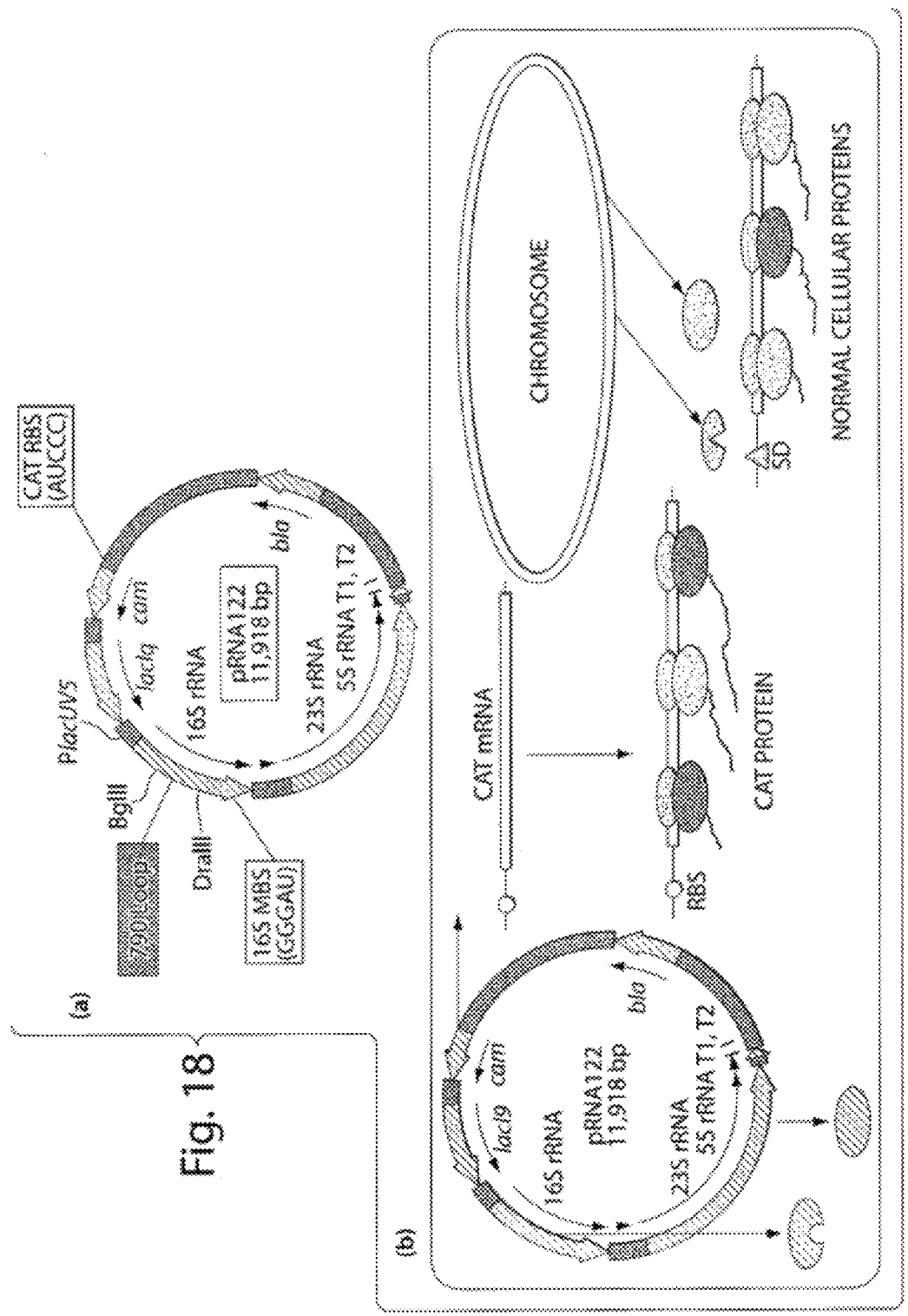

Fig. 19

| Nucleotide | 787 | 788 | 789 | 790 | 791 | 792 | 793 | 794 | 795 |
|---|---|---|---|---|---|---|---|---|---|
| A. Nucleotide distribution of functional mutants[a] | | | | | | | | | |
| A | 54 | 24 | 0 | 69 | 0 | 15 | 18 | 35 | 16 |
| C | 2 | 16 | 0 | 8 | 0 | 24 | 26 | 5 | 34 |
| G | 22 | 21 | 0 | 1 | 78 | 16 | 4 | 9 | 7 |
| U | 0 | 17 | 78 | 0 | 0 | 23 | 30 | 29 | 21 |
| Consensus | R | N | U | M | G | N | H | W | H |
| B. Nucleotide distribution in all known bacteria[b] | | | | | | | | | |
| A | 573 | 0 | 0 | 578 | 1 | 578 | 0 | 577 | 0 |
| C | 3 | 0 | 0 | 0 | 1 | 0 | 0 | 1 | 578 |
| G | 1 | 0 | 0 | 0 | 576 | 0 | 3 | 0 | 0 |
| U | 1 | 578 | 578 | 0 | 0 | 0 | 575 | 0 | 0 |
| Consensus | A | U | U | A | G | A | U | A | C |
| C. Nucleotide distribution in all known organisms[c] | | | | | | | | | |
| A | 1657 | 2 | 1 | 1648 | 2 | 1655 | 5 | 1664 | 1 |
| C | 6 | 1 | 566 | 9 | 1 | 1 | 12 | 1 | 1665 |
| G | 4 | 0 | 0 | 3 | 1662 | 7 | 46 | 2 | 0 |
| U | 1 | 1664 | 1101 | 7 | 3 | 3 | 1605 | 1 | 0 |
| Δ | 0 | 1 | 0 | 1 | 0 | 2 | 0 | 0 | 2 |
| Consensus | A | U | Y | A | G | A | U | A | C |

*Fig. 20*

| Nucleotide[a] | | Mean CAT activity[b] | % Mutant 30 S in | | Thermodynamics[d] | |
|---|---|---|---|---|---|---|
| 787 | 795 | | 30 S peak[c] | 70 S peak[c] | ΔG°₃₇ (kcal/mol) | $T_m$ (°C) |
| A | C | 100 | 46.1 ± 0.8 | 41.7 ± 3.3 | −3.25 | 61.8 |
| A | <u>A</u> | 83.8 ± 2.5 | n.d. | n.d. | −2.90 | 61.3 |
| <u>C</u> | C | 80.5 ± 0.5 | n.d. | n.d. | −2.84 | 60.7 |
| <u>C</u> | <u>U</u> | 74.1 ± 3.4 | n.d. | n.d. | n.d. | n.d. |
| A | <u>U</u> | 72.1 ± 4.5 | 74.3 ± 0.5 | 14.3 ± 1.0 | −5.62 | 75.3 |
| <u>U</u> | <u>U</u> | 72.0 ± 2.4 | n.d. | n.d. | n.d. | n.d. |
| <u>G</u> | <u>U</u> | 70.5 ± 1.8 | 56.1 ± 1.4 | 14.2 ± 0.6 | −4.96 | 68.1 |
| <u>U</u> | C | 65.5 ± 2.1 | n.d. | n.d. | −2.88 | 60.6 |
| <u>C</u> | <u>A</u> | 53.4 ± 1.0 | n.d. | n.d. | n.d. | n.d. |
| <u>G</u> | <u>G</u> | 52.9 ± 0.4 | n.d. | n.d. | −3.70 | 64.9 |
| <u>G</u> | <u>A</u> | 46.0 ± 1.4 | n.d. | n.d. | n.d. | n.d. |
| A | <u>G</u> | 37.5 ± 0.5 | n.d. | n.d. | −3.19 | 63.5 |
| <u>U</u> | <u>A</u> | 36.7 ± 0.4 | 70.8 ± 7.4 | 10.1 ± 0.4 | −5.82 | 74.3 |
| <u>U</u> | <u>G</u> | 13.5 ± 3.3 | 57.7 ± 12.1 | 5.5 ± 3.4 | −5.15 | 69.4 |
| <u>G</u> | C | 5.5 ± 1.8 | 58.3 ± 8.2 | 5.1 ± 1.3 | −7.61 | 83.4 |
| <u>C</u> | <u>G</u> | 1.2 ± 0.1 | n.d. | n.d. | n.d. | n.d. |

*Fig. 21*

```
GACGCCGGGCAAGAGCAACTCGGTCGCCGCATACACTATTCTCAGAATGACT
TGGTTGAGTACTCACCAGTCACAGAAAAGCATCTTACGGATGGCATGACAGT
AAGAGAATTATGCAGTGCTGCCATAACCATGAGTGATAACACTGCGGCCAAC
TTACTTCTGACAACGATCGGAGGACCGAAGGAGCTAACCGCTTTTTTGCACA
ACATGGGGGATCATGTAACTCGCCTTGATCGTTGGGAACCGGAGCTGAATGA
AGCCATACCAAACGACGAGCGTGACACCACGATGCCTGCAGCAATGGCAAC
AACGTTGCGCAAACTATTAACTGGCGAACTACTTACTCTAGCTTCCCGGCAA
CAATTAATAGACTGGATGGAGGCGGATAAAGTTGCAGGACCACTTCTGCGCT
CGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGT
ATCGTAGTTATCTACACGACGGGGAGTCAGGCAACTATGGATGAACGAAAT
AGACAGATCGCTGAGATAGGTGCCTCACTGATTAAGCATTGGTAACTGTCAG
ACCAAGTTTACTCATATATACTTTAGATTGATTTAAAACTTCATTTTTAATTT
AAAAGGATCTAGGTGAAGATCCTTTTTGATAATCTCATGACCAAAATCCCTT
AACGTGAGTTTTCGTTCCACTGAGCGTCAGACCCCTTAATAAGATGATCTTCT
TGAGATCGTTTTGGTCTGCGCGTAATCTCTTGCTCTGAAAACGAAAAAACCG
CCTTGCAGGGCGGTTTTTCGAAGGTTCTCTGAGCTACCAACTCTTTGAACCGA
GGTAACTGGCTTGGAGGAGCGCAGTCACCAAAACTTGTCCTTTCAGTTTAGC
CTTAACCGGCGCATGACTTCAAGACTAACTCCTCTAAATCAATTACCAGTGG
CTGCTGCCAGTGGTGCTTTTGCATGTCTTTCCGGGTTGGACTCAAGACGATAG
TTACCGGATAAGGCGCAGCGGTCGGACTGAACGGGGGGTTCGTGCATACAG
TCCAGCTTGGAGCGAACTGCCTACCCGGAACTGAGTGTCAGGCGTGGAATGA
GACAAACGCGGCCATAACAGCGGAATGACACCGGTAAACCGAAAGGCAGGA
ACAGGAGAGCGCACGAGGGAGCCGCCAGGGGGAAACGCCTGGTATCTTTAT
AGTCCTGTCGGGTTTCGCCACCACTGATTTGAGCGTCAGATTTCGTGATGCTT
GTCAGGGGGGCGGAGCCTATGGAAAAACGGCTTTGCCGCGGCCCTCTCACTT
CCCTGTTAAGTATCTTCCTGGCATCTTCCAGGAAATCTCCGCCCCGTTCGTAA
GCCATTTCCGCTCGCCGCAGTCGAACGACCGAGCGTAGCGAGTCAGTGAGCG
AGGAAGCGGAATATATCCTGTATCACATATTCTGCTGACGCACCGGTGCAGC
CTTTTTTCTCCTGCCACATGAAGCACTTCACTGACACCCTCATCAGTGCCAAC
ATAGTAAGCCAGTATACACTCCGCTAGCATCGTCCATTCCGACAGCATCGCC
AGTCACTATGGCGTGCTGCTAGCGCTATATGCGTTGATGCAATTTCTATGCGC
ACCCGTTCTCGGAGCACTGTCCGACCGCTTTGGCCGCCGCCCAGTCCTGCTCG
CTTCGCTACTTGGAGCCACTATCGACTACGCGATCATGGCGACCACACCCGT
CCTGTGGATCCTCTACGCCGGACGCATCGTGGCCGGCCACGATGCGTCCGGC
GTAGAGGATCTATTTAACGACCCTGCCCTGAACCGACGACCGGGTCGAATTT
GCTTTCGAATTTCTGCCATTCATCCGCTTATTATCACTTATTCAGGCGTAGCA
CCAGGCGTTTAAGGGCACCAATAACTGCCTTAAAAAAATTACGCCCCGCCCT
GCCACTCATCGCAGTACTGTTGTAATTCATTAAGCATTCTGCCGACATGGAA
GCCATCACAGACGGCATGATGAACCTGAATCGCCAGCGGCATCAGCACCTTG
TCGCCTTGCGTATAATATTTGCCCATGGTGAAAACGGGGGCGAAGAAGTTGT
CCATATTGGCCACGTTTAAATCAAAACTGGTGAAACTCACCCAGGGATTGGC
TGAGACGAAAAACATATTCTCAATAAACCCTTTAGGGAAATAGGCCAGGTTT
TCACCGTAACACGCCACATCTTGCGAATATATGTGTAGAAACTGCCGGAAAT
CGTCGTGGTATTCACTCCAGAGCGATGAAAACGTTTCAGTTTGCTCATGGAA
```

*Fig. 22*

```
AACGGTGTAACAAGGGTGAACACTATCCCATATCACCAGCTCACCGTCTTTC
ATTGCCATACGGAATTCCGGATGAGCATTCATCAGGCGGGCAAGAATGTGAA
TAAAGGCCGGATAAAACTTGTGCTTATTTTTCTTTACGGTCTTTAAAAAGGCC
GTAATATCCAGCTGAACGGTCTGGTTATAGGTACATTGAGCAACTGACTGAA
ATGCCTCAAAATGTTCTTTACGATGCCATTGGGATATATCAACGGTGGTATAT
CCAGTGATTTTTTTCTCCATTTCTCGAGCACACTGAAAGCGGCCGCTTCCACA
CATTAAACTAGTTCGATGATTAATTGTCAACAGCTCGCCGCTATATGCGTTGA
TGCAATTTCTATGCGCACCCGTTCTCGGAGCACTGTCCGACCGCTTTGGCCGC
CGCCCAGTCCTGCTCGCTTCGCTACTTGGAGCCACTATCGACTACGCGATCAT
GGCGACCACACCCGTCCTGTGGATCCCAGACGAGTTAAGTCACCATACGTTA
GTACAGGTTGCCACTCTTTTGGCAGACGCAGACCTACGGCTACAATAGCGAA
GCGGTCCTGGTATTCATGTTTAAAAATACTGTCGCGATAGCCAAAACGGCAC
TCTTTGGCAGTTAAGCGCACTTGCTTGCCTGTCGCCAGTTCAACAGAATCAAC
ATAAGCGCAAACTCGCTGTAATTCTACGCCATAAGCACCAATATTCTGGATA
GGTGATGAGCCGACACAACCAGGAATTAATGCCAGATTTTCCAGACCAGGC
ATACCTTCCTGCAAAGTGTATTTTACCAGACGATGCCAGTTTTCTCCGGCTCC
TACATGTAAATACCACGCATCAGGTTCATCATGAATTTCGATACCTTTGATCC
GGTTGATGATCACCGTGCCGCGATAGTCCTCCAGAAAAAGTACATTACTTCC
TTCACCCAGAATAAGAACGGGTTGTCCTTCTGCGGTTGCATACTGCCAGGCA
TTGAGTAATTGTTGTTCGTCTTCGGCACATACAATGTGCTGAGCATTATGATC
AATGCCAAATGTGTTCCAGGGTTTTAAGGAGTGGTTCATAGCTGCTTTCCTGA
TGCAAAAACGAGGCTAGTTTACCGTATCTGTGGGGGGATGGCTTGTAGATAT
GACGACAGGAAGAGTTTGTAGAAACGCAAAAAGGCCATCCGTCAGGATGGC
CTTCTGCTTAATTTGATGCCTGGCAGTTTATGGCGGGCGTCCTGCCCGCCACC
CTCCGGGCCGTTGCTTCGCAACGTTCAAATCCGCTCCCGGCGGATTTGTCCTA
CTCAGGAGAGCGTTCACCGACAAACAACAGATAAAACGAAAGGCCCAGTCT
TTCGACTGAGCCTTTCGTTTTATTTGATGCCTGGCAGTTCCCTACTCTCGCAT
GGGGAGACCCCACACTACCATCGGCGCTACGGCGTTTCACTTCTGAGTTCGG
CATGGGGTCAGGTGGGACCACCGCGCTACTGCCGCCAGGCAAATTCTGTTTT
ATCAGACCGCTTCTGCGTTCTGATTTAATCTGTATCAGGCTGAAAATCTTCTC
TCATCCGCCAAAACAGCTTCGGCGTTGTAAGGTTAAGCCTCACGGTTCATTA
GTACCGGTTAGCTCAACGCATCGCTGCGCTTACACACCCGGCCTATCAACGT
CGTCGTCTTCAACGTTCCTTCAGGACCCTTAAAGGGTCAGGGAGAACTCATC
TCGGGGCAAGTTTCGTGCTTAGATGCTTTCAGCACTTATCTCTTCCGCATTTA
GCTACCGGGCAGTGCCATTGGCATGACAACCCGAACACCAGTGATGCGTCCA
CTCCGGTCCTCTCGTACTAGGAGCAGCCCCCTCAGTTCTCCAGCGCCCACG
GCAGATAGGGACCGAACTGTCTCACGACGTTCTAAACCCAGCTCGCGTACCA
CTTTAAATGGCGAACAGCCATACCCTTGGGACCTACTTCAGCCCCAGGATGT
GATGAGCCGACATCGAGGTGCCAAACACCGCCGTCGATATGAACTCTTGGGC
GGTATCAGCCTGTTATCCCCGGAGTACCTTTTATCCGTTGAGCGATGGCCCTT
CCATTCAGAACCACCGGATCACTATGACCTGCTTTCGCACCTGCTCGCGCCGT
CACGCTCGCAGTCAAGCTGGCTTATGCCATTGCACTAACCTCCTGATGTCCG
ACCAGGATTAGCCAACCTTCGTGCTCCTCCGTTACTCTTTAGGAGGAGACCG
CCCCAGTCAAACTACCCACCAGACACTGTCCGCAACCCGGATTACGGGTCAA
CGTTAGAACATCAAACATTAAAGGGTGGTATTTCAAGGTCGGCTCCATGCAG
```

*Fig. 22*
Cont.

```
ACTGGCGTCCACACTTCAAAGCCTCCCACCTATCCTACACATCAAGGCTCAA
TGTTCAGTGTCAAGCTATAGTAAAGGTTCACGGGGTCTTTCCGTCTTGCCGCG
GGTACACTGCATCTTCACAGCGAGTTCAATTTCACTGAGTCTCGGGTGGAGA
CAGCCTGGCCATCATTACGCCATTCGTGCAGGTCGGAACTTACCCGACAAGG
AATTTCGCTACCTTAGGACCGTTATAGTTACGGCCGCCGTTTACCGGGGCTTC
GATCAAGAGCTTCGCTTGCGCTAACCCCATCAATTAACCTTCCGGCACCGGG
CAGGCGTCACACCGTATACGTCCACTTTCGTGTTTGCACAGTGCTGTGTTTTT
AATAAACAGTTGCAGCCAGCTGGTATCTTCGACTGATTTCAGCTCCATCCGC
GAGGGACCTCACCTACATATCAGCGTGCCTTCTCCCGAAGTTACGGCACCAT
TTTGCCTAGTTCCTTCACCCGAGTTCTCTCAAGCGCCTTGGTATTCTCTACCTG
ACCACCTGTGTCGGTTTGGGGTACGATTTGATGTTACCTGATGCTTAGAGGCT
TTTCCTGGAAGCAGGGCATTTGTTGCTTCAGCACCGTAGTGCCTCGTCATCAC
GCCTCAGCCTTGATTTTCCGGATTTGCCTGGAAAACCAGCCTACACGCTTAA
ACCGGGACAACCGTCGCCCGGCCAACATAGCCTTCTCCGTCCCCCCTTCGCA
GTAACACCAAGTACAGGAATATTAACCTGTTTCCCATCGACTACGCCTTTCG
GCCTCGCCTTAGGGGTCGACTCACCCTGCCCCGATTAACGTTGGACAGGAAC
CCTTGGTCTTCCGGCGAGCGGGCTTTTCACCCGCTTTATCGTTACTTATGTCA
GCATTCGCACTTCTGATACCTCCAGCATGCCTCACAGCACACCTTCGCAGGCT
TACAGAACGCTCCCCTACCCAACAACGCATAAGCGTCGCTGCCGCAGCTTCG
GTGCATGGTTTAGCCCCGTTACATCTTCCGCGCAGGCCGACTCGACCAGTGA
GCTATTACGCTTTCTTTAAATGATGGCTGCTTCTAAGCCAACATCCTGGCTGT
CTGGGCCTTCCCACATCGTTTCCCACTTAACCATGACTTTGGGACCTTAGCTG
GCGGTCTGGGTTGTTTCCCTCTTCACGACGGACGTTAGCACCCGCCGTGTGTC
TCCCGTGATAACATTCTCCGGTATTCGCAGTTTGCATCGGGTTGGTAAGTCGG
GATGACCCCCTTGCCGAAACAGTGCTCTACCCCCGGAGATGAATTCACGAGG
CGCTACCTAAATAGCTTTCGGGGAGAACCAGCTATCTCCCGGTTTGATTGGC
CTTTCACCCCCAGCCACAAGTCATCCGCTAATTTTTCAACATTAGTCGGTTCG
GTCCTCCAGTTAGTGTTACCCAACCTTCAACCTGCCCATGGCTAGATCACCGG
GTTTCGGGTCTATACCCTGCAACTTAACGCCCAGTTAAGACTCGGTTTCCCTT
CGGCTCCCCTATTCGGTTAACCTTGCTACAGAATATAAGTCGCTGACCCATTA
TACAAAAGGTACGCAGTCACACGCCTAAGCGTGCTCCCACTGCTTGTACGTA
CACGGTTTCAGGTTCTTTTTCACTCCCCTCGCCGGGGTTCTTTTCGCCTTTCCC
TCACGGTACTGGTTCACTATCGGTCAGTCAGGAGTATTTAGCCTTGGAGGAT
GGTCCCCCCATATTCAGACAGGATACCACGTGTCCCGCCCTACTCATCGAGC
TCACAGCATGTGCATTTTTGTGTACGGGGCTGTCACCCTGTATCGCGCGCCTT
TCCAGACGCTTCCACTAACACACACACTGATTCAGGCTCTGGGCTGCTCCCC
GTTCGCTCGCCGCTACTGGGGGAATCTCGGTTGATTTCTTTTCCTCGGGGTAC
TTAGATGTTTCAGTTCCCCCGGTTCGCCTCATTAACCTATGGATTCAGTTAAT
GATAGTGTGTCGAAACACACTGGGTTTCCCCATTCGGAAATCGCCGGTTATA
ACGGTTCATATCACCTTACCGACGCTTATCGCAGATTAGCACGTCCTTCATCG
CCTCTGACTGCCAGGGCATCCACCGTGTACGCTTAGTCGCTTAACCTCACAA
CCCGAAGATGTTTCTTTCGATTCATCATCGTGTTGCGAAAATTTGAGAGACTC
ACGAACAACTCTCGTTGTTCAGTGTTTCAATTTTCAGCTTGATCCAGATTTTT
AAAGAGCAAAAATCTCAAACATCACCCGAAGATGAGTTTTGAGATATTAAG
GTCGGCGACTTTCACTCACAAACCAGCAAGTGGCGTCCCCTAGGGGATTCGA
```

*Fig. 22*
Cont.

```
ACCCCTGTTACCGCCGTGAAAGGGCGGTGTCCTGGGCCTCTAGACGAAGGGG
ACACGAAAATTGCTTATCACGCGTTGCGTGATATTTTCGTGTAGGGTGAGCTT
TCATTAATAGAAAGCGAACGGCCTTATTCTCTTCAGCCTCACTCCCAACGCGT
AAACGCCTTGCTTTTCACTTTCTATCAGACAATCTGTGTGAGCACTACAAAGT
ACGCTTCTTTAAGGTAAGTGTGTGATCCAACCGCAGGTTCCCCTACGGTTACC
TTGTTACGACTTCACCCCAGTCATGAATCACAAAGTGGTAAGCGCCCTCCCG
AAGGTTAAGCTACCTACTTCTTTTGCAACCCACTCCCATGGTGTGACGGGCG
GTGTGTACAAGGCCCGGGAACGTATTCACCGTGGCATTCTGATCCACGATTA
CTAGCGATTCCGACTTCATGGAGTCGAGTTGCAGACTCCAATCCGGACTACG
ACGCACTTTATGAGGTCCGCTTGCTCTCGCGAGGTCGCTTCTCTTTGTATGCG
CCATTGTAGCACGTGTGTAGCCCTGGTCGTAAGGGCCATGATGACTTGACGT
CATCCCCACCTTCCTCCAGTTTATCACTGGCAGTCTCCTTTGAGTTCCCGGCC
GGACCGCTGGCAACAAAGGATAAGGGTTGCGCTCGTTGCGGGACTTAACCC
AACATTTCACAACACGAGCTGACGACAGCCATGCAGCACCTGTCTCACGGTT
CCCGAAGGCACATTCTCATCTCTGAAAACTTCCGTGGATGTCAAGACCAGGT
AAGGTTCTTCGCGTTGCATCGAATTAAACCACATGCTCCACCGCTTGTGCGG
GCCCCCGTCAATTCATTTGAGTTTTAACCTTGCGGCCGTACTCCCCAGGCGGT
CGACTTAACGCGTTAGCTCCGGAAGCCACGCCTCAAGGGCACAACCTCCAAG
TCGACATCGTTTACGGCGTGGACTACCAGGGTATCTAATCCTGTTTGCTCCCC
ACGCTTTCGCACCTGAGCGTCAGTCTTCGTCCAGGGGGCCGCCTTCGCCACC
GGTATTCCTCCAGATCTCTACGCATTTCACCGCTACACCTGGAATTCTACCCC
CCTCTACGAGACTCAAGCTTGCCAGTATCAGATGCAGTTCCCAGGTTGAGCC
CGGGGATTTCACATCTGACTTAACAAACCGCCTGCGTGCGCTTTACGCCCAG
TAATTCCGATTAACGCTTGCACCCTCCGTATTACCGCGGCTGCTGGCACGGA
GTTAGCCGGTGCTTCTTCTGCGGGTAACGTCAATGAGCAAAGGTATTAACTT
TACTCCCTTCCTCCCCGCTGAAAGTACTTTACAACCCGAAGGCCTTCTTCATA
CACGCGGCATGGCTGCATCAGGCTTGCGCCCATTGTGCAATATTCCCCACTG
CTGCCTCCCGTAGGAGTCTGGACCGTGTCTCAGTTCCAGTGTGGCTGGTCATC
CTCTCAGACCAGCTAGGGATCGTCGCCTAGGTGAGCCGTTACCCCACCTACT
AGCTAATCCCATCTGGGCACATCCGATGGCAAGAGGCCCGAAGGTCCCCCTC
TTTGGTCTTGCGACGTTATGCGGTATTAGCTACCGTTTCCAGTAGTTATCCCC
CTCCATCAGGCAGTTTCCCAGACATTACTCACCCGTCCGCCACTCGTCAGCA
AAGAAGCAAGCTTCTTCCTGTTACCGTTCGACTTGCATGTGTTAGGCCTGCCG
CCAGCGTTCAATCTGAGCCATGATCAAACTCTTCAATTTAAAAGTTTGACGCT
CAAAGAATTAAACTTCGTAATGAATTACGTGTTCACTCTTGAGACTTGGTATT
CATTTTTCGTCTTGCGACGTTAAGAATCCGTATCTTCGAGTGCCCACACAGAT
TGTCTGATAAATTGTTAAAGAGCAGTGCCGCTTCGCTTTTTCTCAGCGGCCGC
TGTGTGAAATTGTTATCCGCTCACAATTCCACACATTATACGAGCCGGAAGC
ATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCAT
TAATGAATCGGCCAACGCGCGGGGAGAGGCGGTTTGCGTATTGGGCGCCAG
GGTGGTTTTTCTTTTCACCAGTGAGACGGGCAACAGCTGATTGCCCTTCACCG
CCTGGCCCTGAGAGAGTTGCAGCAAGCGGTCCACGCTGGTTTGCCCCAGCAG
GCGAAAATCCTGTTTGATGGTGGTTGACGGCGGGATATAACATGAGCTGTCT
TCGGTATCGTCGTATCCCACTACCGAGATATCCGCACCAACGCGCAGCCCGG
```

*Fig. 22*
Cont.

```
ACTCGGTAATGGCGCGCATTGCGCCCAGCGCCATCTGATCGTTGGCAACCAG
CATCGCAGTGGGAACGATGCCCTCATTCAGCATTTGCATGGTTTGTTGAAAA
CCGGACATGGCACTCCAGTCGCCTTCCCGTTCCGCTATCGGCTGAATTTGATT
GCGAGTGAGATATTTATGCCAGCCAGCCAGACGCAGACGCGCCGAGACAGA
ACTTAATGGGCCCGCTAACAGCGCGATTTGCTGGTGACCCAATGCGACCAGA
TGCTCCACGCCCAGTCGCGTACCGTCTTCATGGGAGAAAATAATACTGTTGA
TGGGTGTCTGGTCAGAGACATCAAGAAATAACGCCGGAACATTAGTGCAGG
CAGCTTCCACAGCAATGGCATCCTGGTCATCCAGCGGATAGTTAATGATCAG
CCCACTGACCCGTTGCGCGAGAAGATTGTGCACCGCCGCTTTACAGGCTTCG
ACGCCGCTTCGTTCTACCATCGACACCACCACGCTGGCACCCAGTTGATCGG
CGCGAGATTTAATCGCCGCGACAATTTGCGACGGCGCGTGCAGGGCCAGACT
GGAGGTGGCAACGCCAATCAGCAACGACTGTTTGCCCGCCAGTTGTTGTGCC
ACGCGGTTGGGAATGTAATTCAGCTCCGCCATCGCCGCTTCCACTTTTTCCCG
CGTTTTCGCAGAAACGTGGCTGGCCTGGTTCACCACGCGGGAAACGGTCTGA
TAAGAGACACCGGCATACTCTGCGACATCGTATAACGTTACTGGTTTCACAT
TCACCACCCTGAATTGACTCTCTTCCGGGCGCTATCATGCCATACCGCGAAA
GGTTTTGCACCATTCGATGGTGTCGGATCCTAGAGCGCACGAATGAGGGCCG
ACAGGAAGCAAAGCTGAAAGGAATCAAATTTGGCCGCAGGCGTACCGTGGA
CAGGAACGTCGTGCTGACGCTTCATCAGAAGGGCACTGGTGCAACGGAAATT
GCTCATCAGCTCAGTATTGCCCGCTCCACGGTTTATAAAATTCTTGAAGACG
AAAGGGCCTCGTGCATACGCCTATTTTTATAGGTTAATGTCATGATAATAAT
GGTTTCTTAGACGTCAGGTGGCACTTTTCGGGGAAATGTGCGCGGAACCCCT
ATTTGTTTATTTTTCTAAATACATTCAAATATGTATCCGCTCATGAGACAATA
ACCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGT
GCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTA
TGTGGCGCGGTATTATCCCGTGTT
```

*Fig. 22*
Cont.

```
GATCCTCTACGCCGGACGCATCGTGGCCGGCCACGATGCGTCCGGCGTAGAG
GATCTATTTAACGACCCTGCCCTGAACCGACGACCGGGTCGAATTTGCTTTC
GAATTTCTGCCATTCATCCGCTTATTATCACTTATTCAGGCGTAGCACCAGGC
GTTTAAGGGCACCAATAACTGCCTTAAAAAAATTACGCCCCGCCCTGCCACT
CATCGCAGTACTGTTGTAATTCATTAAGCATTCTGCCGACATGGAAGCCATC
ACAGACGGCATGATGAACCTGAATCGCCAGCGGCATCAGCACCTTGTCGCCT
TGCGTATAATATTTGCCCATGGTGAAAACGGGGGCGAAGAAGTTGTCCATAT
TGGCCACGTTTAAATCAAAACTGGTGAAACTCACCCAGGGATTGGCTGAGAC
GAAAAACATATTCTCAATAAACCCTTTAGGGAAATAGGCCAGGTTTTCACCG
TAACACGCCACATCTTGCGAATATATGTGTAGAAACTGCCGGAAATCGTCGT
GGTATTCACTCCAGAGCGATGAAAACGTTTCAGTTTGCTCATGGAAAACGGT
GTAACAAGGGTGAACACTATCCCATATCACCAGCTCACCGTCTTTCATTGCC
ATACGGAATTCCGGATGAGCATTCATCAGGCGGGCAAGAATGTGAATAAAG
GCCGGATAAAACTTGTGCTTATTTTTCTTTACGGTCTTTAAAAAGGCCGTAAT
ATCCAGCTGAACGGTCTGGTTATAGGTACATTGAGCAACTGACTGAAATGCC
TCAAAATGTTCTTTACGATGCCATTGGGATATATCAACGGTGGTATATCCAGT
GATTTTTTTCTCCATTTGCGGAGGGATATGAAAGCGGCCGCTTCCACACATTA
AACTAGTTCGATGATTAATTGTCAACAGCTCGCCGGCGGCACCTCGCTAACG
GATTCACCACTCCAAGAATTGGAGCCAATCGATTCTTGCGGAGAACTGTGAA
TGCGCAAACCAACCCTTGGCAGAACATATCCATCGCGTCCGCCATCTCCAGC
AGCCGCACGCGGCGCATCTCGGGCAGCGTTGGGTCCTGGCCACGGGTGCGCA
TGATCGTGCTCCTGTCGTTGAGGACCCGGCTAGGCTGGCGGGGTTGCCTTAC
TGGTTAGCAGAATGAATCACCGATACGCGAGCGAACGTGAAGCGACTGCTG
CTGCAAAACGTCTGCGACCTGAGCAACAACATGAATGGTCTTCGGTTTCCGT
GTTTCGTAAAGTCTGGAAACGCGGAAGTCAGCGCCCTGCACCATTATGTTCC
GGATCTGGGTACCGAGCTCGAATTCACTGGCCGTCGTTTTACAACGTCGTGA
CTGGGAAAACCCTGGCGTTACCCAACTTAATCGCCTTGCAGCACATCCCCCT
TTCGCCAGGCATCGCAGGATGCTGCTGGCTACCCTGTGGAACACCTACATCT
GTATTAACGAAGCGCTGGCATTGACCCTGAGTGATTTTTCTCTGGTCCCGCCG
CATCCATACCGCCAGTTGTTTACCCTCACAACGTTCCAGTAACCGGGCATGTT
CATCATCAGTAACCCGTATCGTGAGCATCCTCTCTCGTTTCATCGGTATCATT
ACCCCCATGAACAGAAATTCCCCCTTACACGGAGGCATCAAGTGACCAAACA
GGAAAAAACCGCCCTTAACATGGCCCGCTTTATCAGAAGCCAGACATTAACG
CTTCTGGAGAAACTCAACGAGCTGGACGCGGATGAACAGGCAGACATCTGT
GAATCGCTTCACGACCACGCTGATGAGCTTTACCGCAGCTGCCTCGCGCGTT
TCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTC
AGCGGGTGTTGGCGGGTGTCGGGGCGCAGCCATGACCCAGTCACGTAGCGA
TAGCGGAGTGTATACTGGCTTAACTATGCGGCATCAGAGCAGATTGTACTGA
GAGTGCACCATATGCGGTGTGAAATACCGCACAGATGCGTAAGGAGAAAAT
ACCGCATCAGGCGCTCTTCCGCTTCCTCGCTCACTGACTCGCTGCGCTCGGTC
GTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGC
AAAAGGCCAGGAACCGTAAAAAGGCCGCGTTGCTGGCGTTTTCCATAGGCT
CCGCCCCCTGACGAGCATCACAAAAATCGACGCTCAAGTCAGAGGTGGCG
AAACCCGACAGGACTATAAAGATACCAGGCGTTTCCCCCTGGAAGCTCCCTC
```

Fig. 23

```
GTGCGCTCTCCTGTTCCGACCCTGCCGCTTACCGGATACCTGTCCGCCTTTCT
CCCTTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTA
AGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACG
GCTACACTAGAAGGACAGTATTTGGTATCTGCGCTCTGCTGAAGCCAGTTAC
CTTCGGAAAAGAGTTGGTAGCTCTTGATCCGGCAAACAAACCACCGCTGGT
AGCGGTGGTTTTTTTGTTTGCAAGCAGCAGATTACGCGCAGAAAAAAGGAT
CTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACC
TAGATCCTTTTAAATTAAAAATGAAGTTTTAAATCAATCTAAAGTATATATG
AGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACC
GCGAGACCCACGCTCACCGGCTCCAGATTTATCAGCAATAAACCAGCCAGCC
GGAAGGGCCGAGCGCAGAAGTGGTCCTGCAACTTTATCCGCCTCCATCCAGT
CTATTAATTGTTGCCGGGAAGCTAGAGTAAGTAGTTCGCCAGTTAATAGTTT
GCGCAACGTTGTTGCCATTGCTGCAGGCATCGTGGTGTCACGCTCGTCGTTTG
GTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCATAA
TTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCC
GGCGTCAACACGGGATAATACCGCGCCACATAGCAGAACTTTAAAAGTGCTC
ATCATTGGAAAACGTTCTTCGGGGCGAAAACTCTCAAGGATCTTACCGCTGT
TGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCG
CAAAAAAGGGAATAAGGGCGACACGGAAATGTTGAATACTCATACTCTTCCT
TTTTCAATATTATTGAAGCATTTATCAGGGTTATTGTCTCATGAGCGGATACA
TATTTGAATGTATTTAGAAAAATAAACAAATAGGGGTTCCGCGCACATTTCC
CCGAAAAGTGCCACCTGACGTCTAAGAAACCATTATTATCATGACATTAACC
TATAAAAATAGGCGTATCACGAGGCCCTTTCGTCTTCAAGAATTCTCATGTTT
GACAGCTTATCATCGATAAGCTTTAATGCGGTAGTTTATCACAGTTAAATTGC
TAACGCAGTCAGGCACCGTGTATGAAATCTAACAATGCGCTCATCGTCATCC
TCGGCACCGTCACCCTGGATGCTGTAGGCATAGGCTTGGTTATGCCGGTACT
GCCGGGCCTCTTGCGGGATATCGTCCATTCCGACAGCATCGCCAGTCACTAT
GGCGTGCTGCTAGCGCTATATGCGTTGATGCAATTTCTATGCGCACCCGTTCT
CGGAGCACTGTCCGACCGCTTTGGCCGCCGCCCAGTCCTGCTCGCTTCGCTAC
TTGGAGCCACTATCGACTACGCGATCATGGCGACCACACCCGTCCTGTGGAT
CCCAGACGAGTTAAGTCACCATACGTTAGTACAGGTTGCCACTCTTTTGGCA
GACGCAGACCTACGGCTACAATAGCGAAGCGGTCCTGGTATTCATGTTTAAA
AATACTGTCGCGATAGCCAAAACGGCACTCTTTGGCAGTTAAGCGCACTTGC
TTGCCTGTCGCCAGTTCAACAGAATCAACATAAGCGCAAACTCGCTGTAATT
CTACGCCATAAGCACCAATATTCTGGATAGGTGATGAGCCGACACAACCAGG
AATTAATGCCAGATTTTCCAGACCAGGCATACCTTCCTGCAAAGTGTATTTTA
```

*Fig. 23*
Cont.

```
CCAGACGATGCCAGTTTTCTCCGGCTCCTACATGTAAATACCACGCATCAGG
TTCATCATGAATTTCGATACCTTTGATCCGGTTGATGATCACCGTGCCGCGAT
AGTCCTCCAGAAAAAGTACATTACTTCCTTCACCCAGAATAAGAACGGGTTG
TCCTTCTGCGGTTGCATACTGCCAGGCATTGAGTAATTGTTGTTCGTCTTCGG
CACATACAATGTGCTGAGCATTATGATCAATGCCAAATGTGTTCCAGGGTTT
TAAGGAGTGGTTCATAGCTGCTTTCCTGATGCAAAAACGAGGCTAGTTTACC
GTATCTGTGGGGGGATGGCTTGTAGATATGACGACAGGAAGAGTTTGTAGAA
ACGCAAAAAGGCCATCCGTCAGGATGGCCTTCTGCTTAATTTGATGCCTGGC
AGTTTATGGCGGGCGTCCTGCCCGCCACCCTCCGGGCCGTTGCTTCGCAACG
TTCAAATCCGCTCCCGGCGGATTTGTCCTACTCAGGAGAGCGTTCACCGACA
AACAACAGATAAAACGAAAGGCCCAGTCTTTCGACTGAGCCTTTCGTTTTAT
TTGATGCCTGGCAGTTCCCTACTCTCGCATGGGGAGACCCCACACTACCATC
GGCGCTACGGCGTTTCACTTCTGAGTTCGGCATGGGGTCAGGTGGGACCACC
GCGCTACTGCCGCCAGGCAAATTCTGTTTTATCAGACCGCTTCTGCGTTCTGA
TTTAATCTGTATCAGGCTGAAAATCTTCTCTCATCCGCCAAAACAGCTTCGGC
GTTGTAAGGTTAAGCCTCACGGTTCATTAGTACCGGTTAGCTCAACGCATCG
CTGCGCTTACACACCCGGCCTATCAACGTCGTCGTCTTCAACGTTCCTTCAGG
ACCCTTAAAGGGTCAGGGAGAACTCATCTCGGGGCAAGTTTCGTGCTTAGAT
GCTTTCAGCACTTATCTCTTCCGCATTTAGCTACCGGGCAGTGCCATTGGCAT
GACAACCCGAACACCAGTGATGCGTCCACTCCGGTCCTCTCGTACTAGGAGC
AGCCCCCCTCAGTTCTCCAGCGCCCACGGCAGATAGGGACCGAACTGTCTCA
CGACGTTCTAAACCCAGCTCGCGTACCACTTTAAATGGCGAACAGCCATACC
CTTGGGACCTACTTCAGCCCCAGGATGTGATGAGCCGACATCGAGGTGCCAA
ACACCGCCGTCGATATGAACTCTTGGGCGGTATCAGCCTGTTATCCCCGGAG
TACCTTTTATCCGTTGAGCGATGGCCCTTCCATTCAGAACCACCGGATCACTA
TGACCTGCTTTCGCACCTGCTCGCGCCGTCACGCTCGCAGTCAAGCTGGCTTA
TGCCATTGCACTAACCTCCTGATGTCCGACCAGGATTAGCCAACCTTCGTGCT
CCTCCGTTACTCTTTAGGAGGAGACCGCCCCAGTCAAACTACCCACCAGACA
CTGTCCGCAACCCGGATTACGGGTCAACGTTAGAACATCAAACATTAAAGGG
TGGTATTTCAAGGTCGGCTCCATGCAGACTGGCGTCCACACTTCAAAGCCTC
CCACCTATCCTACACATCAAGGCTCAATGTTCAGTGTCAAGCTATAGTAAAG
GTTCACGGGGTCTTTCCGTCTTGCCGCGGGTACACTGCATCTTCACAGCGAGT
TCAATTTCACTGAGTCTCGGGTGGAGACAGCCTGGCCATCATTACGCCATTC
GTGCAGGTCGGAACTTACCCGACAAGGAATTTCGCTACCTTAGGACCGTTAT
AGTTACGGCCGCCGTTTACCGGGGCTTCGATCAAGAGCTTCGCTTGCGCTAA
CCCCATCAATTAACCTTCCGGCACCGGGCAGGCGTCACACCGTATACGTCCA
CTTTCGTGTTTGCACAGTGCTGTGTTTTAATAAACAGTTGCAGCCAGCTGGT
ATCTTCGACTGATTTCAGCTCCATCCGCGAGGGACCTCACCTACATATCAGC
GTGCCTTCTCCCGAAGTTACGGCACCATTTTGCCTAGTTCCTTCACCCGAGTT
CTCTCAAGCGCCTTGGTATTCTCTACCTGACCACCTGTGTCGGTTTGGGGTAC
GATTTGATGTTACCTGATGCTTAGAGGCTTTTCCTGGAAGCAGGGCATTTGTT
GCTTCAGCACCGTAGTGCCTCGTCATCACGCCTCAGCCTTGATTTTCCGGATT
TGCCTGGAAAACCAGCCTACACGCTTAAACCGGGACAACCGTCGCCCGGCCA
ACATAGCCTTCTCCGTCCCCCCTTCGCAGTAACACCAAGTACAGGAATATTA
ACCTGTTTCCCATCGACTACGCCTTTCGGCCTCGCCTTAGGGGTCGACTCACC
CTGCCCCGATTAACGTTGGACAGGAACCCTTGGTCTTCCGGCGAGCGGGCTT
```

Fig. 23
Cont.

TTCACCCGCTTTATCGTTACTTATGTCAGCATTCGCACTTCTGATACCTCCAG
CATGCCTCACAGCACACCTTCGCAGGCTTACAGAACGCTCCCCTACCCAACA
ACGCATAAGCGTCGCTGCCGCAGCTTCGGTGCATGGTTTAGCCCCGTTACAT
CTTCCGCGCAGGCCGACTCGACCAGTGAGCTATTACGCTTTCTTTAAATGATG
GCTGCTTCTAAGCCAACATCCTGGCTGTCTGGGCCTTCCCACATCGTTTCCCA
CTTAACCATGACTTTGGGACCTTAGCTGGCGGTCTGGGTTGTTTCCCTCTTCA
CGACGGACGTTAGCACCCGCCGTGTGTCTCCCGTGATAACATTCTCCGGTATT
CGCAGTTTGCATCGGGTTGGTAAGTCGGGATGACCCCCTTGCCGAAACAGTG
CTCTACCCCGGAGATGAATTCACGAGGCGCTACCTAAATAGCTTTCGGGGA
GAACCAGCTATCTCCCGGTTTGATTGGCCTTTCACCCCCAGCCACAAGTCATC
CGCTAATTTTTCAACATTAGTCGGTTCGGTCCTCCAGTTAGTGTTACCCAACC
TTCAACCTGCCCATGGCTAGATCACCGGGTTTCGGGTCTATACCCTGCAACTT
AACGCCCAGTTAAGACTCGGTTTCCCTTCGGCTCCCCTATTCGGTTAACCTTG
CTACAGAATATAAGTCGCTGACCCATTATACAAAAGGTACGCAGTCACACGC
CTAAGCGTGCTCCCACTGCTTGTACGTACACGGTTTCAGGTTCTTTTTCACTC
CCCTCGCCGGGGTTCTTTTCGCCTTTCCCTCACGGTACTGGTTCACTATCGGT
CAGTCAGGAGTATTTAGCCTTGGAGGATGGTCCCCCCATATTCAGACAGGAT
ACCACGTGTCCCGCCCTACTCATCGAGCTCACAGCATGTGCATTTTTGTGTAC
GGGGCTGTCACCCTGTATCGCGCGCCTTCCAGACGCTTCCACTAACACACA
CACTGATTCAGGCTCTGGGCTGCTCCCGTTCGCTCGCCGCTACTGGGGGAA
TCTCGGTTGATTTCTTTTCCTCGGGGTACTTAGATGTTTCAGTTCCCCCGGTTC
GCCTCATTAACCTATGGATTCAGTTAATGATAGTGTGTCGAAACACACTGGG
TTTCCCCATTCGGAAATCGCCGGTTATAACGGTTCATATCACCTTACCGACGC
TTATCGCAGATTAGCACGTCCTTCATCGCCTCTGACTGCCAGGGCATCCACCG
TGTACGCTTAGTCGCTTAACCTCACAACCCGAAGATGTTTCTTTCGATTCATC
ATCGTGTTGCGAAAATTTGAGAGACTCACGAACAACTCTCGTTGTTCAGTGT
TTCAATTTTCAGCTTGATCCAGATTTTTAAAGAGCAAAAATCTCAAACATCAC
CCGAAGATGAGTTTTGAGATATTAAGGTCGGCGACTTTCACTCACAAACCAG
CAAGTGGCGTCCCCTAGGGGATTCGAACCCCTGTTACCGCCGTGAAAGGGCG
GTGTCCTGGGCCTCTAGACGAAGGGGACACGAAAATTGCTTATCACGCGTTG
CGTGATATTTTCGTGTAGGGTGAGCTTTCATTAATAGAAAGCGAACGGCCTT
ATTCTCTTCAGCCTCACTCCCAACGCGTAAACGCCTTGCTTTTCACTTTCTATC
AGACAATCTGTGTGAGCACTACAAAGTACGCTTCTTTAAGGTAATCCCATGA
TCCAACCGCAGGTTCCCCTACGGTTACCTTGTTACGACTTCACCCCAGTCATG
AATCACAAAGTGGTAAGCGCCCTCCCGAAGGTTAAGCTACCTACTTCTTTTG
CAACCCACTCCCATGGTGTGACGGGCGGTGTGTACAAGGCCCGGGAACGTAT
TCACCGTGGCATTCTGATCCACGATTACTAGCGATTCCGACTTCATGGAGTCG
AGTTGCAGACTCCAATCCGGACTACGACGCACTTTATGAGGTCCGCTTGCTC
TCGCGAGGTCGCTTCTCTTTGTATGCGCCATTGTAGCACGTGTGTAGCCCTGG
TCGTAAGGGCCATGATGACTTGACGTCATCCCCACCTTCCTCCAGTTTATCAC
TGGCAGTCTCCTTTGAGTTCCCGGCCGGACCGCTGGCAACAAAGGATAAGGG
TTGCGCTCGTTGCGGGACTTAACCCAACATTTCACAACACGAGCTGACGACA
GCCATGCAGCACCTGTCTCACGGTTCCCGAAGGCACATTCTCATCTCTGAAA
ACTTCCGTGGATGTCAAGACCAGGTAAGGTTCTTCGCGTTGCATCGAATTAA
ACCACATGCTCCACCGCTTGTGCGGGCCCCGTCAATTCATTTGAGTTTTAAC
CTTGCGGCCGTACTCCCCAGGCGGTCGACTTAACGCGTTAGCTCCGGAAGCC

*Fig. 23*
Cont.

ACGCCTCAAGGGCACAACCTCCAAGTCGACATCGTTTACGGCGTGGACTACC
AGGGTATCTAATCCTGTTTGCTCCCCACGCTTTCGCACCTGAGCGTCAGTCTT
CGTCCAGGGGGCCGCCTTCGCCACCGGTATTCCTCCAGATCTCTACGCATTTC
ACCGCTACACCTGGAATTCTACCCCCCTCTACGAGACTCAAGCTTGCCAGTA
TCAGATGCAGTTCCCAGGTTGAGCCCGGGGATTTCACATCTGACTTAACAAA
CCGCCTGCGTGCGCTTTACGCCCAGTAATTCCGATTAACGCTTGCACCCTCCG
TATTACCGCGGCTGCTGGCACGGAGTTAGCCGGTGCTTCTTCTGCGGGTAAC
GTCAATGAGCAAAGGTATTAACTTTACTCCCTTCCTCCCCGCTGAAAGTACTT
TACAACCCGAAGGCCTTCTTCATACACGCGGCATGGCTGCATCAGGCTTGCG
CCCATTGTGCAATATTCCCCACTGCTGCCTCCCGTAGGAGTCTGGACCGTGTC
TCAGTTCCAGTGTGGCTGGTCATCCTCTCAGACCAGCTAGGGATCGTCGCCT
AGGTGAGCCGTTACCCCACCTACTAGCTAATCCCATCTGGGCACATCCGATG
GCAAGAGGCCCGAAGGTCCCCCTCTTTGGTCTTGCGACGTTATGCGGTATTA
GCTACCGTTTCCAGTAGTTATCCCCCTCCATCAGGCAGTTTCCCAGACATTAC
TCACCCGTCCGCCACTCGTCAGCAAAGAAGCAAGCTTCTTCCTGTTACCGTTC
GACTTGCATGTGTTAGGCCTGCCGCCAGCGTTAATCTGAGCCATGATCAAA
CTCTTCAATTTAAAAGTTTGACGCTCAAAGAATTAAACTTCGTAATGAATTAC
GTGTTCACTCTTGAGACTTGGTATTCATTTTCGTCTTGCGACGTTAAGAATC
CGTATCTTCGAGTGCCCACACAGATTGTCTGATAAATTGTTAAAGAGCAGTG
CCGCTTCGCTTTTTCTCAGCGGCCGCTGTGTGAAATTGTTATCCGCTCACAAT
TCCACACATTATACGAGCCGGAAGCATAAAGTGTAAAGCCTGGGGTGCCTAA
TGAGTGAGCTAACTCACATTAATTGCGTTGCGCTCACTGCCCGCTTTCCAGTC
GGGAAACCTGTCGTGCCAGCTGCATTAATGAATCGGCCAACGCGCGGGGAG
AGGCGGTTTGCGTATTGGGCGCCAGGGTGGTTTTTCTTTTCACCAGTGAGAC
GGGCAACAGCTGATTGCCCTTCACCGCCTGGCCCTGAGAGAGTTGCAGCAAG
CGGTCCACGCTGGTTTGCCCCAGCAGGCGAAAATCCTGTTTGATGGTGGTTG
ACGGCGGGATATAACATGAGCTGTCTTCGGTATCGTCGTATCCCACTACCGA
GATATCCGCACCAACGCGCAGCCCGGACTCGGTAATGGCGCGCATTGCGCCC
AGCGCCATCTGATCGTTGGCAACCAGCATCGCAGTGGGAACGATGCCCTCAT
TCAGCATTTGCATGGTTTGTTGAAAACCGGACATGGCACTCCAGTCGCCTTCC
CGTTCCGCTATCGGCTGAATTTGATTGCGAGTGAGATATTTATGCCAGCCAG
CCAGACGCAGACGCGCCGAGACAGAACTTAATGGGCCCGCTAACAGCGCGA
TTTGCTGGTGACCCAATGCGACCAGATGCTCCACGCCCAGTCGCGTACCGTC
TTCATGGGAGAAAATAATACTGTTGATGGGTGTCTGGTCAGAGACATCAAGA
AATAACGCCGGAACATTAGTGCAGGCAGCTTCCACAGCAATGGCATCCTGGT
CATCCAGCGGATAGTTAATGATCAGCCCACTGACCCGTTGCGCGAGAAGATT
GTGCACCGCCGCTTTACAGGCTTCGACGCCGCTTCGTTCTACCATCGACACCA
CCACGCTGGCACCCAGTTGATCGGCGCGAGATTTAATCGCCGCGACAATTTG
CGACGGCGCGTGCAGGGCCAGACTGGAGGTGGCAACGCCAATCAGCAACGA
CTGTTTGCCCGCCAGTTGTTGTGCCACGCGGTTGGGAATGTAATTCAGCTCCG
CCATCGCCGCTTCCACTTTTTCCCGCGTTTTCGCAGAAACGTGGCTGGCCTGG
TTCACCACGCGGGAAACGGTCTGATAAGAGACACCGGCATACTCTGCGACAT
CGTATAACGTTACTGGTTTCACATTCACCACCCTGAATTGACTCTCTTCCGGG
CGCTATCATGCCATACCGCGAAAGGTTTTGCACCATTCGATGGTGTCG
```

*Fig. 23*
Cont.

```
AAATTGAAGAGTTTGATCATGGCTCAGATTGAACGCTGGCGGCAGGCCTAAC
ACATGCAAGTCGAACGGTAACAGGAAGAAGCTTGCTTCTTTGCTGACGAGTG
GCGGACGGGTGAGTAATGTCTGGGAAACTGCCTGATGGAGGGGGATAACTA
CTGGAAACGGTAGCTAATACCGCATAACGTCGCAAGACCAAAGAGGGGGAC
CTTCGGGCCTCTTGCCATCGGATGTGCCCAGATGGGATTAGCTAGTAGGTGG
GGTAACGGCTCACCTAGGCGACGATCCCTAGCTGGTCTGAGAGGATGACCAG
CCACACTGGAACTGAGACACGGTCCAGACTCCTACGGGAGGCAGCAGTGGG
GAATATTGCACAATGGGCGCAAGCCTGATGCAGCCATGCCGCGTGTATGAAG
AAGGCCTTCGGGTTGTAAAGTACTTTCAGCGGGGAGGAAGGGAGTAAAGTT
AATACCTTTGCTCATTGACGTTACCCGCAGAAGAAGCACCGGCTAACTCCGT
GCCAGCAGCCGCGGTAATACGGAGGGTGCAAGCGTTAATCGGAATTACTGG
GCGTAAAGCGCACGCAGGCGGTTTGTTAAGTCAGATGTGAAATCCCCGGGCT
CAACCTGGGAACTGCATCTGATACTGGCAAGCTTGAGTCTCGTAGAGGGGGG
TAGAATTCCAGGTGTAGCGGTGAAATGCGTAGAGATCTGGAGGAATACCGG
TGGCGAAGGCGGCCCCCTGGACGAAGACTGACGCTCAGGTGCGAAAGCGTG
GGGAGCAAACAGGATTAGATACCCTGGTAGTCCACGCCGTAAACGATGTCG
ACTTGGAGGTTGTGCCCTTGAGGCGTGGCTTCCGGAGCTAACGCGTTAAGTC
GACCGCCTGGGGAGTACGGCCGCAAGGTTAAAACTCAAATGAATTGACGGG
GGCCCGCACAAGCGGTGGAGCATGTGGTTTAATTCGATGCAACGCGAAGAA
CCTTACCTGGTC
TTGACATCCACGGAAGTTTTCAGAGATGAGAATGTGCCTTCGGGAACCGTGA
GACAGGTGCTGCATGGCTGTCGTCAGCTCGTGTTGTGAAATGTTGGGTTAAG
TCCCGCAACGAGCGCAACCCTTATCCTTTGTTGCCAGCGGTCCGGCCGGGAA
CTCAAAGGAGACTGCCAGTGATAAACTGGAGGAAGGTGGGGATGACGTCAA
GTCATCATGGCCCTTACGACCAGGGCTACACACGTGCTACAATGGCGCATAC
AAAGAGAAGCGACCTCGCGAGAGCAAGCGGACCTCATAAAGTGCGTCGTAG
TCCGGATTGGAGTCTGCAACTCGACTCCATGAAGTCGGAATCGCTAGTAATC
GTGGATCAGAATGCCACGGTGAATACGTTCCCGGGCCTTGTACACACCGCCC
GTCACACCATGGGAGTGGGTTGCAAAAGAAGTAGGTAGCTTAACCTTCGGG
AGGGCGCTTACCACTTTGTGATTCATGACTGGGGTGAAGTCGTAACAAGGTA
ACCGTAGGGGAACCTGCGGTTGGATCATGGGATTACCTTAAAGAAGCGTACT
TTGTAGTGCTCACACAGATTGTCTGATAGAAAGTGAAAAGCAAGGCGTTTAC
GCGTTGGGAGTGAGGCTGAAGAGAATAAGGCCGTTCGCTTTCTATTAATGAA
AGCTCACCCTACACGAAAATATCACGCAACGCGTGATAAGCAATTTTCGTGT
CCCCTTCGTCTAGAGGCCCAGGACACCGCCCTTTCACGGCGGTAACAGGGGT
TCGAATCCCCTAGGGGACGCCACTTGCTGGTTTGTGAGTGAAAGTCGCCGAC
CTTAATATCTCAAAACTCATCTTCGGGTGATGTTTGAGATTTTTGCTCTTTAA
AAATCTGGATCAAGCTGAAAATTGAAACACTGAACAACGAGAGTTGTTCGTG
AGTCTCTCAAATTTTCGCAACACGATGATGAATCGAAAGAAACATCTTCGGG
TTGT
GAGGTTAAGCGACTAAGCGTACACGGTGGATGCCCTGGCAGTCAGAGGCGA
TGAAGGACGTGCTAATCTGCGATAAGCGTCGGTAAGGTGATATGAACCGTTA
TAACCGGCGATTTCCGAATGGGGAAACCCAGTGTGTTTCGACACACTATCAT
TAACTGAATCCATAGGTTAATGAGGCGAACCGGGGGAACTGAAACATCTAA
GTACCCCGAGGAAAAGAAATCAACCGAGATTCCCCCAGTAGCGGCGAGCGA
```

*Fig. 24*

ACGGGGAGCAGCCCAGAGCCTGAATCAGTGTGTGTGTTAGTGGAAGCGTCTG
GAAAGGCGCGCGATACAGGGTGACAGCCCCGTACACAAAAATGCACATGCT
GTGAGCTCGATGAGTAGGGCGGGACACGTGGTATCCTGTCTGAATATGGGGG
GACCATCCTCCAAGGCTAAATACTCCTGACTGACCGATAGTGAACCAGTACC
GTGAGGGAAAGGCGAAAAGAACCCCGGCGAGGGGAGTGAAAAAGAACCTG
AAACCGTGTACGTACAAGCAGTGGGAGCACGCTTAGGCGTGTGACTGCGTAC
CTTTTGTATAATGGGTCAGCGACTTATATTCTGTAGCAAGGTTAACCGAATA
GGGGAGCCGAAGGGAAACCGAGTCTTAACTGGGCGTTAAGTTGCAGGGTAT
AGACCCGAAACCCGGTGATCTAGCCATGGGCAGGTTGAAGGTTGGGTAACA
CTAACTGGAGGACCGAACCGACTAATGTTGAAAAATTAGCGGATGACTTGTG
GCTGGGGGTGAAAGGCCAATCAAACCGGGAGATAGCTGGTTCTCCCCGAAA
GCTATTTAGGTAGCGCCTCGTGAATTCATCTCCGGGGGTAGAGCACTGTTTC
GGCAAGGGGGTCATCCCGACTTACCAACCCGATGCAAACTGCGAATACCGG
AGAATGTTATCACGGGAGACACACGGCGGGTGCTAACGTCCGTCGTGAAGA
GGGAAACAACCCA
GACCGCCAGCTAAGGTCCCAAAGTCATGGTTAAGTGGGAAACGATGTGGGA
AGGCCCAGACAGCCAGGATGTTGGCTTAGAAGCAGCCATCATTTAAAGAAA
GCGTAATAGCTCACTGGTCGAGTCGGCCTGCGCGGAAGATGTAACGGGGCTA
AACCATGCACCGAAGCTGCGGCAGCGACGCTTATGCGTTGTTGGGTAGGGGA
GCGTTCTGTAAGCCTGCGAAGGTGTGCTGTGAGGCATGCTGGAGGTATCAGA
AGTGCGAATGCTGACATAAGTAACGATAAAGCGGGTGAAAAGCCCGCTCGC
CGGAAGACCAAGGGTTCCTGTCCAACGTTAATCGGGGCAGGGTGAGTCGAC
CCCTAAGGCGAGGCCGAAAGGCGTAGTCGATGGGAAACAGGTTAATATTCC
TGTACTTGGTGTTACTGCGAAGGGGGGACGGAGAAGGCTATGTTGGCCGGGC
GACGGTTGTCCCGGTTTAAGCGTGTAGGCTGGTTTTCCAGGCAAATCCGGAA
AATCAAGGCTGAGGCGTGATGACGAGGCACTACGGTGCTGAAGCAACAAAT
GCCCTGCTTCCAGGAAAAGCCTCTAAGCATCAGGTAACATCAAATCGTACCC
CAAACCGACACAGGTGGTCAGGTAGAGAATACCAAGGCGCTTGAGAGAACT
CGGGTGAAGGAACTAGGCAAAATGGTGCCGTAACTTCGGGAGAAGGCACGC
TGATATGTAGGTGAGGTCCCTCGCGGATGGAGCTGAAATCAGTCGAAGATAC
CAGCTGGCTGCAACTGTTTATTAAAAACACAGCACTGTGCAAACACGAAAGT
GGACGTATACGGTGTGACGCCTGCCCGGTGCCGGAAGGTTAATTGATGGGGT
TAGCGCAAGCGAAGCTCTTGATCGAAGCCCCGGTAAACGGCGGCCGTAACT
ATAACGGTCCTAAGGTAGCGAAATTCCTTGTCGGGTAAGTTCCGACCTGCAC
GAATGGCGTAA
TGATGGCCAGGCTGTCTCCACCCGAGACTCAGTGAAATTGAACTCGCTGTGA
AGATGCAGTGTACCCGCGGCAAGACGGAAAGACCCCGTGAACCTTTACTATA
GCTTGACACTGAACATTGAGCCTTGATGTGTAGGATAGGTGGGAGGCTTTGA
AGTGTGGACGCCAGTCTGCATGGAGCCGACCTTGAAATACCACCCTTTAATG
TTTGATGTTCTAACGTTGACCCGTAATCCGGGTTGCGGACAGTGTCTGGTGG
GTAGTTTGACTGGGGCGGTCTCCTCCTAAAGAGTAACGGAGGAGCACGAAG
GTTGGCTAATCCTGGTCGGACATCAGGAGGTTAGTGCAATGGCATAAGCCAG
CTTGACTGCGAGCGTGACGGCGCGAGCAGGTGCGAAAGCAGGTCATAGTGA
TCCGGTGGTTCTGAATGGAAGGGCCATCGCTCAACGGATAAAAGGTACTCCG
GGGATAACAGGCTGATACCGCCCAAGAGTTCATATCGACGGCGGTGTTTGGC

*Fig. 24*
Cont

```
ACCTCGATGTCGGCTCATCACATCCTGGGGCTGAAGTAGGTCCCAAGGGTAT
GGCTGTTCGCCATTTAAAGTGGTACGCGAGCTGGGTTTAGAACGTCGTGAGA
CAGTTCGGTCCCTATCTGCCGTGGGCGCTGGAGAACTGAGGGGGGCTGCTCC
TAGTACGAGAGGACCGGAGTGGACGCATCACTGGTGTTCGGGTTGTCATGCC
AATGGCACTGCCCGGTAGCTAAATGCGGAAGAGATAAGTGCTGAAAGCATC
TAAGCACGAAACTTGCCCCGAGATGAGTTCTCCCTGACCCTTTAAGGGTCCT
GAAGGAACGTTGAAGACGACGACGTTGATAGGCCGGGTGTGTAAGCGCAGC
GATGCGTTGAGCTAACCGGTACTAATGAACCGTGAGGCTTAACCTTACAACG
CCGAAGCTGTTTTGGCGGATGAGAGAAGATTTTCAGCCTGATACAGATTAAA
TCAGAACGCAGAAGCGGTCTGATAAAACAGAATTTGCCTGGCGGCAGTAGC
GCGGTGGTCCCACCTGACCCCATGCCGAACTCAGAAGTGAAACGCCGTAGCG
CCGATGGTAGTGTGGGGTCTCCCCATGCGAGAGTAGGGA
ACTGCCAGGCATCAAATAAAACGAAAGGCTCAGTCGAAAGACTGGGCCTTT
CGTTTTATCTGTTGTTTGTCGGTGAACGCTCTCCTGAGTAGGACAAATCCGCC
GGGAGCGGATTTGAACGTTGCGAAGCAACGGCCCGGAGGGTGGCGGGCAGG
ACGCCCGCCATAAACTGCCAGGCATCAAATTAAGCAGAAGGCCATCCTGAC
GGATGGCCTTTTGCGTTTCTACAAACTCTTCCTGTCGTCATATCTACAAGCC
ATCCCCCCACAGATACGGTAAACTAGCCTCGTTTTTGCATCAGGAAAGCAGC
TATGAACCACTCCTTAAAACCCTGGAACACATTTGGCATTGATCATAATGCT
CAGCACATTGTATGGGCCTTAAGGGCCCAACAATTACTCAATGCCTGGCAGT
ATGCAACCGCAGAAGGACAACCCGTTCTTATTCTGGGTGAAGGAAGTAATGT
ACTTTTTCTGGAGGACTATCGCGGCACGGTGATCATCAACCGGATCAAAGGT
ATCGAAATTCATGATGAACCTGATGCGTGGTATTTACATGTAGGAGCCGGAG
AAAACTGGCATCGTCTGGTAAAATACACTTTGCAGGAAGGTATGCCTGGTCT
GGAAAATCTGGCATTAATTCCTGGTTGTGTCGGCTCATCACCTATCCAGAAT
ATTGGTGCTTATGGCGTAGAATTACAGCGAGTTTGCGCTTATGTTGATTCTGT
TGAACTGGCGACAGGCAAGCAAGTGCGCTTAACTGCCAAAGAGTGCCGTTTT
GGCTATCGCGACAGTATTTTTAAACATGAATACCAGGACCGCTTCGCTATTG
TAGCCGTAGGTCTGCGTCTGCCAAAAGAGTGGCAACCTGTACTAACGTATGG
TGACTTAACTCGTCTGGGATCCACAGGACGGGTGTGGTCGCCATGATCGCGT
AGTCGATAGTGGCTCCAAGTAGCGAAGCGAGCAGGACTGGGCGGCGGCCAA
AGC
GGTCGGACAGTGCTCCGAGAACGGGTGCGCATAGAAATTGCATCAACGCAT
ATAGCGCTAGCAGCACGCCATAGTGACTGGCGATGCTGTCGGAATGGACGAT
ATCCCGCAAGAGGCCCGGCAGTACCGGCATAACCAAGCCTATGCCTACAGC
ATCCAGGGTGACGGTGCCGAGGATGACGATGAGCGCATTGTTAGATTTCATA
CACGGTGCCTGACTGCGTTAGCAATTTAACTGTGATAAACTACCGCATTAAA
GCTTATCGATGATAAGCTGTCAAACATGAGAATTCTTGAAGACGAAAGGGCC
TCGTGATACGCCTATTTTATAGGTTAATGTCATGATAATAATGGTTTCTTAG
ACGTCAGGTGGCACTTTTCGGGGAAATGTGCGCGGAACCCCTATTTGTTTATT
TTTCTAAATACATTCAAATATGTATCCGCTCATGAGACAATAACCCTGATAA
ATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCC
```

*Fig. 24*
Cont.

CGAAGAACGTTTTCCAATGATGAGCACTTTTAAAGTTCTGCTATGTGGCGCG
GTATTATCCCGTGTTGACGCCGGGCAAGAGCAACTCGGTCGCCGCATACACT
ATTCTCAGAATGACTTGGTTGAGTACTCACCAGTCACAGAAAAGCATCTTAC
GGATGGCATGACAGTAAGAGAATTATGCAGTGCTGCCATAACCATGAGTGAT
AACACTGCGGCCAACTTACTTCTGACAACGATCGGAGGACCGAAGGAGCTA
ACCGCTTTTTTGCACAACATGGGGGATCATGTAACTCGCCTTGATCGTTGGG
AA
CCGGAGCTGAATGAAGCCATACCAAACGACGAGCGTGACACCACGATGCCT
GCAGCAATGGCAACAACGTTGCGCAAACTATTAACTGGCGAACTACTTACTC
TAGCTTCCCGGCAACAATTAATAGACTGGATGGAGGCGGATAAAGTTGCAG
GACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTAT
GGATGAACGAAATAGACAGATCGCTGAGATAGGTGCCTCACTGATTAAGCA
TTGGTAACTGTCAGACCAAGTTTACTCATATATACTTTAGATTGATTTAAAAC
TTCATTTTTAATTTAAAAGGATCTAGGTGAAGATCCTTTTTGATAATCTCATG
ACCAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACC
AAATACTGTCCTTCTAGTGTAGCCGTAGTTAGGCCACCACTTCAAGAACTCT
GTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCG
GATAAGGCGCAGCGGTCGGGCTGAACGGGGGGTTCGTGCACACAGCCCAGC
TTGGAGCGAACGACCTACACCGAACTGAGATACCTACAGCGTGAGCTATGA
GAAAGCGCCACGCTTCCCGAAGGGAGAAAGGCGGACAGGTATCCGGTAAGC
GGC
AGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGC
CTTTTTACGGTTCCTGGCCTTTTGCTGGCCTTTTGCTCACATGTTCTTTCCTGC
GTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAG
CGGAAGAGCGCCTGATGCGGTATTTTCTCCTTACGCATCTGTGCGGTATTTCA
CACCGCATATGGTGCACTCTCAGTACAATCTGCTCTGATGCCGCATAGTTAA
GCCAGTATACACTCCGCTATCGCTACGTGACTGGGTCATGGCTGCGCCCCGA
CACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTT
TTCACCGTCATCACCGAAACGCGCGAGGCAGCTGCGGTAAAGCTCATCAGCG
TGGTCGTGAAGCGATTCACAGATGTCTGCCTGTTCATCCGCGTCCAGCTCGTT
GAGTTTCTCCAGAAGCGTTAATGTCTGGCTTCTGATAAAGCGGGCCATGTTA
AGGGCGGTTTTTTCCTGTTTGGTCACTTGATGCCTCCGTGTAAGGGGGAATTT
CTGTTCATGGGGGTAATGATACCGATGAAACGAGAGAGGATGCTCACGATA
CGGGTTACTGATGATGAACATGCCCGGTTACTGGAACGTTGTGAGGGTAAAC
AACTGGCGGTATGGATGCGGCGGGACCAGAGAAAAATCACTCAGGGTCAAT

*Fig. 24*
Cont.

```
GCCAGCGCTTCGTTAATACAGATGTAGGTGTTCCACAGGGTAGCCAGCAGCA
TCCTGCGATGCCTGGCGAAAGGGGGATGTGCTGCAAGGCGATTAAGTTGGGT
AACGCCAGGGTTTTCCCAGTCACGACGTTGTAAAACGACGGCCAGTGAATTC
GAGCTCGGTACCTGCACTGACGACAGGAAGAG
TTTGTAGAAACGCAAAAAGGCCATCCGTCAGGATGGCCTTCTGCTTAATTTG
ATGCCTGGCAGTTTATGGCGGGCGTCCTGCCCGCCACCCTCCGGGCCGTTGC
TTCGCAACGTTCAAATCCGCTCCCGGCGGATTTGTCCTACTCAGGAGAGCGT
TCACCGACAAACAACAGATAAAACGAAAGGCCCAGTCTTTCGACTGAGCCTT
TCGTTTTATTTGATGCCTGGCAGTTCCCTACTCTCGCATGGGGAGACCCCACA
CTACCATCGGCGCTACGACTAGATTATTTGTAGAGCTCATCCATGCCATGTGT
AATCCCAGCAGCAGTTACAAACTCAAGAAGGACCATGTGGTCACGCTTTTCG
TTGGGATCTTTCGAAAGGGCAGATTGTGTCGACAGGTAATGGTTGTCTGGTA
AAAGGACAGGGCCATCGCCAATTGGAGTATTTTGTTGATAATGGTCTGCTAG
TTGAACGGATCCATCTTCAATGTTGTGGCGAATTTTGAAGTTAGCTTTGATTC
CATTCTTTTGTTTGTCTGCCGTGATGTATACATTGTGTGAGTTATAGTTGTACT
CGAGTTTGTGTCCGAGAATGTTTCCATCTTCTTTAAAATCAATACCTTTTAAC
TCGATACGATTAACAAGGGTATCACCTTCAAACTTGACTTCAGCACGCGTCT
TGTAGTTCCCGTCATCTTTGAAAGATATAGTGCGTTCCTGTACATAACCTTCG
GGCATGGCACTCTTGAAAAAGTCATGCCGTTTCATATGATCCGGATAACGGG
AAAAGCATTGAACACCATAAGAGAAAGTAGTGACAAGTGTTGGCCATGGAA
CAGGTAGTTTTCCAGTAGTGCAAATAAATTTAAGGGTAAGCTTTCCGTATGT
AGCATCACCTTCACCCTCTCCACTGACAGAAAATTTGTGCCCATTAACATCAC
CATCTAATTCAACAAGAATTGGGACAACTCCAGTGAAAAGTTCTTCT
CCTTTGCTCGCAGTGATTTTTTTCTCCATTTGCGGAGGGATATGAAAGCGGCC
GCTTCCACACATTAAACTAGTTCGATGATTAATTGTCAACAGCTCGCCGGCG
GCACCTCGCTAACGGATTCACCACTCCAAGAATTGGAGCCAATCGATTCTTG
CGGAGAACTGTGAATGCGGGTACCCAGATCCGGAACATAATGGTGCAGGGC
GCTGACTTCCGCGTTTCCAGACTTTACGAAACACGGAAACCGAAGACCATTC
ATGTTGTTGCTCAGGTCGCAGACGTTTTGCAGCAGCAGTCGCTTCACGTTCGC
TCGCGTATCGGTGATTCATTCTGCTAACCAGTAAGGCAACCCCGCCAGCCTA
GCCGGGTCCTCAACGACAGGAGCACGATCATGCGCACCCGTGGCCAGGACC
CAACGCTGCCCGAGATGCGCCGCGTGCGGCTGCTGGAGATGGCGGACGCGA
TGGATATGTTCTGCCAAGGGTTGGTTTGCGCATTCACAGTTCTCCGCAAGAAT
CGATTGGCTCCAATTCTTGGAGTGGTGAATCCGTTAGCGAGGTGCCGCCGGC
GAGCTGTTGACAATTAATCATCGAACTAGTTTAATGTGTGGAAGCGGCCGCT
TTCATATCCCTCCGCAAATGGAGAAAAAAATCACTGGATATACCACCGTTGA
TATATCCCAATGGCATCGTAAAGAACATTTTGAGGCATTTCAGTCAGTTGCTC
AATGTACCTATAACCAGACCGTTCAGCTGGATATTACGGCCTTTTTAAAGAC
CGTAAAGAAAAATAAGCACAAGTTTTATCCGGCCTTTATTCACATTCTTGCCC
GCCTGATGAATGCTCATCCGGAATTCCGTATGGCAATGAAAGACGGTGAGCT
GGTGATATGGGATAGTGTTCACCCTTGTTACACCGTTTTCCATGAGCAAACTG
AAACGTTTTCATCGCTCTGGAGTGAATACCACGACGATTTCCGGCAGTTTC
TACACATATATTCGCAAGATGTGGCGTGTTACGGTGAAAACCTGGCCTATTT
CCCTAAAGGGTTTATTGAGAATATGTTTTTCGTCTCAGCCAATCCCTGGGTGA
GTTTCACCAGTTTTGATTTAAACGTGGCCAATATGGACAACTTCTTCGCCCCC
```

*Fig. 24*
Cont.

```
GTTTTCACCATGGGCAAATATTATACGCAAGGCGACAAGGTGCTGATGCCGC
TGGCGATTCAGGTTCATCATGCCGTCTGTGATGGCTTCCATGTCGGCAGAAT
GCTTAATGAATTACAACAGTACTGCGATGAGTGGCAGGGCGGGGCGTAATTT
TTTTAAGGCAGTTATTGGTGCCCTTAAACGCCTGGTGCTACGCCTGAATAAGT
GATAATAAGCGGATGAATGGCAGAAATTCGAAAGCAAATTCGACCCGGTCG
TCGGTTCAGGGCAGGGTCGTTAAATAGCCGCTTATGTCTATTGCTGGTTTACG
GTTTATTGACTACCCGAAGCAGTGTGACCCTGTGCTTCTCAAATGCCTGAGG
GCAGTTTGCTCAGGTCTCCCGTGGGGGGAATAATTAACGGTATGAGCCTTA
CGGCGGACGGATCGTGGCCGCAAGTGGGTCCGGCTAGAGGATCCGACACCA
TCGAATGGTGCAAAACCTTTCGCGGTATGGCATGATAGCGCCCGGAAGAGA
GTCAATTCAGGGTGGTGAATGTGAAACCAGTAACGTTATACGATGTCGCAGA
GTATGCCGGTGTCTCTTATCAGACCGTTTCCCGCGTGGTGAACCAGGCCAGC
CACGTTTCTGCGAAAACGCGGGAAAAAGTGGAAGCGGCGATGGCGGAGCTG
AATTACATTCCCAACCGCGTGGCACAACAACTGGCGGGCAAACAGTCGTTGC
TGATTGGCGTTGCCACCTCCAGTCTGGCCCTGCACGCGCCGTCGCAAATTGTC
GCGGCGATTAAATCTCGCGCCGATCAACTGGGTGCCAGCGTGGTGGTGTCGA
T
GGTAGAACGAAGCGGCGTCGAAGCCTGTAAAGCGGCGGTGCACAATCTTCT
CGCGCAACGGGTCAGTGGGCTGATCATTAACTATCCGCTGGATGACCAGGAT
GCCATTGCTGTGGAAGCTGCCTGCACTAATGTTCCGGCGTTATTTCTTGATGT
CTCTGACCAGACACCCATCAACAGTATTATTTTCTCCCATGAAGACGGTACG
CGACTGGGCGTGGAGCATCTGGTCGCATTGGGTCACCAGCAAATCGCGCTGT
TAGCGGGCCCATTAAGTTCTGTCTCGGCGCGTCTGCGTCTGGCTGGCTGGCAT
AAATATCTCACTCGCAATCAAATTCAGCCGATAGCGGAACGGGAAGGCGAC
TGGAGTGCCATGTCCGGTTTTCAACAAACCATGCAAATGCTGAATGAGGGCA
TCGTTCCCACTGCGATGCTGGTTGCCAACGATCAGATGGCGCTGGGCGCAAT
GCGCGCCATTACCGAGTCCGGGCTGCGCGTTGGTGCGGATATCTCGGTAGTG
GGATACGACGATACCGAAGACAGCTCATGTTATATCCCGCCGTCAACCACCA
TCAAACAGGATTTTCGCCTGCTGGGGCAAACCAGCGcGGACCGCTTGCTGCA
ACTCTCTCAGGGCCAGGCGGTGAAGGGCAATCAGCTGTTGCCCGTCTCACTG
GTGAAAAGAAAAACCACCCTGGCGCCCAATACGCAAACCGCCTCTCCCCGC
GCGTTGGCCGATTCATTAATGCAGCTGGCACGACAGGTTTCCCGACTGGAAA
GCGGGCAGTGAGCGCAACGCAATTAATGTGAGTTAGCTCACTCATTAGGCAC
CCCAGGCTTTACACTTTATGCTTCCGGCTCGTATAATGTGTGGAATTGTGAGC
GGATAACAATTTCACACAGCGGCCGCTGAGAAAAAGCGAAGCGGCACTGCT
CTTTAACAATTTATCAGACAATCTGTGTGGGCACTCGAAGATACGGATTCTT
AACGTCGCAAGACGAAAAATGAATACCAAGTCTCAAGAGTGAACACGTAAT
TCATTACGAAGTTTAATTCTTTGAGCGTCAAACTTTTAACGACGGCCAGTGA
ATTCGAGCTCGGTACCTGCACTGACGACAGGAAGAG
```

*Fig. 24*
Cont.

```
AAATTGAAGAGTTTGATCATGGCTCAGATTGAACGCTGGCGGCAGGCCTAAC
ACATGCAAGTCGAACGGTAACAGGAAGAAGCTTGCTTCTTTGCTGACGAGTG
GCGGACGGGTGAGTAATGTCTGGGAAACTGCCTGATGGAGGGGGATAACTA
CTGGAAACGGTAGCTAATACCGCATAACGTCGCAAGACCAAAGAGGGGGAC
CTTCGGGCCTCTTGCCATCGGATGTGCCCAGATGGGATTAGCTAGTAGGTGG
GGTAACGGCTCACCTAGGCGACGATCCCTAGCTGGTCTGAGAGGATGACCAG
CCACACTGGAACTGAGACACGGTCCAGACTCCTACGGGAGGCAGCAGTGGG
GAATATTGCACAATGGGCGCAAGCCTGATGCAGCCATGCCGCGTGTATGAAG
AAGGCCTTCGGGTTGTAAAGTACTTTCAGCGGGGAGGAAGGGAGTAAAGTT
AATACCTTTGCTCATTGACGTTACCCGCAGAAGAAGCACCGGCTAACTCCGT
GCCAGCAGCCGCGGTAATACGGAGGGTGCAAGCGTTAATCGGAATTACTGG
GCGTAAAGCGCACGCAGGCGGTTTGTTAAGTCAGATGTGAAATCCCCGGGCT
CAACCTGGGAACTGCATCTGATACTGGCAAGCTTGAGTCTCGTAGAGGGGGG
TAGAATTCCAGGTGTAGCGGTGAAATGCGTAGAGATCTGGAGGAATACCGG
TGGCGAAGGCGGCCCCCTGGACGAAGACTGACGCTCAGGTGCGAAAGCGTG
GGGAGCAAACAGGATTAGATACCCTGGTAGTCCACGCCGTAAACGATGTCG
ACTTGGAGGTTGTGCCCTTGAGGCGTGGCTTCCGGAGCTAACGCGTTAAGTC
GACCGCCTGGGGAGTACGGCCGCAAGGTTAAAACTCAAATGAATTGACGGG
GGCCCGCACAAGCGGCGGAGCATGTGGATTAATTCGATGCAACGCGAAGAA
CCTTACCTGGGTTTGACATGCACAGGACGCGTCTAGAGATAGGCGTTCCCTT
GTGGCCTGTGTGCAGGTGGTGCATGGCTGTCGTCAGCTCGTGTCGTGAGATG
TTGGGTTAAGTCCCGCAACGAGCGCAACCCTTGTCTCATGTTGCCAGCACGT
AATGGTGGGGACTCGTGAGAGACTGCCGGGGTCAACTCGGAGGAAGGTGGG
GATGACGTCAAGTCATCATGCCCCTTATGTCCAGGGCTTCACACATGCTACA
ATGGCCGGTACAAAGGGCTGCGATGCCGCGAGGTTAAGCGAATCCTTAAAA
GCCGGTCTCAGTTCGGATCGGGGTCTGCAACTCGACCCCGTGAAGTCGGAGT
CGCTAGTAATCGCAGATCAGCAACGCTGCGGTGAATACGTTCCCGGGCCTTG
TACACACCGCCCGTCACGTCATGAAAGTCGGTAACACCCGAAGCCAGTGGCC
TAACCCTCGGGAGGGAGCTGTCGAAGGTGGGATCGGCGATTGGGACGAAGT
CGTAACAAGGTAACCGTAGGGGAACCTGCGGTTGGATCATGGGATTACCTTA
AAGAAGCGTACTTTGTAGTGCTCACACAGATTGTCTGATAGAAAGTGAAAAG
CAAGGCGTTTACGCGTTGGGAGTGAGGCTGAAGAGAATAAGGCCGTTCGCTT
TCTATTAATGAAAGCTCACCCTACACGAAAATATCACGCAACGCGTGATAAG
CAATTTTCGTGTCCCCTTCGTCTAGAGGCCCAGGACACCGCCCTTTCACGGCG
GTAACAGGGGTTCGAATCCCCTAGGGGACGCCACTTGCTGGTTTGTGAGTGA
AAGTCGCCGACCTTAATATCTCAAAACTCATCTTCGGGTGATGTTTGAGATTT
TTGCTCTTTAAAAATCTGGATCAAGCTGAAAATTGAAACACTGAACAACGAG
AGTTGTTCGTGAGTCTCTCAAATTTTCGCAACACGATGATGAATCGAAAGAA
ACATCTTCGGGTTGTGAGGTTAAGCGACTAAGCGTACACGGTGGATGCCCTG
GCAGTCAGAGGCGATGAAGGACGTGCTAATCTGCGATAAGCGTCGGTAAGG
TGATATGAACCGTTATAACCGGCGATTTCCGAATGGGGAAACCCAGTGTGTT
TCGACACACTATCATTAACTGAATCCATAGGTTAATGAGGCGAACCGGGGGA
ACTGAAACATCTAAGTACCCCGAGGAAAAGAAATCAACCGAGATTCCCCCA
GTAGCGGCGAGCGAACGGGGAGCAGCCCAGAGCCTGAATCAGTGTGTGTGT
TAGTGGAAGCGTCTGGAAAGGCGCGCGATACAGGGTGACAGCCCCGTACAC
```

*Fig. 25*

```
AAAAATGCACATGCTGTGAGCTCGATGAGTAGGGCGGGACACGTGGTATCCT
GTCTGAATATGGGGGGACCATCCTCCAAGGCTAAATACTCCTGACTGACCGA
TAGTGAACCAGTACCGTGAGGGAAAGGCGAAAAGAACCCCGGCGAGGGGA
GTGAAAAAGAACCTGAAACCGTGTACGTACAAGCAGTGGGAGCACGCTTAG
GCGTGTGACTGCGTACCTTTTGTATAATGGGTCAGCGACTTATATTCTGTAGC
AAGGTTAACCGAATAGGGGAGCCGAAGGGAAACCGAGTCTTAACTGGGCGT
TAAGTTGCAGGGTATAGACCCGAAACCCGGTGATCTAGCCATGGGCAGGTTG
AAGGTTGGGTAACACTAACTGGAGGACCGAACCGACTAATGTTGAAAAATT
AGCGGATGACTTGTGGCTGGGGGTGAAAGGCCAATCAAACCGGGAGATAGC
TGGTTCTCCCCGAAAGCTATTTAGGTAGCGCCTCGTGAATTCATCTCCGGGG
GTAGAGCACTGTTTCGGCAAGGGGGTCATCCCGACTTACCAACCCGATGCAA
ACTGCGAATACCGGAGAATGTTATCACGGGAGACACACGGCGGGTGCTAAC
GTCCGTCGTGAAGAGGGAAACAACCCAGACCGCCAGCTAAGGTCCCAAAGT
CATGGTTAAGTGGGAAACGATGTGGGAAGGCCCAGACAGCCAGGATGTTGG
CTTAGAAGCAGCCATCATTTAAAGAAAGCGTAATAGCTCACTGGTCGAGTCG
GCCTGCGCGGAAGATGTAACGGGGCTAAACCATGCACCGAAGCTGCGGCAG
CGACGCTTATGCGTTGTTGGGTAGGGGAGCGTTCTGTAAGCCTGCGAAGGTG
TGCTGTGAGGCATGCTGGAGGTATCAGAAGTGCGAATGCTGACATAAGTAAC
GATAAAGCGGGTGAAAAGCCCGCTCGCCGGAAGACCAAGGGTTCCTGTCCA
ACGTTAATCGGGGCAGGGTGAGTCGACCCCTAAGGCGAGGCCGAAAGGCGT
AGTCGATGGGAAACAGGTTAATATTCCTGTACTTGGTGTTACTGCGAAGGGG
GGACGGAGAAGGCTATGTTGGCCGGGCGACGGTTGTCCCGGTTTAAGCGTGT
AGGCTGGTTTTCCAGGCAAATCCGGAAAATCAAGGCTGAGGCGTGATGACG
AGGCACTACGGTGCTGAAGCAACAAATGCCCTGCTTCCAGGAAAAGCCTCTA
AGCATCAGGTAACATCAAATCGTACCCCAAACCGACACAGGTGGTCAGGTA
GAGAATACCAAGGCGCTTGAGAGAACTCGGGTGAAGGAACTAGGCAAAATG
GTGCCGTAACTTCGGGAGAAGGCACGCTGATATGTAGGTGAGGTCCCTCGCG
GATGGAGCTGAAATCAGTCGAAGATACCAGCTGGCTGCAACTGTTTATTAAA
AACACAGCACTGTGCAAACACGAAAGTGGACGTATACGGTGTGACGCCTGC
CCGGTGCCGGAAGGTTAATTGATGGGGTTAGCGCAAGCGAAGCTCTTGATCG
AAGCCCCGGTAAACGGCGGCCGTAACTATAACGGTCCTAAGGTAGCGAAAT
TCCTTGTCGGGTAAGTTCCGACCTGCACGAATGGCGTAATGATGGCCAGGCT
GTCTCCACCCGAGACTCAGTGAAATTGAACTCGCTGTGAAGATGCAGTGTAC
CCGCGGCAAGACGGAAAGACCCCGTGAACCTTTACTATAGCTTGACACTGAA
CATTGAGCCTTGATGTGTAGGATAGGTGGGAGGCTTTGAAGTGTGGACGCCA
GTCTGCATGGAGCCGACCTTGAAATACCACCCTTTAATGTTTGATGTTCTAAC
GTTGACCCGTAATCCGGGTTGCGGACAGTGTCTGGTGGGTAGTTTGACTGGG
GCGGTCTCCTCCTAAAGAGTAACGGAGGAGCACGAAGGTTGGCTAATCCTGG
TCGGACATCAGGAGGTTAGTGCAATGGCATAAGCCAGCTTGACTGCGAGCGT
GACGGCGCGAGCAGGTGCGAAAGCAGGTCATAGTGATCCGGTGGTTCTGAA
TGGAAGGGCCATCGCTCAACGGATAAAAGGTACTCCGGGGATAACAGGCTG
ATACCGCCCAAGAGTTCATATCGACGGCGGTGTTTGGCACCTCGATGTCGGC
TCATCACATCCTGGGGCTGAAGTAGGTCCCAAGGGTATGGCTGTTCGCCATT
TAAAGTGGTACGCGAGCTGGGTTTAGAACGTCGTGAGACAGTTCGGTCCCTA
TCTGCCGTGGGCGCTGGAGAACTGAGGGGGGCTGCTCCTAGTACGAGAGGA
```

*Fig. 25*
Cont.

```
CCGGAGTGGACGCATCACTGGTGTTCGGGTTGTCATGCCAATGGCACTGCCC
GGTAGCTAAATGCGGAAGAGATAAGTGCTGAAAGCATCTAAGCACGAAACT
TGCCCCGAGATGAGTTCTCCCTGACCCTTTAAGGGTCCTGAAGGAACGTTGA
AGACGACGACGTTGATAGGCCGGGTGTGTAAGCGCAGCGATGCGTTGAGCT
AACCGGTACTAATGAACCGTGAGGCTTAACCTTACAACGCCGAAGCTGTTTT
GGCGGATGAGAGAAGATTTTCAGCCTGATACAGATTAAATCAGAACGCAGA
AGCGGTCTGATAAAACAGAATTTGCCTGGCGGCAGTAGCGCGGTGGTCCCAC
CTGACCCCATGCCGAACTCAGAAGTGAAACGCCGTAGCGCCGATGGTAGTGT
GGGGTCTCCCCATGCGAGAGTAGGGAACTGCCAGGCATCAAATAAAACGAA
AGGCTCAGTCGAAAGACTGGGCCTTTCGTTTTATCTGTTGTTTGTCGGTGAAC
GCTCTCCTGAGTAGGACAAATCCGCCGGGAGCGGATTTGAACGTTGCGAAGC
AACGGCCCGGAGGGTGGCGGGCAGGACGCCCGCCATAAACTGCCAGGCATC
AAATTAAGCAGAAGGCCATCCTGACGGATGGCCTTTTTGCGTTTCTACAAAC
TCTTCCTGTCGTCATATCTACAAGCCATCCCCCACAGATACGGTAAACTAGC
CTCGTTTTTGCATCAGGAAAGCAGCTATGAACCACTCCTTAAAACCCTGGAA
CACATTTGGCATTGATCATAATGCTCAGCACATTGTATGGGCCTTAAGGGCC
CAACAATTACTCAATGCCTGGCAGTATGCAACCGCAGAAGGACAACCCGTTC
TTATTCTGGGTGAAGGAAGTAATGTACTTTTTCTGGAGGACTATCGCGGCAC
GGTGATCATCAACCGGATCAAAGGTATCGAAATTCATGATGAACCTGATGCG
TGGTATTTACATGTAGGAGCCGGAGAAAACTGGCATCGTCTGGTAAAATACA
CTTTGCAGGAAGGTATGCCTGGTCTGGAAAATCTGGCATTAATTCCTGGTTGT
GTCGGCTCATCACCTATCCAGAATATTGGTGCTTATGGCGTAGAATTACAGC
GAGTTTGCGCTTATGTTGATTCTGTTGAACTGGCGACAGGCAAGCAAGTGCG
CTTAACTGCCAAAGAGTGCCGTTTTGGCTATCGCGACAGTATTTTTAAACATG
AATACCAGGACCGCTTCGCTATTGTAGCCGTAGGTCTGCGTCTGCCAAAAGA
GTGGCAACCTGTACTAACGTATGGTGACTTAACTCGTCTGGGATCCACAGGA
CGGGTGTGGTCGCCATGATCGCGTAGTCGATAGTGGCTCCAAGTAGCGAAGC
GAGCAGGACTGGGCGGCGGCCAAAGCGGTCGGACAGTGCTCCGAGAACGGG
TGCGCATAGAAATTGCATCAACGCATATAGCGCTAGCAGCACGCCATAGTGA
CTGGCGATGCTGTCGGAATGGACGATATCCCGCAAGAGGCCCGGCAGTACC
GGCATAACCAAGCCTATGCCTACAGCATCCAGGGTGACGGTGCCGAGGATG
ACGATGAGCGCATTGTTAGATTTCATACACGGTGCCTGACTGCGTTAGCAAT
TTAACTGTGATAAACTACCGCATTAAAGCTTATCGATGATAAGCTGTCAAAC
ATGAGAATTCTTGAAGACGAAAGGGCCTCGTGATACGCCTATTTTTATAGGT
TAATGTCATGATAATAATGGTTTCTTAGACGTCAGGTGGCACTTTTCGGGGA
AATGTGCGCGGAACCCCTATTTGTTTATTTTTCTAAATACATTCAAATATGTA
TCCGCTCATGAGACAATAACCCTGATAAATGCTTCAATAATATTGAAAAAGG
AAGAGTATGAGTATTCAACATTTCCGTGTCGCCCTTATTCCCTTTTTTGCGGC
ATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGC
ACTTTTAAAGTTCTGCTATGTGGCGCGGTATTATCCCGTGTTGACGCCGGGCA
AGAGCAACTCGGTCGCCGCATACACTATTCTCAGAATGACTTGGTTGAGTAC
TCACCAGTCACAGAAAAGCATCTTACGGATGGCATGACAGTAAGAGAATTAT
GCAGTGCTGCCATAACCATGAGTGATAACACTGCGGCCAACTTACTTCTGAC
```

*Fig. 25*
Cont.

```
AACGATCGGAGGACCGAAGGAGCTAACCGCTTTTTTGCACAACATGGGGGA
TCATGTAACTCGCCTTGATCGTTGGGAACCGGAGCTGAATGAAGCCATACCA
AACGACGAGCGTGACACCACGATGCCTGCAGCAATGGCAACAACGTTGCGC
AAACTATTAACTGGCGAACTACTTACTCTAGCTTCCCGGCAACAATTAATAG
ACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGC
GGTATCATTGCAGCACTGGGGCCAGATGGTAAGCCCTCCCGTATCGTAGTTA
TCTACACGACGGGGAGTCAGGCAACTATGGATGAACGAAATAGACAGATCG
CTGAGATAGGTGCCTCACTGATTAAGCATTGGTAACTGTCAGACCAAGTTTA
CTCATATATACTTTAGATTGATTTAAAACTTCATTTTTAATTTAAAAGGATCT
AGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAG
ATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGT
AACTGGCTTCAGCAGAGCGCAGATACCAAATACTGTCCTTCTAGTGTAGCCG
TAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGGGCG
GAGCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGA
CCGAGCGCAGCGAGTCAGTGAGCGAGGAAGCGGAAGAGCGCCTGATGCGGT
ATTTTCTCCTTACGCATCTGTGCGGTATTTCACACCGCATATGGTGCACTCTC
AGTACAATCTGCTCTGATGCCGCATAGTTAAGCCAGTATACACTCCGCTATC
GCTACGTGACTGGGTCATGGCTGCGCCCCGACACCCGCCAACACCCGCTGAC
GCGCCCTGACGGGCTTGTCTGCTCCCGGCATCCGCTTACAGACAAGCTGTGA
CCGTCTCCGGGAGCTGCATGTGTCAGAGGTTTTCACCGTCATCACCGAAACG
CGCGAGGCAGCTGCGGTAAAGCTCATCAGCGTGGTCGTGAAGCGATTCACA
GATGTCTGCCTGTTCATCCGCGTCCAGCTCGTTGAGTTTCTCCAGAAGCGTTA
ATGTCTGGCTTCTGATAAAGCGGGCCATGTTAAGGGCGGTTTTTTCCTGTTTG
GTCACTTGATGCCTCCGTGTAAGGGGGAATTTCTGTTCATGGGGGTAATGAT
ACCGATGAAACGAGAGAGGATGCTCACGATACGGGTTACTGATGATGAACA
TGCCCGGTTACTGGAACGTTGTGAGGGTAAACAACTGGCGGTATGGATGCGG
CGGGACCAGAGAAAAATCACTCAGGGTCAATGCCAGCGCTTCGTTAATACA
GATGTAGGTGTTCCACAGGGTAGCCAGCAGCATCCTGCGATGCCTGGCGAAA
GGGGGATGTGCTGCAAGGCGATTAAGTTGGGTAACGCCAGGGTTTTCCCAGT
CACGACGTTGTAAAACGACGGCCAGTGAATTCGAGCTCGGTACCTGCACTGA
CGACAGGAAGAGTTTGTAGAAACGCAAAAAGGCCATCCGTCAGGATGGCCT
TCTGCTTAATTTGATGCCTGGCAGTTTATGGCGGGCGTCCTGCCCGCCACCCT
CCGGGCCGTTGCTTCGCAACGTTCAAATCCGCTCCCGGCGGATTTGTCCTACT
```

*Fig. 25*
Cont.

```
CAGGAGAGCGTTCACCGACAAACAACAGATAAAACGAAAGGCCCAGTCTTT
CGACTGAGCCTTTCGTTTTATTTGATGCCTGGCAGTTCCCTACTCTCGCATGG
GGAGACCCCACACTACCATCGGCGCTACGACTAGATTATTTGTAGAGCTCAT
CCATGCCATGTGTAATCCCAGCAGCAGTTACAAACTCAAGAAGGACCATGTG
GTCACGCTTTTCGTTGGGATCTTTCGAAAGGGCAGATTGTGTCGACAGGTAA
TGGTTGTCTGGTAAAAGGACAGGGCCATCGCCAATTGGAGTATTTTGTTGAT
AATGGTCTGCTAGTTGAACGGATCCATCTTCAATGTTGTGGCGAATTTTGAA
GTTAGCTTTGATTCCATTCTTTTGTTTGTCTGCCGTGATGTATACATTGTGTGA
GTTATAGTTGTACTCGAGTTTGTGTCCGAGAATGTTTCCATCTTCTTTAAAAT
CAATACCTTTTAACTCGATACGATTAACAAGGGTATCACCTTCAAACTTGACT
TCAGCACGCGTCTTGTAGTTCCCGTCATCTTTGAAAGATATAGTGCGTTCCTG
TACATAACCTTCGGGCATGGCACTCTTGAAAAAGTCATGCCGTTTCATATGA
TCCGGATAACGGGAAAAGCATTGAACACCATAAGAGAAAGTAGTGACAAGT
GTTGGCCATGGAACAGGTAGTTTTCCAGTAGTGCAAATAAATTTAAGGGTAA
GCTTTCCGTATGTAGCATCACCTTCACCCTCTCCACTGACAGAAAATTTGTGC
CCATTAACATCACCATCTAATTCAACAAGAATTGGGACAACTCCAGTGAAAA
GTTCTTCTCCTTTGCTCGCAGTGATTTTTTCTCCATTTGCGGAGGGATATGA
AAGCGGCCGCTTCCACACATTAAACTAGTTCGATGATTAATTGTCAACAGCT
CGCCGGCGGCACCTCGCTAACGGATTCACCACTCCAAGAATTGGAGCCAATC
GATTCTTGCGGAGAACTGTGAATGCGGGTACCCAGATCCGGAACATAATGGT
GCAGGGCGCTGACTTCCGCGTTTCCAGACTTTACGAAACACGGAAACCGAAG
ACCATTCATGTTGTTGCTCAGGTCGCAGACGTTTTGCAGCAGCAGTCGCTTCA
CGTTCGCTCGCGTATCGGTGATTCATTCTGCTAACCAGTAAGGCAACCCCGC
CAGCCTAGCCGGGTCCTCAACGACAGGAGCACGATCATGCGCACCCGTGGCC
AGGACCCAACGCTGCCCGAGATGCGCCGCGTGCGGCTGCTGGAGATGGCGG
ACGCGATGGATATGTTCTGCCAAGGGTTGGTTTGCGCATTCACAGTTCTCCGC
AAGAATCGATTGGCTCCAATTCTTGGAGTGGTGAATCCGTTAGCGAGGTGCC
GCCGGCGAGCTGTTGACAATTAATCATCGAACTAGTTTAATGTGTGGAAGCG
GCCGCTTTCATATCCCTCCGCAAATGGAGAAAAAAATCACTGGATATACCAC
CGTTGATATATCCCAATGGCATCGTAAAGAACATTTTGAGGCATTTCAGTCA
GTTGCTCAATGTACCTATAACCAGACCGTTCAGCTGGATATTACGGCCTTTT
AAAGACCGTAAAGAAAAATAAGCACAAGTTTTATCCGGCCTTTATTCACATT
CTTGCCCGCCTGATGAATGCTCATCCGGAATTCCGTATGGCAATGAAAGACG
GTGAGCTGGTGATATGGGATAGTGTTCACCCTTGTTACACCGTTTTCCATGAG
CAAACTGAAACGTTTTCATCGCTCTGGAGTGAATACCACGACGATTTCCGGC
AGTTTCTACACATATATTCGCAAGATGTGGCGTGTTACGGTGAAAACCTGGC
CTATTTCCCTAAAGGGTTTATTGAGAATATGTTTTTCGTCTCAGCCAATCCCT
GGGTGAGTTTCACCAGTTTTGATTTAAACGTGGCCAATATGGACAACTTCTTC
GCCCCCGTTTTCACCATGGGCAAATATTATACGCAAGGCGACAAGGTGCTGA
TGCCGCTGGCGATTCAGGTTCATCATGCCGTCTGTGATGGCTTCCATGTCGGC
AGAATGCTTAATGAATTACAACAGTACTGCGATGAGTGGCAGGGCGGGGCG
TAATTTTTTTAAGGCAGTTATTGGTGCCCTTAAACGCCTGGTGCTACGCCTGA
ATAAGTGATAATAAGCGGATGAATGGCAGAAATTCGAAAGCAAATTCGACC
CGGTCGTCGGTTCAGGGCAGGGTCGTTAAATAGCCGCTTATGTCTATTGCTG
GTTTACGGTTTATTGACTACCCGAAGCAGTGTGACCCTGTGCTTCTCAAATGC
```

*Fig. 25*
Cont.

```
CTGAGGGCAGTTTGCTCAGGTCTCCCGTGGGGGGAATAATTAACGGTATGA
GCCTTACGGCGGACGGATCGTGGCCGCAAGTGGGTCCGGCTAGAGGATCCG
ACACCATCGAATGGTGCAAAACCTTTCGCGGTATGGCATGATAGCGCCCGGA
AGAGAGTCAATTCAGGGTGGTGAATGTGAAACCAGTAACGTTATACGATGTC
GCAGAGTATGCCGGTGTCTCTTATCAGACCGTTTCCCGCGTGGTGAACCAGG
CCAGCCACGTTTCTGCGAAAACGCGGGAAAAAGTGGAAGCGGCGATGGCGG
AGCTGAATTACATTCCCAACCGCGTGGCACAACAACTGGCGGGCAAACAGTC
GTTGCTGATTGGCGTTGCCACCTCCAGTCTGGCCCTGCACGCGCCGTCGCAA
ATTGTCGCGGCGATTAAATCTCGCGCCGATCAACTGGGTGCCAGCGTGGTGG
TGTCGATGGTAGAACGAAGCGGCGTCGAAGCCTGTAAAGCGGCGGTGCACA
ATCTTCTCGCGCAACGGGTCAGTGGGCTGATCATTAACTATCCGCTGGATGA
CCAGGATGCCATTGCTGTGGAAGCTGCCTGCACTAATGTTCCGGCGTTATTTC
TTGATGTCTCTGACCAGACACCCATCAACAGTATTATTTTCTCCCATGAAGAC
GGTACGCGACTGGGCGTGGAGCATCTGGTCGCATTGGGTCACCAGCAAATCG
CGCTGTTAGCGGGCCCATTAAGTTCTGTCTCGGCGCGTCTGCGTCTGGCTGGC
TGGCATAAATATCTCACTCGCAATCAAATTCAGCCGATAGCGGAACGGGAAG
GCGACTGGAGTGCCATGTCCGGTTTTCAACAAACCATGCAAATGCTGAATGA
GGGCATCGTTCCCACTGCGATGCTGGTTGCCAACGATCAGATGGCGCTGGGC
GCAATGCGCGCCATTACCGAGTCCGGGCTGCGCGTTGGTGCGGATATCTCGG
TAGTGGGATACGACGATACCGAAGACAGCTCATGTTATATCCCGCCGTCAAC
CACCATCAAACAGGATTTTCGCCTGCTGGGGCAAACCAGCGcGGACCGCTTG
CTGCAACTCTCTCAGGGCCAGGCGGTGAAGGGCAATCAGCTGTTGCCCGTCT
CACTGGTGAAAAGAAAAACCACCCTGGCGCCCAATACGCAAACCGCCTCTCC
CCGCGCGTTGGCCGATTCATTAATGCAGCTGGCACGACAGGTTTCCCGACTG
GAAAGCGGGCAGTGAGCGCAACGCAATTAATGTGAGTTAGCTCACTCATTAG
GCACCCCAGGCTTTACACTTTATGCTTCCGGCTCGTATAATGTGTGGAATTGT
GAGCGGATAACAATTTCACACAGCGGCCGCTGAGAAAAGCGAAGCGGCAC
TGCTCTTTAACAATTTATCAGACAATCTGTGTGGGCACTCGAAGATACGGAT
TCTTAACGTCGCAAGACGAAAAATGAATACCAAGTCTCAAGAGTGAACACG
TAATTCATTACGAAGTTTAATTCTTTGAGCGTCAAACTTTT
```

*Fig. 25*
Cont.

```
AAATTGAAGAGTTTGATCATGGCTCAGATTGAACGCTGGCGGCAGGCCTAAC
ACATGCAAGTCGAACGGTAACAGGAAGAAGCTTGCTTCTTTGCTGACGAGTG
GCGGACGGGTGAGTAATGTCTGGGAAACTGCCTGATGGAGGGGGATAACTA
CTGGAAACGGTAGCTAATACCGCATAACGTCGCAAGACCAAAGAGGGGGAC
CTTCGGGCCTCTTGCCATCGGATGTGCCCAGATGGGATTAGCTAGTAGGTGG
GGTAACGGCTCACCTAGGCGACGATCCCTAGCTGGTCTGAGAGGATGACCAG
CCACACTGGAACTGAGACACGGTCCAGACTCCTACGGGAGGCAGCAGTGGG
GAATATTGCACAATGGGCGCAAGCCTGATGCAGCCATGCCGCGTGTATGAAG
AAGGCCTTCGGGTTGTAAAGTACTTTCAGCGGGGAGGAAGGGAGTAAAGTT
AATACCTTTGCTCATTGACGTTACCCGCAGAAGAAGCACCGGCTAACTCCGT
GCCAGCAGCCGCGGTAATACGGAGGGTGCAAGCGTTAATCGGAATTACTGG
GCGTAAAGCGCACGCAGGCGGTTTGTTAAGTCAGATGTGAAATCCCCGGGCT
CAACCTGGGAACTGCATCTGATACTGGCAAGCTTGAGTCTCGTAGAGGGGGG
TAGAATTCCAGGTGTAGCGGTGAAATGCGTAGAGATCTGGAGGAATACCGG
TGGCGAAGGCGGCCCCCTGGACGAAGACTGACGCTCAGGTGCGAAAGCGTG
GGGAGCAAACAGGATTAGATACCCTGGTAGTCCACGCCGTAAACGATGTCG
ACTTGGAGGTTGTGCCCTTGAGGCGTGGCTTCCGGAGCTAACGCGTTAAGTC
GACCGCCTGGGGAGTACGGCCGCAAGGTTAAAACTCAAATGAATTGACGGG
GGCCCGCACAAGCGGCGGAGCATGTGGATTAATTCGATGCAACGCGAAGAA
CCTTACCTGGGTTTGACATGCACAGGACGCGTCTAGAGATAGGCGTTCCCTT
GTGGCCTGTGTGCAGGTGGTGCATGGCTGTCGTCAGCTCGTGTCGTGAGATG
TTGGGTTAAGTCCCGCAACGAGCGCAACCCTTGTCTCATGTTGCCAGCACGT
AATGGTGGGGACTCGTGAGAGACTGCCGGGGTCAACTCGGAGGAAGGTGGG
GATGACGTCAAGTCATCATGCCCCTTATGTCCAGGGCTTCACACATGCTACA
ATGGCCGGTACAAAGGGCTGCGATGCCGCGAGGTTAAGCGAATCCTTAAAA
GCCGGTCTCAGTTCGGATCGGGGTCTGCAACTCGACCCCGTGAAGTCGGAGT
CGCTAGTAATCGCAGATCAGCAACGCTGCGGTGAATACGTTCCCGGGCCTTG
TACACACCGCCCGTCACGTCATGAAAGTCGGTAACACCCGAAGCCAGTGGCC
TAACCCTCGGGAGGGAGCTGTCGAAGGTGGGATCGGCGATTGGGACGAAGT
CGTAACAAGGTAACCGTAGGGGAACCTGCGGTTGGATCATGGGATTACCTTA
AAGAAGCGTACTTTGTAGTGCTCACACAGATTGTCTGATAGAAAGTGAAAAG
CAAGGCGTTTACGCGTTGGGAGTGAGGCTGAAGAGAATAAGGCCGTTCGCTT
TCTATTAATGAAAGCTCACCCTACACGAAAATATCACGCAACGCGTGATAAG
CAATTTTCGTGTCCCCTTCGTCTAGACGTAGCGCCGATGGTAGTGTGGGGTCT
CCCCATGCGAGAGTAGGGAACTGCCAGGCATCAAATAAAACGAAAGGCTCA
GTCGAAAGACTGGGCCTTTCGTTTTATCTGTTGTTTGTCGGTAACGCTCTCC
TGAGTAGGACAAATCCGCCGGGAGCGGATTTGAACGTTGCGAAGCAACGGC
CCGGAGGGTGGCGGGCAGGACGCCCGCCATAAACTGCCAGGCATCAAATTA
AGCAGAAGGCCATCCTGACGGATGGCCTTTTGCGTTTCTACAAACTCTTCCT
GTCGTCACTGCAGGCATGCAAGCTTGGCGTAATCATGGTCATAGCTGTTTCCT
GTGTGAAATTGTTATCCGCTCACAATTCCACACAACATACGAGCCGGAAGCA
TAAAGTGTAAAGCCTGGGGTGCCTAATGAGTGAGCTAACTCACATTAATTGC
GTTGCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCTCTTC
CGCTTCCTCGCTCACTGACTCGCTGCGCTCGGTCGTTCGGCTGCGGCGAGCG
```

*Fig. 26*

```
GTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCG
ACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGT
GCTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGAT
TTTGGTCATGAGATTATCAAAAAGGATCTTCACCTAGATCCTTTTAAATTAAA
AATGAAGTTTTAAATCAATCTAAAGTATATATGAGTAAACTTGGTCTGACAG
TTACCAATGCTTAATCAGTGAGGCACCTATCTCAGCGATCTGTCTATTTCGTT
CATCCATAGTTGCCTGACTCCCCGTCGTGTAGATAACTACGATACGGGAGGG
CTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATT
GCTACAGGCATCGTGGTGTCACGCTCGTCGTTTGGTATGGCTTCATTCAGCTC
CGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAG
TGTTATCACTCATGGTTATGGCAGCACTGCATAATTCTCTTACTGTCATGCCA
TCCGTAAGATGCTTTTCTGTGACTGGTGAGTACTCAACCAAGTCATTCTGAGA
ATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTT
CGGGGCGAAAACTCTCAAGGATCTTACCGCTGTTGAGATCCAGTTCGATGTA
ACCCACTCGTGCACCCAACTGATCTTCAGCATCTTTTACTTTCACCAGCGTTT
CTGGGTGAGCAAAAACAGGAAGGCAAAATGCCGCAAAAAAGGGAATAAGG
GCGACACGGAAATGTTGAATACTCATACTCTTCCTTTTTCAATATTATTGAAG
CATTTATCAGGGTTATTGTCTCATGAGCGGATACATATTTGAATGTATTTAGA
AAAATAAACAAATAGGGGTTCCGCGCACATTTCCCCGAAAAGTGCCACCTGA
CGTCTAAGAAACCATTATTATCATGACATTAACCTATAAAAATAGGCGTATC
ACGAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGGAG
CAGACAAGCCCGTCAGGGCGCGTCAGCGGGTGTTGGCGGGTGTCGGGGCTG
GCTTAACTATGCGGCATCAGAGCAGATTGTACTGAGAGTGCACCATATGCGG
TGTGAAATACCGCACAGATGCGTAAGGAGAAAATACCGCATCAGGCGCCAT
TCGCCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAGTTG
GGTAACGCCAGGGTTTTCCCAGTCACGACGTTGTAAAACGACGGCCAGTGAA
```

*Fig. 26*
Cont.

```
TTCGAGCTCGGTACCTGCAGTGACGACAGGAAGAGTTTGTAGAAACGCAAA
AAGGCCATCCGTCAGGATGGCCTTCTGCTTAATTTGATGCCTGGCAGTTTATG
GCGGGCGTCCTGCCCGCCACCCTCCGGGCCGTTGCTTCGCAACGTTCAAATC
CGCTCCCGGCGGATTTGTCCTACTCAGGAGAGCGTTCACCGACAAACAACAG
ATAAAACGAAAGGCCCAGTCTTTCGACTGAGCCTTTCGTTTTATTTGATGCCT
GGCAGTTCCCTACTCTCGCATGGGGAGACCCCACACTACCATCGGCGCTACG
TCTAGATTATTTGTAGAGCTCATCCATGCCATGTGTAATCCCAGCAGCAGTTA
CAAACTCAAGAAGGACCATGTGGTCACGCTTTTCGTTGGGATCTTTCGAAAG
GGCAGATTGTGTCGACAGGTAATGGTTGTCTGGTAAAAGGACAGGGCCATCG
CCAATTGGAGTATTTTGTTGATAATGGTCTGCTAGTTGAACGGATCCATCTTC
AATGTTGTGGCGAATTTTGAAGTTAGCTTTGATTCCATTCTTTTGTTTGTCTGC
CGTGATGTATACATTGTGTGAGTTATAGTTGTACTCGAGTTTGTGTCCGAGAA
TGTTTCCATCTTCTTTAAAATCAATACCTTTTAACTCGATACGATTAACAAGG
GTATCACCTTCAAACTTGACTTCAGCACGCGTCTTGTAGTTCCCGTCATCTTT
GAAAGATATAGTGCGTTCCTGTACATAACCTTCGGGCATGGCACTCTTGAAA
AAGTCATGCCGTTTCATATGATCCGGATAACGGGAAAAGCATTGAACACCAT
AAGAGAAAGTAGTGACAAGTGTTGGCCATGGAACAGGTAGTTTTCCAGTAGT
GCAAATAAATTTAAGGGTAAGCTTTCCGTATGTAGCATCACCTTCACCCTCTC
CACTGACAGAAAATTTGTGCCCATTAACATCACCATCTAATTCAACAAGAAT
TGGGACAACTCCAGTGAAAAGTTCTTCTCCTTTGCTAGCAGTGATTTTTTTCT
CCATTTGCGGAGGGATATGAAAGCGGCCGCTTCCACACATTAAACTAGTTCG
ATGATTAATTGTCAACAGCTCGCCGGCGGCACCTCGCTAACGGATTCACCAC
TCCAAGAATTGGAGCCAATCGATTCTTGCGGAGAACTGTGAATGCGGGTACC
CAGATCCGGAACATAATGGTGCAGGGCGCTGACTTCCGCGTTTCCAGACTTT
ACGAAACACGGAAACCGAAGACCATTCATGTTGTTGCTCAGGTCGCAGACGT
TTTGCAGCAGCAGTCGCTTCACGTTCGCTCGCGTATCGGTGATTCATTCTGCT
AACCAGTAAGGCAACCCCGCCAGCCTAGCCGGGTCCTCAACGACAGGAGCA
CGATCATGCGCACCCGTGGCCAGGACCCAACGCTGCCCGAGATGCGCCGCGT
GCGGCTGCTGGAGATGGCGGACGCGATGGATATGTTCTGCCAAGGGTTGGTT
TGCGCATTCACAGTTCTCCGCAAGAATCGATTGGCTCCAATTCTTGGAGTGGT
GAATCCGTTAGCGAGGTGCCGCCGGCGAGCTGTTGACAATTAATCATCGAAC
TAGTTTAATGTGTGGAAGCGGCCGCTTTCATATCCCTCCGCAAATGGAGAAA
AAAATCACTGGATATACCACCGTTGATATATCCCAATGGCATCGTAAAGAAC
ATTTTGAGGCATTTCAGTCAGTTGCTCAATGTACCTATAACCAGACCGTTCAG
CTGGATATTACGGCCTTTTTAAAGACCGTAAAGAAAAATAAGCACAAGTTTT
ATCCGGCCTTTATTCACATTCTTGCCCGCCTGATGAATGCTCATCCGGAATTC
CGTATGGCAATGAAAGACGGTGAGCTGGTGATATGGGATAGTGTTCACCCTT
GTTACACCGTTTTCCATGAGCAAACTGAAACGTTTTCATCGCTCTGGAGTGA
ATACCACGACGATTTCCGGCAGTTTCTACACATATATTCGCAAGATGTGGCG
TGTTACGGTGAAAACCTGGCCTATTTCCCTAAAGGGTTTATTGAGAATATGTT
TTTCGTCTCAGCCAATCCCTGGGTGAGTTTCACCAGTTTTGATTTAAACGTGG
CCAATATGGACAACTTCTTCGCCCCCGTTTTCACCATGGGCAAATATTATACG
CAAGGCGACAAGGTGCTGATGCCGCTGGCGATTCAGGTTCATCATGCCGTCT
GTGATGGCTTCCATGTCGGCAGAATGCTTAATGAATTACAACAGTACTGCGA
TGAGTGGCAGGGCGGGGCGTAATTTTTTAAGGCAGTTATTGGTGCCCTTAA
```

*Fig. 26*
Cont.

```
ACGCCTGGTGCTACGCCTGAATAAGTGATAATAAGCGGATGAATGGCAGAA
ATTCGAAAGCAAATTCGACCCGGTCGTCGGTTCAGGGCAGGGTCGTTAAATA
GCCGCTTATGTCTATTGCTGGTTTACGGTTTATTGACTACCCGAAGCAGTGTG
ACCCTGTGCTTCTCAAATGCCTGAGGGCAGTTTGCTCAGGTCTCCCGTGGGG
GGGAATAATTAACGGTATGAGCCTTACGGCGGACGGATCGTGGCCGCAAGT
GGGTCCGGCTAGAGGATCCGACACCATCGAATGGTGCAAAACCTTTCGCGGT
ATGGCATGATAGCGCCCGGAAGAGAGTCAATTCAGGGTGGTGAATGTGAAA
CCAGTAACGTTATACGATGTCGCAGAGTATGCCGGTGTCTCTTATCAGACCG
TTTCCCGCGTGGTGAACCAGGCCAGCCACGTTTCTGCGAAAACGCGGGAAAA
AGTGGAAGCGGCGATGGCGGAGCTGAATTACATTCCCAACCGCGTGGCACA
ACAACTGGCGGGCAAACAGTCGTTGCTGATTGGCGTTGCCACCTCCAGTCTG
GCCCTGCACGCGCCGTCGCAAATTGTCGCGGCGATTAAATCTCGCGCCGATC
AACTGGGTGCCAGCGTGGTGGTGTCGATGGTAGAACGAAGCGGCGTCGAAG
CCTGTAAAGCGGCGGTGCACAATCTTCTCGCGCAACGGGTCAGTGGGCTGAT
TATTAACTATCCGCTGGATGACCAGGATGCCATTGCTGTGGAAGCTGCCTGC
ACTAATGTTCCGGCGTTATTTCTTGATGTCTCTGACCAGACACCCATCAACAG
TATTATTTTCTCCCATGAAGACGGTACGCGACTGGGCGTGGAGCATCTGGTC
GCATTGGGcCACCAGCAAATCGCGCTGTTAGCGGGCCCATTAAGTTCTGTCTC
GGCGCGTCTGCGTCTGGCTGGCTGGCATAAATATCTCACTCGCAATCAAATT
CAGCCGATAGCGGAACGGGAAGGCGACTGGAGTGCCATGTCCGGTTTTCAA
CAAACCATGCAAATGCTGAATGAGGGCATCGTTCCCACTGCGATGCTGGTTG
CCAACGATCAGATGGCGCTGGGCGCAATGCGCGCCATTACCGAGTCCGGGCT
GCGCGTTGGTGCGGATATCTCGGTAGTGGGATACGACGATACCGAAGACAG
CTCATGTTATATCCCGCCGTCAACCACCATCAAACAGGATTTTCGCCTGCTGG
GGCAAACCAGCGTGGACCGCTTGCTGCAACTCTCTCAGGGCCAGGCGGTGAA
GGGCAATCAGCTGTTGCCCGTCTCACTGGTGAAAAGAAAAACCACCCTGGCG
CCCAATACGCAAACCGCCTCTCCCCGCGCGTTGGCCGATTCATTAATGCAGC
TGGCACGACAGGTTTCCCGACTGGAAAGCGGGCAGTGAGCGCAACGCAATT
AATGTGAGTTAGCTCACTCATTAGGCACCCCAGGCTTTACACTTTATGCTTCC
GGCTCGTATAATGTGTGGAATTGTGAGCGGATAACAATTTCACACAGCGGCC
GCTGAGAAAAGCGAAGCGGCACTGCTCTTTAACAATTTATCAGACAATCTG
TGTGGGCACTCGAAGATACGGATTCTTAACGTCGCAAGACGAAAAATGAAT
ACCAAGTCTCAAGAGTGAACACGTAATTCATTACGAAGTTTAATTCTTTGAG
CGTCAAACTTTT
```

*Fig. 26*
Cont.

METHODS AND COMPOSITIONS FOR THE IDENTIFICATION OF ANTIBIOTICS THAT ARE NOT SUSCEPTIBLE TO ANTIBIOTIC RESISTANCE

RELATED APPLICATIONS

The present application is a continuation of U.S. patent application Ser. No. 11/436,349, filed on May 18, 2006, now U.S. Pat. No. 7,709,196; which is a divisional of U.S. patent application Ser. No. 10/612,224, filed on Jul. 1, 2003, now U.S. Pat. No. 7,081,341; which claims priority from U.S. provisional patent application Ser. No. 60/393,237, filed on Jul. 1, 2002, and U.S. provisional patent application Ser. No. 60/452,012, filed on Mar. 5, 2003, all of which are expressly incorporated by reference.

BACKGROUND OF THE INVENTION

Ribosomes are composed of one large and one small subunit containing three or four RNA molecules and over fifty proteins. The part of the ribosome that is directly involved in protein synthesis is the ribosomal RNA (rRNA). The ribosomal proteins are responsible for folding the rRNAs into their correct three-dimensional structures. Ribosomes and the protein synthesis process are very similar in all organisms. One difference between bacteria and other organisms, however, is the way that ribosomes recognize mRNA molecules that are ready to be translated. In bacteria, this process involves a base-pairing interaction between several nucleotides near the beginning of the mRNA and an equal number of nucleotides at the end of the ribosomal RNA molecule in the small subunit. The mRNA sequence is known as the Shine-Dalgarno (SD) sequence and its counterpart on the rRNA is called the Anti-Shine-Dalgarno (ASD) sequence.

There is now extensive biochemical, genetic and phylogenetic evidence indicating that rRNA is directly involved in virtually every aspect of ribosome function (Garrett, R. A., et al. (2000) *The Ribosome: Structure, Function, Antibiotics, and Cellular Interactions*. ASM Press, Washington, D.C.). Genetic and functional analyses of rRNA mutations in *E. coli* and most other organisms have been complicated by the presence of multiple rRNA genes and by the occurrence of dominant lethal rRNA mutations. Because there are seven rRNA operons in *E. coli*, the phenotypic expression of rRNA mutations may be affected by the relative amounts of mutant and wild-type ribosomes in the cell. Thus, detection of mutant phenotypes can be hindered by the presence of wild-type ribosomes. A variety of approaches have been designed to circumvent these problems.

One common approach uses cloned copies of a wild-type rRNA operon (Brosius, J., et al. (1981) *Plasmid* 6: 112-118; Sigmund, C. D. et al. (1982) *Proc. Natl. Acad. Sci. U.S.A.* 79: 5602-5606). Several groups have used this system to detect phenotypic differences caused by a high level of expression of mutant ribosomes. Recently, a strain of *E. coli* was constructed in which the only supply of ribosomal RNA was plasmid encoded (Asai, T., (1999) *J. Bacteriol.* 181: 3803-3809). This system has been used to study transcriptional regulation of rRNA synthesis, as well as ribosomal RNA function (Voulgaris, J., et al. (1999) *J. Bacteriol.* 181: 4170-4175; Koosha, H., et al. (2000) *RNA.* 6: 1166-1173; Sergiev, P. V., et al. (2000) *J. Mol. Biol.* 299: 379-389; O'Connor, M. et al. (2001) *Nuci. Acids Res.* 29: 1420-1425; O'Connor, M., et al. (2001) *Nucl. Acids Res.* 29: 710-715; Vila-Sanjurjo, A. et al. (2001) *J. Mol. Biol.* 308: 457-463); Morosyuk S. V., et al. (2000) *J. Mol. Biol.* 300 (1):113-126; Morosyuk S. V., et al. (2001) *J. Mol. Biol.* 307 (1):197-210; and Morosyuk S. V., et al. (2001) *J. Mol. Biol.* 307 (1):211-228. Hui et al. showed that mRNA could be directed to a specific subset of plasmid-encoded ribosomes by altering the message binding site (MBS) of the ribosome while at the same time altering the ribosome binding site (RBS) of an mRNA (Hui, A., et al. (1987) *Methods Enzymol.* 153: 432-452).

Although each of the above methods has contributed significantly to the understanding of rRNA function, progress in this field has been hampered both by the complexity of translation and by difficulty in applying standard genetic selection techniques to these systems.

Resistance to antibiotics, a matter of growing concern, is caused partly by antibiotic overuse. According to a study published by the Journal of the American Medical Association in 2001, between 1989 to 1999 American adults made some 6.7 million visits a year to the doctor for sore throat. In 73% of those visits, the study found, the patient was treated with antibiotics, though only 5%-17% of sore throats are caused by bacterial infections, the only kind that respond to antibiotics. Macrolide antibiotics in particular are becoming extremely popular for treatment of upper respiratory infections, in part because of their typically short, convenient course of treatment. Research has linked such vast use to a rise in resistant bacteria and the recent development of multiple drug resistance has underscored the need for antibiotics which are highly specific and refractory to the development of drug resistance.

Microorganisms can be resistant to antibiotics by four mechanisms. First, resistance can occur by reducing the amount of antibiotic that accumulates in the cell. Cells can accomplish this by either reducing the uptake of the antibiotic into the cell or by pumping the antibiotic out of the cell. Uptake mediated resistance often occurs, because a particular organism does not have the antibiotic transport protein on the cell surface or occasionally when the constituents of the membrane are mutated in a way that interferes with transport of the antibiotic into a cell. Uptake mediated resistance is only possible in instances where the drug gains entry through a nonessential transport molecule. Efflux mechanisms of antibiotic resistance occur via transporter proteins. These can be highly specific transporters that transport a particular antibiotic, such as tetracycline, out of the cell or they can be more general transporters that transport groups of molecules with similar characteristics out of the cell. The most notorious example of a nonspecific transporter is the multidrug resistance transporter (MDR).

Inactivating the antibiotic is another mechanism by which microorganisms can become resistant to antibiotics. Antibiotic inactivation is accomplished when an enzyme in the cell chemically alters the antibiotic so that it no longer binds to its intended target. These enzymes are usually very specific and have evolved over millions of years, along with the antibiotics that they inactivate. Examples of antibiotics that are enzymatically inactivated are penicillin, chloramphenicol, and kanamycin.

Resistance can also occur by modifying or overproducing the target site. The target molecule of the antibiotic is either mutated or chemically modified so that it no long binds the antibiotic. This is possible only if modification of the target does not interfere with normal cellular functions. Target site overproduction is less common but can also produce cells that are resistant to antibiotics.

Lastly, target bypass is a mechanism by which microorganisms can become resistant to antibiotics. In bypass mechanisms, two metabolic pathways or targets exist in the cell and one is not sensitive to the antibiotic. Treatment with the antibiotic selects cells with more reliance on the second, antibiotic-resistant pathway.

Among these mechanisms, the greatest concern for new antibiotic development is target site modification. Enzymatic inactivation and specific transport mechanisms require the existence of a substrate specific enzyme to inactivate or transport the antibiotic out of the cell. Enzymes have evolved over millions of years in response to naturally occurring antibiotics. Since microorganisms cannot spontaneously generate new enzymes, these mechanisms are unlikely to pose a significant threat to the development of new synthetic antibiotics. Target bypass only occurs in cells where redundant metabolic pathways exist. As understanding of the MDR transporters increases, it is increasingly possible to develop drugs that are not transported out of the cell by them. Thus, target site modification poses the greatest risk for the development of antibiotic resistance for new classes of antibiotic and this is particularly true for those antibiotics that target ribosomes. The only new class of antibiotics in thirty-five years, the oxazolidinones, is a recent example of an antibiotic that has been compromised because of target site modification. Resistant strains containing a single mutation in rRNA developed within seven months of its use in the clinical settings.

SUMMARY OF THE INVENTION

The present invention provides compositions and methods which may be used to identify antibiotics that are not susceptible to the development of antibiotic resistance. In particular, rRNA genes from *E. coli* and other disease causing organisms are genetically engineered to allow identification of functional mutant ribosomes that may be used as drug targets, e.g., to screen chemical and peptide libraries to identify compounds that bind to all functional mutant ribosomes but do not bind to human ribosomes. Antibiotics that recognize all biologically active forms of the target molecule and are therefore not susceptible to the development of drug resistance by target site modification are thus identified.

The invention provides plasmid constructs comprising an rRNA gene having a mutant ASD sequence set forth in FIGS. 12 (SEQ ID NOS:24-47), 13 (SEQ ID NOS:48-61), 15 (SEQ ID NOS:62-111), and 16 (SEQ ID NOS:112-159), at least one mutation in the rRNA gene, and a genetically engineered gene which encodes a selectable marker having a mutant SD sequence set forth in FIGS. 12, 13, 15, and 16. The mutant SD-ASD sequences are mutually compatible pairs and therefore permit translation of only the mRNA containing the compatible mutant SD sequence, i.e., translation of the selectable marker. In one embodiment, the selectable marker is chosen from the group consisting of chloramphenicol acetyltransferase (CAT), green fluorescent protein (GFP), or both CAT and GFP. In another embodiment, the DNA sequence encoding the rRNA gene is under the control of an inducible promoter.

The rRNA gene may be selected from a variety of species, thereby providing for the identification of functional mutant ribosomes that may be used as drug targets to identify drug candidates that are effective against the selected species. Examples of species include, without limitation, *Mycobacterium tuberculosis* (tuberculosis), *Pseudomonas aeruginosa* (multidrug resistant nosocomial infections), *Salmonella typhi* (typhoid fever), *Yersenia pestis* (plague), *Staphylococcus aureus* (multidrug resistant infections causing impetigo, folliculitis, abcesses, boils, infected lacerations, endocarditis, meningitis, septic arthritis, pneumonia, osteomyelitis, and toxic shock), *Streptococcus pyogenes* (streptococcal sore throat, scarlet fever, impetigo, erysipelas, puerperal fever, and necrotizing fascitis), *Enterococcus faecalis* (vancomycin resistant nosocomial infections, endocarditis, and bacteremia), *Chlamydia trachomatis* (lymphogranuloma venereum, trachoma and inclusion conjunctivitis, nongonococcal urethritis, epididymitis, cervicitis, urethritis, infant pneumonia, pelvic inflammatory diseases, Reiter's syndrome (oligoarthritis) and neonatal conjunctivitis), *Saccharomyces cerevesiae, Candida albicans*, and trypanosomes. In one embodiment, the rRNA gene is from *Mycobacterium tuberculosis* (see, e.g., Example 6 and FIG. 17).

In still other embodiments of the invention, the rRNA genes are mitochondrial rRNA genes, i.e., eukaryotic rRNA genes (e.g., human mitochondrial rRNA genes).

The plasmid constructs of the invention, such as the plasmid constructs set forth in FIGS. 22-26, may include novel mutant ASD and SD sequences set forth herein. In particular, the present invention provides novel mutant ASD sequences and novel mutant SD sequences, set forth in FIGS. 12, 13, 15, and 16, which may be used in the plasmid constructs and methods of the invention. The mutant ASD and mutant SD sequences may be used as mutually compatible pairs (see FIGS. 12, 13, 15, and 16). It will be appreciated that the mutually compatible pairs of mutant ASD and SD sequences interact as pairs in the form of RNA and permit translation of only the mRNAs containing the compatible mutant SD sequence.

In another aspect, the present invention provides a plasmid comprising an *E. coli* 16S rRNA gene having a mutant ASD sequence, at least one mutation in said 16S rRNA gene, and a genetically engineered gene which encodes a selectable marker, e.g., GFP, having a mutant SD sequence. In another embodiment, the 16S rRNA gene is from a species other than *E. coli*. In one embodiment, the mutant ASD sequence is selected from the sequences set forth in FIGS. 12, 13, 15, and 16. In another embodiment, the mutant SD sequence is selected from the sequences set forth in FIGS. 12, 13, 15, and 16. In yet another embodiment, the mutant ASD sequence and the mutant SD sequence are in mutually compatible pairs (see FIGS. 12, 13, 15, and 16). Each mutually compatible mutant SD and mutant ASD pair permits translation by the selectable marker.

In one embodiment, the invention features a cell comprising a plasmid of the invention. In another embodiment, the cell is a bacterial cell.

In one embodiment, the invention provides a method for identifying functional mutant ribosomes comprising:

(a) transforming a host cell with a plasmid comprising an rRNA gene having a mutant ASD sequence, at least one mutation in said rRNA gene, and a genetically engineered gene which encodes a selectable marker having a mutant SD sequence, wherein the mutant ASD and mutant SD sequences are a mutually compatible pair;

(b) isolating cells via the selectable marker; and (c) identifying the rRNA from the cells from step (b), thereby identifying functional mutant ribosomes.

In another embodiment, the invention features a method for identifying functional mutant ribosomes comprising:

(a) transforming a host cell with a plasmid comprising an *E. coli* 16S rRNA gene having a mutant ASD sequence, at least one mutation in said 16S rRNA gene, and a genetically engineered gene which encodes GFP having a mutant SD sequence wherein the mutant ASD and mutant SD sequences are a mutually compatible pair;

(b) isolating cells via the GFP; and (c) identifying the rRNA from the cells from step (b), thereby identifying functional mutant ribosomes.

In yet another embodiment, the invention features a method for identifying functional mutant ribosomes that may be suitable as drug targets comprising:

(a) transforming a host cell with a plasmid comprising an rRNA gene having a mutant ASD sequence, at least one mutation in said rRNA gene, and a genetically engineered gene which encodes a selectable marker having a mutant SD sequence, wherein the mutant ASD and mutant SD sequences are a mutually compatible pair;

(b) isolating cells via the selectable marker;

(c) identifying and sequencing the rRNA from the cells from step (b), thereby identifying regions of interest;

(d) selecting regions of interest from step (c);

(e) mutating the regions of interest from step (d);

(f) inserting the mutated regions of interest from step (e) into a plasmid comprising an rRNA gene having a mutant ASD sequence and a genetically engineered gene which encodes a selectable marker having a mutant SD sequence, wherein the mutant ASD and mutant SD sequences are a mutually compatible pair;

(g) transforming a host cell with the plasmid from step (f);

(h) isolating cells of step (g) via the selectable marker; and (i) identifying the rRNA from step (h), thereby identifying functional mutant ribosomes that may be suitable as drug targets.

In a further embodiment, the invention provides a method for identifying functional mutant ribosomes that may be suitable as drug targets comprising:

(a) transforming a host cell with a plasmid comprising an *E. coli* 16S rRNA gene having a mutant ASD sequence, at least one mutation in said 16S rRNA gene, and a genetically engineered gene which encodes GFP having a mutant SD sequence wherein the mutant ASD and mutant SD sequences are a mutually compatible pair;

(b) isolating cells via the GFP;

(c) identifying and sequencing the rRNA from the cells from step (b), thereby identifying regions of interest;

(d) selecting the regions of interest from step (c);

(e) mutating the regions of interest from step (d);

(f) inserting the mutated regions of interest from step (e) into a plasmid comprising an *E. coli* 16S rRNA gene having a mutant ASD sequence and a genetically engineered gene which encodes GFP having a mutant SD sequence, wherein the mutant ASD and mutant SD sequences are a mutually compatible pair;

(g) transforming a host cell with the plasmid from step (f);

(h) isolating cells of step (g) via the GFP; and (i) identifying the rRNA from step (h), thereby identifying functional mutant ribosomes that may be suitable as drug targets.

In one embodiment, the invention features a method for identifying drug candidates comprising:

(a) transforming a host cell with a plasmid comprising an rRNA gene having a mutant ASD sequence, at least one point mutation in said rRNA gene, and a genetically engineered gene which encodes a selectable marker having a mutant SD sequence, wherein the mutant ASD and mutant SD sequences are a mutually compatible pair;

(b) isolating cells via the selectable marker;

(c) identifying and sequencing the rRNA from step (b) to identify the regions of interest;

(d) selecting the regions of interest from step (c);

(e) mutating the regions of interest from step (d);

(f) inserting the mutated regions of interest from step (e) into a plasmid comprising an rRNA gene having a mutant ASD sequence and a genetically engineered gene which encodes a selectable marker having a mutant SD sequence, wherein the mutant ASD and mutant SD sequences are a mutually compatible pair;

(g) transforming a host cell with the plasmid from step (f);

(h) isolating the cells from step (g) via the selectable marker;

(i) identifying the rRNA from step (h) to identify the functional mutant ribosomes;

(j) screening drug candidates against functional mutant ribosomes from step (i);

(k) identifying the drug candidates from step (j) that bound to the functional mutant ribosomes from step (i);

(l) screening the drug candidates from step (k) against human rRNA; and (m) identifying the drug candidates from step (l) that do not bind to human rRNA, thereby identifying drug candidates.

In one embodiment, the invention provides a method for identifying drug candidates comprising:

(a) transforming a host cell with a plasmid comprising an *E. coli* 16S rRNA gene having a mutant ASD sequence, at least one point mutation in said 16S rRNA gene, and a genetically engineered gene which encodes GFP having a mutant SD sequence, wherein the mutant ASD and mutant SD sequences are a mutually compatible pair;

(b) isolating the cells via the selectable marker;

(c) identifying and sequencing the rRNA from step (b) to identify the regions of interest;

(d) selecting the regions of interest from step (c);

(e) mutating the regions of interest from step (d);

(f) inserting the mutated regions of interest from step (e) into a plasmid comprising an *E. coli* 16S rRNA gene having a mutant ASD sequence and a genetically engineered gene which encodes GFP having a mutant SD sequence, wherein the mutant ASD and mutant SD sequences are a mutually compatible pair;

(g) transforming a host cell with the plasmid from step (f);

(h) isolating cells from step (g) via the selectable marker;

(i) identifying the rRNA from step (h) to identify the functional mutant ribosomes;

(j) screening drug candidates against the functional mutant ribosomes from step (i);

(k) identifying the drug candidates from step (j) that bound to the functional mutant ribosomes from step (i);

(l) screening the drug candidates from step (k) against human 16S rRNA; and (m) identifying the drug candidates from step (l) that do not bind to the human 16S rRNA, thereby identifying drug candidates.

It will be appreciated that the rRNA gene used in the methods of the present invention may be from the 16S rRNA, 23S rRNA, and 55S rRNA gene.

Other features and advantages of the invention will be apparent from the following detailed description and claims.

BRIEF DESCRIPTION OF THE DRAWINGS

FIG. 1 depicts the plasmid construct pRNA123. The locations of specific sites in pRNA123 are as follows: the 16S rRNA *E. coli* rrnB operon corresponds to nucleic acids 1-1542; the 16S MBS (message binding sequence) GGGAU corresponds to nucleic acids 1536-1540; the 16S-23S spacer region corresponds to nucleic acids 1543-1982; the 23S rRNA of *E. coli* rrnB operon corresponds to nucleic acids 1983-4886; the 23S-5S spacer region corresponds to nucleic acids 4887-4982; the 5S rRNA of *E. coli* rrnB operon corresponds to nucleic acids 4983-5098; the terminator T1 of *E.* coli rrnB operon corresponds to nucleic acids 5102-5145; the terminator T2 of E. coli rrnB operon corresponds to nucleic acids 5276-5305; the bla (β-lactamase; ampicillin resistance) corresponds to nucleic acids 6575-7432; the replication origin corresponds to nucleic acids 7575-8209; the rop (Rop protein) corresponds to nucleic acids 8813-8622; the GFP corresponds to nucleic acids 10201-9467; the GFP RBS (ribosome binding sequence) AUCCC corresponds to nucleic acids 10213-10209; the trp$^c$ promoter corresponds to nucleic acids 10270-10230; the trp$^c$ promoter corresponds to nucleic acids 10745-10785; the CAT RBS AUCCC corresponds to nucleic acids 10802-10806; the cam (chloramphenicol acetyltransferase: CAT) corresponds to nucleic acids 10814-11473; the lacI$^q$ promoter corresponds to nucleic acids 11782-11859; the lacI$^q$ (lac repressor) corresponds to nucleic acids 11860-12942; and the lacUV5 promoter corresponds to nucleic acids 12985-13026.

Figure 2:
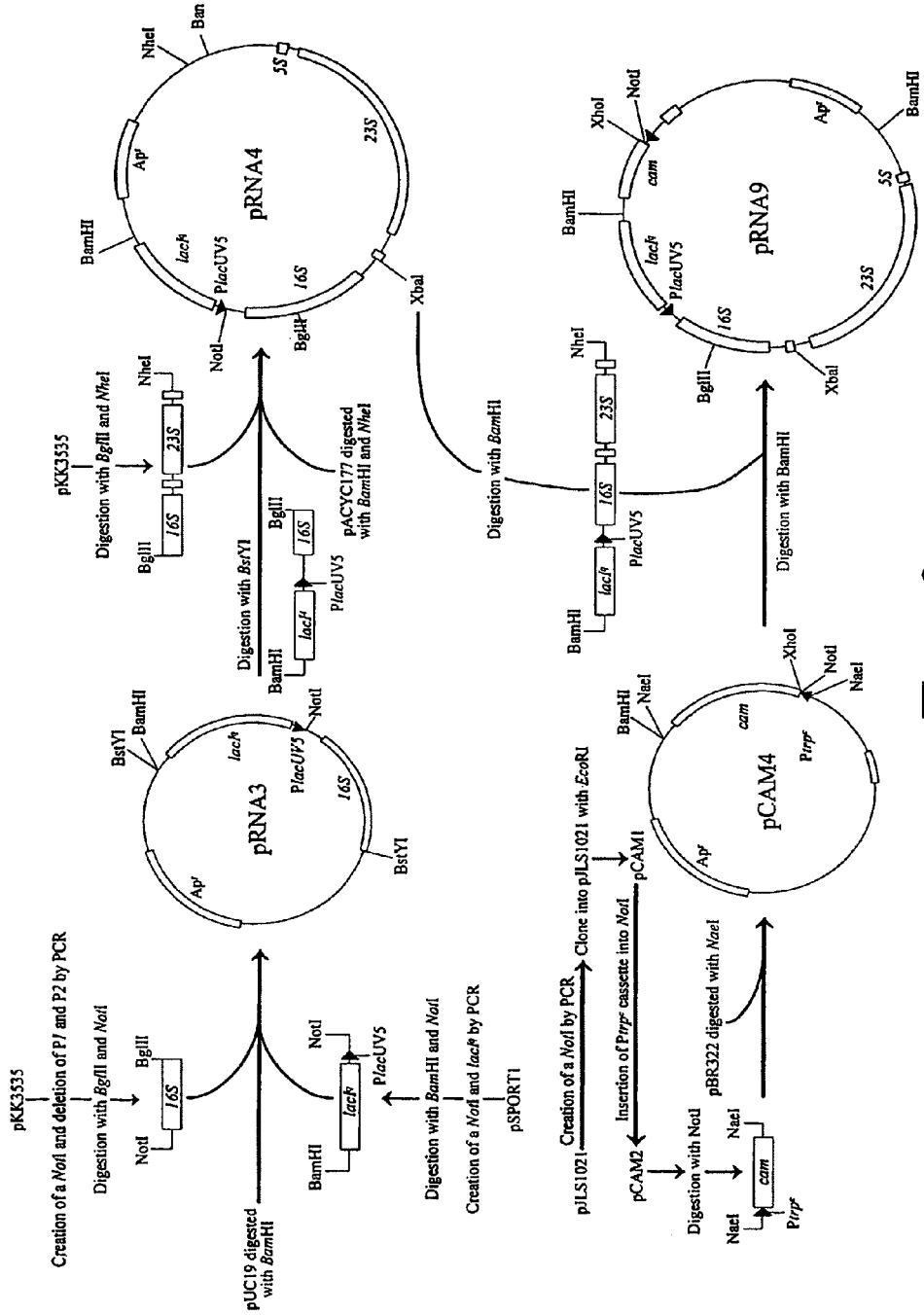

FIG. 2 depicts a scheme for construction of pRNA9. The abbreviations in FIG. 2 are defined as follows: Ap$^r$, ampicillin resistance; cam, CAT gene; lacI$^q$, lactose repressor; PlacUV5, lacUV5 promoter; Ptrp$^c$, constitutive trp promoter. The restriction sites used are also indicated.

Figure 3:
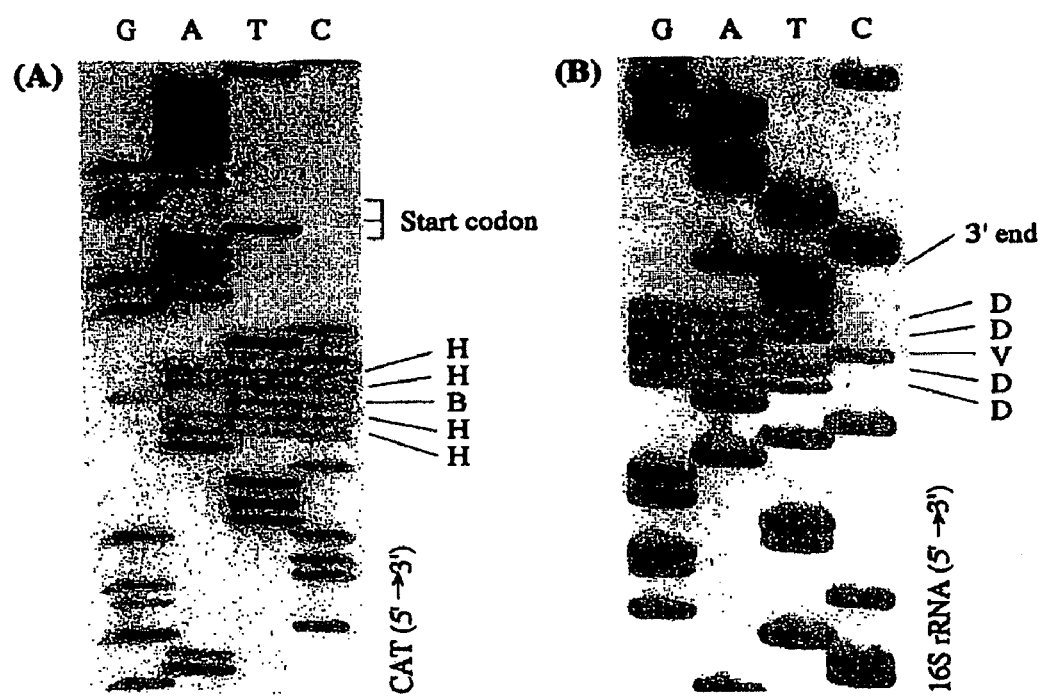

FIG. 3 depicts an autoradiogram of sequencing gels with pRNA8-rMBS-rRBS. The mutagenic MBS and RBS are shown: B 5 C, G, T; D 5 A, G, T; H 5 A, C, T; V 5 A, C, G. The start codon of cam and the 39 end of 16S rRNA are indicated. Panel A depicts the RBS of the CAT gene. Panel B depicts the MBS of the 16S rRNA gene.

Figure 4:
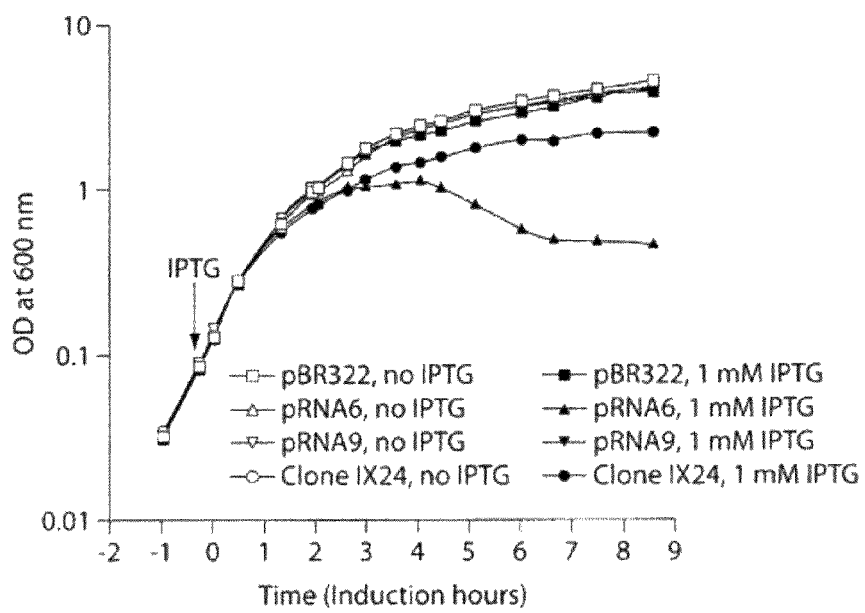

FIG. 4 depicts a graph of the effect of MBSs on growth. The abbreviations in FIG. 4 are defined as follows: pBR322; vector: pRNA6; RBS 5 GUGUG, MBS 5 CACAC: pRNA9; RBS 5 GGAGG (wt), MBS 5 CCUCC (wt): and Clone IX24; RBS 5 AUCCC, MBS 5 GGGAU.

Figure 5:
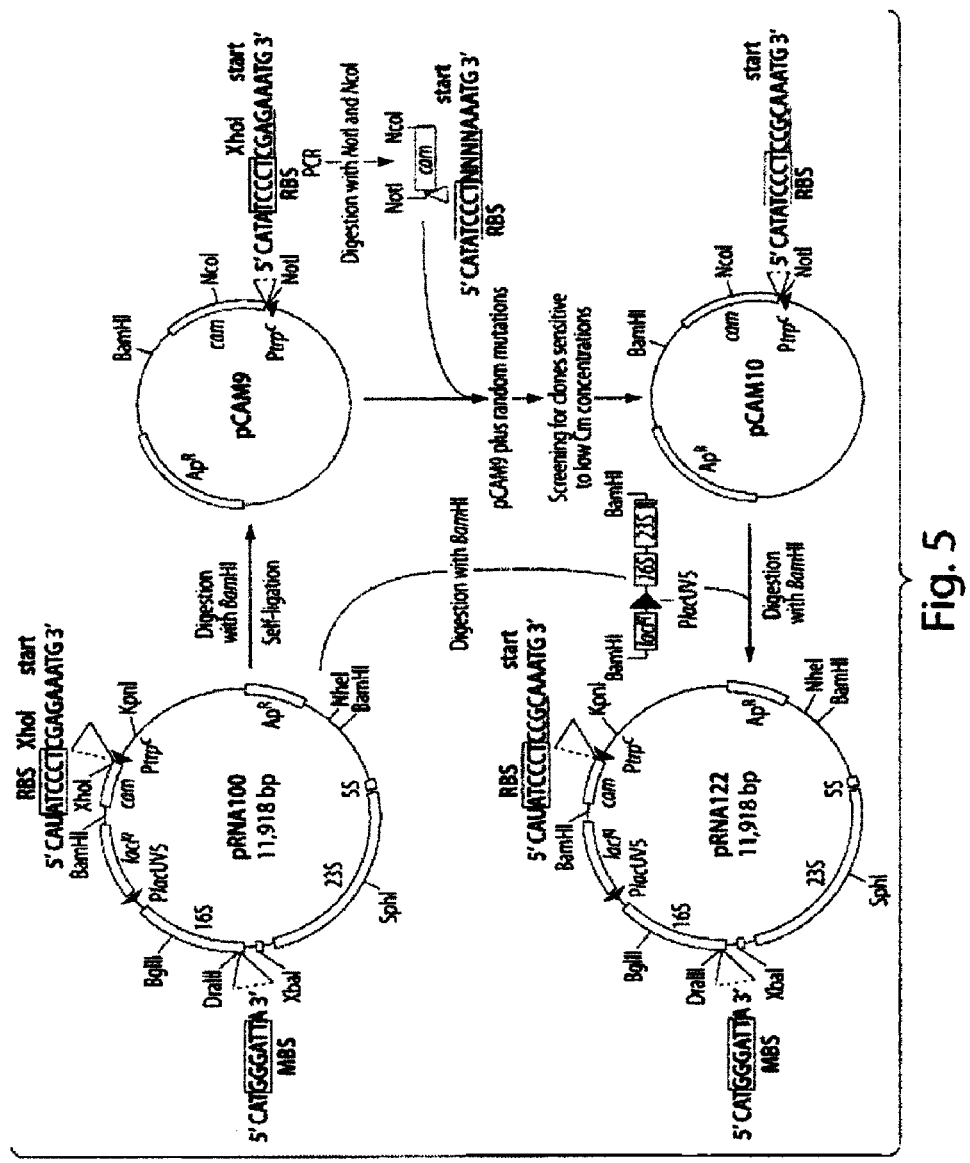

FIG. 5 depicts a scheme for construction of pRNA122. The abbreviations in FIG. 5 are defined as follows: Ap$^r$, ampicillin resistance; cam, CAT gene; lacI$^q$, lactose repressor; PlacUV5, lacUV5 promoter; Ptrp$^c$, constitutive trp promoter; N 5 A, C, G, and T. The four nucleotides mutated are underlined and the restriction sites used are indicated.

Figure 6:
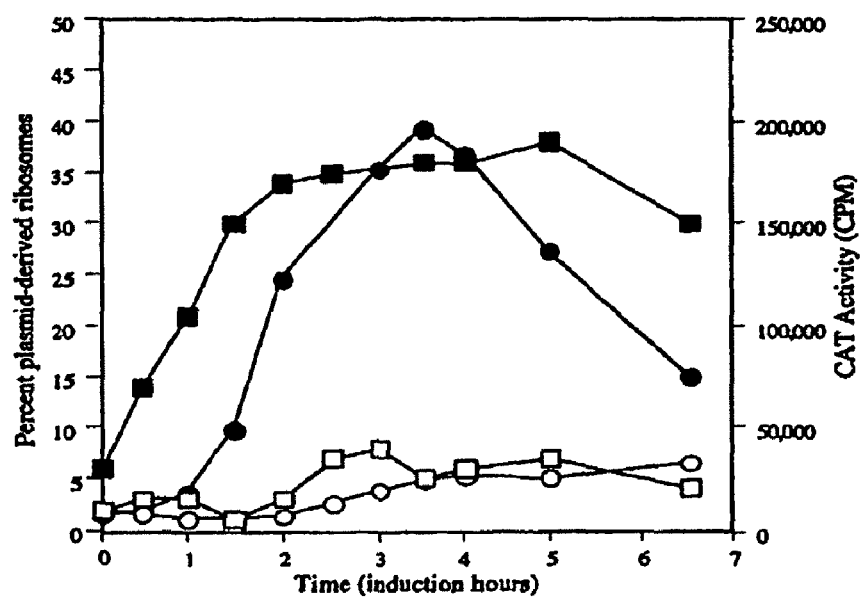

FIG. 6 depicts a plasmid-derived ribosome distribution and CAT activity. Cultures were induced (or not) in early log phase (as shown in FIG. 4) and samples were withdrawn for CAT assay and total RNA preparation at the points indicated. Open squares represent the percent plasmid-derived rRNA in uninduced cells. Closed squares represent the percent plasmid-derived rRNA in induced cells. Open circles represent CAT activity in uninduced cells. Closed circles represent CAT activity in induced cells.

Figure 7:
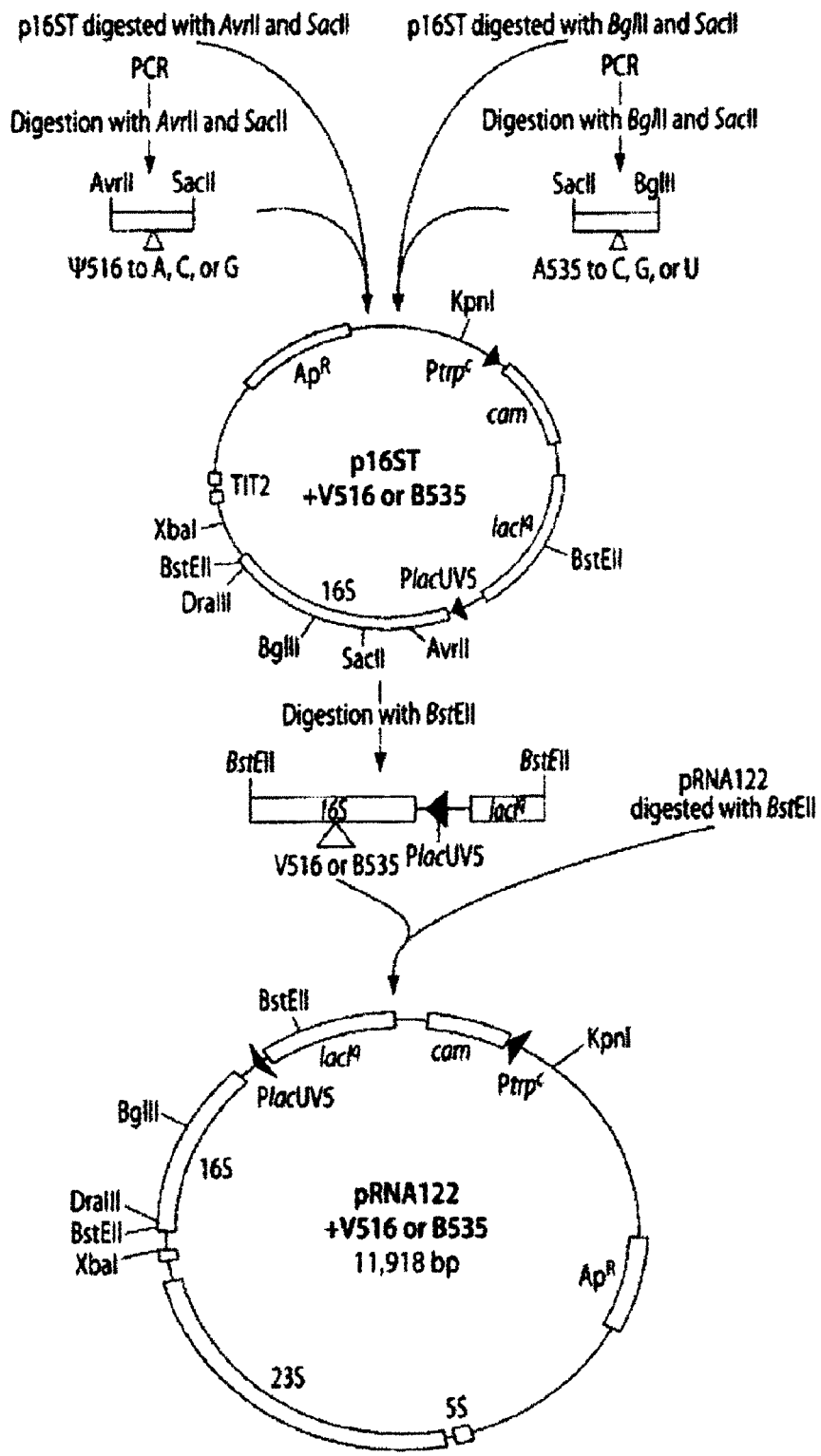

FIG. 7 depicts a scheme for construction of single mutations at positions 516 or 535. The abbreviations in FIG. 7 are defined as follows: Ap$^r$, ampicillin resistance; cam, CAT gene; lacI$^q$, lactose repressor; PlacUV5, lacUV5 promoter; Ptrp$^c$, constitutive trp promoter. C516 was substituted to V (A, C, or G) and A535 was substituted to B (C, G, or T,) in pRNA122 and the restriction sites that were used are also indicated.

Figure 8:
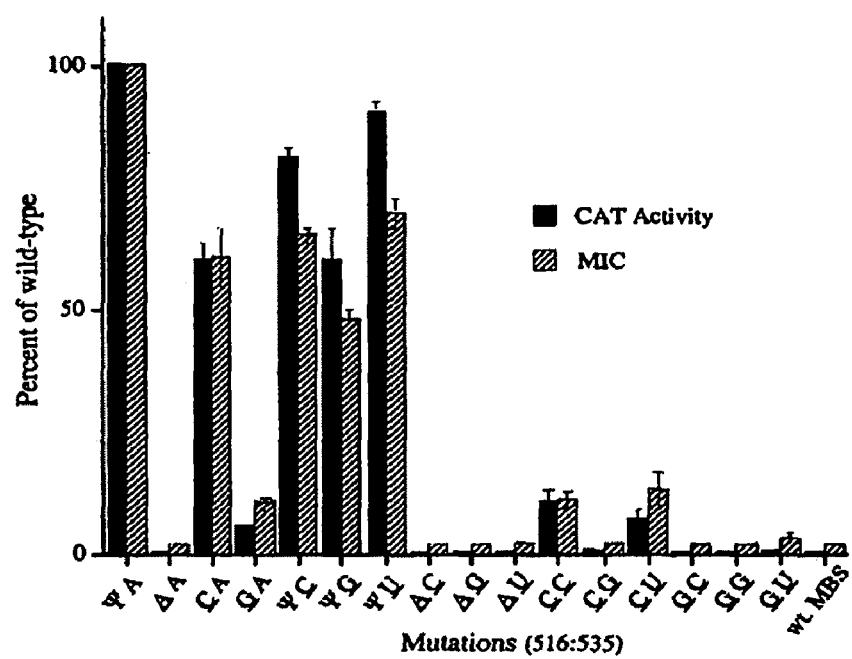

FIG. 8 depicts the functional analysis of mutations constructed at positions 516 and 535 of 16S rRNA in pRNA122. Nucleotide identities are indicated in the order of 516:535 and mutations are underlined. pRNA122 containing the wild-type MBS (wt. MBS) was used as a negative control to assess the degree of MIC and the level of CAT activity due to CAT mRNA translation by wild-type ribosomes. Standard error of the mean is used to indicate the range of the assay results.

FIG. 9 depicts a description and use of oligodeoxynucleotides (SEQ ID NOS:6-23). Primer binding sites are indicated by the number of nucleotides from the 5' nucleotide of the coding region. Negative numbers indicate binding sites 5' to the coding region.

FIG. 10 describes several plasmids used in Example 4.

FIG. 11 depicts the specificity of the selected recombinants. The concentrations of chloramphenicol used are indicated and the unit of MIC is micrograms of chloramphenicol/mL.

FIG. 12 depicts novel mutant ASD sequences and novel mutant SD sequences of the present invention (SEQ ID NOS: 24-47). FIG. 12 also shows a sequence analysis of chloramphenicol resistant isolates. The mutated nucleotides are underlined and potential duplex formations are boxed. CAT activity was measured twice for each culture and the unit is CPM/0.1 µL of culture/OD600. Induction was measured by dividing CAT activity in induced cells with CAT activity in uninduced cells. A -1 indicates no induction, while a +1 indicates induction with 1 mM IPTG.

FIG. 13 depicts novel mutant ASD sequences and novel mutant SD sequences of the present invention (SEQ ID NOS: 48-61). FIG. 13 also shows a sequence analysis of CAT mRNA mutants. Potential duplex formations are boxed and the mutated nucleotides are underlined. The start codon (AUG) is in bold. A -1 indicates no induction, while a +1 indicates induction with 1 mM IPTG.

FIG. 14 depicts the effect of Pseudouridine516 Substitutions on subunit assembly. The percent plasmid-derived 30S data are presented as the percentage of the total 30S in each peak and in crude ribosomes.

FIG. 15 depicts novel mutant ASD sequences and novel mutant SD sequences of the present invention (SEQ ID NOS: 62-111).

FIG. 16 depicts novel mutant ASD sequences and novel mutant SD sequences of the present invention (SEQ ID NOS: 112-159).

FIG. 17 depicts a hybrid construct. This hybrid construct contains a 16S rRNA from Mycobacterium tuberculosis. The specific sites on the hybrid construct are as follows: the part of rRNA from E. coli rrnB operon corresponds to nucleic acids 1-931; the part of 16S rRNA from Mycobacterium tuberculosis rrn operon corresponds to nucleic acids 932-1542; the 16S MBS (message binding sequence) GGGAU corresponds to nucleic acids 1536-1540; the terminator T1 of E. coli rrnB operon corresponds to nucleic acids 1791-1834; the terminator T2 of E. coli rrnB operon corresponds to nucleic acids 1965-1994; the replication origin corresponds to nucleic acids 3054-2438; the bla (β-lactamase; ampicillin resistance) corresponds to nucleic acids 3214-4074; the GFP corresponds to nucleic acids 5726-4992; the GFP RBS (ribosome binding sequence) AUCCC corresponds to nucleic acids 5738-5734; the trp$^c$ promoter corresponds to nucleic acids 5795-5755; the trp$^c$ promoter corresponds to nucleic acids 6270-6310; the CAT RBS (ribosome binding sequence) AUCCC corresponds to nucleic acids 6327-6331; the cam (chloramphenicol acetyltransferase; CAT) corresponds to nucleic acids 6339-6998; the lacI$^q$ promoter corresponds to nucleic acids 7307-7384; the lacI$^q$ (lac repressor) corresponds to nucleic acids 7385-8467; and the lacUV5 promoter corresponds to nucleic acids 8510-8551.

FIG. 18 depicts a plasmid map of pRNA122.

FIG. 19 depicts a table of sequences and MICs of functional mutants (SEQ ID NOS:160-238). Sequences are ranked by the minimum inhibitory concentration ("MIC") of chloramphenicol required to fully inhibit growth of cells expressing the mutant ribosomes. The nucleotide sequences ("Nucleotide sequence") are the 790 loop sequences selected from the pool of functional, randomized mutants. Mutations are underlined. The number of mutations ("Number of mutations") in each mutant sequence are indicated, as well as the number of occurrences ("Number of occurrences") which represents the number of clones with the indicated sequence. The sequence and activity of the unmutated control, pRNA122 (WT, wild-type) is depicted in the first row of FIG. 19, in which the MIC is 600 µg/ml.

FIG. 20 depicts the 790-loop sequence variation. In the consensus sequence R=A or G; N=A, C, G or U; M=A or C; H=A, C or U; W=A or U; Y=C or U; ∆=deletion; and underlined numbers indicate the wild-type E. coli sequence.

FIG. 21 depicts functional and thermodynamic analysis of positions 787 and 795. Mutations have been underlined and "n.d." represents not determined. FIG. 21 shows site-directed mutations ("Nucleotide") that were constructed using PCR, as described for the random mutants, except that the mutagenic primers contained substitutions corresponding only to positions 787 and 795. In order to determine ribosome function ("Mean CAT activity"), each strain was grown and assayed for CAT activity at least twice, the data were averaged, and presented as percentages of the unmutated control, pRNA122+ the standard error of the mean. The ratio of plasmid to chromosome-derived rRNA in 30S and 70 S ribosomes ("% Mutant 30S in 30S peak/70S peak") was determined by primer extension. Cultures were grown and assayed at least twice and the mean values are presented as a percentage of the total 30S in each peak ±the standard error of the mean. Thermodynamic parameters ("Thermodynamics") are for the higher-temperature transition of model oligonucleotides and are the average of results for four or five different oligomer concentrations. Standard errors for the $\Delta G° 37$ are ±5% (1 kcal=4184 J). Errors in $T_m$ are estimated as ±1° C. All solutions were at pH 7.

FIG. 22 depicts the DNA sequence of pRNA8 (SEQ ID NO:1).

FIG. 23 depicts the DNA sequence of pRNA122 (SEQ ID NO:2).

FIG. 24 depicts the DNA sequence of pRNA123 (SEQ ID NO:3).

FIG. 25 depicts the DNA sequence of pRNA123 Mycobacterium tuberculosis-2 (pRNA123 containing a hybrid of E. coli and Mycobacterium tuberculosis 16S rRNA genes) (SEQ ID NO:4).

FIG. 26 depicts the DNA sequence of pRep-Mycobacterium tuberculosis-2 (containing a puc19 derivative containing the rRNA operon from pRNA122; however, the 23S and 5S rRNA genes are deleted) (SEQ ID NO:5).

FIGS. 2-14 may be found in Lee, K., et al. Genetic Approaches to Studying Protein Synthesis Effects of Mutations at Pseudouridine 516 and A535 in Escherichia coli 16S rRNA. Symposium: Translational Control: A Mechanistic Perspective at the Experimental Biology 2001 Meeting (2001); and FIGS. 18-21 may be found in Lee, K. et al., J. Mol. Biol. 269: 732-743 (1997), all of which are expressly incorporated by reference herein.

DETAILED DESCRIPTION OF THE INVENTION

Compositions and methods are provided to identify functional mutant ribosomes suitable as drug targets. The compositions and methods allow isolation and analysis of mutations that would normally be lethal and allow direct selection of rRNA mutants with predetermined levels of ribosome function. The compositions and methods of the present invention may be used to identify antibiotics to treat generally and/or selectively human pathogens.

According to one embodiment of the invention, a functional genomics database for rRNA genes of a variety of species may be generated. In particular, the rRNA gene is randomly mutated using a generalized mutational strategy. A host cell is then transformed with a mutagenized plasmid of the invention comprising: an rRNA gene having a mutant ASD sequence, the mutated rRNA gene, and a genetically engineered gene which encodes a selectable marker having a mutant SD sequence. The selectable marker gene, such as CAT, may be used to select mutants that are functional, e.g., by plating the transformed cells onto growth medium containing chloramphenicol. The mutant rRNA genes contained in each plasmid DNA of the individual clones from each colony are selected and characterized. The function of each of the mutant rRNA genes is assessed by measuring the amount of an additional selectable marker gene, such as GFP, produced by each clone upon induction of the rRNA operon. A functional genomics database may thus be assembled, which contains the sequence and functional data of the functional mutant rRNA genes. In particular, functionally important regions of the rRNA gene that will serve as drug targets are identified by comparing the sequences of the functional genomics database and correlating the sequence with the amount of GFP protein produced.

In another embodiment, the nucleotides in the functionally important target regions identified in the above methods may be simultaneously randomly mutated, e.g., by using standard methods of molecular mutagenesis, and cloned into a plasmid of the invention to form a plasmid pool containing random mutations at each of the nucleotide positions in the target region. The resulting pool of plasmids containing random mutations is then used to transform cells, e.g., E. coli cells, and form a library of clones, each of which contains a unique combination of mutations in the target region. The library of mutant clones are grown in the presence of IPTG to induce production of the mutant rRNA genes and a selectable marker is used, such as CAT, to select clones of rRNA mutants containing nucleotide combinations of the target region that produce functional ribosomes. The rRNA genes producing functional ribosomes are sequenced and may be incorporated into a database.

In yet another embodiment, a series of oligonucleotides may be synthesized that contain the functionally-important nucleotides and nucleotide motifs within the target region and may be used to sequentially screen compounds and compound libraries to identify compounds that recognize (bind to) the functionally important sequences and motifs. The compounds that bind to all of the oligonucleotides are then counterscreened against oligonucleotides and/or other RNA containing molecules to identify drug candidates. Drug candidates selected by the methods of the present invention are thus capable of recognizing all of the functional variants of the target sequence, i.e., the target cannot be mutated in a way that the drug cannot bind, without causing loss of function to the ribosome.

In still another embodiment, after the first stage mutagenesis of the entire rRNA is performed using techniques known in the art, e.g., error-prone PCR mutagenesis, the mutants are analyzed to identify regions within the rRNA that are important for function. These regions are then sorted based on their phylogenetic conservation, as described herein, and are then used for further mutagenesis.

Ribosomal RNA sequences from each species are different and the more closely related two species are, the more their rRNAs are alike. For instance, humans and monkeys have very similar rRNA sequences, but humans and bacteria have very different rRNA sequences. These differences may be utilized for the development of very specific drugs with a narrow spectrum of action and also for the development of broad-spectrum drugs that inhibit large groups of organisms that are only distantly related, such as all bacteria.

In another embodiment, the functionally important regions identified above are divided into groups based upon whether or not they occur in closely related groups of organisms. For instance, some regions of rRNA are found in all bacteria but not in other organisms. Other areas of rRNA are found only in closely related groups of bacteria, such as all of the members of a particular species, e.g., members of the genus *Mycobacterium* or *Streptococcus*.

In a further embodiment, the regions found in very large groups of organisms, e.g., all bacteria or all fungi, are used to develop broad-spectrum antibiotics that may be used to treat infections from a large number of organisms within that group. The methods of the present invention may be performed on these regions and functional mutant ribosomes identified. These functional mutant ribosomes may be screened, for example, with compound libraries.

In yet another embodiment, regions that are located only in relatively small groups of organisms, such as all members of the genus *Streptococcus* or all members of the genus *Mycobacterium*, may be used to design narrow spectrum antibiotics that will only inhibit the growth of organisms that fall within these smaller groups. The methods of the present invention may be performed on these regions and functional mutant ribosomes identified. These functional mutant ribosomes will be screened, e.g., compound libraries.

The invention provides novel plasmid constructs, e.g. pRNA123 (FIGS. 1 and 24). The novel plasmid constructs of the present invention employ novel mutant ASD and mutant SD sequences set forth in FIGS. 12, 13, 15 and 16. The mutant ASD and mutant SD sequences may be used as mutually compatible pairs (see FIGS. 12, 13, 15 and 16). It will be appreciated that the mutually compatible pairs of mutant ASD and SD sequences interact as pairs in the form of RNA, to permit translation of only the mRNAs containing the altered SD sequence.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

As used herein, the term "mutation" includes an alteration in the nucleotide sequence of a given gene or regulatory sequence from the naturally occurring or normal nucleotide sequence. A mutation may be a single nucleotide alteration (e.g., deletion, insertion, substitution, including a point mutation), or a deletion, insertion, or substitution of a number of nucleotides.

By the term "selectable marker" is meant a gene whose expression allows one to identify functional mutant ribosomes.

Various aspects of the invention are described in further detail in the following subsections:

I. Isolated Nucleic Acid Molecules

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention, e.g., a nucleic acid molecule having the nucleotide sequence set forth in FIGS. 12, 13, 15, and 16, or a portion thereof, can be isolated using standard molecular biology techniques and the sequence information provided herein. Using all or portion of the nucleic acid sequence set forth in FIGS. 12, 13, 15, and 16 as a hybridization probe, the nucleic acid molecules of the present invention can be isolated using standard hybridization and cloning techniques (e.g., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989).

Moreover, a nucleic acid molecule encompassing all or a portion of the sequence set forth in FIGS. 12, 13, 15, and 16 can be isolated by the polymerase chain reaction (PCR) using synthetic oligonucleotide primers designed based upon the sequence set forth in FIGS. 12, 13, 15, and 16.

A nucleic acid of the invention can be amplified using cDNA, mRNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequences of the present invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence set forth in FIGS. 12, 13, 15, and 16, or a portion of any of these nucleotide sequences. A nucleic acid molecule which is complementary to the nucleotide sequence shown in FIGS. 12, 13, 15, and 16, is one which is sufficiently complementary to the nucleotide sequence shown in FIGS. 12, 13, 15, and 16, such that it can hybridize to the nucleotide sequence shown in FIGS. 12, 13, 15, and 16, respectively, thereby forming a stable duplex.

II. Recombinant Expression Vectors and Host Cells

Another aspect of the invention pertains to vectors, preferably expression vectors, containing a nucleic acid molecule of the present invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301-315) and pET 11d (Studier et al. (1990) *Methods Enzymol.* 185:60-89). Target gene expression from the pTrc vector relies on host RNA polymerase transcription from a hybrid trp-lac fusion promoter. Target gene expression from the pET 11d vector relies on transcription from a T7 gn 10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119-128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111-2118). Such alteration of nucleic acid sequences of the invention can be carried out by standard DNA synthesis techniques.

In another embodiment, the expression vector may be a yeast expression vector. Examples of vectors for expression in yeast *S. cerevisiae* include pYepSec1 (Baldari et al. (1987) *Embo J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, Calif.), and picZ (Invitrogen Corp, San Diego, Calif.).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., *Molecular Cloning: A Laboratory Manual. 2nd ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) *Science* 249:374-379).

Another aspect of the invention pertains to host cells into which a the nucleic acid molecule of the invention is introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Nucleic acid encoding a selectable marker can be introduced into a host cell on the same vector as that encoding a protein or can be introduced on a separate vector. Cells stably transfected with the introduced nucleic acid can be identified by drug selection (e.g., cells that have incorporated the selectable marker gene will survive, while the other cells die).

III. Uses and Methods of the Invention

The nucleic acid molecules described herein may be used in a plasmid construct, e.g. pRNA123, to carry out one or more of the following methods: (1) creation of a functional genomics database of the rRNA genes generated by the methods of the present invention; (2) mining of the database to identify functionally important regions of the rRNA; (3) identification of functionally important sequences and structural motifs within each target region; (4) screening compounds and compound libraries against a series of functional variants of the target sequence to identify compounds that bind to all functional variants of the target sequence; and (5) counter-screening the compounds against nontarget RNAs, such as human ribosomes or ribosomal RNA sequences.

This invention is further illustrated by the following examples, which should not be construed as limiting. The contents of all references, patents and published patent applications cited throughout this application, as well as the Figures and Appendices, are incorporated herein by reference.

SPECIFIC EXAMPLES

Example 1

Identification of Mutant SD and Mutant ASD Combinations

It has been shown that by coordinately changing the SD and ASD, a particular mRNA containing an altered SD could be targeted to ribosomes containing the altered ASD. This and all other efforts to modify the ASD, however, have proved lethal, as cells containing these mutations died within two hours after the genes containing them were activated.

Using random mutagenesis and genetic selection, mutant SD-ASD combinations were screened in order to identify nonlethal SD-ASD combinations. The mutant SD-ASD mutually compatible pairs are set forth in FIGS. 12, 13 15 and 16. The mutually compatible pairs of mutant sequences interact as pairs in the form of RNA. The novel mutant SD-ASD sequence combinations of the present invention permit translation of only the mRNAs containing the altered SD sequence.

Example 2

Construction of the pRNA123 Plasmid

A plasmid construct of the present invention identified as the pRNA123 plasmid, is set forth in FIGS. 1 and 24. *E. coli* cells contain a single chromosome with seven copies of the rRNA genes and all of the genes for the ribosomal proteins. The plasmid, pRNA123, in the cell contains a genetically engineered copy of one of the rRNA genes from *E. coli* and two genetically engineered genes that are not normally found in *E. coli*, referred to herein as a "selectable markers." One gene encodes the protein chloramphenicol acetyltransferase (CAT). This protein renders cells resistant to chloramphenicol by chemically modifying the antibiotic. Another gene, the Green Fluorescent Protein (GFP), is also included in the system. GFP facilitates high-throughput functional analysis. The amount of green light produced upon irradiation with ultraviolet light is proportional to the amount of GFP present in the cell.

Ribosomes from pRNA123 have an altered ASD sequence. Therefore, the ribosomes can only translate mRNAs that have an altered SD sequence. Only two genes in the cell produce mRNAs with altered SD sequences that may be translated by the plasmid-encoded ribosomes: the CAT and GFP gene. Mutations in rRNA affect the ability of the resulting mutant ribosome to make protein. The present invention thus provides a system whereby the mutations in the plasmid-encoded rRNA gene only affect the amount of GFP and CAT produced. A decrease in plasmid ribosome function makes the cell more sensitive to chloramphenicol and reduces the amount of green fluorescence of the cells. Translation of the other mRNAs in the cell is unaffected since these mRNAs are translated only by ribosomes that come from the chromosome. Hence, cells containing functional mutants may be identified and isolated via the selectable marker.

Example 3

Genetic System for Functional Analysis of Ribosomal RNA

Identification of Functionally Important Regions of rRNA. Functionally important regions of rRNA molecules that may be used as drug targets using a functional genomics approach may be identified through a series of steps. Namely, in step I.a., the entire rRNA gene is randomly mutated using error-prone PCR or another generalized mutational strategy. In step I.b., a host cell is then transformed with a mutagenized plasmid comprising: an rRNA gene having a mutant ASD sequence, at least one mutation in said rRNA gene, and a genetically engineered gene which encodes a selectable marker having a mutant SD sequence, and production of the rRNA genes from the plasmid are induced by growing the cells in the presence of IPTG. In step I.c., the CAT gene is used to select mutants that are functional by plating the transformed cells onto growth medium containing chloramphenicol. In step I.d., individual clones from each of the colonies obtained in step I.c. are isolated. In step I.e., the plasmid DNA from each of the individual clones from step I.d. is isolated. In step I.f., the rRNA genes contained in each of the plasmids that had been isolated in step I.e. are sequenced. In step I.g., the function of each of the mutants from step I.f. is assessed by measuring the amount of GFP produced by each clone from step I.e. upon induction of the rRNA operon. In step I.h., a functional genomics database is assembled containing the sequence and functional data from steps I.f. and I.g. In step I.i., functionally important regions of the rRNA gene that will serve as drug targets are identified. Functionally important regions may be identified by comparing the sequences of all of the functional genomics database constructed in step I.g. and correlating the sequence with the amount of GFP protein produced. Contiguous sequences of three or more rRNA nucleotides, in which substitution of the nucleotides in the region produces significant loss of function, will constitute a functionally important region and therefore a potential drug target.

Isolation of Functional Variants of the Target Regions. A second aspect of the invention features identification of mutations of the target site that might lead to antibiotic resistance using a process termed, "instant evolution", as described below. In step II.a., for a given target region identified in step I.i., each of the nucleotides in the target region is simultaneously randomly mutated using standard methods of molecular mutagenesis, such as cassette mutagenesis or PCR mutagenesis, and cloned into the plasmid of step I.b. to form a plasmid pool containing random mutations at each of the nucleotide positions in the target region. In step II.b., the resulting pool of plasmids containing random mutations from step II.a. is used to transform $E.$ $coli$ cells and form a library of clones, each of which contains a unique combination of mutations in the target region. In step II.c., the library of mutant clones from step II.b. is grown in the presence of IPTG to induce production of the mutant rRNA genes. In step II.d., the induced mutants are plated on medium containing chloramphenicol, and CAT is used to select clones of rRNA mutants containing nucleotide combinations of the target region that produce functional ribosomes. In step II.e., the functional clones isolated in step II.d. are sequenced and GFP is used to measure ribosome function in each one. In step II.f., the data from step II.e. are incorporated into a mutational database.

Isolation of Drug Leads. In step III.a., the database in step II.f. is analyzed to identify functionally-important nucleotides and nucleotide motifs within the target region. In step III.b., the information from step III.a. is used to synthesize a series of oligonucleotides that contain the functionally important nucleotides and nucleotide motifs identified in step III.a. In step III.c., the oligonucleotides from step III.b. are used to sequentially screen compounds and compound libraries to identify compounds that recognize (bind to) the functionally important sequences and motifs. In step III.d., compounds that bind to all of the oligonucleotides are counterscreened against oligonucleotides and/or other RNA containing molecules to identify drug candidates. "Drug candidates" are compounds that 1) bind to all of the oligonucleotides containing the functionally important nucleotides and nucleotide motifs, but do not bind to molecules that do not contain the functionally important nucleotides and nucleotide motifs and 2) do not recognize human ribosomes. Drug candidates selected by the methods of the present invention therefore recognize all of the functional variants of the target sequence, i.e., the target cannot be mutated in a way that the drug cannot bind, without causing loss of function to the ribosome.

Example 4

Genetic System for Studying Protein Synthesis

Materials and Methods

Reagents. All reagents and chemicals were as in Lee, K., et al. (1996) $RNA$ 2: 1270-1285. PCR-directed mutagenesis was performed essentially by the method of Higuchi, R. (1989) $PCR$ $Technology$ (Erlich, H. A., ed.), pp. 61-70. Stockton Press, New York, N.Y. The primers used in the present invention are listed in FIG. 9. The plasmids used in the present invention are listed in FIG. 10.

Bacterial strains and media. All plasmids were maintained and expressed in $E.$ $coli$ DH5 (supE44, hsdR17, recA1, endA1, gyrA96, thi-1 and relA1) (36). To induce synthesis of plasmid-derived rRNA from the lacUV5 promoter, IPTG was added to a final concentration of 1 mM. Chloramphenicol acetyltransferase activity was determined essentially as described by Nielsen et al. (1989) $Anal.$ $Biochem.$ 179: 19-23. Cultures for CAT assays were grown in LB-Ap100. MIC were determined by standard methods in microtiter plates as described in Lee, K., et al. (1997) $J.$ $Mol.$ $Biol.$ 269: 732-743.

Primer extension. To determine the ratio of plasmid to chromosome-derived rRNA, pRNA104 containing cells growing in LB-Ap100 were harvested at the time intervals indicated and total RNA was extracted using the Qiagen RNeasy kit (Chatsworth, Calif.). The 30S, 70S, and crude ribosomes were isolated from 200 mL of induced, plasmid containing cells by the method of Powers and Noller (Powers, T. et al. (1991) $EMBO$ $J.$ 10: 2203-2214). The purified RNA was analyzed by primer extension according to Sigmund, C. D., et al. (1988) $Methods$ $Enzymol.$ 164: 673-690.

Experimental Procedures

Generation of pRNA9 construct. The initial construct, pRNA9, was generated using the following methods. Plasmid pRNA9 contains a copy of the rrnB operon from pKK3535 under transcriptional regulation of the lacUV5 promoter; this well-characterized promoter is not subject to catabolic repression and is easily and reproducibly inducible with isopropyl-β-D-thiogalactoside (IPTG). To minimize transcription in the absence of inducer, PCR was used to amplify and subclone the lac repressor variant, lacI$^q$ (Calos, M. P. (1978) $Nature$ 274: 762-765) from pSPORT1 (Life Technologies, Rockville, Md.). The chloramphenicol acetyltransferase gene (cam) is present and transcribed constitutively from a mutant tryptophan promoter, trp$^c$ (De Boer, H. A., et al. (1983) $Proc.$ $Natl.$ $Acad.$ $Sci.$ $U.S.A.$ 80: 21-25; Hui, A., et al. (1987) $Proc.$ $Natl.$ $Acad.$ $Sci.$ $U.S.A.$ 84: 4762-4766). The β-lactamase gene is also present to allow maintenance of plasmids in the host strain. To allow genetic selection, the CAT structural gene from pJLS1021 (Schottel, J. L., et al. (1984) $Gene$ 28: 177-193) was amplified and placed downstream of a constitutive trp$^c$ promoter using PCR. Expression of the CAT gene in $E.$ $coli$ renders the cell resistant to chloramphenicol and the minimal inhibitory concentration, hereinafter referred to as MIC, of chloramphenicol increases proportionally with the amount of CAT protein produced (Lee, K., et al. (1996) $RNA$ 2: 1270-1285; Lee, K., et al. (1997) $J.$ $Mol.$ $Biol.$ 269: 732-743) An overview of the steps used to construct the system is shown in FIG. 2.

Selection of a new MBS-RBS pair. To isolate message binding site-ribosome binding site, hereinafter referred to as MBS-RBS, combinations that are nonlethal and efficiently translated only by plasmid-derived ribosomes, a random mutagenesis and selection scheme were used. In particular, the plasmid-encoded 16S MBS and CAT RBS were randomly mutated using PCR so that the wild-type nucleotide at each position was excluded. An autoradiogram of sequencing gels with pRNA8-rMBS-rBBS is provided in FIG. 3. The resulting $2.5 \times 10^6$ doubly mutated transformants were induced for 3.5 hours in SOC medium containing 1 mM IPTG and plated on Luria broth medium containing 100 μg/mL ampicillin, 350 μg/mL chloramphenicol and 1 mM IPTG. To confirm the presence of all three alternative nucleotides at each mutated position, plasmid DNA from approximately $2.0 \times 10^5$ transformants was sequenced (FIG. 3).

Results

The data show that all of the nonexcluded nucleotides were equally represented in the random pool. Of the $2.5 \times 10^6$ transformants plated, 536 survived the chloramphenicol selection. The efficiency of the selected MBS-RBS combinations was determined by measuring the minimal inhibitory concentration, hereinafter referred to as MIC, of chloramphenicol for each survivor in the presence and absence of inducer (FIG. 11) (Lee, K., et al. (1996) *RNA* 2: 1270-1285; Lee, K., et al. (1997) *J. Mol. Biol.* 269: 732-743). Nine of the isolates (1.7%) showed MIC in the presence of inducer, which were lower than the 350 μg/mL concentration at which they were selected. These were slow growing mutants that appeared after 48 hours during the initial isolation. The MIC, however, were scored after only 24 hours. The MIC for 451 of the isolates (84.1%) were between 400 and 600 μg/mL, and the remaining 76 clones (14.2%) were 600 μg/mL. The difference in chloramphenicol resistance between induced and uninduced cells (ΔMIC) is the amount of CAT translation by plasmid-derived ribosomes only. A specific interaction between plasmid-derived ribosomes and CAT mRNA was indicated in 79 (14.7%) of the clones, which showed four- to eightfold increases in CAT resistance upon addition of IPTG (FIG. 11).

Based on these analyses, 11 clones were retained for additional study. The MBS and RBS in plasmids from these clones were sequenced and CAT assays and growth curves were performed (FIGS. 4 and 12). Although a wide range of inducibility was observed, there was no correlation between specificity and predicted free energy ($\Delta G^{-37}$). Purines were preferred in all of the MBS positions, but the RBS did not show this sort of selectivity. This can be explained partially by the observation that the selected RBS can base pair with sequences adjacent to the mutated region of 16S rRNA (Lee, K., et al. (1996)*RNA* 2: 1270-1285).

Growth curves were performed for all of the selected mutants and compared with strains containing control constructs (FIG. 4). Only one mutant (IX24) is shown in FIG. 4, but all strains containing the selected MBS/RBS sequences showed the same pattern of growth as this mutant. Because of its induction profile, strain IX24 (containing plasmid pRNA100) was chosen for additional experimentation. To eliminate the possibility that mutations outside the MBS and RBS had been inadvertently selected, the DraIII and XbaI fragment containing the MBS and the KpnI and XhoI fragment containing the RBS sequence from pRNA100 (FIG. 5) were transferred to pRNA9.

Specificity of the system. The rate of ribosome induction and the ratio of plasmid to chromosome-derived rRNA at each stage of growth were determined. For this, a pRNA100 derivative, pRNA104, which contains a C1192U mutation in 16S rRNA was constructed (Sigmund, C. D., et al. (1984) *Nucleic Acids Res.* 12: 4653-4663; Triman, K., et al. (1989) *J. Mol. Biol.* 209: 645-653) so that plasmid-derived rRNA could be differentiated from wild-type rRNA by primer extension.

The C1192U mutation does not affect ribosome function in other expression systems (Sigmund, C. D., et al. (1984) *Nucleic Acids Res.* 12: 4653-4663; Makosky, P. C. et al. (1987) *Biochimie* 69: 885-889). To show that the same is true in the present system, CAT activity was measured after 3 hours induction with 1 mM IPTG in DH5 cells expressing pRNA100 or pRNA104 and the two were compared. In these experiments, no significant difference between cells expressing pRNA104 (99.2±2.8%) or pRNA100 (100%) was observed.

To determine the percentage of plasmid-derived ribosomes in cells containing the plasmid, total RNA was isolated from DH5 cells carrying pRNA104 before and after induction with IPTG and subjected to primer extension analysis (Lee, K., et al. (1997) *J. Mol. Biol.* 269: 732-743; Sigmund, C. D., et al. (1984) *Nucleic Acids Res.* 12: 4653-4663; Makosky, P. C. et al. (1987) *Biochimie* 69: 885-889). Maximum induction of plasmid-derived ribosomes occurred 3 hours after induction at which point they constituted approximately 40% of the total ribosome pool (FIG. 6). CAT activities in these cells paralleled induction of plasmid-derived ribosomes and began to decrease 4 hours after induction, presumably due to protein degradation during stationary phase. In uninduced cells, approximately 3% of the total ribosome pool contains plasmid-derived ribosomes because of basal level transcription from the lacUV5 promoter.

Optimization of the system. Chloramphenicol resistance in uninduced cells containing pRNA100 is 75 μg/mL (FIG. 13, MIC=100 μg/mL). By measuring CAT resistance in a derivative of pRNA100 containing a wild-type 16S rRNA gene, it was determined that approximately one-half of this background activity was due to CAT translation by wild-type ribosomes (FIG. 13, pRNA100 1 wt MBS). The remaining activity in uninduced cells is presumably due to leakiness of the lacUV5 promoter (FIG. 6). The nucleotide sequence located between the RBS and the start codon in mRNA affects translational efficiency (Calos, M. P. (1978) *Nature* 274: 762-765; Stormo, G. D., et al. (1982) *Nucleic Acids Res.* 10: 2971-2996; Chen, H., et al. (1994) *Nucl. Acids Res.* 22: 4953-4957). In pRNA100, three of the nucleotides found in this region of the CAT mRNA are complementary with the 3' terminus of wild-type *E. coli* 16S RNA (FIG. 11, pRNA100 1 wt MBS). To eliminate the possibility that this was contributing to CAT translation in the absence of plasmid-encoded ribosomes, four nucleotides in the CAT gene (underlined in FIG. 11) were randomly mutagenized and screened to identify mutants with reduced translation by host ribosomes. A total of 2000 clones were screened in the absence of plasmid-encoded ribosomes using pCAM9 and six poorly translated CAT sequences were isolated (FIG. 13). Next, the BamHI fragment of pRNA100 containing lacI$^q$ and the rrnB operon was added, and MIC, CAT assays and growth curves were performed on cells expressing these constructs (data not shown).

Based on these data, pRNA122 was chosen because it produced a slightly better induction profile than the others (FIGS. 11 and 23). Translation of the pRNA122 CAT message by wild-type ribosomes (FIG. 11, pRNA122 1 wt MBS) produces cells that are sensitive to chloramphenicol concentrations <10 μg/mL. In the presence of specialized ribosomes (FIG. 13, pRNA122), the background chloramphenicol MIC is between 40 and 50 μg/mL and the MIC for induced cells is between 550 and 600 μg/mL, producing an approximately 13-fold increase in CAT expression upon induction in pRNA122. Induction of the rrnB operon in pRNA100 produces only an eightfold increase.

Use of the system. To test the system, the effects of nucleotide substitutions at the sole pseudouridine in *E. coli* 16S rRNA, located at position 516 were examined. Because pseudouridine and U form equally stable base pairs with adenosine (Maden, B. E. (1990) *Prog. Nucleic Acid Res.* Mol. Biol. 39: 241-303), mutations at A535 were also constructed to determine whether the potential for base pair formation between these two loci affected ribosome function. The mutations were constructed initially in a pUC19 (Yanisch-Perron, C., et al. (1985) *Gene* 33: 103-119) derivative containing the 16S RNA gene, p16ST, as shown in FIG. 7 and then transferred to pRNA122 for analysis. This two-step process was used, because the SacII restriction site located between the two mutated positions is unique in pRNA16ST and is not unique in pRNA122. The effect of the mutations in pRNA122 on protein synthesis in vivo was determined by measuring the MIC and CAT activity of the mutant cells (FIG. 8). At position 516, ribosomes containing the single transition mutation, pseudouridine516C, produced approximately 60% of the amount of functional CAT protein produced by wild-type ribosomes. The transversion mutations, pseudouridine516A or pseudouridine516G, however, reduced ribosome function by >90%. All of the single mutations at position 535 retained >50% of the function of wild-type ribosomes. To examine the possibility that the potential for base pairing between positions 516 and 535 is necessary for ribosome function, all possible mutations between these loci were also constructed and analyzed (FIG. 8). These data show that all of the double mutants were inactive (10% or less of the wild-type) regardless of the potential to base pair. To examine the reasons for loss of function in the 516 mutants, ribosomes from cells expressing single mutations at position 516 were fractionated by sucrose density gradient centrifugation and the 30S and 70S peaks were analyzed by primer extension to determine the percentage of plasmid-derived 30S subunits present. The data in FIG. 14 show a strong correlation between ribosome function and the presence of plasmid-derived ribosomes in the 70S ribosomal fraction, indicating that mutations at positions 516 affect the ability of the mutant 30S subunits to form 70S ribosomes.

The references cited in Example 4 may be found in Lee, K., et al. Genetic Approaches to Studying Protein Synthesis: Effects of Mutations at Pseudouridine516 and A535 in *Escherichia coli* 16S rRNA. *Symposium: Translational Control: A Mechanistic Perspective* at the Experimental Biology 2001 Meeting (2001) and at Lee, K. et al. (2001) Genetic Approaches to Studying Protein Synthesis: Effects of Mutations at Pseudouridine516 and A535 in *Escherichia coli* 16S rRNA. *J. Nutrition* 131 (11):2994-3004.

Example 5

In Vivo Determination of RNA Structure-Function Relationships

Materials and Methods

Reagents. Restriction enzymes, ligase, AMV reverse transcriptase and calf intestine alkaline phosphatase were from New England Biolabs and from Gibco-BRL. Sequenase modified DNA polymerase, nucleotides and sequencing buffers were from USB/Amersham. Oligonucleotides were synthesized on-site using a Beckman Oligo 1000 DNA synthesizer. Amplitaq DNA polymerase and PCR reagents were from Perkin-Elmer-Cetus. [$^3$H]Chloramphenicol (30.1 Ci/mmol) was from Amersham and [α-$^{35}$S]dATP (1000 Ci/mmol) was from New England Nuclear. Other chemicals were from Sigma.

pRNA122. The key features of this construct are: (1) it contains a copy of the rrnB operon from pKK3535 (Brosius. J., et al. (1981) *Plasmid* 6:112-118.) under transcriptional regulation of the lacUV5 promoter; (2) it contains a copy of the lactose repressor allele lacI$^q$ (Calos, M. P. (1978) *Nature* 274:762-769; (3) the chloramphenicol acetyltransferase gene (cam) is present and transcribed constitutively from a mutant tryptophan promoter, trp$^c$ (de Boer, H. A., et al. (1983) *Proc. Natl. Acad. Sci. USA* 80:21-25); (4) the RBS of the CAT message has been changed from the wild-type, 5'-GGAGG to 5'-AUCCC, and the MBS of the 16S rRNA gene has been changed to 5'-GGGAU; and (5) the β-lactamase gene is present to allow maintenance of plasmids in the host strain.

Bacterial strains and media. Plasmids were maintained and expressed in *E. coli* DH5 (supE44, hsdR17, recA1, endA1, gyrA96, thi-1; Hanahan, D. (1983) *J. Mol. Biol.* 166:557-580). Cultures were grown in LB medium (Luria, S. E. & Burrous, J. W. (1957) *J. Bacteriol.* 74:461-476) or LB medium containing 100 μg/ml ampicillin (LB-Ap100). To induce synthesis of plasmid-derived rRNA from the lacUV5 promoter, IPTG was added to a final concentration of 1 mM at the times indicated in each experiment. Strains were transformed by electroporation (Dower, W. J., et al. (1988) *Nucl. Acids Res.* 16: 6127) using a Gibco-BRL Cell Porator. Unless otherwise indicated, transformants were grown in SOC medium (Hanahan, 1983, supra) for one hour prior to plating on selective medium to allow expression of plasmid-derived genes.

Chloramphenicol acetyltransferase assays. CAT activity was determined essentially as described (Nielsen, D. A. et al. (1989) *Anal. Biochem.* 60:191-227). Cultures for CAT assays were grown in LB-Ap100. Briefly, 0.5 ml aliquots of mid-log cultures (unless otherwise indicated) were added to an equal volume of 500 mM Tris-HCl (pH8) and lysed using 0.01% (w/v) SDS and chloroform (Miller, J. H. (1992) A Short Course in Bacterial Genetics, (Miller, J. H., ed.), pp. 71-80, Cold Spring Harbor Laboratory Press, Cold Spring Harbor, N.Y.). The resulting lysate was either used directly or diluted in assay buffer prior to use. Assay mixtures contained cell extract (5 μl or 10 μl), 250 mM Tris (pH 8), 214 μM butyryl-coenzyme A (Bu-CoA), and 40 μM [$^3$H]chloramphenicol in a 125 μl volume. Two concentrations of lysate were assayed for one hour at 37° C. to ensure that the signal was proportional to protein concentrations. The product, butyryl-[$^3$H]chloramphenicol was extracted into 2,6,10,14-tetramethylpentadecane:xylenes (2:1) and measured directly in a Beckman LS-3801 liquid scintillation counter. Blanks were prepared exactly as described above, except that uninoculated LB medium was used instead of culture.

Minimum inhibitory concentration determination. MICs were determined by standard methods in microtiter plates or on solid medium. Overnight cultures grown in LB-Ap100 were diluted and induced in the same medium containing 1 mM IPTG for three hours. Approximately $10^4$ induced cells were then added to wells (or spotted onto solid medium) containing LB-Ap100+ IPTG (1 mM) and chloramphenicol at increasing concentrations. Cultures were grown for 24 hours and the lowest concentration of chloramphenicol that completely inhibited growth was designated as the MIC.

Random mutagenesis and selection. Random mutagenesis of the 790 loop was performed essentially by the method of Higuchi (1989) using PCR and cloned in pRNA122 using the unique BglII and DraIII restriction sites (Higuchi, R. (1989) PCR Technology (Erlich, H. A., ed.), pp. 61-70, Stockton Press, New York) (FIG. 18). For each set of mutations, four primers were used: two "outside" primers and two "inside" primers. The two outside primers were designed to anneal to either side of the BglII and DraIII restriction sites in pRNA122 (FIG. 2). These primers were 16S-DraIII, 5'-GA-CAATCTGTGTGAGCACTA-3' (SEQ ID NO:239) and 16S-535, 5'-TGCCAGCAGCCGCGGTAATACGGAGGGT-GCAAGCGT-3' (SEQ ID NO:240). The inside primers were 16S-786R, 5'-CCTGTTTGCTCCCCACGCTTTCGCAC-CTGAGCG-3' (SEQ ID NO:241) and 16S-ASS-3,5'-CT-CAGGTGCGAAAGCGTGGGGAGCAAACAGG CCTG-GTAGTCC ACGCC GTAA-3' (SEQ ID NO:242) (N=A, T, C and G). Thus, $4^9$=262,144 possible combinations were created, with the exception of 320 sequences that were eliminated because they formed either BglII or DraIII recognition sites (256 BglII sites and 64 DraIII sites).

Transformants were incubated in SOC medium containing 1 mM IPTG for four hours to induce rRNA synthesis and then plated on LB agar containing 100 µg/ml chloramphenicol. A total of 2×10⁶ transformants were plated yielding approximately 2000 chloramphenicol-resistant survivors. Next, 736 of these survivors were randomly chosen and assayed to determine the MIC of chloramphenicol necessary to completely inhibit growth in cells expressing mutant ribosomes. From this pool, 182 transformants with MICs greater than 100 µg/ml were randomly selected and sequenced.

Site-directed mutation of positions 787 and 795. Mutations at positions 787 and 795 were constructed as described above for the random mutants, except that the inside primers were 16S-786R (see above) and 16S-ASS-4,5'-CTCAGGTGC-GAAAGCGTGGGGAGCAAACAGGNTTAGA-TANCCTGGTAGTCC ACGCCGTAA-3' (SEQ ID NO:243) (N=A, T, C and G). Transformants were selected on LB-Ap100 agar plates and grouped according to their MICs for chloramphenicol. Representatives from each group were then sequenced to identify the mutations.

Primer extension. To determine the ratio of plasmid to chromosome-derived rRNA, 30S and 70 S ribosomes were isolated from 200 ml of induced, plasmid containing cells by the method of Powers & Noller (1991). The purified RNA was then used in primer extension experiments (Triman, K., et al. (1989) *J. Mol. Biol.* 209:643-653). End-labeled primers complementary to sequences 3' to the 788 and 795 mutation sites were annealed to rRNA from induced cells and extended through the mutation site using AMV reverse transcriptase. The primers used were: 16S-806R, 5'-GGACTACCAGGG-TATCT-3' (SEQ ID NO:244); 16S-814R, 5'-TACGGCGTG-GACTACCA-3' (SEQ ID NO:245). For wild-type pRNA122 ribosomes, position 1192 in the 16S RNA gene was changed from C to U and primers were constructed as described above (Triman et al., 1989, supra). This mutation has previously been shown not to affect subunit association (Sigmund, C. D., et al. (1988) *Methods Enzymol.* 164:673-689). The extension mixture contained a mixture of three deoxyribonucleotides and one dideoxyribonucleotide. The cDNAs were resolved by PAGE and the ratios of mutant to non-mutant ribosomes were determined by comparing the amount of radioactivity in each of the two bands.

Oligoribonucleotide synthesis. Oligoribonucleotides were synthesized on solid support with the phosphoramidite method (Capaldi, D. & Reese, C. (1994) *Nucl. Acids Res.* 22:2209-2216) on a Cruachem PS 250 DNA/RNA synthesizer. Oligomers were removed from solid support and deprotected by treatment with ammonia and acid following the manufacturer's recommendations. The RNA was purified on a silica gel Si500F TLC plate (Baker) eluted for five hours with n-propanol/ammonia/water (55:35:10, by vol.). Bands were visualized with an ultraviolet lamp and the least mobile band was cut out and eluted three times with 1 ml of purified water. Oligomers were further purified with a Sep-pak C-18 cartridge (Waters) and desalted by continuous-flow dialysis (BRL). Purities were checked by analytical C-8 HPLC (Perceptive Biosystems) and were greater than 95%.

Experimental Procedures

Sequence analysis of functional mutants. Random mutations were introduced simultaneously at all nine positions (787 to 795) in the 790 loop. Functional (chloramphenicol-resistant) mutants were then selected in *E. coli* DH5 cells (Hanahan, 1983, supra) and the effects of these mutations on ribosome function were determined A total of 182 mutants that retained chloramphenicol resistance were randomly selected and sequenced. Wild-type 790-loop sequences were obtained from 81 of the sequenced transformants, while the remaining 101 contained mutant sequences. One of the transformants was chloramphenicol-resistant in the absence of inducer, presumably due to a spontaneous mutation in the CAT gene, and was excluded from further analysis. Of 100 sequenced functional mutants, 14 were duplicates and four sequences occurred three times. Thus, 78 different, functional, 790-loop mutants were analyzed (FIG. 19). According to resampling theory, this distribution indicates that of the $4^9$=262,144 possible sequences, only 190 (standard deviation 30) unique sequences exist in the pool of selected functional mutants. Of the 78 mutants, 44 contained four to six substitutions out of the nine bases mutated and 21 of these retained greater than 50% of the wild-type activity. The minimal inhibitory concentration (MIC) of chloramphenicol for cells expressing wild-type rRNA from pRNA122 is 600 µg/ml. MICs of the mutants ranged from 150 to 550 µg/ml with a mean of 320 µg/ml (standard deviation 89). The median and mode were both 350 µg/ml.

Functional 790-loop mutants showed strong nucleotide preferences at all mutated positions, except positions 788 and 792, which showed a random distribution (FIG. 20) but significant covariation. No mutations were observed at U789 or G791. Mutations at these positions, however, were present in mutants that were selected for loss of function (not shown). Thus, these nucleotides appear to be directly involved in ribosome function. U789 is strictly conserved among bacteria but is frequently C789 among other organisms (FIG. 20). Chemical protection studies have shown that G791 is specifically protected from kethoxal modification in 70 S ribosomes and polysomes (Brow, D. A. & Noller, H. F. (1983) *J. Mol. Biol.* 163: 112-118; Moazed, D. & Noller, H. F. (1986) J. Mol. Biol. 191: 483-493); and by poly(U) (Moazed & Noller, 1986, supra) and that G791 becomes more accessible to kethoxal modification when 30S subunits are converted from the "inactive" to "active" conformation (Moazed et al., 1986, supra).

Purines were strongly selected at position 787 (97.4%) while A and, to a lesser extent, C were preferred at position 790 (98.7%) and U was completely excluded at both positions. At both position 793 and 795, A, C and U were equally distributed but G was selected against. Adenine and uracil were preferred at position 794 (81.8%).

Non-random distribution of nucleotides among the selected functional clones indicates that nucleotide identity affects the level of ribosome function. To examine this, the mean activities (MICs) of ribosomes containing all mutations at a given position were compared by single-factor analysis of variance between ribosome function (MIC) and nucleotide identity at each mutated position. Positions that showed a significant effect of nucleotide identity upon the level of ribosome function were 787 (P <0.001), 788 (P <0.05) and 795 (P<0.001). The absence of mutations at positions U789 and G791 in the functional clones prevents statistical analysis of these positions but mutations at these positions presumably strongly affect ribosome function as well.

FIG. 20 shows a comparison of the selected functional mutants with current phylogenetic data (R. Gutell, unpublished results; Gutell, R. R. (1994) *Nucl. Acids Res.* 22(17): 3502-3507; Maidak, B. L. et al. (1996) *Nucl. Acids Res.* 24: 82-85). While nucleotide preferences in the selected mutants are similar to those observed in the phylogenetic data, the mutant sequences selected in this study show much more variability than those found in nature. This may be because all of the positions in the loop were mutated simultaneously, allowing normally deleterious mutations in one position to be compensated for by mutations at other positions, a process that is unlikely to occur in nature. In addition, none of the mutants was as functional as the wild-type, suggesting that wild-type 790-loop sequences have been selected for optimal activity or that other portions of the translational machinery have been optimized to function with the wild-type sequence.

To identify potential nucleotide covariation within the loop, the paired distribution of selected nucleotides was examined for goodness of fit. The most significant covariations were observed between positions 787 and 795 (P <0.001) and between positions 790 and 793 (P <0.001). For positions 790 and 793, only eight double mutants were available for analysis; therefore, the covariation observed between these positions should be regarded with caution. Position 788, which showed no nucleotide specificity, did show significant covariation with positions 787 (P<0.01), 794 (P <0.01) and 795 (P <0.01).

Analysis of site-directed mutations constructed at the base of the loop:

Functional analysis of mutations at positions 787 and 795. The observed covariations among positions 787, 788 and 795 are particularly interesting, since nucleotide identity at these positions correlated with the level of ribosome function. Further analysis of nucleotides at positions 787 and 795 revealed that 72 of the 78 functional mutants have the potential to form mismatched base-pairs (A.C, G.U, A.A and G.G). Other mismatches, such as G.A and U.G, however, were not found. In addition, only four sequences with an A.U Watson-Crick pair and no sequences with a U.A, G.C or C.G pair were present, suggesting that strong base-pairs between these positions inhibit ribosome function. Therefore all possible nucleotide combinations at positions 787 and 795 were constructed and analyzed without changing other nucleotides in the 790 loop. Ribosome function of the mutants (FIG. 21) varied from 84% (A.A) to 1% (C.G) of the wild-type. As predicted by analysis of the pool of functional random mutants, site-directed mutants with G.C, C.G and U.A Watson-Crick pairs between positions 787 and 795 were strongly inhibitory.

Results

These data suggest that strong pairing between nucleotides at positions 787 and 795 inhibits ribosome function. In addition, some of the site-directed substitutions at positions 787 and 795 that produced functional ribosomes were largely excluded from the pool of mutants in which all of the loop positions were mutated simultaneously (e.g. CC, CU, UU and UC). The observed nucleotide preferences at positions 787 and 795 in the selected random pool presumably reflect interaction of nucleotides at these positions with other nucleotides in the loop. This is consistent with our findings of extensive covariations among these sites.

Perturbations of the 790 loop have been shown to affect ribosomal subunit association (Herr, W., et al. (1979) *J. Mol. Biol.* 130: 433-449; Tapprich, W. & Hill, W., (1986) *Proc. Natl. Acad. Sci. USA* 83: 556-560; Tapprich, W., et al. (1989) *Proc. Natl. Acad. Sci. USA* 86: 4927-4931). Therefore several of the 787 to 795 mutants were tested for their ability to form 70 S ribosomes. Ribosomes were isolated from selected mutants and the distribution of mutant ribosomes in both the 70 S and 30S peaks was determined by primer extension (FIG. 21). These data show that CAT activity correlates with the presence of mutant 30S subunits in the 70 S ribosome pool. Thus, loss of function may be due to the inability of mutant 30S and 50 S subunits to associate. Another explanation for this observation is that the mutations may directly affect a stage of the protein synthesis process prior to subunit association, such as initiation, which prevents subsequent steps from occurring. Other mutations in the 16S rRNA have been identified for which this appears to be the case (Cunningham, P., et al. (1993) *Biochemistry* 32: 7172-7180).

The references cited in Example 5 may be found in Lee, K. et al., *J. Mol. Biol.* 269: 732-743 (1997), expressly incorporated by reference herein.

Example 6

Construction of a Hybrid Construct

A plasmid construct of the present invention identified as the hybrid construct, is set forth in FIGS. 17 and 25. This hybrid construct contains a 16S rRNA from *Mycobacterium tuberculosis*. The specific sites on the hybrid construct are as follows: the part of rRNA from *E. coli* rrnB operon corresponds to nucleic acids 1-931; the part of 16S rRNA from *Mycobacterium tuberculosis* rrn operon corresponds to nucleic acids 932-1542; the 16S MBS GGGAU corresponds to nucleic acids 1536-1540; the terminator T1 of *E. coli* rrnB operon corresponds to nucleic acids 1791-1834; the terminator T2 of *E. coli* rrnB operon corresponds to nucleic acids 1965-1994; the replication origin corresponds to nucleic acids 3054-2438; the bla (β-lactamase; ampicillin resistance) corresponds to nucleic acids 3214-4074; the GFP corresponds to nucleic acids 5726-4992; the GFP RBS (ribosome binding sequence) AUCCC corresponds to nucleic acids 5738-5734; the trp$^c$ promoter corresponds to nucleic acids 5795-5755; the trp$^c$ promoter corresponds to nucleic acids 6270-6310; the CAT RBS (ribosome binding sequence) AUCCC corresponds to nucleic acids 6327-6331; the cam (chloramphenicol acetyltransferase; CAT) corresponds to nucleic acids 6339-6998; the lacI$^q$ promoter corresponds to nucleic acids 7307-7384; the lacI$^q$ (lac repressor) corresponds to nucleic acids 7385-8467; and the lac UV5 promoter corresponds to nucleic acids 8510-8551.

All references cited herein are expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 245

<210> SEQ ID NO 1
<211> LENGTH: 10903
<212> TYPE: DNA
<213> ORGANISM: Artificial Sequence
<220> FEATURE:
<223> OTHER INFORMATION: primer

<400> SEQUENCE: 1

| | | | | | |
|---|---|---|---|---|---|
| gacgccgggc | aagagcaact | cggtcgccgc | atacactatt | ctcagaatga | cttggttgag | 60 |
| tactcaccag | tcacagaaaa | gcatcttacg | gatggcatga | cagtaagaga | attatgcagt | 120 |
| gctgccataa | ccatgagtga | taacactgcg | gccaacttac | ttctgacaac | gatcggagga | 180 |
| ccgaaggagc | taaccgcttt | tttgcacaac | atggggggatc | atgtaactcg | ccttgatcgt | 240 |
| tgggaaccgg | agctgaatga | agccatacca | aacgacgagc | gtgacaccac | gatgcctgca | 300 |
| gcaatggcaa | caacgttgcg | caaactatta | actggcgaac | tacttactct | agcttcccgg | 360 |
| caacaattaa | tagactggat | ggaggcggat | aaagttgcag | gaccacttct | gcgctcggcc | 420 |
| cttccggctg | gctggtttat | tgctgataaa | tctggagccg | gtgagcgtgg | gtctcgcggt | 480 |
| atcattgcag | cactggggcc | agatggtaag | ccctcccgta | tcgtagttat | ctacacgacg | 540 |
| gggagtcagg | caactatgga | tgaacgaaat | agacagatcg | ctgagatagg | tgcctcactg | 600 |
| attaagcatt | ggtaactgtc | agaccaagtt | tactcatata | tactttagat | tgatttaaaa | 660 |
| cttcattttt | aatttaaaag | gatctaggtg | aagatccttt | ttgataatct | catgaccaaa | 720 |
| atcccttaac | gtgagttttc | gttccactga | gcgtcagacc | ccttaataag | atgatcttct | 780 |
| tgagatcgtt | ttggtctgcg | cgtaatctct | tgctctgaaa | acgaaaaaac | cgccttgcag | 840 |
| ggcggttttt | cgaaggttct | ctgagctacc | aactctttga | accgaggtaa | ctggcttgga | 900 |
| ggagcgcagt | caccaaaact | tgtcctttca | gtttagcctt | aaccggcgca | tgacttcaag | 960 |
| actaactcct | ctaaatcaat | taccagtggc | tgctgccagt | ggtgcttttg | catgtctttc | 1020 |
| cgggttggac | tcaagacgat | agttaccgga | taaggcgcag | cggtcggact | gaacggggggg | 1080 |
| ttcgtgcata | cagtccagct | tggagcgaac | tgcctacccg | gaactgagtg | tcaggcgtgg | 1140 |
| aatgagacaa | acgcggccat | aacagcgaaa | tgacaccggt | aaaccgaaag | gcaggaacag | 1200 |
| gagagcgcac | gagggagccg | ccaggggaa | acgcctggta | tctttatagt | cctgtcgggt | 1260 |
| ttcgccacca | ctgatttgag | cgtcagattt | cgtgatgctt | gtcagggggg | cggagcctat | 1320 |
| ggaaaaacgg | ctttgccgcg | gccctctcac | ttccctgtta | agtatcttcc | tggcatcttc | 1380 |
| caggaaatct | ccgccccgtt | cgtaagccat | ttccgctcgc | cgcagtcgaa | cgaccgagcg | 1440 |
| tagcgagtca | gtgagcgagg | aagcggaata | tatcctgtat | cacatattct | gctgacgcac | 1500 |
| cggtgcagcc | ttttttctcc | tgccacatga | agcacttcac | tgacaccctc | atcagtgcca | 1560 |
| acatagtaag | ccagtataca | ctccgctagc | atcgtccatt | ccgacagcat | cgccagtcac | 1620 |
| tatggcgtgc | tgctagcgct | atatgcgttg | atgcaatttc | tatgcgcacc | cgttctcgga | 1680 |
| gcactgtccg | accgctttgg | ccgccgccca | gtcctgctcg | cttcgctact | tggagccact | 1740 |
| atcgactacg | cgatcatggc | gaccacaccc | gtcctgtgga | tcctctacgc | cggacgcatc | 1800 |
| gtggccggcc | acgatgcgtc | cggcgtagag | gatctattta | cgaccctgc | cctgaaccga | 1860 |
| cgaccgggtc | gaatttgctt | tcgaatttct | gccattcatc | cgcttattat | cacttattca | 1920 |
| ggcgtagcac | caggcgttta | agggcaccaa | taactgcctt | aaaaaaatta | cgccccgccc | 1980 |

```
tgccactcat cgcagtactg ttgtaattca ttaagcattc tgccgacatg gaagccatca    2040
cagacggcat gatgaacctg aatcgccagc ggcatcagca ccttgtcgcc ttgcgtataa    2100
tatttgccca tggtgaaaac gggggcgaag aagttgtcca tattggccac gtttaaatca    2160
aaactggtga aactcaccca gggattggct gagacgaaaa acatattctc aataaaccct    2220
ttagggaaat aggccaggtt ttcaccgtaa cacgccacat cttgcgaata tatgtgtaga    2280
aactgccgga atcgtcgtg gtattcactc cagagcgatg aaaacgtttc agtttgctca     2340
tggaaaacgg tgtaacaagg gtgaacacta tcccatatca ccagctcacc gtctttcatt    2400
gccatacgga attccggatg agcattcatc aggcgggcaa gaatgtgaat aaaggccgga    2460
taaaacttgt gcttattttt ctttacggtc tttaaaaagg ccgtaatatc cagctgaacg    2520
gtctggttat aggtacattg agcaactgac tgaaatgcct caaaatgttc tttacgatgc    2580
cattgggata tatcaacggt ggtatatcca gtgatttttt tctccatttc tcgagcacac    2640
tgaaagcggc cgcttccaca cattaaacta gttcgatgat taattgtcaa cagctcgccg    2700
ctatatgcgt tgatgcaatt tctatgcgca cccgttctcg gagcactgtc cgaccgcttt    2760
ggccgccgcc cagtcctgct cgcttcgcta cttggagcca ctatcgacta cgcgatcatg    2820
gcgaccacac ccgtcctgtg gatcccagac gagttaagtc accatacgtt agtacaggtt    2880
gccactcttt tggcagacgc agacctacgg ctacaatagc gaagcggtcc tggtattcat    2940
gtttaaaaat actgtcgcga tagccaaaac ggcactcttt ggcagttaag cgcacttgct    3000
tgcctgtcgc cagttcaaca gaatcaacat aagcgcaaac tcgctgtaat tctacgccat    3060
aagcaccaat attctggata ggtgatgagc cgacacaacc aggaattaat gccagatttt    3120
ccagaccagg catccttcc tgcaaagtgt attttaccag acgatgccag ttttctccgg      3180
ctcctacatg taaataccac gcatcaggtt catcatgaat ttcgatacct ttgatccggt    3240
tgatgatcac cgtgccgcga tagtcctcca gaaaaagtac attacttcct tcacccagaa    3300
taagaacggg ttgtccttct gcggttgcat actgccaggc attgagtaat tgttgttcgt    3360
cttcggcaca tacaatgtgc tgagcattat gatcaatgcc aaatgtgttc caggttttta    3420
aggagtggtt catagctgct ttcctgatgc aaaaacgagg ctagtttacc gtatctgtgg    3480
ggggatggct tgtagatatg acgacaggaa gagtttgtag aaacgcaaaa aggccatccg    3540
tcaggatggc cttctgctta atttgatgcc tggcagttta tggcgggcgt cctgcccgcc    3600
accctccggg ccgttgcttc gcaacgttca aatccgctcc cggcggattt gtcctactca    3660
ggagagcgtt caccgacaaa caacagataa aacgaaaggc ccagtctttc gactgagcct    3720
ttcgttttat ttgatgcctg gcagttccct actctcgcat ggggagaccc cacactacca    3780
tcggcgctac ggcgtttcac ttctgagttc ggcatgggt caggtgggac caccgcgcta     3840
ctgccgccag gcaaattctg ttttatcaga ccgcttctgc gttctgattt aatctgtatc    3900
aggctgaaaa tcttctctca tccgccaaaa cagcttcggc gttgtaaggt taagcctcac    3960
ggttcattag taccggttag ctcaacgcat cgctgcgctt acacacccgg cctatcaacg    4020
tcgtcgtctt caacgttcct tcaggaccct taaagggtca gggagaactc atctcggggc    4080
aagtttcgtg cttagatgct ttcagcactt atctcttccg catttagcta ccgggcagtg    4140
ccattggcat gacaacccga acaccagtga tgcgtccact ccgtcctct cgtactagga     4200 gcagccccc tcagttctcc agcgcccacg gcagataggg accgaactgt ctcacgacgt     4260
tctaaaccca gctcgcgtac cactttaaat ggcgaacagc catacccttg ggacctactt    4320
cagccccagg atgtgatgag ccgacatcga ggtgccaaac accgccgtcg atatgaactc    4380
```

```
ttgggcggta tcagcctgtt atccccggag tacctttat ccgttgagcg atggccttc      4440
cattcagaac caccggatca ctatgacctg ctttcgcacc tgctcgcgcc gtcacgctcg    4500
cagtcaagct ggcttatgcc attgcactaa cctcctgatg tccgaccagg attagccaac    4560
cttcgtgctc ctccgttact ctttaggagg agaccgcccc agtcaaacta cccaccagac    4620
actgtccgca acccggatta cgggtcaacg ttagaacatc aaacattaaa gggtggtatt    4680
tcaaggtcgg ctccatgcag actggcgtcc acacttcaaa gcctcccacc tatcctacac    4740
atcaaggctc aatgttcagt gtcaagctat agtaaaggtt cacggggtct ttccgtcttg    4800
ccgcgggtac actgcatctt cacagcgagt tcaatttcac tgagtctcgg gtggagacag    4860
cctggccatc attacgccat tcgtgcaggt cggaacttac ccgacaagga atttcgctac    4920
cttaggaccg ttatagttac ggccgccgtt taccggggct tcgatcaaga gcttcgcttg    4980
cgctaaccc atcaattaac cttccggcac cgggcaggcg tcacaccgta tacgtccact    5040
ttcgtgtttg cacagtgctg tgtttttaat aaacagttgc agccagctgg tatcttcgac    5100
tgatttcagc tccatccgcg agggacctca cctacatatc agcgtgcctt ctcccgaagt    5160
tacggcacca ttttgcctag ttccttcacc cgagttctct caagcgcctt ggtattctct    5220
acctgaccac ctgtgtcggt ttggggtacg atttgatgtt acctgatgct tagaggcttt    5280
tcctggaagc agggcatttg ttgcttcagc accgtagtgc ctcgtcatca cgcctcagcc    5340
ttgattttcc ggatttgcct ggaaaaccag cctacacgct taaaccggga caaccgtcgc    5400
ccggccaaca tagccttctc cgtccccct tcgcagtaac accaagtaca ggaatattaa     5460
cctgttccc atcgactacg ccttcggcc tcgccttagg ggtcgactca ccctgccccg      5520
attaacgttg gacaggaacc cttggtcttc cggcgagcgg gcttttcacc cgctttatcg    5580
ttacttatgt cagcattcgc acttctgata cctccagcat gcctcacagc acaccttcgc    5640
aggcttacag aacgctcccc tacccaacaa cgcataagcg tcgctgccgc agcttcggtg    5700
catggtttag ccccgttaca tcttccgcgc aggccgactc gaccagtgag ctattacgct    5760
ttctttaaat gatggctgct tctaagccaa catcctggct gtctgggcct tcccacatcg    5820
tttcccactt aaccatgact ttgggacctt agctggcggt ctgggttgtt tccctcttca    5880
cgacggacgt tagcacccgc cgtgtgtctc ccgtgataac attctccggt attcgcagtt    5940
tgcatcgggt tggtaagtcg ggatgacccc cttgccgaaa cagtgctcta ccccggaga    6000
tgaattcacg aggcgctacc taaatagctt tcggggagaa ccagctatct cccggtttga    6060
ttggcctttc accccagcc acaagtcatc cgctaatttt tcaacattag tcggttcggt     6120
cctccagtta gtgttaccca accttcaacc tgcccatggc tagatcaccg ggtttcgggt    6180
ctatacctg caacttaacg cccagttaag actcggtttc cttcggctc ccctattcgg     6240
ttaaccttgc tacagaatat aagtcgctga cccattatac aaaaggtacg cagtcacacg    6300
cctaagcgtg ctcccactgc ttgtacgtac acgtttcag gttctttttc actcccctcg     6360
ccggggttct tttcgccttt ccctcacggt actggttcac tatcggtcag tcaggagtat    6420
ttagccttgg aggatggtcc ccccatattc agacaggata ccacgtgtcc cgccctactc    6480
atcgagctca cagcatgtgc attttgtgt acggggctgt caccctgtat cgcgcgcctt     6540
tccagacgct tccactaaca cacacactga ttcaggctct gggctgctcc ccgttcgctc    6600
gccgctactg ggggaatctc ggttgatttc ttttcctcgg ggtacttaga tgtttcagtt    6660
cccccggttc gcctcattaa cctatggatt cagttaatga tagtgtgtcg aaacacactg    6720
ggtttcccca ttcggaaatc gccggttata acggttcata tcaccttacc gacgcttatc    6780
```

```
gcagattagc acgtccttca tcgcctctga ctgccagggc atccaccgtg tacgcttagt   6840
cgcttaacct cacaacccga agatgtttct ttcgattcat catcgtgttg cgaaaatttg   6900
agagactcac gaacaactct cgttgttcag tgtttcaatt ttcagcttga tccagatttt   6960
taaagagcaa aaatctcaaa catcacccga agatgagttt tgagatatta aggtcggcga   7020
ctttcactca caaaccagca agtggcgtcc cctagggat tcgaacccct gttaccgccg    7080
tgaaagggcg gtgtcctggg cctctagacg aaggggacac gaaaattgct tatcacgcgt   7140
tgcgtgatat tttcgtgtag ggtgagcttt cattaataga aagcgaacgg ccttattctc   7200
ttcagcctca ctcccaacgc gtaaacgcct tgcttttcac tttctatcag acaatctgtg   7260
tgagcactac aaagtacgct tctttaaggt aagtgtgtga tccaaccgca ggttccccta   7320
cggttacctt gttacgactt cacccccagtc atgaatcaca aagtggtaag cgccctcccg   7380
aaggttaagc tacctacttc ttttgcaacc cactcccatg gtgtgacggg cggtgtgtac   7440
aaggcccggg aacgtattca ccgtggcatt ctgatccacg attactagcg attccgactt   7500
catggagtcg agttgcagac tccaatccgg actacgacgc actttatgag gtccgcttgc   7560
tctcgcgagg tcgcttctct ttgtatgcgc cattgtagca cgtgtgtagc cctggtcgta   7620
agggccatga tgacttgacg tcatccccac cttcctccag tttatcactg gcagtctcct   7680
ttgagttccc ggccggaccg ctggcaacaa aggataaggg ttgcgctcgt tgcgggactt   7740
aacccaacat ttcacaacac gagctgacga cagccatgca gcacctgtct cacggttccc   7800
gaaggcacat tctcatctct gaaaacttcc gtggatgtca agaccaggta aggttcttcg   7860
cgttgcatcg aattaaaacca catgctccac cgcttgtgcg ggccccgtc aattcatttg    7920 agttttaacc ttgcggccgt actcccagg cggtcgactt aacgcgttag ctccggaagc    7980
cacgcctcaa gggcacaacc tccaagtcga catcgtttac ggcgtggact accagggtat   8040
ctaatcctgt ttgctcccca cgctttcgca cctgagcgtc agtcttcgtc caggggccg    8100 ccttcgccac cggtattcct ccagatctct acgcatttca ccgctacacc tggaattcta   8160 ccccctcta cgagactcaa gcttgccagt atcagatgca gttcccaggt tgagcccggg    8220
gatttcacat ctgacttaac aaaccgcctg cgtgcgcttt acgcccagta attccgatta   8280
acgcttgcac cctccgtatt accgcggctg ctggcacgga gttagccggt gcttcttctg   8340
cgggtaacgt caatgagcaa aggtattaac tttactcccct tcctcccgc tgaaagtact   8400 ttacaacccg aaggccttct tcatacacgc ggcatggctg catcaggctt gcgcccattg   8460
tgcaatattc cccactgctg cctcccgtag gagtctggac cgtgtctcag ttccagtgtg   8520
gctggtcatc ctctcagacc agctagggat cgtcgcctag gtgagccgtt accccaccta   8580
ctagctaatc ccatctgggc acatccgatg gcaagaggcc cgaaggtccc cctctttggt   8640
cttgcgacgt tatgcggtat tagctaccgt ttccagtagt tatcccccc catcaggcag   8700 tttcccagac attactcacc cgtccgccac tcgtcagcaa agaagcaagc ttcttcctgt   8760
taccgttcga cttgcatgtg ttaggcctgc cgccagcgtt caatctgagc catgatcaaa   8820
ctcttcaatt taaagttttg acgctcaaag aattaaactt cgtaatgaat tacgtgttca   8880
ctcttgagac ttggtattca ttttttcgtct tgcgacgtta agaatccgta tcttcgagtg   8940
cccacacaga ttgtctgata aattgttaaa gagcagtgcc gcttcgcttt ttctcagcgg   9000
ccgctgtgtg aaattgttat ccgctcacaa ttccacacat tatacgagcc ggaagcataa   9060
agtgtaaagc ctggggtgcc taatgagtga gctaactcac attaattgcg ttgcgctcac   9120
tgcccgcttt ccagtcggga aacctgtcgt gccagctgca ttaatgaatc ggccaacgcg   9180
```

```
cggggagagg cggtttgcgt attgggcgcc agggtggttt ttcttttcac cagtgagacg    9240
ggcaacagct gattgccctt caccgcctgg ccctgagaga gttgcagcaa gcggtccacg    9300
ctggtttgcc ccagcaggcg aaaatcctgt tgatggtggg ttgacggcgg gatataacat    9360
gagctgtctt cggtatcgtc gtatcccact accgagatat ccgcaccaac gcgcagcccg    9420
gactcggtaa tggcgcgcat tgcgcccagc gccatctgat cgttggcaac cagcatcgca    9480
gtgggaacga tgccctcatt cagcatttgc atggtttgtt gaaaaccgga catggcactc    9540
cagtcgcctt cccgttccgc tatcggctga atttgattgc gagtgagata tttatgccag    9600
ccagccagac gcagacgcgc cgagacagaa cttaatgggc ccgctaacag cgcgatttgc    9660
tggtgaccca atgcgaccag atgctccacg cccagtcgcg taccgtcttc atgggagaaa    9720
ataatactgt tgatgggtgt ctggtcagag acatcaagaa ataacgccgg aacattagtg    9780
caggcagctt ccacagcaat ggcatcctgg tcatccagcg gatagttaat gatcagccca    9840
ctgacccgtt gcgcgagaag attgtgcacc gccgctttac aggcttcgac gccgcttcgt    9900
tctaccatcg acaccaccac gctggcaccc agttgatcgg cgcgagattt aatcgccgcg    9960
acaatttgcg acggcgcgtg cagggccaga ctggaggtgg caacgccaat cagcaacgac   10020
tgtttgcccg ccagttgttg tgccacgcgg ttgggaatgt aattcagctc cgccatcgcc   10080
gcttccactt ttttcccgcgt tttcgcagaa acgtggctgg cctggttcac cacgcgggaa   10140
acggtctgat aagagacacc ggcatactct gcgacatcgt ataacgttac tggtttcaca   10200
ttcaccaccc tgaattgact ctcttccggg cgctatcatg ccataccgcg aaaggttttg   10260
caccattcga tggtgtcgga tcctagagcg cacgaatgag ggccgacagg aagcaaagct   10320
gaaaggaatc aaatttggcc gcaggcgtac cgtggacagg aacgtcgtgc tgacgcttca   10380
tcagaagggc actggtgcaa cggaaattgc tcatcagctc agtattgccc gctccacggt   10440
ttataaaatt cttgaagacg aaagggcctc gtgcatacgc ctattttat aggttaatgt   10500
catgataata atggtttctt agacgtcagg tggcactttt cggggaaatg tgcgcggaac   10560
ccctatttgt ttattttct aaatacattc aaatatgtat ccgctcatga cacaataacc   10620
ctgataaatg cttcaataat attgaaaaag gaagagtatg agtattcaac atttccgtgt   10680
cgcccttatt cccttttttg cggcattttg ccttcctgtt tttgctcacc cagaaacgct   10740
ggtgaaagta aaagatgctg aagatcagtt gggtgcacga gtgggttaca tcgaactgga   10800
tctcaacagc ggtaagatcc ttgagagttt tcgccccgaa gaacgttttc caatgatgag   10860
cacttttaaa gttctgctat gtggcgcggt attatcccgt gtt                     10903

<210> SEQ ID NO 2
<211> LENGTH: 11918
<212> TYPE: DNA
<213> ORGANISM: Artificial Sequence
<220> FEATURE:
<223> OTHER INFORMATION: primer

<400> SEQUENCE: 2
gatcctctac gccggacgca tcgtggccgg ccacgatgcg tccggcgtag aggatctatt      60
taacgaccct gccctgaacc gacgaccggg tcgaatttgc tttcgaattt ctgccattca     120
tccgcttatt atcacttatt caggcgtagc accaggcgtt taagggcacc ataactgcc      180
ttaaaaaaat tacgccccgc cctgccactc atcgcagtac tgttgtaatt cattaagcat     240
tctgccgaca tggaagccat cacagacggc atgatgaacc tgaatcgcca gcggcatcag     300
caccttgtcg ccttgcgtat aatatttgcc catggtgaaa acgggggcga agaagttgtc     360
```

```
catattggcc acgtttaaat caaaactggt gaaactcacc cagggattgg ctgagacgaa    420
aaacatattc tcaataaacc ctttagggaa ataggccagg ttttcaccgt aacacgccac    480
atcttgcgaa tatatgtgta gaaactgccg gaaatcgtcg tggtattcac tccagagcga    540
tgaaaacgtt tcagtttgct catggaaaac ggtgtaacaa gggtgaacac tatcccatat    600
caccagctca ccgtctttca ttgccatacg gaattccgga tgagcattca tcaggcgggc    660
aagaatgtga ataaaggccg gataaaactt gtgcttattt ttctttacgg tctttaaaaa    720
ggccgtaata tccagctgaa cggtctggtt ataggtacat tgagcaactg actgaaatgc    780
ctcaaaatgt tctttacgat gccattggga tatatcaacg gtggtatatc cagtgatttt    840
tttctccatt tgcggaggga tatgaaagcg ccgcttcca cacattaaac tagttcgatg     900
attaattgtc aacagctcgc cggcggcacc tcgctaacgg attcaccact ccaagaattg    960
gagccaatcg attcttgcgg agaactgtga atgcgcaaac caaccccttgg cagaacatat  1020
ccatcgcgtc cgccatctcc agcagccgca cgcggcgcat ctcgggcagc gttgggtcct   1080
ggccacgggt gcgcatgatc gtgctcctgt cgttgaggac ccggctaggc tggcggggtt   1140
gccttactgg ttagcagaat gaatcaccga tacgcgagcg aacgtgaagc gactgctgct   1200
gcaaaacgtc tgcgacctga gcaacaacat gaatggtctt cggtttccgt gtttcgtaaa   1260
gtctggaaac gcggaagtca gcgccctgca ccattatgtt ccggatctgg gtaccgagct   1320
cgaattcact ggccgtcgtt ttacaacgtc gtgactggga aaaccctggc gttacccaac   1380
ttaatcgcct tgcagcacat ccccctttcg ccaggcatcg caggatgctg ctggctaccc   1440
tgtggaacac ctacatctgt attaacgaag cgctggcatt gaccctgagt gatttttctc   1500
tggtcccgcc gcatccatac cgccagttgt taccctcac aacgttccag taaccgggca    1560
tgttcatcat cagtaacccg tatcgtgagc atcctctctc gtttcatcgg tatcattacc   1620
cccatgaaca gaaattcccc cttacacgga ggcatcaagt gaccaaacag gaaaaaaccg   1680
cccttaacat ggcccgcttt atcagaagcc agacattaac gcttctggag aaactcaacg   1740
agctggacgc ggatgaacag gcagacatct gtgaatcgct tcacgaccac gctgatgagc   1800
tttaccgcag ctgcctcgcg cgtttcggtg atgacggtga aaacctctga cacatgcagc   1860
tcccggagac ggtcacagct tgtctgtaag cggatgccgg gagcagacaa gcccgtcagg   1920
gcgcgtcagc gggtgttggc gggtgtcggg gcgcagccat gacccagtca cgtagcgata   1980
gcggagtgta tactggctta actatgcggc atcagagcag attgtactga gagtgcacca   2040
tatgcggtgt gaaataccgc acagatgcgt aaggagaaaa taccgcatca ggcgctcttc   2100
cgcttcctcg ctcactgact cgctgcgctc ggtcgttcgg ctgcggcgag cggtatcagc   2160
tcactcaaag gcggtaatac ggttatccac agaatcaggg gataacgcag gaaagaacat   2220
gtgagcaaaa ggccagcaaa aggccaggaa ccgtaaaaag gccgcgttgc tggcgttttt   2280
ccataggctc cgcccccctg acgagcatca caaaaatcga cgctcaagtc agaggtggcg   2340
aaacccgaca ggactataaa gataccaggc gtttccccct ggaagctccc tcgtgcgctc   2400
tcctgttccg accctgccgc ttaccggata cctgtccgcc tttctccctt cgggaagcgt   2460
ggcgctttct catagctcac gctgtaggta tctcagttcg gtgtaggtcg ttcgctccaa   2520
gctgggctgt gtgcacgaac ccccgttca gcccgaccgc tgcgccttat ccggtaacta   2580
tcgtcttgag tccaacccgg taagacacga cttatcgcca ctggcagcag ccactggtaa   2640
caggattagc agagcgaggt atgtaggcgg tgctacagag ttcttgaagt ggtggcctaa   2700
ctacggctac actagaagga cagtatttgg tatctgcgct ctgctgaagc cagttacctt   2760
```

```
cggaaaaaga gttggtagct cttgatccgg caaacaaacc accgctggta gcggtggttt    2820
ttttgtttgc aagcagcaga ttacgcgcag aaaaaaagga tctcaagaag atcctttgat    2880
cttttctacg gggtctgacg ctcagtggaa cgaaaactca cgttaaggga ttttggtcat    2940
gagattatca aaaaggatct tcacctagat ccttttaaat taaaaatgaa gttttaaatc    3000
aatctaaagt atatatgagt aaacttggtc tgacagttac caatgcttaa tcagtgaggc    3060
acctatctca gcgatctgtc tatttcgttc atccatagtt gcctgactcc ccgtcgtgta    3120
gataactacg atacgggagg gcttaccatc tggccccagt gctgcaatga taccgcgaga    3180
cccacgctca ccggctccag atttatcagc aataaaccag ccagccggaa gggccgagcg    3240
cagaagtggt cctgcaactt tatccgcctc catccagtct attaattgtt gccgggaagc    3300
tagagtaagt agttcgccag ttaatagttt gcgcaacgtt gttgccattg ctgcaggcat    3360
cgtggtgtca cgctcgtcgt ttggtatggc ttcattcagc tccggttccc aacgatcaag    3420
gcgagttaca tgatccccca tgttgtgcaa aaaagcggtt agctccttcg gtcctccgat    3480
cgttgtcaga agtaagttgg ccgcagtgtt atcactcatg gttatggcag cactgcataa    3540
ttctcttact gtcatgccat ccgtaagatg ctttttctgtg actggtgagt actcaaccaa    3600
gtcattctga gaatagtgta tgcggcgacc gagttgctct tgcccggcgt caacacggga    3660
taataccgcg ccacatagca gaactttaaa agtgctcatc attggaaaac gttcttcggg    3720
gcgaaaactc tcaaggatct taccgctgtt gagatccagt tcgatgtaac ccactcgtgc    3780
acccaactga tcttcagcat cttttacttt caccagcgtt tctgggtgag caaaaacagg    3840
aaggcaaaat gccgcaaaaa agggaataag ggcgacacgg aaatgttgaa tactcatact    3900 cttcctttt caatattatt gaagcattta tcagggttat tgtctcatga gcggatacat    3960
atttgaatgt atttagaaaa ataaacaaat aggggttccg cgcacatttc cccgaaaagt    4020
gccacctgac gtctaagaaa ccattattat catgacatta acctataaaa ataggcgtat    4080
cacgaggccc tttcgtcttc aagaattctc atgtttgaca gcttatcatc gataagcttt    4140
aatgcggtag tttatcacag ttaaattgct aacgcagtca ggcaccgtgt atgaaatcta    4200
acaatgcgct catcgtcatc ctcggcaccg tcaccctgga tgctgtaggc ataggcttgg    4260
ttatgccggt actgccgggc ctcttgcggg atatcgtcca ttccgacagc atcgccagtc    4320 actatgcgt gctgctagcg ctatatgcgt tgatgcaatt tctatgcgca cccgttctcg    4380
gagcactgtc cgaccgcttt ggccgccgcc cagtcctgct cgcttcgcta cttggagcca    4440
ctatcgacta cgcgatcatg gcgaccacac ccgtcctgtg gatcccagac gagttaagtc    4500
accatacgtt agtacaggtt gccactcttt tggcagacgc agacctacgg ctacaatagc    4560
gaagcggtcc tggtattcat gtttaaaaat actgtcgcga tagccaaaac ggcactcttt    4620
ggcagttaag cgcacttgct tgcctgtcgc cagttcaaca gaatcaacat aagcgcaaac    4680
tcgctgtaat tctacgccat aagcaccaat attctggata ggtgatgagc cgacacaacc    4740
aggaattaat gccagatttt ccagaccagg cataccttcc tgcaaagtgt attttaccag    4800
acgatgccag ttttctccgg ctcctacatg taaataccac gcatcaggtt catcatgaat    4860
ttcgatacct tgatccggt tgatgatcac cgtgccgcga tagtcctcca gaaaaagtac    4920
attacttcct tcacccagaa taagaacggg ttgtccttct gcggttgcat actgccaggc    4980
attgagtaat tgttgttcgt cttcggcaca tacaatgtgc tgagcattat gatcaatgcc    5040
aaatgtgttc cagggtttta aggagtggtt catagctgct ttcctgatgc aaaaacgagg    5100
ctagtttacc gtatctgtgg ggggatggct tgtagatatg acgacaggaa gagtttgtag    5160
```

```
aaacgcaaaa aggccatccg tcaggatggc cttctgctta atttgatgcc tggcagttta   5220
tggcgggcgt cctgcccgcc accctccggg ccgttgcttc gcaacgttca aatccgctcc   5280
cggcggattt gtcctactca ggagagcgtt caccgacaaa caacagataa aacgaaaggc   5340
ccagtctttc gactgagcct ttcgttttat ttgatgcctg gcagttccct actctcgcat   5400
ggggagaccc cacactacca tcggcgctac ggcgtttcac ttctgagttc ggcatggggt   5460
caggtgggac caccgcgcta ctgccgccag gcaaattctg ttttatcaga ccgcttctgc   5520
gttctgattt aatctgtatc aggctgaaaa tcttctctca tccgccaaaa cagcttcggc   5580
gttgtaaggt taagcctcac ggttcattag taccggttag ctcaacgcat cgctgcgctt   5640
acacacccgg cctatcaacg tcgtcgtctt caacgttcct tcaggaccct aaagggtca    5700 gggagaactc atctcgggc aagtttcgtg cttagatgct ttcagcactt atctcttccg    5760
catttagcta ccgggcagtg ccattggcat gacaacccga acaccagtga tgcgtccact   5820
ccggtcctct cgtactagga gcagcccccc tcagttctcc agcgcccacg gcagataggg   5880
accgaactgt ctcacgacgt tctaaaccca gctcgcgtac cactttaaat ggcgaacagc   5940
catacccttg ggacctactt cagcccagg atgtgatgag ccgacatcga ggtgccaaac    6000
accgccgtcg atatgaactc ttgggcggta tcagcctgtt atccccggag tacctttat    6060 ccgttgagcg atggcccttc cattcagaac caccggatca ctatgacctg ctttcgcacc   6120
tgctcgcgcc gtcacgctcg cagtcaagct ggcttatgcc attgcactaa cctcctgatg   6180
tccgaccagg attagccaac cttcgtgctc ctccgttact cttaggagg agaccgcccc    6240 agtcaaacta cccaccagac actgtccgca acccggatta cgggtcaacg ttagaacatc   6300
aaacattaaa gggtggtatt tcaaggtcgg ctccatgcag actggcgtcc acacttcaaa   6360
gcctcccacc tatcctacac atcaaggctc aatgttcagt gtcaagctat agtaaaggtt   6420
cacggggtct ttccgtcttg ccgcgggtac actgcatctt cacagcgagt tcaatttcac   6480
tgagtctcgg gtggagacag cctggccatc attacgccat tcgtgcaggt cggaacttac   6540
ccgacaagga atttcgctac cttaggaccg ttatagttac ggccgccgtt taccggggct   6600
tcgatcaaga gcttcgcttg cgctaacccc atcaattaac cttccggcac cgggcaggcg   6660
tcacaccgta tacgtccact ttcgtgtttg cacagtgctg tgttttaat aaacagttgc     6720 agccagctgg tatcttcgac tgatttcagc tccatccgcg agggacctca cctacatatc   6780
agcgtgcctt ctcccgaagt tacggcacca ttttgcctag ttccttcacc cgagttctct   6840
caagcgcctt ggtattctct acctgaccac ctgtgtcggt ttggggtacg atttgatgtt   6900
acctgatgct tagaggcttt tcctggaagc agggcatttg ttgcttcagc accgtagtgc   6960
ctcgtcatca cgcctcagcc ttgatttttcc ggatttgcct ggaaaaccag cctacacgct   7020
taaaccggga caaccgtcgc ccggccaaca tagccttctc cgtccccct tcgcagtaac    7080 accaagtaca ggaatattaa cctgtttccc atcgactacg cctttcggcc tcgccttagg   7140
ggtcgactca ccctgccccg attaacgttg gacaggaacc cttggtcttc cggcgagcgg   7200
gcttttcacc cgctttatcg ttacttatgt cagcattcgc acttctgata cctccagcat   7260
gcctcacagc acaccttcgc aggcttacag aacgctcccc tacccaacaa cgcataagcg   7320
tcgctgccgc agcttcggtg catggtttag ccccgttaca tcttccgcgc aggccgactc   7380
gaccagtgag ctattacgct ttctttaaat gatggctgct tctaagccaa catcctggct   7440
gtctgggcct tccacatccg tttcccactt aaccatgact ttgggacctt agctggcggt   7500
ctgggttgtt tccctcttca cgacggacgt tagcacccgc cgtgtgtctc ccgtgataac   7560
```

```
attctccggt attcgcagtt tgcatcgggt tggtaagtcg ggatgacccc cttgccgaaa   7620
cagtgctcta cccccggaga tgaattcacg aggcgctacc taaatagctt tcggggagaa   7680
ccagctatct cccggtttga ttggcctttc accccccagcc acaagtcatc cgctaatttt  7740
tcaacattag tcggttcggt cctccagtta gtgttaccca accttcaacc tgcccatggc   7800
tagatcaccg ggtttcgggt ctataccctg caacttaacg cccagttaag actcggtttc   7860
ccttcggctc ccctattcgg ttaaccttgc tacagaatat aagtcgctga cccattatac   7920
aaaaggtacg cagtcacacg cctaagcgtg ctcccactgc ttgtacgtac acggtttcag   7980
gttcttttc actcccctcg ccggggttct tttcgccttt ccctcacggt actggttcac    8040
tatcggtcag tcaggagtat ttagccttgg aggatggtcc ccccatattc agacaggata   8100
ccacgtgtcc cgccctactc atcgagctca cagcatgtgc attttttgtgt acggggctgt  8160
caccctgtat cgcgcgcctt ccagacgct tccactaaca cacacactga ttcaggctct    8220
gggctgctcc ccgttcgctc gccgctactg ggggaatctc ggttgatttc ttttcctcgg   8280
ggtacttaga tgtttcagtt cccccggttc gcctcattaa cctatggatt cagttaatga   8340
tagtgtgtcg aaacacactg gtttccccca ttcggaaatc gccggttata acggttcata   8400
tcaccttacc gacgcttatc gcagattagc acgtccttca tcgcctctga ctgccagggc   8460
atccaccgtg tacgcttagt cgcttaacct cacaacccga agatgtttct ttcgattcat   8520
catcgtgttg cgaaaatttg agagactcac gaacaactct cgttgttcag tgtttcaatt   8580
ttcagcttga tccagatttt taaagagcaa aaatctcaaa catcacccga agatgagttt   8640
tgagatatta aggtcggcga cttcactca caaaccagca agtggcgtcc cctaggggat    8700
tcgaacccct gttaccgccg tgaaagggcg gtgtcctggg cctctagacg aaggggacac   8760
gaaaattgct tatcacgcgt gcgtgatat tttcgtgtag ggtgagcttt cattaataga    8820
aagcgaacgg ccttattctc ttcagcctca ctcccaacgc gtaaacgcct tgcttttcac   8880
tttctatcag acaatctgtg tgagcactac aaagtacgct tctttaaggt aatcccatga   8940
tccaaccgca ggttcccta cggttaccttt gttacgactt cacccccagtc atgaatcaca   9000
aagtggtaag cgcccctcccg aaggttaagc tacctacttc ttttgcaacc cactcccatg   9060
gtgtgacggg cggtgtgtac aaggcccggg aacgtattca ccgtggcatt ctgatccacg   9120
attactagcg attccgactt catggagtcg agttgcagac tccaatccgg actacgacgc   9180
actttatgag gtccgcttgc tctcgcgagg tcgcttctct ttgtatgcgc cattgtagca   9240
cgtgtgtagc cctggtcgta agggccatga tgacttgacg tcatccccac cttcctccag   9300
tttatcactg gcagtctcct ttgagttccc ggccggaccg ctggcaacaa aggataaggg   9360
ttgcgctcgt tgcgggactt aacccaacat ttcacaacac gagctgacga cagccatgca   9420
gcacctgtct cacggttccc gaaggcacat tctcatctct gaaaacttcc gtggatgtca   9480
agaccaggta aggttcttcg cgttgcatcg aattaaacca catgctccac cgcttgtgcg   9540
ggcccccgtc aattcatttg agttttaacc ttgcggccgt actccccagg cggtcgactt   9600
aacgcgttag ctccggaagc cacgcctcaa gggcacaacc tccaagtcga catcgtttac   9660
ggcgtggact accagggtat ctaatcctgt ttgctcccca cgctttcgca cctgagcgtc   9720
agtcttcgtc caggggccg ccttcgccac cggtattcct ccagatctct acgcatttca    9780
ccgctacacc tggaattcta cccccctcta cgagactcaa gcttgccagt atcagatgca   9840
gttcccaggt tgagcccggg gatttcacat ctgacttaac aaaccgcctg cgtgcgcttt   9900
acgcccagta attccgatta acgcttgcac cctccgtatt accgcggctg ctggcacgga   9960
```

```
gttagccggt gcttcttctg cgggtaacgt caatgagcaa aggtattaac tttactccct    10020
tcctccccgc tgaaagtact ttacaacccg aaggccttct tcatacacgc ggcatggctg    10080
catcaggctt gcgcccattg tgcaatattc cccactgctg cctcccgtag gagtctggac    10140
cgtgtctcag ttccagtgtg gctggtcatc ctctcagacc agctagggat cgtcgcctag    10200
gtgagccgtt accccaccta ctagctaatc ccatctgggc acatccgatg caagaggcc    10260
cgaaggtccc cctctttggt cttgcgacgt tatgcggtat tagctaccgt ttccagtagt    10320
tatcccctc catcaggcag tttcccagac attactcacc cgtccgccac tcgtcagcaa    10380
agaagcaagc ttcttcctgt taccgttcga cttgcatgtg ttaggcctgc cgccagcgtt    10440
caatctgagc catgatcaaa ctcttcaatt taaaagtttg acgctcaaag aattaaactt    10500
cgtaatgaat tacgtgttca ctcttgagac ttggtattca tttttcgtct tgcgacgtta    10560
agaatccgta tcttcgagtg cccacacaga ttgtctgata aattgttaaa gagcagtgcc    10620
gcttcgcttt ttctcagcgg ccgctgtgtg aaattgttat ccgctcacaa ttccacacat    10680
tatacgagcc ggaagcataa agtgtaaagc ctggggtgcc taatgagtga gctaactcac    10740
attaattgcg ttgcgctcac tgcccgcttt ccagtcggga aacctgtcgt gccagctgca    10800
ttaatgaatc ggccaacgcg cggggagagg cggtttgcgt attgggcgcc agggtggttt    10860
ttcttttcac cagtgagacg ggcaacagct gattgccctt caccgcctgg ccctgagaga    10920
gttgcagcaa gcggtccacg ctggtttgcc ccagcaggcg aaaatcctgt ttgatggtgg    10980
ttgacgcgg gatataacat gagctgtctt cggtatcgtc gtatcccact accgagatat    11040
ccgcaccaac gcgcagcccg gactcggtaa tggcgcgcat tgcgcccagc gccatctgat    11100
cgttggcaac cagcatcgca gtgggaacga tgccctcatt cagcatttgc atggtttgtt    11160
gaaaaccgga catggcactc cagtcgcctt cccgttccgc tatcggctga atttgattgc    11220
gagtgagata tttatgccag ccagccagac gcagacgcgc cgagacagaa cttaatgggc    11280
ccgctaacag cgcgatttgc tggtgaccca atgcgaccag atgctccacg cccagtcgcg    11340
taccgtcttc atgggagaaa ataatactgt tgatgggtgt ctggtcagag acatcaagaa    11400
ataacgccgg aacattagtg caggcagctt ccacagcaat ggcatcctgg tcatccagcg    11460
gatagttaat gatcagccca ctgacccgtt gcgcgagaag attgtgcacc gccgctttac    11520
aggcttcgac gccgcttcgt tctaccatcg acaccaccac gctggcaccc agttgatcgg    11580
cgcgagattt aatcgccgcg acaatttgcg acggcgcgtg cagggccaga ctggaggtgg    11640
caacgccaat cagcaacgac tgtttgcccg ccagttgttg tgccacgcgg ttgggaatgt    11700
aattcagctc cgccatcgcc gcttccactt tttcccgcgt tttcgcagaa acgtggctgg    11760
cctggttcac cacgcgggaa acggtctgat aagagacacc ggcatactct gcgacatcgt    11820
ataacgttac tggtttcaca ttcaccaccc tgaattgact ctcttccggg cgctatcatg    11880
ccataccgcg aaaggttttg caccattcga tggtgtcg                          11918
```

<210> SEQ ID NO 3
<211> LENGTH: 13278
<212> TYPE: DNA
<213> ORGANISM: Artificial Sequence
<220> FEATURE:
<223> OTHER INFORMATION: primer

<400> SEQUENCE: 3

```
aaattgaaga gtttgatcat ggctcagatt gaacgctggc ggcaggccta acacatgcaa    60
gtcgaacggt aacaggaaga agcttgcttc tttgctgacg agtggcggac gggtgagtaa    120
```

```
tgtctgggaa actgcctgat ggaggggat aactactgga aacggtagct aataccgcat    180
aacgtcgcaa gaccaaagag ggggaccttc gggcctcttg ccatcggatg tgcccagatg    240
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420 tcggttgta aagtactttc agcggggagg aaggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660 gtagagggg gtagaattcc aggtgtagcg gtgaaatgcg tagagatctg gaggaatacc    720
ggtggcgaag gcggcccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctgggag tacggccgca    900 aggttaaaac tcaaatgaat tgacggggc ccgcacaagc ggtggagcat gtggtttaat    960
tcgatgcaac gcgaagaacc ttacctggtc ttgacatcca cggaagtttt cagagatgag   1020
aatgtgcctt cgggaaccgt gagacaggtg ctgcatggct gtcgtcagct cgtgttgtga   1080
aatgttgggt taagtcccgc aacgagcgca acccttatcc tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca aagagaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct gtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcatgggat taccttaaag aagcgtactt   1560
tgtagtgctc acacagattg tctgatagaa agtgaaaagc aaggcgttta cgcgttggga   1620
gtgaggctga agagaataag gccgttcgct ttctattaat gaaagctcac cctacacgaa   1680
aatatcacgc aacgcgtgat aagcaatttt cgtgtcccct tcgtctagag gcccaggaca   1740 ccgcccttc acggcggtaa caggggttcg aatcccctag gggacgccac ttgctggttt   1800
gtgagtgaaa gtcgccgacc ttaatatctc aaaactcatc ttcgggtgat gtttgagatt   1860
tttgctcttt aaaaatctgg atcaagctga aaattgaaac actgaacaac gagagttgtt   1920
cgtgagtctc tcaaattttc gcaacacgat gatgaatcga agaaacatc ttcggggttgt   1980 gaggttaagc gactaagcgt acacggtgga tgccctggca gtcagaggcg atgaaggacg   2040
tgctaatctg cgataagcgt cggtaaggtg atatgaaccg ttataaccgg cgatttccga   2100 atgggaaac ccagtgtgtt tcgacacact atcattaact gaatccatag gttaatgagg   2160
cgaaccgggg gaactgaaac atctaagtac cccgaggaaa agaaatcaac cgagattccc   2220
ccagtagcgg cgagcgaacg gggagcagcc cagagcctga atcagtgtgt gtgttagtgg   2280
aagcgtctgg aaaggcgcgc gatacagggt gacagcccg tacacaaaaa tgcacatgct   2340
gtgagctcga tgagtagggc gggacacgtg gtatcctgtc tgaatatggg gggaccatcc   2400
tccaaggcta aatactcctg actgaccgat agtgaaccag taccgtgagg gaaaggcgaa   2460
aagaaccccg gcgaggggag tgaaaaagaa cctgaaaccg tgtacgtaca agcagtggga   2520
```

```
gcacgcttag gcgtgtgact gcgtaccttt tgtataatgg gtcagcgact tatattctgt   2580
agcaaggtta accgaatagg ggagccgaag ggaaaccgag tcttaactgg gcgttaagtt   2640
gcagggtata gacccgaaac ccggtgatct agccatgggc aggttgaagg ttgggtaaca   2700
ctaactggag gaccgaaccg actaatgttg aaaaattagc ggatgacttg tggctggggg   2760
tgaaaggcca atcaaaccgg gagatagctg gttctccccg aaagctattt aggtagcgcc   2820
tcgtgaattc atctccgggg gtagagcact gtttcggcaa ggggtcatc ccgacttacc   2880 aacccgatgc aaactgcgaa taccggagaa tgttatcacg ggagacacac ggcgggtgct   2940
aacgtccgtc gtgaagaggg aaacaaccca gaccgccagc taaggtccca aagtcatggt   3000
taagtgggaa acgatgtggg aaggcccaga cagccaggat gttggcttag aagcagccat   3060
catttaaaga aagcgtaata gctcactggt cgagtcggcc tgcgcggaag atgtaacggg   3120
gctaaaccat gcaccgaagc tgcggcagcg acgcttatgc gttgttgggt aggggagcgt   3180
tctgtaagcc tgcgaaggtg tgctgtgagg catgctggag gtatcagaag tgcgaatgct   3240
gacataagta acgataaagc gggtgaaaag cccgctcgcc ggaagaccaa gggttcctgt   3300
ccaacgttaa tcggggcagg gtgagtcgac ccctaaggcg aggccgaaag gcgtagtcga   3360
tgggaaacag gttaatattc ctgtacttgg tgttactgcg aagggggggac ggagaaggct   3420 atgttggccg ggcgacggtt gtcccggttt aagcgtgtag gctggttttc caggcaaatc   3480
cggaaaatca aggctgaggc gtgatgacga ggcactacgg tgctgaagca acaaatgccc   3540
tgcttccagg aaaagcctct aagcatcagg taacatcaaa tcgtacccca aaccgacaca   3600
ggtggtcagg tagagaatac caaggcgctt gagagaactc gggtgaagga actaggcaaa   3660
atggtgccgt aacttcggga gaaggcacgc tgatatgtag gtgaggtccc tcgcggatgg   3720
agctgaaatc agtcgaagat accagctggc tgcaactgtt tattaaaaac acagcactgt   3780
gcaaacacga aagtggacgt atacggtgtg acgcctgccc ggtgccggaa ggttaattga   3840
tggggttagc gcaagcgaag ctcttgatcg aagcccggt aaacggcggc cgtaactata   3900
acggtcctaa ggtagcgaaa ttccttgtcg ggtaagttcc gacctgcacg aatggcgtaa   3960
tgatggccag gctgtctcca cccgagactc agtgaaattg aactcgctgt gaagatgcag   4020
tgtacccgcg gcaagacgga aagacccgt gaacctttac tatagcttga cactgaacat   4080
tgagccttga tgtgtaggat aggtgggagg ctttgaagtg tggacgccag tctgcatgga   4140
gccgaccttg aaataccacc ctttaatgtt tgatgttcta acgttgaccc gtaatccggg   4200
ttgcggacag tgtctggtgg gtagtttgac tggggcggtc tcctcctaaa gagtaacgga   4260
ggagcacgaa ggttggctaa tcctggtcgg acatcaggag gttagtgcaa tggcataagc   4320
cagcttgact gcgagcgtga cggcgcgagc aggtgcgaaa gcaggtcata gtgatccggt   4380
ggttctgaat ggaagggcca tcgctcaacg gataaaaggt actccgggga taacaggctg   4440
ataccgccca agagttcata tcgacggcgg tgtttggcac ctcgatgtcg gctcatcaca   4500
tcctggggct gaagtaggtc ccaagggtat ggctgttcgc catttaaagt ggtacgcgag   4560
ctgggtttag aacgtcgtga gacagttcgg tccctatctg ccgtgggcgc tggagaactg   4620
aggggggctg ctcctagtac gagaggaccg gagtggacgc atcactggtg ttcgggttgt   4680
catgccaatg gcactgcccg gtagctaaat gcggaagaga taagtgctga aagcatctaa   4740
gcacgaaact gccccgaga tgagttctcc ctgacccttt aagggtcctg aaggaacgtt   4800
gaagacgacg acgttgatag gccgggtgtg taagcgcagc gatgcgttga gctaaccggt   4860
actaatgaac cgtgaggctt aaccttacaa cgccgaagct gttttggcgg atgagagaag   4920
```

```
attttcagcc tgatacagat taaatcagaa cgcagaagcg gtctgataaa acagaatttg   4980
cctggcggca gtagcgcggt ggtcccacct gaccccatgc cgaactcaga agtgaaacgc   5040
cgtagcgccg atggtagtgt ggggtctccc catgcgagag tagggaactg ccaggcatca   5100
aataaaacga aaggctcagt cgaaagactg ggcctttcgt tttatctgtt gtttgtcggt   5160
gaacgctctc ctgagtagga caaatccgcc gggagcggat ttgaacgttg cgaagcaacg   5220
gcccggaggg tggcgggcag gacgcccgcc ataaactgcc aggcatcaaa ttaagcagaa   5280
ggccatcctg acggatggcc ttttgcgtt tctacaaact cttcctgtcg tcatatctac   5340
aagccatccc cccacagata cggtaaacta gcctcgtttt tgcatcagga aagcagctat   5400
gaaccactcc ttaaaaccct ggaacacatt tggcattgat cataatgctc agcacattgt   5460
atgggcctta agggcccaac aattactcaa tgcctggcag tatgcaaccg cagaaggaca   5520
acccgttctt attctgggtg aaggaagtaa tgtacttttt ctggaggact atcgcggcac   5580
ggtgatcatc aaccggatca aaggtatcga aattcatgat gaacctgatg cgtggtattt   5640
acatgtagga gccggagaaa actggcatcg tctggtaaaa tacactttgc aggaaggtat   5700
gcctggtctg gaaaatctgg cattaattcc tggttgtgtc ggctcatcac ctatccagaa   5760
tattggtgct tatggcgtag aattacagcg agtttgcgct tatgttgatt ctgttgaact   5820
ggcgacaggc aagcaagtgc gcttaactgc caaagagtgc cgttttggct atcgcgacag   5880
tattttaaa catgaatacc aggaccgctt cgctattgta gccgtaggtc tgcgtctgcc   5940
aaaagagtgg caacctgtac taacgtatgg tgacttaact cgtctgggat ccacaggacg   6000
ggtgtggtcg ccatgatcgc gtagtcgata gtggctccaa gtagcgaagc gagcaggact   6060
gggcggcggc caaagcggtc ggacagtgct ccgagaacgg gtgcgcatag aaattgcatc   6120
aacgcatata gcgctagcag cacgccatag tgactggcga tgctgtcgga atggacgata   6180
tcccgcaaga ggcccggcag taccggcata accaagccta tgcctacagc atccagggtg   6240
acggtgccga ggatgacgat gagcgcattg ttagatttca tacacggtgc ctgactgcgt   6300
tagcaattta actgtgataa actaccgcat taaagcttat cgatgataag ctgtcaaaca   6360
tgagaattct tgaagacgaa agggcctcgt gatacgccta ttttttatagg ttaatgtcat   6420
gataataatg gtttcttaga cgtcaggtgg cacttttcgg ggaaatgtgc gcggaacccc   6480
tatttgttta ttttttctaaa tacattcaaa tatgtatccg ctcatgagac aataaccctg   6540
ataaatgctt caataatatt gaaaaggaa gagtatgagt attcaacatt tccgtgtcgc   6600
ccttattccc ttttttgcgg catttttgcct tcctgttttt gctcacccag aaacgctggt   6660
gaaagtaaaa gatgctgaag atcagttggg tgcacgagtg ggttacatcg aactggatct   6720
caacagcgg aagatccttg agagttttcg ccccgaagaa cgttttccaa tgatgagcac   6780
ttttaaagtt ctgctatgtg gcgcggtatt atcccgtgtt gacgccgggc aagagcaact   6840
cggtcgccgc atacactatt ctcagaatga cttggttgag tactcaccag tcacagaaaa   6900
gcatcttacg gatggcatga cagtaagaga attatgcagt gctgccataa ccatgagtga   6960
taacactgcg gccaacttac ttctgacaac gatcggagga ccgaaggagc taaccgcttt   7020
tttgcacaac atgggggatc atgtaactcg ccttgatcgt tgggaaccgg agctgaatga   7080
agccatacca aacgacgagc gtgacaccac gatgcctgca gcaatggcaa caacgttgcg   7140
caaactatta actggcgaac tacttactct agcttcccgg caacaattaa tagactggat   7200
ggaggcggat aaagttgcag gaccacttct gcgctcggcc cttccggctg gctggtttat   7260
tgctgataaa tctggagccg gtgagcgtgg gtctcgcggt atcattgcag cactggggcc   7320
```

-continued

```
agatggtaag ccctcccgta tcgtagttat ctacacgacg gggagtcagg caactatgga    7380
tgaacgaaat agacagatcg ctgagatagg tgcctcactg attaagcatt ggtaactgtc    7440
agaccaagtt tactcatata tactttagat tgatttaaaa cttcattttt aatttaaaag    7500
gatctaggtg aagatccttt ttgataatct catgaccaaa atcccttaac gtgagttttc    7560
gttccactga gcgtcagacc ccgtagaaaa gatcaaagga tcttcttgag atcctttttt    7620
tctgcgcgta atctgctgct tgcaaacaaa aaaaccaccg ctaccagcgg tggtttgttt    7680
gccggatcaa gagctaccaa ctcttttttcc gaaggtaact ggcttcagca gagcgcagat    7740
accaaatact gtccttctag tgtagccgta gttaggccac cacttcaaga actctgtagc    7800
accgcctaca tacctcgctc tgctaatcct gttaccagtg gctgctgcca gtggcgataa    7860
gtcgtgtctt accgggttgg actcaagacg atagttaccg gataaggcgc agcggtcggg    7920
ctgaacgggg ggttcgtgca cacagcccag cttggagcga acgacctaca ccgaactgag    7980
atacctacag cgtgagctat gagaaagcgc cacgcttccc gaaggagaa aggcggacag    8040
gtatccggta agcggcaggg tcggaacagg agagcgcacg agggagcttc caggggggaaa    8100
cgcctggtat ctttatagtc ctgtcgggtt tcgccacctc tgacttgagc gtcgattttt    8160
gtgatgctcg tcaggggggc ggagcctatg gaaaaacgcc agcaacgcgg cctttttacg    8220
gttcctggcc ttttgctggc cttttgctca catgttcttt cctgcgttat cccctgattc    8280
tgtggataac cgtattaccg cctttgagtg agctgatacc gctcgccgca gccgaacgac    8340
cgagcgcagc gagtcagtga gcgaggaagc ggaagagcgc ctgatgcggt attttctcct    8400
tacgcatctg tgcggtattt cacaccgcat atggtgcact ctcagtacaa tctgctctga    8460
tgccgcatag ttaagccagt atacactccg ctatcgctac gtgactgggt catggctgcg    8520
ccccgacacc cgccaacacc cgctgacgcg ccctgacggg cttgtctgct cccggcatcc    8580
gcttacagac aagctgtgac cgtctccggg agctgcatgt gtcagaggtt ttcaccgtca    8640
tcaccgaaac gcgcgaggca gctgcggtaa agctcatcag cgtggtcgtg aagcgattca    8700
cagatgtctg cctgttcatc cgcgtccagc tcgttgagtt tctccagaag cgttaatgtc    8760
tggcttctga taaagcgggc catgttaagg gcggtttttt cctgtttggt cacttgatgc    8820
ctccgtgtaa gggggaattt ctgttcatgg gggtaatgat accgatgaaa cgagagagga    8880
tgctcacgat acgggttact gatgatgaac atgcccggtt actggaacgt tgtgagggta    8940
aacaactggc ggtatggatg cggcgggacc agagaaaaat cactcagggt caatgccagc    9000
gcttcgttaa tacagatgta ggtgttccac agggtagcca gcagcatcct gcgatgcctg    9060
gcgaaagggg gatgtgctgc aaggcgatta agttgggtaa cgccagggtt ttcccagtca    9120
cgacgttgta aaacgacggc cagtgaattc gagctcggta cctgcactga cgacaggaag    9180
agtttgtaga aacgcaaaaa ggccatccgt caggatggcc ttctgcttaa tttgatgcct    9240
ggcagtttat gcgggcgtc ctgcccgcca ccctccgggc cgttgcttcg caacgttcaa    9300
atccgctccc ggcggatttg tcctactcag gagagcgttc accgacaaac aacagataaa    9360
acgaaaggcc cagtctttcg actgagcctt tcgttttatt tgatgcctgg cagttcccta    9420
ctctcgcatg gggagacccc acactaccat cggcgctacg actagattat tgtagagct    9480
catccatgcc atgtgtaatc ccagcagcag ttacaaactc aagaaggacc atgtggtcac    9540
gcttttcgtt gggatctttc gaaagggcag attgtgtcga caggtaatgg ttgtctggta    9600
aaaggacagg gccatcgcca attggagtat tttgttgata atggtctgct agttgaacgg    9660
atccatcttc aatgttgtgg cgaattttga agttagcttt gattccattc ttttgtttgt    9720
```

```
ctgccgtgat gtatacattg tgtgagttat agttgtactc gagtttgtgt ccgagaatgt    9780
ttccatcttc tttaaaatca ataccttta actcgatacg attaacaagg gtatcacctt    9840
caaacttgac ttcagcacgc gtcttgtagt tcccgtcatc tttgaaagat atagtgcgtt    9900
cctgtacata accttcgggc atggcactct tgaaaaagtc atgccgtttc atatgatccg    9960
gataacggga aaagcattga acaccataag agaaagtagt gacaagtgtt ggccatggaa   10020
caggtagttt tccagtagtg caaataaatt taagggtaag cttccgtat gtagcatcac    10080 cttcaccctc tccactgaca gaaaatttgt gcccattaac atcaccatct aattcaacaa   10140
gaattgggac aactccagtg aaaagttctt ctcctttgct cgcagtgatt tttttctcca   10200
tttgcggagg gatatgaaag cggccgcttc cacacattaa actagttcga tgattaattg   10260
tcaacagctc gccggcggca cctcgctaac ggattcacca ctccaagaat tggagccaat   10320
cgattcttgc ggagaactgt gaatgcgggt acccagatcc ggaacataat ggtgcagggc   10380
gctgacttcc gcgtttccag actttacgaa acacggaaac cgaagaccat tcatgttgtt   10440
gctcaggtcg cagacgtttt gcagcagcag tcgcttcacg ttcgctcgcg tatcggtgat   10500
tcattctgct aaccagtaag gcaaccccgc cagcctagcc gggtcctcaa cgacaggagc   10560
acgatcatgc gcacccgtgg ccaggaccca acgctgcccg agatgcgccg cgtgcggctg   10620
ctggagatgg cggacgcgat ggatatgttc tgccaagggt tggtttgcgc attcacagtt   10680
ctccgcaaga atcgattggc tccaattctt ggagtggtga atccgttagc gaggtgccgc   10740
cggcgagctg ttgacaatta atcatcgaac tagtttaatg tgtggaagcg gccgctttca   10800
tatccctccg caaatggaga aaaaaatcac tggatatacc accgttgata tatcccaatg   10860
gcatcgtaaa gaacattttg aggcatttca gtcagttgct caatgtacct ataaccagac   10920
cgttcagctg gatattacgg cctttttaaa gaccgtaaag aaaaataagc acaagtttta   10980
tccggccttt attcacattc ttgcccgcct gatgaatgct catccggaat tccgtatggc   11040
aatgaaagac ggtgagctgg tgatatggga tagtgttcac ccttgttaca ccgttttcca   11100
tgagcaaact gaaacgtttt catcgctctg gagtgaatac cacgacgatt tccggcagtt   11160
tctacacata tattcgcaag atgtggcgtg ttacggtgaa aacctggcct atttccctaa   11220
agggtttatt gagaatatgt ttttcgtctc agccaatccc tgggtgagtt tcaccagttt   11280
tgatttaaac gtggccaata tggacaactt cttcgccccc gttttcacca tgggcaaata   11340
ttatacgcaa ggcgacaagg tgctgatgcc gctggcgatt caggttcatc atgccgtctg   11400
tgatggcttc catgtcggca gaatgcttaa tgaattacaa cagtactgcg atgagtggca   11460
gggcggggcg taattttttt aaggcagtta ttggtgccct taaacgcctg gtgctacgcc   11520
tgaataagtg ataataagcg gatgaatggc agaaattcga aagcaaattc gacccggtcg   11580
tcggttcagg gcagggtcgt taaatagccg cttatgtcta ttgctggttt acggtttatt   11640
gactacccga agcagtgtga ccctgtgctt ctcaaatgcc tgaggcagt ttgctcaggt    11700 ctcccgtggg ggggaataat taacggtatg agccttacgg cggacggatc gtggccgcaa   11760
gtgggtccgg ctagaggatc cgacaccatc gaatggtgca aaacctttcg cggtatggca   11820
tgatagcgcc cggaagagag tcaattcagg gtggtgaatg tgaaaccagt aacgttatac   11880
gatgtcgcag agtatgccgg tgtctcttat cagaccgttt cccgcgtggt gaaccaggcc   11940
agccacgttt ctgcgaaaac gcgggaaaaa gtggaagcgg cgatggcgga gctgaattac   12000
attcccaacc gcgtggcaca acaactggcg ggcaaacagt cgttgctgat tggcgttgcc   12060
acctccagtc tggccctgca cgcgccgtcg caaattgtcg cggcgattaa atctcgcgcc   12120
```

-continued

```
gatcaactgg gtgccagcgt ggtggtgtcg atggtagaac gaagcggcgt cgaagcctgt      12180
aaagcggcgg tgcacaatct tctcgcgcaa cgggtcagtg ggctgatcat taactatccg      12240
ctggatgacc aggatgccat tgctgtggaa gctgcctgca ctaatgttcc ggcgttattt      12300
cttgatgtct ctgaccagac acccatcaac agtattattt tctcccatga agacggtacg      12360
cgactgggcg tggagcatct ggtcgcattg ggtcaccagc aaatcgcgct gttagcgggc      12420
ccattaagtt ctgtctcggc gcgtctgcgt ctggctggct ggcataaata tctcactcgc      12480
aatcaaattc agccgatagc ggaacgggaa ggcgactgga gtgccatgtc cggttttcaa      12540
caaaccatgc aaatgctgaa tgagggcatc gttcccactg cgatgctggt tgccaacgat      12600
cagatggcgc tgggcgcaat gcgcgccatt accgagtccg ggctgcgcgt tggtgcggat      12660
atctcggtag tgggatacga cgataccgaa gacagctcat gttatatccc gccgtcaacc      12720
accatcaaac aggattttcg cctgctgggg caaaccagcg cggaccgctt gctgcaactc      12780
tctcagggcc aggcggtgaa gggcaatcag ctgttgcccg tctcactggt gaaaagaaaa      12840
accaccctgg cgcccaatac gcaaaccgcc tctccccgcg cgttggccga ttcattaatg      12900
cagctggcac gacaggtttc ccgactggaa agcgggcagt gagcgcaacg caattaatgt      12960
gagttagctc actcattagg caccccaggc tttacacttt atgcttccgg ctcgtataat      13020
gtgtggaatt gtgagcggat aacaatttca cacagcggcc gctgagaaaa agcgaagcgg      13080
cactgctctt taacaattta tcagacaatc tgtgtgggca ctcgaagata cggattctta      13140
acgtcgcaag acgaaaaatg aataccaagt ctcaagagtg aacacgtaat tcattacgaa      13200
gtttaattct ttgagcgtca aacttttaac gacggccagt gaattcgagc tcggtacctg      13260
cactgacgac aggaagag                                                   13278
```

<210> SEQ ID NO 4
<211> LENGTH: 13227
<212> TYPE: DNA
<213> ORGANISM: Artificial Sequence
<220> FEATURE:
<223> OTHER INFORMATION: primer

<400> SEQUENCE: 4

```
aaattgaaga gtttgatcat ggctcagatt gaacgctggc ggcaggccta acacatgcaa        60
gtcgaacggt aacaggaaga agcttgcttc tttgctgacg agtggcggac gggtgagtaa       120
tgtctgggaa actgcctgat ggaggggggat aactactgga aacggtagct aataccgcat      180
aacgtcgcaa gaccaaagag ggggaccttc gggcctcttg ccatcggatg tgcccagatg      240
ggattagcta gtaggtgggg taacggctca cctaggcgac gatccctagc tggtctgaga      300
ggatgaccag ccacactgga actgagacac ggtccagact cctacgggag gcagcagtgg      360
ggaatattgc acaatgggcg caagcctgat gcagccatgc cgcgtgtatg aagaaggcct      420
tcgggttgta aagtactttc agcggggagg aaggagtaa agttaatacc tttgctcatt      480
gacgttaccc gcagaagaag caccggctaa ctccgtgcca gcagccgcgg taatacggag      540
ggtgcaagcg ttaatcggaa ttactgggcg taaagcgcac gcaggcggtt tgttaagtca      600
gatgtgaaat ccccgggctc aacctggaa ctgcatctga tactggcaag cttgagtctc       660 gtagagggggg gtagaattcc aggtgtagcg gtgaaatgcg tagagatctg gaggaatacc      720
ggtggcgaag gcggccccct ggacgaagac tgacgctcag gtgcgaaagc gtgggagca       780 aacaggatta gataccctgg tagtccacgc cgtaaacgat gtcgacttgg aggttgtgcc      840
cttgaggcgt ggcttccgga gctaacgcgt taagtcgacc gcctggggag tacggccgca      900
```

-continued

```
aggttaaaac tcaaatgaat tgacgggggc ccgcacaagc ggcggagcat gtggattaat    960
tcgatgcaac gcgaagaacc ttacctgggt ttgacatgca caggacgcgt ctagagatag   1020
gcgttccctt gtggcctgtg tgcaggtggt gcatggctgt cgtcagctcg tgtcgtgaga   1080
tgttgggtta agtcccgcaa cgagcgcaac ccttgtctca tgttgccagc acgtaatggt   1140
ggggactcgt gagagactgc cggggtcaac tcggaggaag gtgggatga cgtcaagtca   1200
tcatgcccct tatgtccagg gcttcacaca tgctacaatg gccggtacaa agggctgcga   1260
tgccgcgagg ttaagcgaat ccttaaaagc cggtctcagt tcggatcggg gtctgcaact   1320
cgaccccgtg aagtcggagt cgctagtaat cgcagatcag caacgctgcg gtgaatacgt   1380
tcccgggcct tgtacacacc gcccgtcacg tcatgaaagt cggtaacacc cgaagccagt   1440
ggcctaaccc tcgggaggga gctgtcgaag gtgggatcgg cgattgggac gaagtcgtaa   1500
caaggtaacc gtaggggaac ctgcggttgg atcatgggat taccttaaag aagcgtactt   1560
tgtagtgctc acacagattg tctgatagaa agtgaaaagc aaggcgttta cgcgttggga   1620
gtgaggctga agagaataag gccgttcgct ttctattaat gaaagctcac cctacacgaa   1680
aatatcacgc aacgcgtgat aagcaatttt cgtgtcccct tcgtctagag gcccaggaca   1740
ccgcccttc acggcggtaa caggggttcg aatcccctag gggacgccac ttgctggttt   1800
gtgagtgaaa gtcgccgacc ttaatatctc aaaactcatc ttcgggtgat gtttgagatt   1860
tttgctcttt aaaaatctgg atcaagctga aaattgaaac actgaacaac gagagttgtt   1920
cgtgagtctc tcaaattttc gcaacacgat gatgaatcga agaaacatc ttcgggttgt   1980
gaggttaagc gactaagcgt acacggtgga tgccctggca gtcagaggcg atgaaggacg   2040
tgctaatctg cgataagcgt cggtaaggtg atatgaaccg ttataaccgg cgatttccga   2100
atggggaaac ccagtgtgtt tcgacacact atcattaact gaatccatag gttaatgagg   2160
cgaaccgggg gaactgaaac atctaagtac cccgaggaaa agaaatcaac cgagattccc   2220
ccagtagcgg cgagcgaacg gggagcagcc cagagcctga atcagtgtgt gtgttagtgg   2280
aagcgtctgg aaaggcgcgc gatacagggt gacagccccg tacacaaaaa tgcacatgct   2340
gtgagctcga tgagtagggc gggacacgtg gtatcctgtc tgaatatggg gggaccatcc   2400
tccaaggcta aatactcctg actgaccgat agtgaaccag taccgtgagg gaaaggcgaa   2460
aagaaccccg gcgaggggag tgaaaaagaa cctgaaaccg tgtacgtaca agcagtggga   2520
gcacgcttag gcgtgtgact gcgtacccttt tgtataatgg gtcagcgact tatattctgt   2580
agcaaggtta accgaatagg ggagccgaag ggaaaccgag tcttaactgg gcgttaagtt   2640
gcagggtata gacccgaaac ccggtgatct agccatgggc aggttgaagg ttgggtaaca   2700
ctaactggag gaccgaaccg actaatgttg aaaaattagc ggatgacttg tggctggggg   2760
tgaaaggcca atcaaaccgg gagatagctg gttctccccg aaagctattt aggtagcgcc   2820
tcgtgaattc atctccgggg gtagagcact gtttcggcaa ggggggtcatc ccgacttacc   2880
aacccgatgc aaactgcgaa taccggagaa tgttatcacg ggagacacac ggcgggtgct   2940
aacgtccgtc gtgaagaggg aaacaaccca gaccgccagc taaggtccca aagtcatggt   3000
taagtgggaa acgatgtggg aaggcccaga cagccaggat gttggcttag aagcagccat   3060
catttaaaga aagcgtaata gctcactggt cgagtcggcc tgcgcggaag atgtaacggg   3120
gctaaaccat gcaccgaagc tgcggcagcg acgcttatgc gttgttgggt aggggagcgt   3180
tctgtaagcc tgcgaaggtg tgctgtgagg catgctggag gtatcagaag tgcgaatgct   3240
gacataagta acgataaagc gggtgaaaag cccgctcgcc ggaagaccaa gggttcctgt   3300
```

```
ccaacgttaa tcggggcagg gtgagtcgac ccctaaggcg aggccgaaag gcgtagtcga    3360
tgggaaacag gttaatattc ctgtacttgg tgttactgcg aaggggggac ggagaaggct    3420
atgttggccg ggcgacggtt gtcccggttt aagcgtgtag gctggttttc caggcaaatc    3480
cggaaaatca aggctgaggc gtgatgacga ggcactacgg tgctgaagca acaaatgccc    3540
tgcttccagg aaaagcctct aagcatcagg taacatcaaa tcgtacccca accgacaca    3600
ggtggtcagg tagagaatac caaggcgctt gagagaactc gggtgaagga actaggcaaa    3660
atggtgccgt aacttcggga aaggcacgc tgatatgtag gtgaggtccc tcgcggatgg     3720
agctgaaatc agtcgaagat accagctggc tgcaactgtt tattaaaaac acagcactgt    3780
gcaaacacga aagtggacgt atacggtgtg acgcctgccc ggtgccggaa ggttaattga    3840
tggggttagc gcaagcgaag ctcttgatcg aagcccggt aaacggcggc cgtaactata    3900
acggtcctaa ggtagcgaaa ttccttgtcg ggtaagttcc gacctgcacg aatggcgtaa   3960
tgatggccag gctgtctcca cccgagactc agtgaaattg aactcgctgt gaagatgcag    4020
tgtacccgcg gcaagacgga aagaccccgt gaaccttac tatagcttga cactgaacat     4080
tgagccttga tgtgtaggat aggtgggagg ctttgaagtg tggacgccag tctgcatgga    4140
gccgaccttg aaataccacc ctttaatgtt tgatgttcta acgttgaccc gtaatccggg    4200
ttgcggacag tgtctggtgg gtagtttgac tggggcggtc tcctcctaaa gagtaacgga    4260
ggagcacgaa ggttggctaa tcctggtcgg acatcaggag gttagtgcaa tggcataagc    4320
cagcttgact gcgagcgtga cggcgcgagc aggtgcgaaa gcaggtcata gtgatccggt    4380
ggttctgaat ggaagggcca tcgctcaacg gataaaaggt actccgggga taacaggctg    4440
ataccgccca agagttcata tcgacggcgg tgtttggcac ctcgatgtcg gctcatcaca    4500
tcctggggct gaagtaggtc ccaagggtat ggctgttcgc catttaaagt ggtacgcgag    4560
ctgggtttag aacgtcgtga gacagttcgg tccctatctg ccgtgggcgc tggagaactg    4620
agggggctg ctcctagtac gagaggaccg gagtggacgc atcactggtg ttcgggttgt     4680
catgccaatg gcactgcccg gtagctaaat gcggaagaga taagtgctga aagcatctaa    4740
gcacgaaact tgccccgaga tgagttctcc ctgacccttt aagggtcctg aaggaacgtt    4800
gaagacgacg acgttgatag gccgggtgtg taagcgcagc gatgcgttga gctaaccggt    4860
actaatgaac cgtgaggctt aaccttacaa cgccgaagct gttttggcgg atgagagaag    4920
attttcagcc tgatacagat taaatcagaa cgcagaagcg gtctgataaa acagaatttg    4980
cctggcggca gtagcgcggt ggtcccacct gaccccatgc cgaactcaga agtgaaacgc    5040
cgtagcgccg atggtagtgt ggggtctccc catgcgagag tagggaactg ccaggcatca    5100
aataaaacga aaggctcagt cgaaagactg gcctttcgt tttatctgtt gtttgtcggt     5160
gaacgctctc ctgagtagga caaatccgcc gggagcggat ttgaacgttg cgaagcaacg    5220
gcccggaggg tggcgggcag gacgcccgcc ataaactgcc aggcatcaaa ttaagcagaa    5280
ggccatcctg acggatggcc ttttgcgtt tctacaaact cttcctgtcg tcatatctac     5340
aagccatccc cccacagata cggtaaacta gcctcgtttt tgcatcagga aagcagctat    5400
gaaccactcc ttaaaaccct ggaacacatt tggcattgat cataatgctc agcacattgt    5460
atgggcctta agggcccaac aattactcaa tgcctggcag tatgcaaccg cagaaggaca    5520
acccgttctt attctgggtg aaggaagtaa tgtactttt ctggaggact atcgcggcac     5580
ggtgatcatc aaccggatca aaggtatcga aattcatgat gaacctgatg cgtggtattt    5640
acatgtagga gccggagaaa actggcatcg tctggtaaaa tacactttgc aggaaggtat    5700
```

```
gcctggtctg gaaaatctgg cattaattcc tggttgtgtc ggctcatcac ctatccagaa    5760
tattggtgct tatggcgtag aattacagcg agtttgcgct tatgttgatt ctgttgaact    5820
ggcgacaggc aagcaagtgc gcttaactgc caaagagtgc cgttttggct atcgcgacag    5880
tatttttaaa catgaatacc aggaccgctt cgctattgta gccgtaggtc tgcgtctgcc    5940
aaaagagtgg caacctgtac taacgtatgg tgacttaact cgtctgggat ccacaggacg    6000
ggtgtggtcg ccatgatcgc gtagtcgata gtggctccaa gtagcgaagc gagcaggact    6060
gggcggcggc caaagcggtc ggacagtgct ccgagaacgg gtgcgcatag aaattgcatc    6120
aacgcatata gcgctagcag cacgccatag tgactggcga tgctgtcgga atggacgata    6180
tcccgcaaga ggcccggcag taccggcata accaagccta tgcctacagc atccagggtg    6240
acggtgccga ggatgacgat gagcgcattg ttagatttca tacacggtgc ctgactgcgt    6300
tagcaattta actgtgataa actaccgcat taaagcttat cgatgataag ctgtcaaaca    6360
tgagaattct tgaagacgaa agggcctcgt gatacgccta ttttatagg ttaatgtcat    6420 gataataatg gtttcttaga cgtcaggtgg cacttttcgg ggaaatgtgc gcggaacccc    6480
tatttgttta ttttttctaaa tacattcaaa tatgtatccg ctcatgagac aataaccctg    6540
ataaatgctt caataatatt gaaaaaggaa gagtatgagt attcaacatt tccgtgtcgc    6600
ccttattccc ttttttgcgg cattttgcct tcctgttttt gctcacccag aaacgctggt    6660
gaaagtaaaa gatgctgaag atcagttggg tgcacgagtg ggttacatcg aactggatct    6720
caacagcggt aagatccttg agagttttcg ccccgaagaa cgttttccaa tgatgagcac    6780
ttttaaagtt ctgctatgtg gcgcggtatt atcccgtgtt gacgccgggc aagagcaact    6840
cggtcgccgc atacactatt ctcagaatga cttggttgag tactcaccag tcacagaaaa    6900
gcatcttacg gatggcatga cagtaagaga attatgcagt gctgccataa ccatgagtga    6960
taacactgcg gccaacttac ttctgacaac gatcggagga ccgaaggagc taaccgcttt    7020
tttgcacaac atgggggatc atgtaactcg ccttgatcgt tgggaaccgg agctgaatga    7080
agccatacca aacgacgagc gtgacaccac gatgcctgca gcaatggcaa caacgttgcg    7140
caaactatta actggcgaac tacttactct agcttcccgg caacaattaa tagactggat    7200
ggaggcggat aaagttgcag gaccacttct gcgctcggcc cttccggctg gctggtttat    7260
tgctgataaa tctggagccg gtgagcgtgg gtctcgcggt atcattgcag cactggggcc    7320
agatggtaag ccctcccgta tcgtagttat ctacacgacg gggagtcagg caactatgga    7380
tgaacgaaat agacagatcg ctgagatagg tgcctcactg attaagcatt ggtaactgtc    7440
agaccaagtt tactcatata ctttagat tgatttaaaa cttcatttt aatttaaaag    7500 gatctaggtg aagatccttt ttgataatct catgaccaaa atcccttaac gtgagttttc    7560
gttccactga gcgtcagacc ccgtagaaaa gatcaaagga tcttcttgag atccttttt    7620 tctgcgcgta atctgctgct tgcaaacaaa aaaaccaccg ctaccagcgg tggtttgttt    7680
gccggatcaa gagctaccaa ctcttttcc gaaggtaact ggcttcagca gagcgcagat    7740
accaaatact gtccttctag tgtagccgta gttaggccac cacttcaaga actctgtagc    7800
accgcctaca tacctcgctc tgctaatcct gttaccagtg gctgctgcca gtggcgataa    7860
gtcgtgtctt accgggttgg actcaagacg atagttaccg gataaggcgc agcggtcggg    7920
ctgaacgggg ggttcgtgca cacagcccag cttggagcga acgacctaca ccgaactgag    7980
atacctacag cgtgagctat gagaaagcgc cacgcttccc gaagggagaa aggcggacag    8040
gtatccggta agcggcaggg tcggaacagg agagcgcacg agggagcttc caggggggaaa    8100
```

```
cgcctggtat ctttatagtc ctgtcgggtt tcgccacctc tgacttgagc gtcgattttt    8160
gtgatgctcg tcagggggc ggagcctatg gaaaaacgcc agcaacgcgg ccttttacg      8220 gttcctggcc ttttgctggc cttttgctca catgttcttt cctgcgttat ccctgattc      8280 tgtggataac cgtattaccg cctttgagtg agctgatacc gctcgccgca gccgaacgac    8340
cgagcgcagc gagtcagtga gcgaggaagc ggaagagcgc ctgatgcggt attttctcct    8400
tacgcatctg tgcggtattt cacaccgcat atggtgcact ctcagtacaa tctgctctga    8460
tgccgcatag ttaagccagt atacactccg ctatcgctac gtgactgggt catggctgcg    8520
ccccgacacc cgccaacacc cgctgacgcg ccctgacggg cttgtctgct cccggcatcc    8580
gcttacagac aagctgtgac cgtctccggg agctgcatgt gtcagaggtt ttcaccgtca    8640
tcaccgaaac gcgcgaggca gctgcggtaa agctcatcag cgtggtcgtg aagcgattca    8700
cagatgtctg cctgttcatc cgcgtccagc tcgttgagtt tctccagaag cgttaatgtc    8760
tggcttctga taaagcgggc catgttaagg cggttttttt cctgtttggt cacttgatgc    8820
ctccgtgtaa gggggaattt ctgttcatgg gggtaatgat accgatgaaa cgagagagga    8880
tgctcacgat acgggttact gatgatgaac atgcccggtt actggaacgt tgtgagggta    8940
aacaactggc ggtatggatg cggcgggacc agagaaaaat cactcagggt caatgccagc    9000
gcttcgttaa tacagatgta ggtgttccac agggtagcca gcagcatcct gcgatgcctg    9060
gcgaaggggg gatgtgctgc aaggcgatta agttgggtaa cgccagggtt ttcccagtca    9120
cgacgttgta aaacgacggc cagtgaattc gagctcggta cctgcactga cgacaggaag    9180
agtttgtaga aacgcaaaaa ggccatccgt caggatggcc ttctgcttaa tttgatgcct    9240
ggcagtttat ggcgggcgtc ctgcccgcca ccctccgggc cgttgcttcg caacgttcaa    9300
atccgctccc ggcggatttg tcctactcag gagagcgttc accgacaaac aacagataaa    9360
acgaaaggcc cagtctttcg actgagcctt tcgtttatt tgatgcctgg cagttcccta    9420
ctctcgcatg gggagacccc acactaccat cggcgctacg actagattat tgtagagct    9480 catccatgcc atgtgtaatc ccagcagcag ttacaaactc aagaaggacc atgtggtcac    9540
gcttttcgtt gggatctttc gaaagggcag attgtgtcga caggtaatgg ttgtctggta    9600
aaaggacagg gccatcgcca attggagtat tttgttgata atggtctgct agttgaacgg    9660
atccatcttc aatgttgtgg cgaattttga agttagcttt gattccattc ttttgtttgt    9720
ctgccgtgat gtatacattg tgtgagttat agttgtactc gagtttgtgt ccgagaatgt    9780
ttccatcttc tttaaaatca ataccttta actcgatacg attaacaagg gtatcaccct    9840
caaacttgac ttcagcacgc gtcttgtagt tcccgtcatc tttgaaagat atagtgcgtt    9900
cctgtacata accttcgggc atggcactct tgaaaaagtc atgccgtttc atatgatccg    9960
gataacggga aaagcattga acaccataag agaaagtagt gacaagtgtt ggccatggaa    10020
caggtagttt tccagtagtg caaataaatt taagggtaag ctttccgtat gtagcatcac    10080 cttcacccctc tccactgaca gaaaatttgt gcccattaac atcaccatct aattcaacaa    10140
gaattgggac aactccagtg aaaagttctt ctcctttgct cgcagtgatt tttttctcca    10200
tttgcggagg gatatgaaag cggccgcttc cacacattaa actagttcga tgattaattg    10260
tcaacagctc gccggcggca cctcgctaac ggattcacca ctccaagaat tggagccaat    10320
cgattcttgc ggagaactgt gaatgcgggt acccagatcc ggaacataat ggtgcagggc    10380
gctgacttcc gcgtttccag actttacgaa acacggaaac cgaagaccat tcatgttgtt    10440
gctcaggtcg cagacgtttt gcagcagcag tcgcttcacg ttcgctcgcg tatcggtgat    10500
```

```
tcattctgct aaccagtaag gcaaccccgc cagcctagcc gggtcctcaa cgacaggagc   10560
acgatcatgc gcaccgtgg ccaggaccca acgctgcccg agatgcgccg cgtgcggctg   10620
ctggagatgg cggacgcgat ggatatgttc tgccaagggt tggtttgcgc attcacagtt   10680
ctccgcaaga atcgattggc tccaattctt ggagtggtga atccgttagc gaggtgccgc   10740
cggcgagctg ttgacaatta atcatcgaac tagtttaatg tgtggaagcg gccgctttca   10800
tatccctccg caaatggaga aaaaaatcac tggatatacc accgttgata tatcccaatg   10860
gcatcgtaaa gaacattttg aggcatttca gtcagttgct caatgtacct ataaccagac   10920
cgttcagctg gatattacgg cctttttaaa gaccgtaaag aaaaataagc acaagtttta   10980
tccggccttt attcacattc ttgcccgcct gatgaatgct catccggaat tccgtatggc   11040
aatgaaagac ggtgagctgg tgatatggga tagtgttcac ccttgttaca cgttttcca   11100 tgagcaaact gaaacgtttt catcgctctg gagtgaatac cacgacgatt tccggcagtt   11160
tctacacata tattcgcaag atgtggcgtg ttacggtgaa aacctggcct atttccctaa   11220
agggtttatt gagaatatgt ttttcgtctc agccaatccc tgggtgagtt tcaccagttt   11280
tgatttaaac gtggccaata tggacaactt cttcgccccc gttttcacca tgggcaaata   11340
ttatacgcaa ggcgacaagg tgctgatgcc gctggcgatt caggttcatc atgccgtctg   11400
tgatggcttc catgtcggca gaatgcttaa tgaattacaa cagtactgcg atgagtggca   11460
gggcggggcg tattttttt aaggcagtta ttggtgccct aaacgcctg gtgctacgcc   11520 tgaataagtg ataataagcg gatgaatggc agaaattcga aagcaaattc gacccggtcg   11580
tcggttcagg gcagggtcgt taaatagccg cttatgtcta ttgctggttt acggtttatt   11640
gactacccga agcagtgtga ccctgtgctt ctcaaatgcc tgagggcagt ttgctcaggt   11700
ctcccgtggg gggaataat taacggtatg agccttacgg cggacggatc gtggccgcaa   11760
gtgggtccgg ctagaggatc cgacaccatc gaatggtgca aaccttttcg cggtatggca   11820
tgatagcgcc cggaagagag tcaattcagg gtggtgaatg tgaaaccagt aacgttatac   11880
gatgtcgcag agtatgccgg tgtctcttat cagaccgttt cccgcgtggt gaaccaggcc   11940
agccacgttt ctgcgaaaac gcgggaaaaa gtggaagcgg cgatggcgga gctgaattac   12000
attcccaacc gcgtggcaca acaactggcg gcaaacagt cgttgctgat tggcgttgcc   12060
acctccagtc tggccctgca cgcgccgtcg caaattgtcg cggcgattaa atctcgcgcc   12120
gatcaactgg gtgccagcgt ggtggtgtcg atggtagaac gaagcggcgt cgaagcctgt   12180
aaagcggcgg tgcacaatct tctcgcgcaa cgggtcagtg gctgatcat taactatccg   12240 ctggatgacc aggatgccat tgctgtggaa gctgcctgca ctaatgttcc ggcgttattt   12300
cttgatgtct ctgaccagac acccatcaac agtattattt tctcccatga agacggtacg   12360
cgactgggcg tggagcatct ggtcgcattg ggtcaccagc aaatcgcgct gttagcgggc   12420
ccattaagtt ctgtctcggc gcgtctgcgt ctggctggc ggcataaata tctcactcgc   12480
aatcaaattc agccgatagc ggaacgggaa ggcgactgga gtgccatgtc cggttttcaa   12540
caaaccatgc aaatgctgaa tgagggcatc gttcccactg cgatgctggt tgccaacgat   12600
cagatggcgc tgggcgcaat gcgcgccatt accgagtccg ggctgcgcgt tggtgcggat   12660
atctcggtag tgggatacga cgataccgaa gacagctcat gttatatccc gccgtcaacc   12720
accatcaaac aggattttcg cctgctgggg caaaccagcg cggaccgctt gctgcaactc   12780
tctcagggcc aggcggtgaa gggcaatcag ctgttgcccg tctcactggt gaaaagaaaa   12840
accaccctgg cgcccaatac gcaaaccgcc tctccccgcg cgttggccga ttcattaatg   12900
```

-continued

| | | |
|---|---|---|
| cagctggcac gacaggtttc ccgactggaa agcgggcagt gagcgcaacg caattaatgt | 12960 |
| gagttagctc actcattagg cacccaggc tttacactttt atgcttccgg ctcgtataat | 13020 |
| gtgtggaatt gtgagcggat aacaatttca cacagcggcc gctgagaaaa agcgaagcgg | 13080 |
| cactgctctt taacaattta tcagacaatc tgtgtgggca ctcgaagata cggattctta | 13140 |
| acgtcgcaag acgaaaaatg aataccaagt ctcaagagtg aacacgtaat tcattacgaa | 13200 |
| gtttaattct ttgagcgtca aactttt | 13227 |

<210> SEQ ID NO 5
<211> LENGTH: 8752
<212> TYPE: DNA
<213> ORGANISM: Artificial Sequence
<220> FEATURE:
<223> OTHER INFORMATION: primer

<400> SEQUENCE: 5

| | | |
|---|---|---|
| aaattgaaga gtttgatcat ggctcagatt gaacgctggc ggcaggccta acacatgcaa | 60 |
| gtcgaacggt aacaggaaga agcttgcttc tttgctgacg agtggcggac gggtgagtaa | 120 |
| tgtctgggaa actgcctgat ggagggggat aactactgga aacggtagct aataccgcat | 180 |
| aacgtcgcaa gaccaaagag ggggaccttc gggcctcttg ccatcggatg tgcccagatg | 240 |
| ggattagcta gtaggtgggg taacggctca cctaggcgac gatccctagc tggtctgaga | 300 |
| ggatgaccag ccacactgga actgagacac ggtccagact cctacgggag gcagcagtgg | 360 |
| ggaatattgc acaatgggcg caagcctgat gcagccatgc cgcgtgtatg aagaaggcct | 420 |
| tcgggttgta aagtactttc agcggggagg aagggagtaa agttaatacc tttgctcatt | 480 |
| gacgttaccc gcagaagaag caccggctaa ctccgtgcca gcagccgcgg taatacggag | 540 |
| ggtgcaagcg ttaatcggaa ttactgggcg taaagcgcac gcaggcggtt tgttaagtca | 600 |
| gatgtgaaat ccccgggctc aacctggaa ctgcatctga tactggcaag cttgagtctc | 660 |
| gtagaggggg gtagaattcc aggtgtagcg gtgaaatgcg tagagatctg gaggaatacc | 720 |
| ggtggcgaag gcggccccct ggacgaagac tgacgctcag gtgcgaaagc gtgggagca | 780 |
| aacaggatta gataccctgg tagtccacgc cgtaaacgat gtcgacttgg aggttgtgcc | 840 |
| cttgaggcgt ggcttccgga gctaacgcgt taagtcgacc gcctggggag tacggccgca | 900 |
| aggttaaaac tcaaatgaat tgacgggggc ccgcacaagc ggcggagcat gtggattaat | 960 |
| tcgatgcaac gcgaagaacc ttacctgggt ttgacatgca caggacgcgt ctagagatag | 1020 |
| gcgttccctt gtggcctgtg tgcaggtggt gcatggctgt cgtcagctcg tgtcgtgaga | 1080 |
| tgttgggtta agtcccgcaa cgagcgcaac ccttgtctca tgttgccagc acgtaatggt | 1140 |
| ggggactcgt gagagactgc cggggtcaac tcggaggaag gtgggggatga cgtcaagtca | 1200 |
| tcatgcccct tatgtccagg gcttcacaca tgctacaatg gccggtacaa agggctgcga | 1260 |
| tgccgcgagg ttaagcgaat cctaaaagc cggtctcagt tcggatcggg gtctgcaact | 1320 |
| cgaccccgtg aagtcggagt gctagtaat cgcagatcag caacgctgcg gtgaatacgt | 1380 |
| tcccgggcct tgtacacacc gcccgtcacg tcatgaaagt cggtaacacc cgaagccagt | 1440 |
| ggcctaaccc tcgggaggga gctgtcgaag gtgggatcgg cgattgggac gaagtcgtaa | 1500 |
| caaggtaacc gtaggggaac ctgcggttgg atcatgggat taccttaaag aagcgtactt | 1560 |
| tgtagtgctc acacagattg tctgatagaa agtgaaaagc aaggcgttta cgcgttggga | 1620 |
| gtgaggctga agagaataag gccgttcgct ttctattaat gaaagctcac cctacacgaa | 1680 |
| aatatcacgc aacgcgtgat aagcaatttt cgtgtcccct tcgtctagac gtagcgccga | 1740 |

```
tggtagtgtg gggtctcccc atgcgagagt agggaactgc caggcatcaa ataaaacgaa    1800
aggctcagtc gaaagactgg gcctttcgtt ttatctgttg tttgtcggtg aacgctctcc    1860
tgagtaggac aaatccgccg ggagcggatt tgaacgttgc gaagcaacgg cccggagggt    1920
ggcgggcagg acgcccgcca taaactgcca ggcatcaaat taagcagaag ccatcctga    1980 cggatggcct ttttgcgttt ctacaaactc ttcctgtcgt cactgcaggc atgcaagctt    2040
ggcgtaatca tggtcatagc tgtttcctgt gtgaaattgt tatccgctca caattccaca    2100
caacatacga gccggaagca taaagtgtaa agcctggggt gcctaatgag tgagctaact    2160
cacattaatt gcgttgcgct cactgcccgc tttccagtcg ggaaacctgt cgtgccagct    2220
gcattaatga atcggccaac gcgcggggag aggcggtttg cgtattgggc gctcttccgc    2280
ttcctcgctc actgactcgc tgcgctcggt cgttcggctg cggcgagcgg tatcagctca    2340
ctcaaaggcg gtaatacggt tatccacaga atcagggat aacgcaggaa agaacatgtg     2400
agcaaaaggc cagcaaaagg ccaggaaccg taaaaaggcc gcgttgctgg cgttttccca    2460
taggctccgc cccctgacg agcatcacaa aaatcgacgc tcaagtcaga ggtggcgaaa     2520
cccgacagga ctataaagat accaggcgtt tcccctgga agctccctcg tgcgctctcc     2580
tgttccgacc ctgccgctta ccggatacct gtccgccttt ctcccttcgg gaagcgtggc    2640
gctttctcat agctcacgct gtaggtatct cagttcggtg taggtcgttc gctccaagct    2700
gggctgtgtg cacgaacccc ccgttcagcc cgaccgctgc gccttatccg gtaactatcg    2760
tcttgagtcc aacccggtaa gacacgactt atcgccactg gcagcagcca ctggtaacag    2820
gattagcaga gcgaggtatg taggcggtgc tacagagttc ttgaagtggt ggcctaacta    2880
cggctacact agaaggacag tatttggtat ctgcgctctg ctgaagccag ttaccttcgg    2940
aaaaagagtt ggtagctctt gatccggcaa acaaaccacc gctggtagcg gtggtttttt    3000
tgtttgcaag cagcagatta cgcgcagaaa aaaaggatct caagaagatc ctttgatctt    3060
ttctacgggg tctgacgctc agtggaacga aaactcacgt taagggattt tggtcatgag    3120
attatcaaaa aggatcttca cctagatcct tttaaattaa aaatgaagtt ttaaatcaat    3180
ctaaagtata tatgagtaaa cttggtctga cagttaccaa tgcttaatca gtgaggcacc    3240
tatctcagcg atctgtctat ttcgttcatc catagttgcc tgactccccg tcgtgtagat    3300
aactacgata cgggagggct taccatctgg ccccagtgct gcaatgatac cgcgagaccc    3360
acgctcaccg gctccagatt tatcagcaat aaaccagcca gccggaaggg ccgagcgcag    3420
aagtggtcct gcaactttat ccgcctccat ccagtctatt aattgttgcc gggaagctag    3480
agtaagtagt tcgccagtta atagtttgcg caacgttgtt gccattgcta caggcatcgt    3540
ggtgtcacgc tcgtcgtttg gtatggcttc attcagctcc ggttcccaac gatcaaggcg    3600
agttacatga tcccccatgt tgtgcaaaaa agcggttagc tccttcggtc ctccgatcgt    3660
tgtcagaagt aagttggccg cagtgttatc actcatggtt atggcagcac tgcataattc    3720
tcttactgtc atgccatccg taagatgctt ttctgtgact ggtgagtact caaccaagtc    3780
attctgagaa tagtgtatgc ggcgaccgag ttgctcttgc ccggcgtcaa tacgggataa    3840
taccgcgcca catagcagaa ctttaaaagt gctcatcatt ggaaaacgtt cttcggggcg    3900
aaaactctca aggatcttac cgctgttgag atccagttcg atgtaaccca ctcgtgcacc    3960
caactgatct tcagcatctt ttactttcac cagcgtttct gggtgagcaa aaacaggaag    4020
gcaaaatgcc gcaaaaaagg gaataagggc gacacgaaaa tgttgaatac tcatactctt    4080 ccttttttcaa tattattgaa gcatttatca gggttattgt ctcatgagcg gatacatatt    4140
```

```
tgaatgtatt tagaaaaata aacaaatagg ggttccgcgc acatttcccc gaaaagtgcc    4200
acctgacgtc taagaaacca ttattatcat gacattaacc tataaaaata ggcgtatcac    4260
gaggcccttt cgtctcgcgc gtttcggtga tgacggtgaa aacctctgac acatgcagct    4320
cccggagacg gtcacagctt gtctgtaagc ggatgccggg agcagacaag cccgtcaggg    4380
cgcgtcagcg ggtgttggcg ggtgtcgggg ctggcttaac tatgcggcat cagagcagat    4440
tgtactgaga gtgcaccata tgcggtgtga ataccgcac agatgcgtaa ggagaaaata    4500
ccgcatcagg cgccattcgc cattcaggct gcgcaactgt tgggaagggc gatcggtgcg    4560
ggcctcttcg ctattacgcc agctggcgaa agggggatgt gctgcaaggc gattaagttg    4620
ggtaacgcca gggttttccc agtcacgacg ttgtaaaacg acggccagtg aattcgagct    4680
cggtacctgc agtgacgaca ggaagagttt gtagaaacgc aaaaaggcca tccgtcagga    4740
tggccttctg cttaatttga tgcctggcag tttatggcgg gcgtcctgcc cgccaccctc    4800
cgggccgttc ttcgcaacg ttcaaatccg ctcccggcgg atttgtccta ctcaggagag    4860
cgttcaccga caaacaacag ataaaacgaa aggcccagtc tttcgactga gcctttcgtt    4920
ttatttgatg cctggcagtt ccctactctc gcatggggag accccacact accatcggcg    4980
ctacgtctag attatttgta gagctcatcc atgccatgtg taatcccagc agcagttaca    5040
aactcaagaa ggaccatgtg gtcacgcttt tcgttgggat ctttcgaaag ggcagattgt    5100
gtcgacaggt aatggttgtc tggtaaaagg acagggccat cgccaattgg agtattttgt    5160
tgataatggt ctgctagttg aacggatcca tcttcaatgt tgtggcgaat tttgaagtta    5220
gctttgattc cattcttttg tttgtctgcc gtgatgtata cattgtgtga gttatagttg    5280
tactcgagtt tgtgtccgag aatgtttcca tcttctttaa aatcaatacc ttttaactcg    5340
atacgattaa caagggtatc accttcaaac ttgacttcag cacgcgtctt gtagttcccg    5400
tcatctttga aagatatagt gcgttcctgt ataaccctt cgggcatggc actcttgaaa    5460
aagtcatgcc gtttcatatg atccggataa cgggaaaagc attgaacacc ataagagaaa    5520
gtagtgacaa gtgttggcca tggaacaggt agttttccag tagtgcaaat aaatttaagg    5580
gtaagctttc cgtatgtagc atcaccttca ccctctccac tgacagaaaa tttgtgccca    5640
ttaacatcac catctaattc aacaagaatt gggacaactc cagtgaaaag ttcttctcct    5700
ttgctagcag tgatttttt ctccatttgc ggagggatat gaaagcggcc gcttccacac    5760
attaaactag ttcgatgatt aattgtcaac agctcgccgg cggcacctcg ctaacggatt    5820
caccactcca agaattggag ccaatcgatt cttgcggaga actgtgaatg cgggtaccca    5880
gatccggaac ataatggtgc agggcgctga cttccgcgtt tccagacttt acgaaacacg    5940
gaaaccgaag accattcatg ttgttgctca ggtcgcagac gttttgcagc agcagtcgct    6000
tcacgttcgc tcgcgtatcg gtgattcatt ctgctaacca gtaaggcaac cccgccagcc    6060
tagccgggtc ctcaacgaca ggagcacgat catgcgcacc cgtggccagg acccaacgct    6120
gcccgagatg cgccgcgtgc ggctgctgga gatggcggac gcgatggata tgttctgcca    6180
agggttggtt tgcgcattca cagttctccg caagaatcga ttggctccaa ttcttggagt    6240
ggtgaatccg ttagcgaggt gccgccggcg agctgttgac aattaatcat cgaactagtt    6300
taatgtgtgg aagcggccgc tttcatatcc ctccgcaaat ggagaaaaaa atcactggat    6360
ataccaccgt tgatatatcc caatggcatc gtaaagaaca ttttgaggca tttcagtcag    6420
ttgctcaatg tacctataac cagaccgttc agctggatat tacggccttt ttaaagaccg    6480
taaagaaaaa taagcacaag ttttatccgg cctttattca cattcttgcc cgcctgatga    6540
```

-continued

```
atgctcatcc ggaattccgt atggcaatga agacggtga gctggtgata tgggatagtg    6600
ttcacccttg ttacaccgtt ttccatgagc aaactgaaac gttttcatcg ctctggagtg    6660
aataccacga cgatttccgg cagtttctac acatatattc gcaagatgtg gcgtgttacg    6720
gtgaaaacct ggcctatttc cctaaagggt ttattgagaa tatgttttt c gtctcagcca    6780
atccctgggt gagtttcacc agttttgatt taaacgtggc caatatggac aacttcttcg    6840
cccccgtttt caccatgggc aaatattata cgcaaggcga caaggtgctg atgccgctgg    6900
cgattcaggt tcatcatgcc gtctgtgatg gcttccatgt cggcagaatg cttaatgaat    6960
tacaacagta ctgcgatgag tggcagggcg gggcgtaatt ttttaaggc agttattggt    7020
gcccttaaac gcctggtgct acgcctgaat aagtgataat aagcggatga atggcagaaa    7080
ttcgaaagca aattcgaccc ggtcgtcggt tcagggcagg gtcgttaaat agccgcttat    7140
gtctattgct ggtttacggt ttattgacta cccgaagcag tgtgaccctg tgcttctcaa    7200
atgcctgagg gcagtttgct caggtctccc gtgggggga ataattaacg gtatgagcct    7260
tacggcggac ggatcgtggc cgcaagtggg tccggctaga ggatccgaca ccatcgaatg    7320
gtgcaaaacc tttcgcggta tggcatgata gcgcccggaa gagagtcaat tcagggtggt    7380
gaatgtgaaa ccagtaacgt tatacgatgt cgcagagtat gccggtgtct cttatcagac    7440
cgtttcccgc gtggtgaacc aggccagcca cgtttctgcg aaaacgcggg aaaaagtgga    7500
agcggcgatg gcggagctga attacattcc caaccgcgtg gcacaacaac tggcgggcaa    7560
acagtcgttg ctgattggcg ttgccacctc cagtctggcc ctgcacgcgc cgtcgcaaat    7620
tgtcgcggcg attaaatctc gcgccgatca actgggtgcc agcgtggtgg tgtcgatggt    7680
agaacgaagc ggcgtcgaag cctgtaaagc ggcggtgcac aatcttctcg cgcaacgggt    7740
cagtgggctg attattaact atccgctgga tgaccaggat gccattgctg tggaagctgc    7800
ctgcactaat gttccggcgt tatttcttga tgtctctgac cagacaccca tcaacagtat    7860
tattttctcc catgaagacg gtacgcgact gggcgtggag catctggtcg cattgggcca    7920
ccagcaaatc gcgctgttag cgggcccatt aagttctgtc tcggcgcgtc tgcgtctggc    7980
tggctggcat aaatatctca ctcgcaatca aattcagccg atagcggaac gggaaggcga    8040
ctggagtgcc atgtccggtt ttcaacaaac catgcaaatg ctgaatgagg gcatcgttcc    8100
cactgcgatg ctggttgcca acgatcagat ggcgctgggc gcaatgcgcg ccattaccga    8160
gtccgggctg cgcgttggtg cggatatctc ggtagtggga tacgacgata ccgaagacag    8220
ctcatgttat atcccgccgt caaccaccat caaacaggat tttcgcctgc tggggcaaac    8280
cagcgtggac cgcttgctgc aactctctca gggccaggcg gtgaagggca atcagctgtt    8340
gcccgtctca ctggtgaaaa gaaaaaccac cctggcgccc aatacgcaaa ccgcctctcc    8400
ccgcgcgttg gccgattcat taatgcagct ggcacgacag gtttcccgac tggaaagcgg    8460
gcagtgagcg caacgcaatt aatgtgagtt agctcactca ttaggcaccc caggctttac    8520
actttatgct tccggctcgt ataatgtgtg gaattgtgag cggataacaa tttcacacag    8580
cggccgctga gaaaaagcga agcggcactg ctctttaaca attttatcaga caatctgtgt    8640
gggcactcga agatacggat tcttaacgtc gcaagacgaa aaatgaatac caagtctcaa    8700
gagtgaacac gtaattcatt acgaagttta attctttgag cgtcaaactt tt            8752
```

<210> SEQ ID NO 6
<211> LENGTH: 20
<212> TYPE: DNA
<213> ORGANISM: Artificial Sequence
<220> FEATURE:

<223> OTHER INFORMATION: primer

<400> SEQUENCE: 6 atagggttc cgcgcacatt					20

<210> SEQ ID NO 7
<211> LENGTH: 48
<212> TYPE: DNA
<213> ORGANISM: Artificial Sequence
<220> FEATURE:
<223> OTHER INFORMATION: primer

<400> SEQUENCE: 7
ctcgagcctc ctgaaagcgg ccgcaactca aaaatacgc ccggtagt					48

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aaatcgtcgt ggtattcact					20

<210> SEQ ID NO 9
<211> LENGTH: 44
<212> TYPE: DNA
<213> ORGANISM: Artificial Sequence
<220> FEATURE:
<223> OTHER INFORMATION: primer

<400> SEQUENCE: 9
gcggccgctt tcaggaggct cgagaaatgg agaaaaaaat cact					44

<210> SEQ ID NO 10
<211> LENGTH: 59
<212> TYPE: DNA
<213> ORGANISM: Artificial Sequence
<220> FEATURE:
<223> OTHER INFORMATION: primer

<400> SEQUENCE: 10
ggccgctagc cggcgagctg ttgacaatta atcatcgaac tagtttaatg tgtggaagc					59

<210> SEQ ID NO 11
<211> LENGTH: 59
<212> TYPE: DNA
<213> ORGANISM: Artificial Sequence
<220> FEATURE:
<223> OTHER INFORMATION: primer

<400> SEQUENCE: 11
ggccgcttcc acacattaaa ctagttcgat gattaattgt caacagctcg ccggctagc					59

<210> SEQ ID NO 12
<211> LENGTH: 17
<212> TYPE: DNA
<213> ORGANISM: Artificial Sequence
<220> FEATURE:
<223> OTHER INFORMATION: primer

<400> SEQUENCE: 12
tcgagcacac tgaaagc					17

<210> SEQ ID NO 13

```
<211> LENGTH: 17
<212> TYPE: DNA
<213> ORGANISM: Artificial Sequence
<220> FEATURE:
<223> OTHER INFORMATION: primer

<400> SEQUENCE: 13
ggccgctttc agtgtgc                                                    17

<210> SEQ ID NO 14
<211> LENGTH: 68
<212> TYPE: DNA
<213> ORGANISM: Artificial Sequence
<220> FEATURE:
<223> OTHER INFORMATION: primer

<400> SEQUENCE: 14
ggtcataggc ggccgctgtg tgaaattgtt atccgctcac aattccacac attatacgag     60
ccggaagc                                                              68

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
ttggatccga caccatcgaa tggtgcaaaa cctt                                 34

<210> SEQ ID NO 16
<211> LENGTH: 29
<212> TYPE: DNA
<213> ORGANISM: Artificial Sequence
<220> FEATURE:
<223> OTHER INFORMATION: primer

<400> SEQUENCE: 16
gaagggatcc ggcgaagatg tttctctgg                                       29

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
gcggccgctt aaaataattt tctgacc                                         27

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
ccacaagctt cgcacctgag cgtcagtctt c                                    31

<210> SEQ ID NO 19
<211> LENGTH: 37
<212> TYPE: DNA
<213> ORGANISM: Artificial Sequence
<220> FEATURE:
<223> OTHER INFORMATION: primer
```

-continued

<400> SEQUENCE: 19
aaaattattt taagcggccg ctgagaaaaa gcgaagc                          37

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
ggcgactttc actcacaaac                                            20

<210> SEQ ID NO 21
<211> LENGTH: 65
<212> TYPE: DNA
<213> ORGANISM: Artificial Sequence
<220> FEATURE:
<223> OTHER INFORMATION: primer

<400> SEQUENCE: 21
gtcgaagctt ggtaaccgta ggggaacctg cggttggatc acacacttac cttaaagaag  60
cgtac                                                            65

<210> SEQ ID NO 22
<211> LENGTH: 54
<212> TYPE: DNA
<213> ORGANISM: Artificial Sequence
<220> FEATURE:
<223> OTHER INFORMATION: primer
<221> NAME/KEY: misc_feature
<222> LOCATION: 34, 35, 36, 37
<223> OTHER INFORMATION: n = A,T,C or G

<400> SEQUENCE: 22
ttaatgtgtg aagcggccg ctttcatatc cctnnnnaaa tggagaaaaa aatc        54

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
cagcaccttg tcgccttgc                                             19

<210> SEQ ID NO 24
<211> LENGTH: 11
<212> TYPE: DNA
<213> ORGANISM: Artificial Sequence
<220> FEATURE:
<223> OTHER INFORMATION: primer

<400> SEQUENCE: 24
caggaggcuc g                                                     11

<210> SEQ ID NO 25
<211> LENGTH: 11
<212> TYPE: RNA
<213> ORGANISM: Artificial Sequence
<220> FEATURE:
<223> OTHER INFORMATION: primer

<400> SEQUENCE: 25
ucaccuccuu a                                                     11

<210> SEQ ID NO 26
<211> LENGTH: 11
<212> TYPE: RNA
<213> ORGANISM: Artificial Sequence
<220> FEATURE:
<223> OTHER INFORMATION: primer

<400> SEQUENCE: 26
cagugugcuc g                                                              11

<210> SEQ ID NO 27
<211> LENGTH: 11
<212> TYPE: RNA
<213> ORGANISM: Artificial Sequence
<220> FEATURE:
<223> OTHER INFORMATION: primer

<400> SEQUENCE: 27
ucacacacuu a                                                              11

<210> SEQ ID NO 28
<211> LENGTH: 11
<212> TYPE: RNA
<213> ORGANISM: Artificial Sequence
<220> FEATURE:
<223> OTHER INFORMATION: primer

<400> SEQUENCE: 28
cauaucccuc g                                                              11

<210> SEQ ID NO 29
<211> LENGTH: 11
<212> TYPE: RNA
<213> ORGANISM: Artificial Sequence
<220> FEATURE:
<223> OTHER INFORMATION: primer

<400> SEQUENCE: 29
ucagggauuu a                                                              11

<210> SEQ ID NO 30
<211> LENGTH: 11
<212> TYPE: RNA
<213> ORGANISM: Artificial Sequence
<220> FEATURE:
<223> OTHER INFORMATION: primer

<400> SEQUENCE: 30
caaacaccuc g                                                              11

<210> SEQ ID NO 31
<211> LENGTH: 11
<212> TYPE: RNA
<213> ORGANISM: Artificial Sequence
<220> FEATURE:
<223> OTHER INFORMATION: primer

<400> SEQUENCE: 31
ucaagagguu a                                                              11

<210> SEQ ID NO 32
<211> LENGTH: 11
<212> TYPE: RNA
<213> ORGANISM: Artificial Sequence
<220> FEATURE:
<223> OTHER INFORMATION: primer

```
<400> SEQUENCE: 32
cauaccucuc g                                                    11

<210> SEQ ID NO 33
<211> LENGTH: 11
<212> TYPE: RNA
<213> ORGANISM: Artificial Sequence
<220> FEATURE:
<223> OTHER INFORMATION: primer

<400> SEQUENCE: 33
ucaugagguu a                                                    11

<210> SEQ ID NO 34
<211> LENGTH: 11
<212> TYPE: RNA
<213> ORGANISM: Artificial Sequence
<220> FEATURE:
<223> OTHER INFORMATION: primer

<400> SEQUENCE: 34
cauaauccuc g                                                    11

<210> SEQ ID NO 35
<211> LENGTH: 11
<212> TYPE: RNA
<213> ORGANISM: Artificial Sequence
<220> FEATURE:
<223> OTHER INFORMATION: primer

<400> SEQUENCE: 35
ucagaggauu a                                                    11

<210> SEQ ID NO 36
<211> LENGTH: 11
<212> TYPE: RNA
<213> ORGANISM: Artificial Sequence
<220> FEATURE:
<223> OTHER INFORMATION: primer

<400> SEQUENCE: 36
caaauaccuc g                                                    11

<210> SEQ ID NO 37
<211> LENGTH: 11
<212> TYPE: RNA
<213> ORGANISM: Artificial Sequence
<220> FEATURE:
<223> OTHER INFORMATION: primer

<400> SEQUENCE: 37
ucaugagguu a                                                    11

<210> SEQ ID NO 38
<211> LENGTH: 11
<212> TYPE: RNA
<213> ORGANISM: Artificial Sequence
<220> FEATURE:
<223> OTHER INFORMATION: primer

<400> SEQUENCE: 38
cacauaccuc g                                                    11

<210> SEQ ID NO 39
<211> LENGTH: 11
```

```
<212> TYPE: RNA
<213> ORGANISM: Artificial Sequence
<220> FEATURE:
<223> OTHER INFORMATION: primer

<400> SEQUENCE: 39
ucaugagguu a                                                            11

<210> SEQ ID NO 40
<211> LENGTH: 11
<212> TYPE: RNA
<213> ORGANISM: Artificial Sequence
<220> FEATURE:
<223> OTHER INFORMATION: primer

<400> SEQUENCE: 40
caccgaccuc g                                                            11

<210> SEQ ID NO 41
<211> LENGTH: 11
<212> TYPE: RNA
<213> ORGANISM: Artificial Sequence
<220> FEATURE:
<223> OTHER INFORMATION: primer

<400> SEQUENCE: 41
ucaagagguu a                                                            11

<210> SEQ ID NO 42
<211> LENGTH: 11
<212> TYPE: RNA
<213> ORGANISM: Artificial Sequence
<220> FEATURE:
<223> OTHER INFORMATION: primer

<400> SEQUENCE: 42
cauaucccuc g                                                            11

<210> SEQ ID NO 43
<211> LENGTH: 11
<212> TYPE: RNA
<213> ORGANISM: Artificial Sequence
<220> FEATURE:
<223> OTHER INFORMATION: primer

<400> SEQUENCE: 43
ucaugggauu a                                                            11

<210> SEQ ID NO 44
<211> LENGTH: 11
<212> TYPE: RNA
<213> ORGANISM: Artificial Sequence
<220> FEATURE:
<223> OTHER INFORMATION: primer

<400> SEQUENCE: 44
caacuaccuc g                                                            11

<210> SEQ ID NO 45
<211> LENGTH: 11
<212> TYPE: RNA
<213> ORGANISM: Artificial Sequence
<220> FEATURE:
<223> OTHER INFORMATION: primer

<400> SEQUENCE: 45
ucaugagguu a                                                            11
```

<210> SEQ ID NO 46
<211> LENGTH: 11
<212> TYPE: RNA
<213> ORGANISM: Artificial Sequence
<220> FEATURE:
<223> OTHER INFORMATION: primer

<400> SEQUENCE: 46
cauauaccuc g                                                        11

<210> SEQ ID NO 47
<211> LENGTH: 11
<212> TYPE: RNA
<213> ORGANISM: Artificial Sequence
<220> FEATURE:
<223> OTHER INFORMATION: primer

<400> SEQUENCE: 47
ucaagagguu a                                                        11

<210> SEQ ID NO 48
<211> LENGTH: 18
<212> TYPE: RNA
<213> ORGANISM: Artificial Sequence
<220> FEATURE:
<223> OTHER INFORMATION: primer

<400> SEQUENCE: 48
cauaucccuc gagaaaug                                                 18

<210> SEQ ID NO 49
<211> LENGTH: 14
<212> TYPE: RNA
<213> ORGANISM: Artificial Sequence
<220> FEATURE:
<223> OTHER INFORMATION: primer

<400> SEQUENCE: 49
ggaucauggg auua                                                     14

<210> SEQ ID NO 50
<211> LENGTH: 18
<212> TYPE: RNA
<213> ORGANISM: Artificial Sequence
<220> FEATURE:
<223> OTHER INFORMATION: primer

<400> SEQUENCE: 50
cauaucccuc gagaaaug                                                 18

<210> SEQ ID NO 51
<211> LENGTH: 14
<212> TYPE: RNA
<213> ORGANISM: Artificial Sequence
<220> FEATURE:
<223> OTHER INFORMATION: primer

<400> SEQUENCE: 51
ggaucaccuc cuua                                                     14

<210> SEQ ID NO 52
<211> LENGTH: 18
<212> TYPE: RNA
<213> ORGANISM: Artificial Sequence
<220> FEATURE:
<223> OTHER INFORMATION: primer

```
<400> SEQUENCE: 52
cauaucccuc cgcaaaug                                              18

<210> SEQ ID NO 53
<211> LENGTH: 14
<212> TYPE: RNA
<213> ORGANISM: Artificial Sequence
<220> FEATURE:
<223> OTHER INFORMATION: primer

<400> SEQUENCE: 53
ggaucauggg auua                                                  14

<210> SEQ ID NO 54
<211> LENGTH: 18
<212> TYPE: RNA
<213> ORGANISM: Artificial Sequence
<220> FEATURE:
<223> OTHER INFORMATION: primer

<400> SEQUENCE: 54
cauaucccuc cgcaaaug                                              18

<210> SEQ ID NO 55
<211> LENGTH: 14
<212> TYPE: RNA
<213> ORGANISM: Artificial Sequence
<220> FEATURE:
<223> OTHER INFORMATION: primer

<400> SEQUENCE: 55
ggaucaccuc cuua                                                  14

<210> SEQ ID NO 56
<211> LENGTH: 18
<212> TYPE: RNA
<213> ORGANISM: Artificial Sequence
<220> FEATURE:
<223> OTHER INFORMATION: primer

<400> SEQUENCE: 56
cauaucccuc cugaaaug                                              18

<210> SEQ ID NO 57
<211> LENGTH: 14
<212> TYPE: RNA
<213> ORGANISM: Artificial Sequence
<220> FEATURE:
<223> OTHER INFORMATION: primer

<400> SEQUENCE: 57
ggaucauggg auua                                                  14

<210> SEQ ID NO 58
<211> LENGTH: 17
<212> TYPE: RNA
<213> ORGANISM: Artificial Sequence
<220> FEATURE:
<223> OTHER INFORMATION: primer

<400> SEQUENCE: 58
cauaucccuc ccaaaug                                               17

<210> SEQ ID NO 59
<211> LENGTH: 14
```

```
<212> TYPE: RNA
<213> ORGANISM: Artificial Sequence
<220> FEATURE:
<223> OTHER INFORMATION: primer

<400> SEQUENCE: 59
ggaucauggg auua                                                          14

<210> SEQ ID NO 60
<211> LENGTH: 18
<212> TYPE: RNA
<213> ORGANISM: Artificial Sequence
<220> FEATURE:
<223> OTHER INFORMATION: primer

<400> SEQUENCE: 60
cauaucccuc cacaaaug                                                      18

<210> SEQ ID NO 61
<211> LENGTH: 14
<212> TYPE: RNA
<213> ORGANISM: Artificial Sequence
<220> FEATURE:
<223> OTHER INFORMATION: primer

<400> SEQUENCE: 61
ggaucauggg auua                                                          14

<210> SEQ ID NO 62
<211> LENGTH: 11
<212> TYPE: RNA
<213> ORGANISM: Artificial Sequence
<220> FEATURE:
<223> OTHER INFORMATION: primer

<400> SEQUENCE: 62
caggaggcuc g                                                             11

<210> SEQ ID NO 63
<211> LENGTH: 11
<212> TYPE: RNA
<213> ORGANISM: Artificial Sequence
<220> FEATURE:
<223> OTHER INFORMATION: primer

<400> SEQUENCE: 63
ucaccuccuu a                                                             11

<210> SEQ ID NO 64
<211> LENGTH: 11
<212> TYPE: RNA
<213> ORGANISM: Artificial Sequence
<220> FEATURE:
<223> OTHER INFORMATION: primer

<400> SEQUENCE: 64
caauccccuc g                                                             11

<210> SEQ ID NO 65
<211> LENGTH: 11
<212> TYPE: RNA
<213> ORGANISM: Artificial Sequence
<220> FEATURE:
<223> OTHER INFORMATION: primer

<400> SEQUENCE: 65
ucaagggauu a                                                             11
```

<210> SEQ ID NO 66
<211> LENGTH: 11
<212> TYPE: RNA
<213> ORGANISM: Artificial Sequence
<220> FEATURE:
<223> OTHER INFORMATION: primer

<400> SEQUENCE: 66
cauaccucuc g                                                              11

<210> SEQ ID NO 67
<211> LENGTH: 11
<212> TYPE: RNA
<213> ORGANISM: Artificial Sequence
<220> FEATURE:
<223> OTHER INFORMATION: primer

<400> SEQUENCE: 67
ucaauggguu a                                                              11

<210> SEQ ID NO 68
<211> LENGTH: 11
<212> TYPE: RNA
<213> ORGANISM: Artificial Sequence
<220> FEATURE:
<223> OTHER INFORMATION: primer

<400> SEQUENCE: 68
cacaguccuc g                                                              11

<210> SEQ ID NO 69
<211> LENGTH: 11
<212> TYPE: RNA
<213> ORGANISM: Artificial Sequence
<220> FEATURE:
<223> OTHER INFORMATION: primer

<400> SEQUENCE: 69
ucagacgauu a                                                              11

<210> SEQ ID NO 70
<211> LENGTH: 11
<212> TYPE: RNA
<213> ORGANISM: Artificial Sequence
<220> FEATURE:
<223> OTHER INFORMATION: primer

<400> SEQUENCE: 70
caaaccacuc g                                                              11

<210> SEQ ID NO 71
<211> LENGTH: 11
<212> TYPE: RNA
<213> ORGANISM: Artificial Sequence
<220> FEATURE:
<223> OTHER INFORMATION: primer

<400> SEQUENCE: 71
ucagugauuu a                                                              11

<210> SEQ ID NO 72
<211> LENGTH: 11
<212> TYPE: RNA
<213> ORGANISM: Artificial Sequence
<220> FEATURE:
<223> OTHER INFORMATION: primer

```
<400> SEQUENCE: 72
cauagcccuc g                                                              11

<210> SEQ ID NO 73
<211> LENGTH: 11
<212> TYPE: RNA
<213> ORGANISM: Artificial Sequence
<220> FEATURE:
<223> OTHER INFORMATION: primer

<400> SEQUENCE: 73 ucauugggguu a                                                             11

<210> SEQ ID NO 74
<211> LENGTH: 11
<212> TYPE: RNA
<213> ORGANISM: Artificial Sequence
<220> FEATURE:
<223> OTHER INFORMATION: primer

<400> SEQUENCE: 74
caucuuccuc g                                                              11

<210> SEQ ID NO 75
<211> LENGTH: 11
<212> TYPE: RNA
<213> ORGANISM: Artificial Sequence
<220> FEATURE:
<223> OTHER INFORMATION: primer

<400> SEQUENCE: 75
ucaggagguu a                                                              11

<210> SEQ ID NO 76
<211> LENGTH: 11
<212> TYPE: RNA
<213> ORGANISM: Artificial Sequence
<220> FEATURE:
<223> OTHER INFORMATION: primer

<400> SEQUENCE: 76
caauuaucuc g                                                              11

<210> SEQ ID NO 77
<211> LENGTH: 11
<212> TYPE: RNA
<213> ORGANISM: Artificial Sequence
<220> FEATURE:
<223> OTHER INFORMATION: primer

<400> SEQUENCE: 77
ucagaauuuu a                                                              11

<210> SEQ ID NO 78
<211> LENGTH: 11
<212> TYPE: RNA
<213> ORGANISM: Artificial Sequence
<220> FEATURE:
<223> OTHER INFORMATION: primer

<400> SEQUENCE: 78
cacagaacuc g                                                              11

<210> SEQ ID NO 79
<211> LENGTH: 11
```

```
<212> TYPE: RNA
<213> ORGANISM: Artificial Sequence
<220> FEATURE:
<223> OTHER INFORMATION: primer

<400> SEQUENCE: 79
ucaaucaguu a                                                              11

<210> SEQ ID NO 80
<211> LENGTH: 11
<212> TYPE: RNA
<213> ORGANISM: Artificial Sequence
<220> FEATURE:
<223> OTHER INFORMATION: primer

<400> SEQUENCE: 80
caaaguucuc g                                                              11

<210> SEQ ID NO 81
<211> LENGTH: 11
<212> TYPE: RNA
<213> ORGANISM: Artificial Sequence
<220> FEATURE:
<223> OTHER INFORMATION: primer

<400> SEQUENCE: 81
ucaaugaguu a                                                              11

<210> SEQ ID NO 82
<211> LENGTH: 11
<212> TYPE: RNA
<213> ORGANISM: Artificial Sequence
<220> FEATURE:
<223> OTHER INFORMATION: primer

<400> SEQUENCE: 82
caauucacuc g                                                              11

<210> SEQ ID NO 83
<211> LENGTH: 11
<212> TYPE: RNA
<213> ORGANISM: Artificial Sequence
<220> FEATURE:
<223> OTHER INFORMATION: primer

<400> SEQUENCE: 83
ucagugaauu a                                                              11

<210> SEQ ID NO 84
<211> LENGTH: 11
<212> TYPE: RNA
<213> ORGANISM: Artificial Sequence
<220> FEATURE:
<223> OTHER INFORMATION: primer

<400> SEQUENCE: 84
caacucacuc g                                                              11

<210> SEQ ID NO 85
<211> LENGTH: 11
<212> TYPE: RNA
<213> ORGANISM: Artificial Sequence
<220> FEATURE:
<223> OTHER INFORMATION: primer

<400> SEQUENCE: 85
ucagaguguu a                                                              11
```

<210> SEQ ID NO 86
<211> LENGTH: 11
<212> TYPE: RNA
<213> ORGANISM: Artificial Sequence
<220> FEATURE:
<223> OTHER INFORMATION: primer

<400> SEQUENCE: 86
caacccacuc g                                                              11

<210> SEQ ID NO 87
<211> LENGTH: 11
<212> TYPE: RNA
<213> ORGANISM: Artificial Sequence
<220> FEATURE:
<223> OTHER INFORMATION: primer

<400> SEQUENCE: 87
ucaugggauu a                                                              11

<210> SEQ ID NO 88
<211> LENGTH: 11
<212> TYPE: RNA
<213> ORGANISM: Artificial Sequence
<220> FEATURE:
<223> OTHER INFORMATION: primer

<400> SEQUENCE: 88
caucguucuc g                                                              11

<210> SEQ ID NO 89
<211> LENGTH: 11
<212> TYPE: RNA
<213> ORGANISM: Artificial Sequence
<220> FEATURE:
<223> OTHER INFORMATION: primer

<400> SEQUENCE: 89
ucaaagaguu a                                                              11

<210> SEQ ID NO 90
<211> LENGTH: 11
<212> TYPE: RNA
<213> ORGANISM: Artificial Sequence
<220> FEATURE:
<223> OTHER INFORMATION: primer

<400> SEQUENCE: 90
cacaccacuc g                                                              11

<210> SEQ ID NO 91
<211> LENGTH: 11
<212> TYPE: RNA
<213> ORGANISM: Artificial Sequence
<220> FEATURE:
<223> OTHER INFORMATION: primer

<400> SEQUENCE: 91
ucaugguuuu a                                                              11

<210> SEQ ID NO 92
<211> LENGTH: 11
<212> TYPE: RNA
<213> ORGANISM: Artificial Sequence
<220> FEATURE:
<223> OTHER INFORMATION: primer

```
<400> SEQUENCE: 92
cacccaccuc g                                                          11

<210> SEQ ID NO 93
<211> LENGTH: 11
<212> TYPE: RNA
<213> ORGANISM: Artificial Sequence
<220> FEATURE:
<223> OTHER INFORMATION: primer

<400> SEQUENCE: 93
ucaaaggguu a                                                          11

<210> SEQ ID NO 94
<211> LENGTH: 11
<212> TYPE: RNA
<213> ORGANISM: Artificial Sequence
<220> FEATURE:
<223> OTHER INFORMATION: primer

<400> SEQUENCE: 94
caucccacuc g                                                          11

<210> SEQ ID NO 95
<211> LENGTH: 11
<212> TYPE: RNA
<213> ORGANISM: Artificial Sequence
<220> FEATURE:
<223> OTHER INFORMATION: primer

<400> SEQUENCE: 95
ucaagggguu a                                                          11

<210> SEQ ID NO 96
<211> LENGTH: 11
<212> TYPE: RNA
<213> ORGANISM: Artificial Sequence
<220> FEATURE:
<223> OTHER INFORMATION: primer

<400> SEQUENCE: 96
caaacuccuc g                                                          11

<210> SEQ ID NO 97
<211> LENGTH: 11
<212> TYPE: RNA
<213> ORGANISM: Artificial Sequence
<220> FEATURE:
<223> OTHER INFORMATION: primer

<400> SEQUENCE: 97
ucauacuauu a                                                          11

<210> SEQ ID NO 98
<211> LENGTH: 11
<212> TYPE: RNA
<213> ORGANISM: Artificial Sequence
<220> FEATURE:
<223> OTHER INFORMATION: primer

<400> SEQUENCE: 98
cauacaucuc g                                                          11

<210> SEQ ID NO 99
<211> LENGTH: 11
```

```
<212> TYPE: RNA
<213> ORGANISM: Artificial Sequence
<220> FEATURE:
<223> OTHER INFORMATION: primer

<400> SEQUENCE: 99
ucaagaguuu a                                                          11

<210> SEQ ID NO 100
<211> LENGTH: 11
<212> TYPE: RNA
<213> ORGANISM: Artificial Sequence
<220> FEATURE:
<223> OTHER INFORMATION: primer

<400> SEQUENCE: 100
caacucucuc g                                                          11

<210> SEQ ID NO 101
<211> LENGTH: 11
<212> TYPE: RNA
<213> ORGANISM: Artificial Sequence
<220> FEATURE:
<223> OTHER INFORMATION: primer

<400> SEQUENCE: 101
ucaggagauu a                                                          11

<210> SEQ ID NO 102
<211> LENGTH: 11
<212> TYPE: RNA
<213> ORGANISM: Artificial Sequence
<220> FEATURE:
<223> OTHER INFORMATION: primer

<400> SEQUENCE: 102
caaauaucuc g                                                          11

<210> SEQ ID NO 103
<211> LENGTH: 11
<212> TYPE: RNA
<213> ORGANISM: Artificial Sequence
<220> FEATURE:
<223> OTHER INFORMATION: primer

<400> SEQUENCE: 103
ucagagauuu a                                                          11

<210> SEQ ID NO 104
<211> LENGTH: 11
<212> TYPE: RNA
<213> ORGANISM: Artificial Sequence
<220> FEATURE:
<223> OTHER INFORMATION: primer

<400> SEQUENCE: 104
cauaccucuc g                                                          11

<210> SEQ ID NO 105
<211> LENGTH: 11
<212> TYPE: RNA
<213> ORGANISM: Artificial Sequence
<220> FEATURE:
<223> OTHER INFORMATION: primer

<400> SEQUENCE: 105
ucaugagguu a                                                          11
```

<210> SEQ ID NO 106
<211> LENGTH: 11
<212> TYPE: RNA
<213> ORGANISM: Artificial Sequence
<220> FEATURE:
<223> OTHER INFORMATION: primer

<400> SEQUENCE: 106
cauaguacuc g                                                              11

<210> SEQ ID NO 107
<211> LENGTH: 11
<212> TYPE: RNA
<213> ORGANISM: Artificial Sequence
<220> FEATURE:
<223> OTHER INFORMATION: primer

<400> SEQUENCE: 107
ucauggauuu a                                                              11

<210> SEQ ID NO 108
<211> LENGTH: 11
<212> TYPE: RNA
<213> ORGANISM: Artificial Sequence
<220> FEATURE:
<223> OTHER INFORMATION: primer

<400> SEQUENCE: 108
caauccacuc g                                                              11

<210> SEQ ID NO 109
<211> LENGTH: 11
<212> TYPE: RNA
<213> ORGANISM: Artificial Sequence
<220> FEATURE:
<223> OTHER INFORMATION: primer

<400> SEQUENCE: 109
ucaguggauu a                                                              11

<210> SEQ ID NO 110
<211> LENGTH: 11
<212> TYPE: RNA
<213> ORGANISM: Artificial Sequence
<220> FEATURE:
<223> OTHER INFORMATION: primer

<400> SEQUENCE: 110
cacagaucuc g                                                              11

<210> SEQ ID NO 111
<211> LENGTH: 11
<212> TYPE: RNA
<213> ORGANISM: Artificial Sequence
<220> FEATURE:
<223> OTHER INFORMATION: primer

<400> SEQUENCE: 111
ucaggcuuuu a                                                              11

<210> SEQ ID NO 112
<211> LENGTH: 11
<212> TYPE: RNA
<213> ORGANISM: Artificial Sequence
<220> FEATURE:
<223> OTHER INFORMATION: primer

```
<400> SEQUENCE: 112
cauagcacuc g                                                    11

<210> SEQ ID NO 113
<211> LENGTH: 11
<212> TYPE: RNA
<213> ORGANISM: Artificial Sequence
<220> FEATURE:
<223> OTHER INFORMATION: primer

<400> SEQUENCE: 113
ucaugcuauu a                                                    11

<210> SEQ ID NO 114
<211> LENGTH: 11
<212> TYPE: RNA
<213> ORGANISM: Artificial Sequence
<220> FEATURE:
<223> OTHER INFORMATION: primer

<400> SEQUENCE: 114
caacuaacuc g                                                    11

<210> SEQ ID NO 115
<211> LENGTH: 11
<212> TYPE: RNA
<213> ORGANISM: Artificial Sequence
<220> FEATURE:
<223> OTHER INFORMATION: primer

<400> SEQUENCE: 115
ucauaguguu a                                                    11

<210> SEQ ID NO 116
<211> LENGTH: 11
<212> TYPE: RNA
<213> ORGANISM: Artificial Sequence
<220> FEATURE:
<223> OTHER INFORMATION: primer

<400> SEQUENCE: 116
caaauaucuc g                                                    11

<210> SEQ ID NO 117
<211> LENGTH: 11
<212> TYPE: RNA
<213> ORGANISM: Artificial Sequence
<220> FEATURE:
<223> OTHER INFORMATION: primer

<400> SEQUENCE: 117
ucaagguauu a                                                    11

<210> SEQ ID NO 118
<211> LENGTH: 11
<212> TYPE: RNA
<213> ORGANISM: Artificial Sequence
<220> FEATURE:
<223> OTHER INFORMATION: primer

<400> SEQUENCE: 118
caaauaucuc g                                                    11

<210> SEQ ID NO 119
<211> LENGTH: 11
```

<212> TYPE: RNA
<213> ORGANISM: Artificial Sequence
<220> FEATURE:
<223> OTHER INFORMATION: primer

<400> SEQUENCE: 119
ucaggagauu a        11

<210> SEQ ID NO 120
<211> LENGTH: 11
<212> TYPE: RNA
<213> ORGANISM: Artificial Sequence
<220> FEATURE:
<223> OTHER INFORMATION: primer

<400> SEQUENCE: 120
cacuccucuc g        11

<210> SEQ ID NO 121
<211> LENGTH: 11
<212> TYPE: RNA
<213> ORGANISM: Artificial Sequence
<220> FEATURE:
<223> OTHER INFORMATION: primer

<400> SEQUENCE: 121
ucagaggauu a        11

<210> SEQ ID NO 122
<211> LENGTH: 11
<212> TYPE: RNA
<213> ORGANISM: Artificial Sequence
<220> FEATURE:
<223> OTHER INFORMATION: primer

<400> SEQUENCE: 122
cauauuccuc g        11

<210> SEQ ID NO 123
<211> LENGTH: 11
<212> TYPE: RNA
<213> ORGANISM: Artificial Sequence
<220> FEATURE:
<223> OTHER INFORMATION: primer

<400> SEQUENCE: 123
ucauggaauu a        11

<210> SEQ ID NO 124
<211> LENGTH: 11
<212> TYPE: RNA
<213> ORGANISM: Artificial Sequence
<220> FEATURE:
<223> OTHER INFORMATION: primer

<400> SEQUENCE: 124
caaccuacuc g        11

<210> SEQ ID NO 125
<211> LENGTH: 11
<212> TYPE: RNA
<213> ORGANISM: Artificial Sequence
<220> FEATURE:
<223> OTHER INFORMATION: primer

<400> SEQUENCE: 125
ucaggagauu a        11

<210> SEQ ID NO 126
<211> LENGTH: 11
<212> TYPE: RNA
<213> ORGANISM: Artificial Sequence
<220> FEATURE:
<223> OTHER INFORMATION: primer

<400> SEQUENCE: 126
caauccacuc g                                                          11

<210> SEQ ID NO 127
<211> LENGTH: 11
<212> TYPE: RNA
<213> ORGANISM: Artificial Sequence
<220> FEATURE:
<223> OTHER INFORMATION: primer

<400> SEQUENCE: 127
ucaggagauu a                                                          11

<210> SEQ ID NO 128
<211> LENGTH: 11
<212> TYPE: RNA
<213> ORGANISM: Artificial Sequence
<220> FEATURE:
<223> OTHER INFORMATION: primer

<400> SEQUENCE: 128 caaccccuc g                                                           11

<210> SEQ ID NO 129
<211> LENGTH: 11
<212> TYPE: RNA
<213> ORGANISM: Artificial Sequence
<220> FEATURE:
<223> OTHER INFORMATION: primer

<400> SEQUENCE: 129
ucagaggguu a                                                          11

<210> SEQ ID NO 130
<211> LENGTH: 11
<212> TYPE: RNA
<213> ORGANISM: Artificial Sequence
<220> FEATURE:
<223> OTHER INFORMATION: primer

<400> SEQUENCE: 130
caaacaucuc g                                                          11

<210> SEQ ID NO 131
<211> LENGTH: 11
<212> TYPE: RNA
<213> ORGANISM: Artificial Sequence
<220> FEATURE:
<223> OTHER INFORMATION: primer

<400> SEQUENCE: 131
ucaagauguu a                                                          11

<210> SEQ ID NO 132
<211> LENGTH: 11
<212> TYPE: RNA
<213> ORGANISM: Artificial Sequence
<220> FEATURE:
<223> OTHER INFORMATION: primer

```
<400> SEQUENCE: 132
caucccacuc g                                                    11

<210> SEQ ID NO 133
<211> LENGTH: 11
<212> TYPE: RNA
<213> ORGANISM: Artificial Sequence
<220> FEATURE:
<223> OTHER INFORMATION: primer

<400> SEQUENCE: 133
ucaggguauu a                                                    11

<210> SEQ ID NO 134
<211> LENGTH: 11
<212> TYPE: RNA
<213> ORGANISM: Artificial Sequence
<220> FEATURE:
<223> OTHER INFORMATION: primer

<400> SEQUENCE: 134
cacugaucuc g                                                    11

<210> SEQ ID NO 135
<211> LENGTH: 11
<212> TYPE: RNA
<213> ORGANISM: Artificial Sequence
<220> FEATURE:
<223> OTHER INFORMATION: primer

<400> SEQUENCE: 135
ucagaggauu a                                                    11

<210> SEQ ID NO 136
<211> LENGTH: 11
<212> TYPE: RNA
<213> ORGANISM: Artificial Sequence
<220> FEATURE:
<223> OTHER INFORMATION: primer

<400> SEQUENCE: 136
cauaucccuc g                                                    11

<210> SEQ ID NO 137
<211> LENGTH: 11
<212> TYPE: RNA
<213> ORGANISM: Artificial Sequence
<220> FEATURE:
<223> OTHER INFORMATION: primer

<400> SEQUENCE: 137 ucaggauuu a                                                     11

<210> SEQ ID NO 138
<211> LENGTH: 11
<212> TYPE: RNA
<213> ORGANISM: Artificial Sequence
<220> FEATURE:
<223> OTHER INFORMATION: primer

<400> SEQUENCE: 138
caaacaccuc g                                                    11

<210> SEQ ID NO 139
<211> LENGTH: 11
```

```
<212> TYPE: RNA
<213> ORGANISM: Artificial Sequence
<220> FEATURE:
<223> OTHER INFORMATION: primer

<400> SEQUENCE: 139
ucaagagguu a                                                        11

<210> SEQ ID NO 140
<211> LENGTH: 11
<212> TYPE: RNA
<213> ORGANISM: Artificial Sequence
<220> FEATURE:
<223> OTHER INFORMATION: primer

<400> SEQUENCE: 140
caacgaacuc g                                                        11

<210> SEQ ID NO 141
<211> LENGTH: 11
<212> TYPE: RNA
<213> ORGANISM: Artificial Sequence
<220> FEATURE:
<223> OTHER INFORMATION: primer

<400> SEQUENCE: 141
ucagaguguu a                                                        11

<210> SEQ ID NO 142
<211> LENGTH: 11
<212> TYPE: RNA
<213> ORGANISM: Artificial Sequence
<220> FEATURE:
<223> OTHER INFORMATION: primer

<400> SEQUENCE: 142
caucuaucuc g                                                        11

<210> SEQ ID NO 143
<211> LENGTH: 11
<212> TYPE: RNA
<213> ORGANISM: Artificial Sequence
<220> FEATURE:
<223> OTHER INFORMATION: primer

<400> SEQUENCE: 143
ucaggagauu a                                                        11

<210> SEQ ID NO 144
<211> LENGTH: 11
<212> TYPE: RNA
<213> ORGANISM: Artificial Sequence
<220> FEATURE:
<223> OTHER INFORMATION: primer

<400> SEQUENCE: 144
cauaccucuc g                                                        11

<210> SEQ ID NO 145
<211> LENGTH: 11
<212> TYPE: RNA
<213> ORGANISM: Artificial Sequence
<220> FEATURE:
<223> OTHER INFORMATION: primer

<400> SEQUENCE: 145
ucaugagguu a                                                        11
```

<210> SEQ ID NO 146
<211> LENGTH: 11
<212> TYPE: RNA
<213> ORGANISM: Artificial Sequence
<220> FEATURE:
<223> OTHER INFORMATION: primer

<400> SEQUENCE: 146
cauauaacuc g                                                              11

<210> SEQ ID NO 147
<211> LENGTH: 11
<212> TYPE: RNA
<213> ORGANISM: Artificial Sequence
<220> FEATURE:
<223> OTHER INFORMATION: primer

<400> SEQUENCE: 147
ucaagagauu a                                                              11

<210> SEQ ID NO 148
<211> LENGTH: 11
<212> TYPE: RNA
<213> ORGANISM: Artificial Sequence
<220> FEATURE:
<223> OTHER INFORMATION: primer

<400> SEQUENCE: 148
caaauaccuc g                                                              11

<210> SEQ ID NO 149
<211> LENGTH: 11
<212> TYPE: RNA
<213> ORGANISM: Artificial Sequence
<220> FEATURE:
<223> OTHER INFORMATION: primer

<400> SEQUENCE: 149
ucaugagguu a                                                              11

<210> SEQ ID NO 150
<211> LENGTH: 11
<212> TYPE: RNA
<213> ORGANISM: Artificial Sequence
<220> FEATURE:
<223> OTHER INFORMATION: primer

<400> SEQUENCE: 150
cacauaccuc g                                                              11

<210> SEQ ID NO 151
<211> LENGTH: 11
<212> TYPE: RNA
<213> ORGANISM: Artificial Sequence
<220> FEATURE:
<223> OTHER INFORMATION: primer

<400> SEQUENCE: 151
ucaugagguu a                                                              11

<210> SEQ ID NO 152
<211> LENGTH: 11
<212> TYPE: RNA
<213> ORGANISM: Artificial Sequence
<220> FEATURE:
<223> OTHER INFORMATION: primer

```
<400> SEQUENCE: 152
caccgaccuc g                                                          11

<210> SEQ ID NO 153
<211> LENGTH: 11
<212> TYPE: RNA
<213> ORGANISM: Artificial Sequence
<220> FEATURE:
<223> OTHER INFORMATION: primer

<400> SEQUENCE: 153
ucaagagguu a                                                          11

<210> SEQ ID NO 154
<211> LENGTH: 11
<212> TYPE: RNA
<213> ORGANISM: Artificial Sequence
<220> FEATURE:
<223> OTHER INFORMATION: primer

<400> SEQUENCE: 154
cauaucccuc g                                                          11

<210> SEQ ID NO 155
<211> LENGTH: 11
<212> TYPE: RNA
<213> ORGANISM: Artificial Sequence
<220> FEATURE:
<223> OTHER INFORMATION: primer

<400> SEQUENCE: 155
ucaugggguu a                                                          11

<210> SEQ ID NO 156
<211> LENGTH: 11
<212> TYPE: RNA
<213> ORGANISM: Artificial Sequence
<220> FEATURE:
<223> OTHER INFORMATION: primer

<400> SEQUENCE: 156
caacuaccuc g                                                          11

<210> SEQ ID NO 157
<211> LENGTH: 11
<212> TYPE: RNA
<213> ORGANISM: Artificial Sequence
<220> FEATURE:
<223> OTHER INFORMATION: primer

<400> SEQUENCE: 157
ucaugagguu a                                                          11

<210> SEQ ID NO 158
<211> LENGTH: 11
<212> TYPE: RNA
<213> ORGANISM: Artificial Sequence
<220> FEATURE:
<223> OTHER INFORMATION: primer

<400> SEQUENCE: 158
cauauaccuc g                                                          11

<210> SEQ ID NO 159
<211> LENGTH: 11
```

-continued

```
<212> TYPE: RNA
<213> ORGANISM: Artificial Sequence
<220> FEATURE:
<223> OTHER INFORMATION: primer

<400> SEQUENCE: 159
ucaagagguu a                                                              11

<210> SEQ ID NO 160
<211> LENGTH: 9
<212> TYPE: RNA
<213> ORGANISM: Artificial Sequence
<220> FEATURE:
<223> OTHER INFORMATION: primer

<400> SEQUENCE: 160 auuagauac                                                                  9

<210> SEQ ID NO 161
<211> LENGTH: 9
<212> TYPE: RNA
<213> ORGANISM: Artificial Sequence
<220> FEATURE:
<223> OTHER INFORMATION: primer

<400> SEQUENCE: 161 auuagguaa                                                                  9

<210> SEQ ID NO 162
<211> LENGTH: 9
<212> TYPE: RNA
<213> ORGANISM: Artificial Sequence
<220> FEATURE:
<223> OTHER INFORMATION: primer

<400> SEQUENCE: 162 auucgacau                                                                  9

<210> SEQ ID NO 163
<211> LENGTH: 9
<212> TYPE: RNA
<213> ORGANISM: Artificial Sequence
<220> FEATURE:
<223> OTHER INFORMATION: primer

<400> SEQUENCE: 163 aauagguac                                                                  9

<210> SEQ ID NO 164
<211> LENGTH: 9
<212> TYPE: RNA
<213> ORGANISM: Artificial Sequence
<220> FEATURE:
<223> OTHER INFORMATION: primer

<400> SEQUENCE: 164 aauagucuc                                                                  9

<210> SEQ ID NO 165
<211> LENGTH: 9
<212> TYPE: RNA
<213> ORGANISM: Artificial Sequence
<220> FEATURE:
<223> OTHER INFORMATION: primer

<400> SEQUENCE: 165 auuagcuac                                                                  9
```

```
<210> SEQ ID NO 166
<211> LENGTH: 9
<212> TYPE: RNA
<213> ORGANISM: Artificial Sequence
<220> FEATURE:
<223> OTHER INFORMATION: primer

<400> SEQUENCE: 166 auucgacac                                                                 9

<210> SEQ ID NO 167
<211> LENGTH: 9
<212> TYPE: RNA
<213> ORGANISM: Artificial Sequence
<220> FEATURE:
<223> OTHER INFORMATION: primer

<400> SEQUENCE: 167 acuagcaca                                                                 9

<210> SEQ ID NO 168
<211> LENGTH: 9
<212> TYPE: RNA
<213> ORGANISM: Artificial Sequence
<220> FEATURE:
<223> OTHER INFORMATION: primer

<400> SEQUENCE: 168 acuagcuuc                                                                 9

<210> SEQ ID NO 169
<211> LENGTH: 9
<212> TYPE: RNA
<213> ORGANISM: Artificial Sequence
<220> FEATURE:
<223> OTHER INFORMATION: primer

<400> SEQUENCE: 169 aauagauac                                                                 9

<210> SEQ ID NO 170
<211> LENGTH: 9
<212> TYPE: RNA
<213> ORGANISM: Artificial Sequence
<220> FEATURE:
<223> OTHER INFORMATION: primer

<400> SEQUENCE: 170 aauaguauc                                                                 9

<210> SEQ ID NO 171
<211> LENGTH: 9
<212> TYPE: RNA
<213> ORGANISM: Artificial Sequence
<220> FEATURE:
<223> OTHER INFORMATION: primer

<400> SEQUENCE: 171 aaucgccuc                                                                 9

<210> SEQ ID NO 172
<211> LENGTH: 9
<212> TYPE: RNA
<213> ORGANISM: Artificial Sequence
<220> FEATURE:
<223> OTHER INFORMATION: primer
```

```
<400> SEQUENCE: 172 gauagguau                                                              9

<210> SEQ ID NO 173
<211> LENGTH: 9
<212> TYPE: RNA
<213> ORGANISM: Artificial Sequence
<220> FEATURE:
<223> OTHER INFORMATION: primer

<400> SEQUENCE: 173 auuaggcac                                                              9

<210> SEQ ID NO 174
<211> LENGTH: 9
<212> TYPE: RNA
<213> ORGANISM: Artificial Sequence
<220> FEATURE:
<223> OTHER INFORMATION: primer

<400> SEQUENCE: 174 aauagguuc                                                              9

<210> SEQ ID NO 175
<211> LENGTH: 9
<212> TYPE: RNA
<213> ORGANISM: Artificial Sequence
<220> FEATURE:
<223> OTHER INFORMATION: primer

<400> SEQUENCE: 175 aauagucaa                                                              9

<210> SEQ ID NO 176
<211> LENGTH: 9
<212> TYPE: RNA
<213> ORGANISM: Artificial Sequence
<220> FEATURE:
<223> OTHER INFORMATION: primer

<400> SEQUENCE: 176 aaucgucuc                                                              9

<210> SEQ ID NO 177
<211> LENGTH: 9
<212> TYPE: RNA
<213> ORGANISM: Artificial Sequence
<220> FEATURE:
<223> OTHER INFORMATION: primer

<400> SEQUENCE: 177 auuagaaaa                                                              9

<210> SEQ ID NO 178
<211> LENGTH: 9
<212> TYPE: RNA
<213> ORGANISM: Artificial Sequence
<220> FEATURE:
<223> OTHER INFORMATION: primer

<400> SEQUENCE: 178 auuagcgac                                                              9

<210> SEQ ID NO 179
<211> LENGTH: 9
```

```
<212> TYPE: RNA
<213> ORGANISM: Artificial Sequence
<220> FEATURE:
<223> OTHER INFORMATION: primer

<400> SEQUENCE: 179 auuaggagc                                                                    9

<210> SEQ ID NO 180
<211> LENGTH: 9
<212> TYPE: RNA
<213> ORGANISM: Artificial Sequence
<220> FEATURE:
<223> OTHER INFORMATION: primer

<400> SEQUENCE: 180 auuaggcaa                                                                    9

<210> SEQ ID NO 181
<211> LENGTH: 9
<212> TYPE: RNA
<213> ORGANISM: Artificial Sequence
<220> FEATURE:
<223> OTHER INFORMATION: primer

<400> SEQUENCE: 181 aguagccuc                                                                    9

<210> SEQ ID NO 182
<211> LENGTH: 9
<212> TYPE: RNA
<213> ORGANISM: Artificial Sequence
<220> FEATURE:
<223> OTHER INFORMATION: primer

<400> SEQUENCE: 182 aguagcuuc                                                                    9

<210> SEQ ID NO 183
<211> LENGTH: 9
<212> TYPE: RNA
<213> ORGANISM: Artificial Sequence
<220> FEATURE:
<223> OTHER INFORMATION: primer

<400> SEQUENCE: 183 aguaggauc                                                                    9

<210> SEQ ID NO 184
<211> LENGTH: 9
<212> TYPE: RNA
<213> ORGANISM: Artificial Sequence
<220> FEATURE:
<223> OTHER INFORMATION: primer

<400> SEQUENCE: 184 aguagguuc                                                                    9

<210> SEQ ID NO 185
<211> LENGTH: 9
<212> TYPE: RNA
<213> ORGANISM: Artificial Sequence
<220> FEATURE:
<223> OTHER INFORMATION: primer

<400> SEQUENCE: 185 aguagucuc                                                                    9
```

<210> SEQ ID NO 186
<211> LENGTH: 9
<212> TYPE: RNA
<213> ORGANISM: Artificial Sequence
<220> FEATURE:
<223> OTHER INFORMATION: primer

<400> SEQUENCE: 186 acuagauau                                                                9

<210> SEQ ID NO 187
<211> LENGTH: 9
<212> TYPE: RNA
<213> ORGANISM: Artificial Sequence
<220> FEATURE:
<223> OTHER INFORMATION: primer

<400> SEQUENCE: 187 acuagaucc                                                                9

<210> SEQ ID NO 188
<211> LENGTH: 9
<212> TYPE: RNA
<213> ORGANISM: Artificial Sequence
<220> FEATURE:
<223> OTHER INFORMATION: primer

<400> SEQUENCE: 188 acuagcaac                                                                9

<210> SEQ ID NO 189
<211> LENGTH: 9
<212> TYPE: RNA
<213> ORGANISM: Artificial Sequence
<220> FEATURE:
<223> OTHER INFORMATION: primer

<400> SEQUENCE: 189 acuagcauc                                                                9

<210> SEQ ID NO 190
<211> LENGTH: 9
<212> TYPE: RNA
<213> ORGANISM: Artificial Sequence
<220> FEATURE:
<223> OTHER INFORMATION: primer

<400> SEQUENCE: 190 acuagcuaa                                                                9

<210> SEQ ID NO 191
<211> LENGTH: 9
<212> TYPE: RNA
<213> ORGANISM: Artificial Sequence
<220> FEATURE:
<223> OTHER INFORMATION: primer

<400> SEQUENCE: 191 acuaggcuc                                                                9

<210> SEQ ID NO 192
<211> LENGTH: 9
<212> TYPE: RNA
<213> ORGANISM: Artificial Sequence
<220> FEATURE:
<223> OTHER INFORMATION: primer -continued

```
<400> SEQUENCE: 192 acuaguaac                                                                          9

<210> SEQ ID NO 193
<211> LENGTH: 9
<212> TYPE: RNA
<213> ORGANISM: Artificial Sequence
<220> FEATURE:
<223> OTHER INFORMATION: primer

<400> SEQUENCE: 193 acuaguauc                                                                          9

<210> SEQ ID NO 194
<211> LENGTH: 9
<212> TYPE: RNA
<213> ORGANISM: Artificial Sequence
<220> FEATURE:
<223> OTHER INFORMATION: primer

<400> SEQUENCE: 194 acuaguuuc                                                                          9

<210> SEQ ID NO 195
<211> LENGTH: 9
<212> TYPE: RNA
<213> ORGANISM: Artificial Sequence
<220> FEATURE:
<223> OTHER INFORMATION: primer

<400> SEQUENCE: 195 aauagauuc                                                                          9

<210> SEQ ID NO 196
<211> LENGTH: 9
<212> TYPE: RNA
<213> ORGANISM: Artificial Sequence
<220> FEATURE:
<223> OTHER INFORMATION: primer

<400> SEQUENCE: 196 aauagcagc                                                                          9

<210> SEQ ID NO 197
<211> LENGTH: 9
<212> TYPE: RNA
<213> ORGANISM: Artificial Sequence
<220> FEATURE:
<223> OTHER INFORMATION: primer

<400> SEQUENCE: 197 aauagccaa                                                                          9

<210> SEQ ID NO 198
<211> LENGTH: 9
<212> TYPE: RNA
<213> ORGANISM: Artificial Sequence
<220> FEATURE:
<223> OTHER INFORMATION: primer

<400> SEQUENCE: 198 aauagccac                                                                          9

<210> SEQ ID NO 199
<211> LENGTH: 9
```

```
<212> TYPE: RNA
<213> ORGANISM: Artificial Sequence
<220> FEATURE:
<223> OTHER INFORMATION: primer

<400> SEQUENCE: 199 aauagccua                                                                 9

<210> SEQ ID NO 200
<211> LENGTH: 9
<212> TYPE: RNA
<213> ORGANISM: Artificial Sequence
<220> FEATURE:
<223> OTHER INFORMATION: primer

<400> SEQUENCE: 200 aauagcuaa                                                                 9

<210> SEQ ID NO 201
<211> LENGTH: 9
<212> TYPE: RNA
<213> ORGANISM: Artificial Sequence
<220> FEATURE:
<223> OTHER INFORMATION: primer

<400> SEQUENCE: 201 guuaguuau                                                                 9

<210> SEQ ID NO 202
<211> LENGTH: 9
<212> TYPE: RNA
<213> ORGANISM: Artificial Sequence
<220> FEATURE:
<223> OTHER INFORMATION: primer

<400> SEQUENCE: 202 gguaguagu                                                                 9

<210> SEQ ID NO 203
<211> LENGTH: 9
<212> TYPE: RNA
<213> ORGANISM: Artificial Sequence
<220> FEATURE:
<223> OTHER INFORMATION: primer

<400> SEQUENCE: 203 gguagucag                                                                 9

<210> SEQ ID NO 204
<211> LENGTH: 9
<212> TYPE: RNA
<213> ORGANISM: Artificial Sequence
<220> FEATURE:
<223> OTHER INFORMATION: primer

<400> SEQUENCE: 204 gauaguagu                                                                 9

<210> SEQ ID NO 205
<211> LENGTH: 9
<212> TYPE: RNA
<213> ORGANISM: Artificial Sequence
<220> FEATURE:
<223> OTHER INFORMATION: primer

<400> SEQUENCE: 205 aauagaaac                                                                 9
```

```
<210> SEQ ID NO 206
<211> LENGTH: 9
<212> TYPE: RNA
<213> ORGANISM: Artificial Sequence
<220> FEATURE:
<223> OTHER INFORMATION: primer

<400> SEQUENCE: 206 guuagauag                                                                 9

<210> SEQ ID NO 207
<211> LENGTH: 9
<212> TYPE: RNA
<213> ORGANISM: Artificial Sequence
<220> FEATURE:
<223> OTHER INFORMATION: primer

<400> SEQUENCE: 207 gguagcuuu                                                                 9

<210> SEQ ID NO 208
<211> LENGTH: 9
<212> TYPE: RNA
<213> ORGANISM: Artificial Sequence
<220> FEATURE:
<223> OTHER INFORMATION: primer

<400> SEQUENCE: 208 gguaguuug                                                                 9

<210> SEQ ID NO 209
<211> LENGTH: 9
<212> TYPE: RNA
<213> ORGANISM: Artificial Sequence
<220> FEATURE:
<223> OTHER INFORMATION: primer

<400> SEQUENCE: 209 auucggaaa                                                                 9

<210> SEQ ID NO 210
<211> LENGTH: 9
<212> TYPE: RNA
<213> ORGANISM: Artificial Sequence
<220> FEATURE:
<223> OTHER INFORMATION: primer

<400> SEQUENCE: 210 auuggagac                                                                 9

<210> SEQ ID NO 211
<211> LENGTH: 9
<212> TYPE: RNA
<213> ORGANISM: Artificial Sequence
<220> FEATURE:
<223> OTHER INFORMATION: primer

<400> SEQUENCE: 211 acuagacgc                                                                 9

<210> SEQ ID NO 212
<211> LENGTH: 9
<212> TYPE: RNA
<213> ORGANISM: Artificial Sequence
<220> FEATURE:
<223> OTHER INFORMATION: primer
```

```
<400> SEQUENCE: 212 acuagccaa                                                                   9

<210> SEQ ID NO 213
<211> LENGTH: 9
<212> TYPE: RNA
<213> ORGANISM: Artificial Sequence
<220> FEATURE:
<223> OTHER INFORMATION: primer

<400> SEQUENCE: 213 acuaggcua                                                                   9

<210> SEQ ID NO 214
<211> LENGTH: 9
<212> TYPE: RNA
<213> ORGANISM: Artificial Sequence
<220> FEATURE:
<223> OTHER INFORMATION: primer

<400> SEQUENCE: 214 aauagcaca                                                                   9

<210> SEQ ID NO 215
<211> LENGTH: 9
<212> TYPE: RNA
<213> ORGANISM: Artificial Sequence
<220> FEATURE:
<223> OTHER INFORMATION: primer

<400> SEQUENCE: 215 aauagucau                                                                   9

<210> SEQ ID NO 216
<211> LENGTH: 9
<212> TYPE: RNA
<213> ORGANISM: Artificial Sequence
<220> FEATURE:
<223> OTHER INFORMATION: primer

<400> SEQUENCE: 216 aauagucca                                                                   9

<210> SEQ ID NO 217
<211> LENGTH: 9
<212> TYPE: RNA
<213> ORGANISM: Artificial Sequence
<220> FEATURE:
<223> OTHER INFORMATION: primer

<400> SEQUENCE: 217 cuuaguuaa                                                                   9

<210> SEQ ID NO 218
<211> LENGTH: 9
<212> TYPE: RNA
<213> ORGANISM: Artificial Sequence
<220> FEATURE:
<223> OTHER INFORMATION: primer

<400> SEQUENCE: 218 guuagagau                                                                   9

<210> SEQ ID NO 219
<211> LENGTH: 9
```

```
<212> TYPE: RNA
<213> ORGANISM: Artificial Sequence
<220> FEATURE:
<223> OTHER INFORMATION: primer

<400> SEQUENCE: 219 guuagucau                                                                9

<210> SEQ ID NO 220
<211> LENGTH: 9
<212> TYPE: RNA
<213> ORGANISM: Artificial Sequence
<220> FEATURE:
<223> OTHER INFORMATION: primer

<400> SEQUENCE: 220 gguagccuu                                                                9

<210> SEQ ID NO 221
<211> LENGTH: 9
<212> TYPE: RNA
<213> ORGANISM: Artificial Sequence
<220> FEATURE:
<223> OTHER INFORMATION: primer

<400> SEQUENCE: 221 gguaggaau                                                                9

<210> SEQ ID NO 222
<211> LENGTH: 9
<212> TYPE: RNA
<213> ORGANISM: Artificial Sequence
<220> FEATURE:
<223> OTHER INFORMATION: primer

<400> SEQUENCE: 222 gguagguag                                                                9

<210> SEQ ID NO 223
<211> LENGTH: 9
<212> TYPE: RNA
<213> ORGANISM: Artificial Sequence
<220> FEATURE:
<223> OTHER INFORMATION: primer

<400> SEQUENCE: 223 gguagguuu                                                                9

<210> SEQ ID NO 224
<211> LENGTH: 9
<212> TYPE: RNA
<213> ORGANISM: Artificial Sequence
<220> FEATURE:
<223> OTHER INFORMATION: primer

<400> SEQUENCE: 224 gguaguuuu                                                                9

<210> SEQ ID NO 225
<211> LENGTH: 9
<212> TYPE: RNA
<213> ORGANISM: Artificial Sequence
<220> FEATURE:
<223> OTHER INFORMATION: primer

<400> SEQUENCE: 225 gauagccuu                                                                9
```

-continued

<210> SEQ ID NO 226
<211> LENGTH: 9
<212> TYPE: RNA
<213> ORGANISM: Artificial Sequence
<220> FEATURE:
<223> OTHER INFORMATION: primer

<400> SEQUENCE: 226 gauaguccu                                                                 9

<210> SEQ ID NO 227
<211> LENGTH: 9
<212> TYPE: RNA
<213> ORGANISM: Artificial Sequence
<220> FEATURE:
<223> OTHER INFORMATION: primer

<400> SEQUENCE: 227 auuagauga                                                                 9

<210> SEQ ID NO 228
<211> LENGTH: 9
<212> TYPE: RNA
<213> ORGANISM: Artificial Sequence
<220> FEATURE:
<223> OTHER INFORMATION: primer

<400> SEQUENCE: 228 aguagcuuu                                                                 9

<210> SEQ ID NO 229
<211> LENGTH: 9
<212> TYPE: RNA
<213> ORGANISM: Artificial Sequence
<220> FEATURE:
<223> OTHER INFORMATION: primer

<400> SEQUENCE: 229 aguaguuag                                                                 9

<210> SEQ ID NO 230
<211> LENGTH: 9
<212> TYPE: RNA
<213> ORGANISM: Artificial Sequence
<220> FEATURE:
<223> OTHER INFORMATION: primer

<400> SEQUENCE: 230 agucgccuc                                                                 9

<210> SEQ ID NO 231
<211> LENGTH: 9
<212> TYPE: RNA
<213> ORGANISM: Artificial Sequence
<220> FEATURE:
<223> OTHER INFORMATION: primer

<400> SEQUENCE: 231 acuagaguc                                                                 9

<210> SEQ ID NO 232
<211> LENGTH: 9
<212> TYPE: RNA
<213> ORGANISM: Artificial Sequence
<220> FEATURE:
<223> OTHER INFORMATION: primer

```
<400> SEQUENCE: 232 aaucgcagc                                                          9

<210> SEQ ID NO 233
<211> LENGTH: 9
<212> TYPE: RNA
<213> ORGANISM: Artificial Sequence
<220> FEATURE:
<223> OTHER INFORMATION: primer

<400> SEQUENCE: 233 cauaguuuu                                                          9

<210> SEQ ID NO 234
<211> LENGTH: 9
<212> TYPE: RNA
<213> ORGANISM: Artificial Sequence
<220> FEATURE:
<223> OTHER INFORMATION: primer

<400> SEQUENCE: 234 gguagaugu                                                          9

<210> SEQ ID NO 235
<211> LENGTH: 9
<212> TYPE: RNA
<213> ORGANISM: Artificial Sequence
<220> FEATURE:
<223> OTHER INFORMATION: primer

<400> SEQUENCE: 235 gguagucgu                                                          9

<210> SEQ ID NO 236
<211> LENGTH: 9
<212> TYPE: RNA
<213> ORGANISM: Artificial Sequence
<220> FEATURE:
<223> OTHER INFORMATION: primer

<400> SEQUENCE: 236 ggucgcuau                                                          9

<210> SEQ ID NO 237
<211> LENGTH: 9
<212> TYPE: RNA
<213> ORGANISM: Artificial Sequence
<220> FEATURE:
<223> OTHER INFORMATION: primer

<400> SEQUENCE: 237 gcuaguaag                                                          9

<210> SEQ ID NO 238
<211> LENGTH: 9
<212> TYPE: RNA
<213> ORGANISM: Artificial Sequence
<220> FEATURE:
<223> OTHER INFORMATION: primer

<400> SEQUENCE: 238 gguagguug                                                          9

<210> SEQ ID NO 239
<211> LENGTH: 20
```

```
<212> TYPE: DNA
<213> ORGANISM: Artificial Sequence
<220> FEATURE:
<223> OTHER INFORMATION: primer

<400> SEQUENCE: 239
gacaatctgt gtgagcacta                                           20

<210> SEQ ID NO 240
<211> LENGTH: 36
<212> TYPE: DNA
<213> ORGANISM: Artificial Sequence
<220> FEATURE:
<223> OTHER INFORMATION: primer

<400> SEQUENCE: 240
tgccagcagc cgcggtaata cggagggtgc aagcgt                         36

<210> SEQ ID NO 241
<211> LENGTH: 33
<212> TYPE: DNA
<213> ORGANISM: Artificial Sequence
<220> FEATURE:
<223> OTHER INFORMATION: primer

<400> SEQUENCE: 241
cctgtttgct ccccacgctt tcgcacctga gcg                            33

<210> SEQ ID NO 242
<211> LENGTH: 60
<212> TYPE: DNA
<213> ORGANISM: Artificial Sequence
<220> FEATURE:
<223> OTHER INFORMATION: primer
<221> NAME/KEY: misc_feature
<222> LOCATION: 32, 33, 34, 35, 36, 37, 38, 39, 40
<223> OTHER INFORMATION: n = A,T,C or G

<400> SEQUENCE: 242
ctcaggtgcg aaagcgtggg gagcaaacag gnnnnnnnnn cctggtagtc cacgccgtaa    60

<210> SEQ ID NO 243
<211> LENGTH: 60
<212> TYPE: DNA
<213> ORGANISM: Artificial Sequence
<220> FEATURE:
<223> OTHER INFORMATION: primer
<221> NAME/KEY: misc_feature
<222> LOCATION: 32, 40
<223> OTHER INFORMATION: n = A,T,C or G

<400> SEQUENCE: 243
ctcaggtgcg aaagcgtggg gagcaaacag gnttagatan cctggtagtc cacgccgtaa    60

<210> SEQ ID NO 244
<211> LENGTH: 17
<212> TYPE: DNA
<213> ORGANISM: Artificial Sequence
<220> FEATURE:
<223> OTHER INFORMATION: primer

<400> SEQUENCE: 244
ggactaccag ggtatct                                              17

<210> SEQ ID NO 245
<211> LENGTH: 17
<212> TYPE: DNA
<213> ORGANISM: Artificial Sequence
```

-continued

<220> FEATURE:
<223> OTHER INFORMATION: primer

<400> SEQUENCE: 245
tacggcgtgg actacca                                                    17

What is claimed is:

1. A method for identifying functional mutant ribosomes comprising:
   (a) transforming a set of host cells with a set of plasmids, each plasmid comprising a mutant rRNA gene and a selectable marker gene;
   wherein said mutant rRNA gene comprises at least one mutation in addition to a mutant Anti-Shine-Dalgarno sequence; and said selectable marker gene comprises a mutant Shine-Dalgarno sequence; and
   wherein said mutant Anti-Shine-Dalgarno and said mutant Shine-Dalgarno sequence are a mutually compatible pair;
   thereby forming a set of transformed host cells;
   (b) isolating from the set of transformed host cells those host cells which express the selectable marker gene product; and
   (c) sequencing the mutant rRNA gene from each host cell isolated in step (b), thereby identifying functional mutant ribosomes, wherein the functional mutant ribosomes comprise functionally important target regions of interest, which comprise nucleotide sequences of one or more nucleic acids or nucleotide motifs which are conserved in each mutant rRNA gene sequenced.

2. The method of claim 1 wherein said mutant rRNA gene is a mutant *E. coli* 16S rRNA gene and said selectable marker gene is a green fluorescent protein gene.

3. A method for identifying functional mutant ribosomes that may be suitable as drug targets comprising: identifying functional mutant ribosomes according to the method of claim 1, thereby identifying functionally important target regions of interest, wherein said regions of interest comprise sequences of one or more nucleic acids or nucleotide motifs which are conserved in each mutant rRNA gene sequenced;
   (d) generating a second plurality of mutant rRNA genes wherein said target regions of interest are mutated; and each of said rRNA genes of said second plurality of mutant rRNA genes further comprises a second mutant Anti-Shrine-Dalgarno sequence;
   (e) inserting the second plurality of mutant rRNA genes comprising the mutated regions of interest from step (d) into a second plurality of plasmids; wherein said second plurality of plasmids further comprise a second genetically engineered gene which encodes a second selectable marker having a second mutant Shine-Dalgarno sequence, wherein the second mutant Anti-Shine-Dalgarno and the second mutant Shine-Dalgarno sequence are a mutually compatible pair;
   (f) transforming a second set of host cells with the plasmids from step (e), thereby forming a second set of transformed host cells;
   (g) isolating from the second set of transformed host cells of step (f) those host cells which express the second selectable marker gene product; and
   (h) sequencing the rRNA gene from each host cell isolated in step (g), thereby identifying functional mutant ribosomes that may be suitable as drug targets.

4. The method of claim 1, wherein said mutant rRNA gene is selected from the rRNA genes of *Escherichia coli, Mycobacterium tuberculosis, Pseudomonas aeruginosa, Salmonella typhi, Yersenia pestis, Staphylococcus aureus, Streptococcus pyogenes, Enterococcus faecalis, Chlamydia trachomatis, Saccharomyces cerevesiae, Candida albicans*, and trypanosomes.

5. The method of claim 1, wherein said mutant rRNA gene is a 16S rRNA gene.

6. The method of claim 1, wherein the selectable marker is selected from the group consisting of chloramphenicol acetyltransferase (CAT), green fluorescent protein (GFP), and mixtures thereof.

7. The method of claim 1, wherein the selectable marker gene is green fluorescent protein.

8. The method of claim 1, wherein said mutant Shine-Dalgarno sequence is selected from the group consisting of the sequences set forth in SEQ. ID. NOS: 24-159; and said mutant Anti-Shine-Dalgarno sequence is selected from the group consisting of the sequences set forth in SEQ. ID. NOS: 24-159.

9. The method of claim 2, wherein said mutant Shine-Dalgarno sequence is selected from the group consisting of the sequences set forth in SEQ. ID. NOS: 24-159; and said mutant Anti-Shine-Dalgarno sequence is selected from the group consisting of the sequences set forth in SEQ. ID. NOS: 24-159.

10. The method of claim 3, wherein said first mutant rRNA gene is selected from the rRNA genes of *Escherichia coli, Mycobacterium tuberculosis, Pseudomonas aeruginosa, Salmonella typhi, Yersenia pestis, Staphylococcus aureus, Streptococcus pyogenes, Enterococcus faecalis, Chlamydia trachomatis, Saccharomyces cerevesiae, Candida albicans*, and trypanosomes.

11. The method of claim 3, wherein said first mutant rRNA gene is a 16S rRNA gene.

12. The method of claim 3, wherein the first selectable marker is selected from the group consisting of chloramphenicol acetyltransferase (CAT), green fluorescent protein (GFP), and mixtures thereof.

13. The method of claim 3, wherein the first selectable marker gene is green fluorescent protein.

14. The method of claim 3, wherein the second selectable marker is selected from the group consisting of chloramphenicol acetyltransferase (CAT), green fluorescent protein (GFP), and mixtures thereof.

15. The method of claim 3, wherein the second selectable marker gene is green fluorescent protein.

16. The method of claim 3, wherein said first mutant Shine-Dalgarno sequence is selected from the group consisting of the sequences set forth in SEQ. ID. NOS: 24-159; and said first mutant Anti-Shine-Dalgarno sequence is selected from the group consisting of the sequences set forth in SEQ. ID. NOS: 24-159.

17. The method of claim 3, wherein said second mutant Shine-Dalgarno sequence is selected from the group consisting of the sequences set forth in SEQ. ID. NOS: 24-159; and said second mutant Anti-Shine-Dalgarno sequence is selected from the group consisting of the sequences set forth in SEQ. ID. NOS: 24-159.

* * * * *